US009458172B2

(12) United States Patent
Bair et al.

(10) Patent No.: US 9,458,172 B2
(45) Date of Patent: Oct. 4, 2016

(54) PYRIDINYL AND PYRIMIDINYL SULFOXIDE AND SULFONE DERIVATIVES

(71) Applicants: Kenneth W Bair, Watertown, MA (US); Timm R Baumeister, Watertown, MA (US); Peter Dragovich, South San Francisco, CA (US); Francis Gosselin, South San Francisco, CA (US); Po-Wai Yuen, Beijing BDA (CN); Mark Zak, South San Francisco, CA (US); Xiaozhang Zheng, Watertown, MA (US)

(72) Inventors: Kenneth W Bair, Watertown, MA (US); Timm R Baumeister, Watertown, MA (US); Peter Dragovich, South San Francisco, CA (US); Francis Gosselin, South San Francisco, CA (US); Po-Wai Yuen, Beijing BDA (CN); Mark Zak, South San Francisco, CA (US); Xiaozhang Zheng, Watertown, MA (US)

( * ) Notice: Subject to any disclaimer, the term of this patent is extended or adjusted under 35 U.S.C. 154(b) by 0 days.

(21) Appl. No.: 14/382,123

(22) PCT Filed: Mar. 1, 2013

(86) PCT No.: PCT/CN2013/000214
§ 371 (c)(1),
(2) Date: Aug. 29, 2014

(87) PCT Pub. No.: WO2013/127267
PCT Pub. Date: Sep. 6, 2013

(65) Prior Publication Data
US 2015/0175621 A1 Jun. 25, 2015

(30) Foreign Application Priority Data

Mar. 2, 2012 (CN) .................. PCT/CN2012/071872

(51) Int. Cl.
| C07D 498/00 | (2006.01) |
| C07D 413/00 | (2006.01) |
| C07D 487/00 | (2006.01) |
| C07D 401/00 | (2006.01) |
| C07D 221/02 | (2006.01) |
| C07D 471/02 | (2006.01) |
| A61K 31/4965 | (2006.01) |
| A61K 31/519 | (2006.01) |
| A61K 31/44 | (2006.01) |
| A61K 31/47 | (2006.01) |
| C07D 495/04 | (2006.01) |
| C07D 471/04 | (2006.01) |
| C07D 491/048 | (2006.01) |
| A61K 45/06 | (2006.01) |
| A61K 31/455 | (2006.01) |
| A61K 31/706 | (2006.01) |
| A61K 31/444 | (2006.01) |
| A61K 31/4545 | (2006.01) |
| A61K 31/496 | (2006.01) |
| A61K 31/506 | (2006.01) |
| A61K 31/5377 | (2006.01) |
| C07D 487/04 | (2006.01) |

(52) U.S. Cl.
CPC ............ *C07D 495/04* (2013.01); *A61K 31/444* (2013.01); *A61K 31/455* (2013.01); *A61K 31/4545* (2013.01); *A61K 31/496* (2013.01); *A61K 31/506* (2013.01); *A61K 31/519* (2013.01); *A61K 31/5377* (2013.01); *A61K 31/706* (2013.01); *A61K 45/06* (2013.01); *C07D 471/04* (2013.01); *C07D 487/04* (2013.01); *C07D 491/048* (2013.01)

(58) Field of Classification Search
None
See application file for complete search history.

(56) References Cited

FOREIGN PATENT DOCUMENTS

| WO | 2005014554 A1 | 2/2005 |
| WO | 2010137351 A1 | 2/2010 |
| WO | 2012061926 A1 | 5/2012 |
| WO | 2012031197 A1 | 8/2012 |

OTHER PUBLICATIONS

International Search Report and Written Opinion for International Application No. PCT/CN2013/000214, mailed on Jun. 13, 2013.
Written Opinion of Singapore Patent Application No. 11201405055T, mailed on Apr. 20, 2015.
Extended European Search Report, for European Patent Application No. 13754209.8, mailed on Jun. 7, 2015.
First Office Action in Chinese Patent Application No. 201380022895.2, dated Oct. 9, 2015.
A von Heideman et al., Safety and efficacy of NAD depleting cancer drugs—results of a phase I clinical trial of CHS 828 and overview of published data, Cancer Chemother Pharmacol. (2010) 65(6):1165-72.
K Wosikowski et al., WK175, a Novel Antitumor Agent, Decreases the Intracellular Nicotinamide Adenine Dinucleotide Concentration and Induces the Apoptotic Cascade in Human Leukemia Cells, Cancer Res. (2002) 62: 1057.
T Wang et al., Structure of Nampt/PBEF/visfatin, a mammalian NAD+ biosynthetic enzyme, Nature Structural & Mol. Biol., (2006) 13(7): 661-662.
H Yang et al., Nutrient-sensitive mitochondrial NAD+ levels dictate cell survival, cell (2007) 130(6): 1095-1107, 21.

(Continued)

*Primary Examiner* — Jeffrey S Lundgren
*Assistant Examiner* — Michael Schmitt
(74) *Attorney, Agent, or Firm* — Gearhart Law, LLC.

(57) ABSTRACT

Disclosed are certain pyridinyl and pyrimidinyl sulfoxide and sulfone compounds, pharmaceutical compositions comprising such compounds and methods of treatment using such compounds.

20 Claims, No Drawings

(56) References Cited

OTHER PUBLICATIONS

JR Revollo et al., Nampt/PBEF/visfatin regulates insulin secretion in β cells as a systemic NAD biosynthetic enzyme (including supplementals), cell metabolism, (2007) 6(5): 363-375.

P Martinsson et al., Cell death with atypical features induced by the novel antitumoral drug CHS 828, in human U-937 GTB cells, Eur. J. Pharmacol. (2001) 417: 181-187.

P Martinsson et al., Temporal effects of the novel antitumour pyridyl cyanoguanidine (CHS 828) on human lymphoma cells, Eur. J. Cancer, (2001) 37: 260-267.

P Martinsson et al., The combination of the antitumoural pyridyl cyanoguanidine CHS 828 and etoposide in vitro—from cytotoxic synergy to complete inhibition of apoptosis, British J. Pharmacol. (2002) 137: 568-573.

EL Jacobson et al., Mapping the role of NAD metabolism in prevention and treatment of carcinogenesis, Mol. Cellular Biochem. (1999) 193: 69-74.

H Lövborg et al., Multiparametric evaluation of apoptosis: effects of standard cytotoxic agents and the cyanoguanidine CHS 828, Mol. Cancer Ther. (2004) 3(5): 521-526.

H Lövborg et al., Action of a Novel Anticancer Agent, CHS 828, on Mouse Fibroblasts Increased Sensitivity of Cells Lacking Poly (ADP-Ribose) Polymerase-1, Cancer Res. (2002) 62: 4206-4211.

H Lövborg et al., Modulation of pyridyl cyanoguanidine (CHS 828) induced cytotoxicity by 3-aminobenzamide in U-937 GTB cells, Biochem Pharmacol. (2002) 63: 1491-1498.

CP Hsu et al., Nicotinamide phosphoribosyltransferase regulates cell survival through NAD+ synthesis in cardiac myocytes, Circ. Res. (2009) 105: 481-491.

SB Hassan et al., Model for time dependency of cytotoxic effect of CHS 828 in vitro suggests two different mechanisms of action, J. Pharmacol. Exp. Ther. (2001) 299(3): 1140-1147.

L Formentini et al., Detection and pharmacological modulation of nicotinamide mononucleotide (NMN) in vitro and in vivo, Biochem. pharmacol. (2009) 77: 1612-1620.

S Ekelund et al., Early stimulation of acidification rate by novel cytotoxic pyridyl cyanoguanidines in human tumor cells: comparison with m-iodobenzylguanidine, Biochem. pharmacol. (2000) 60: 839-849.

M Dvir-Ginzberg et al., Regulation of cartilage-specific gene expression in human chondrocytes by SirT1 and nicotinamide phosphoribosyltransferase, J. Biol. Chem. (2008) 283: 36300-36310.

D. Fuchs et al., Metronomic administration of the drug GMX1777, a cellular NAD synthesis inhibitor, results in neuroblastoma regression and vessel maturation without inducing drug resistance, Int. J. Cancer (2010) 126(12): 2773-2789.

M Watson et al., The small molecule GMX1778 is a potent inhibitor of NAD+ biosynthesis: strategy for enhanced therapy in nicotinic acid phosphoribosyltransferase 1-deficient tumors, Mol. Cellular Biol. (2009) 29(21): 5872-5888.

Rongvaux, A., et al. Nicotinamide Phosphoribosyl Transferase/Pre-B Cell Colony-Enhancing Factor/Visfatin Is Required for Lymphocyte Development and Cellular Resistance to Genotoxic Stress, J. Immunol. (2008) 181: 4685-4695.

Hasmann M. and Schemainda I., FK866, a Highly Specific Non-competitive Inhibitor of Nicotinamide Phosphoribosyltransferase, Represents a Novel Mechanism for Induction of Tumor Cell Apoptosis, Cancer Res. (2003) 63: 7436-7442.

Drevs, J. et al., Antiangiogenic potency of FK866/K22.175, a new inhibitor of intracellular NAD biosynthesis, in murine renal cell carcinoma, Anticancer Res. (2003) 23: 4853-4858 (Abstract only).

Olesen, U. H. et al., Anticancer agent CHS-828 inhibits cellular synthesis of NAD, Biochem. Biophys. Res. Commun. (2008) 367: 799-804.

Ravaud, A. et al, Phase I study and guanidine kinetics of CHS-828, a guanidine-containing compound, administered orally as a single dose every 3 weeks in solid tumors: an ECSG/EORTC study, Eur. J. Cancer 2005, 41, 702-707.

Hovstadius, P. et al., A Phase I study of CHS 828 in patients with solid tumor malignancy, Clin Cancer Res (2002) 8: 2843.

K. Nolen et al., The pharmacokinetics, toxicities, and biologic effects of FK866, a nicotinamide adenine dinucleotide biosynthesis inhibitor, Invest New Drugs (2008) 26:45-51.

Khan, JA et al., Nicotinamide adenine dinucleotide metabolism as an attractive target for drug discovery, Expert Opin. Ther. Targets (2007) 11: 695-705.

M. Galli et al., The Nicotinamide Phosphoribosyltransferase: A Molecular Link between Metabolism, Inflammation, and Cancer, Cancer Res (2010) 70(1): 8-11 [Published OnlineFirst Dec. 22, 2009].

A. Garten et al., Nampt: Linking NAD biology, metabolism, and cancer, Trends Endocrinol Metab. (2009) 20(3): 130-138.

S. Imai et al."Clocks" in the NAD World: NAD as a metabolic oscillator for the regulation of metabolism and aging, Biochimica et Biophysica Acta (BBA)—Proteins and Proteomics (2010) 1804(8): 1584-1590.

U Galli et al., Synthesis and biological evaluation of isosteric analogues of FK866, an inhibitor of NAD salvage, ChemMedChem (2008) 3: 771-779.

Kato et al., Efficacy of combining GMX1777 with radiation therapy for human head and neck carcinoma, Clin Cancer Res.(2010) 16: 898-911.

E Jonsson et al., In vivo activity of CHS 828 on hollow-fibre cultures of primary human tumour cells from patients, Cancer Lett. (2001) 162(2): 193-200.

P. V. Hjarnaa et al., CHS 828, a Novel Pyridyl Cyanoguanidine with Potent Antitumor Activity in Vitro and in Vivo, Cancer Res. (1999) 59: 5751-5757.

Le Friberg et al., Pharmacokinetic—pharmacodynamic modelling of the schedule-dependent effect of the anti-cancer agent CHS 828 in a rat hollow fibre model, Eur. J. Pharmaceutical Sci. (2005) 25: 163-173.

D Fuchs et al, Regression of orthotopic neuroblastoma in mice by targeting the endothelial and tumor cell compartments, J. Transl. Med. (2009) 7:16-27.

S Bruzzone et al., Catastrophic NAD+ depletion in activated T lymphocytes through Nampt inhibition reduces demyelination and disability in EAE, PLoS ONE (2009) 4(11): e7897.

CL Crowley, The NAD+ precursors, nicotinic acid and nicotinamide protect cells against apoptosis induced by a multiple stress inducer, deoxycholate, Cell Death and Differentiation (2000) 7: 314-326.

PYRIDINYL AND PYRIMIDINYL SULFOXIDE AND SULFONE DERIVATIVES

PRIORITY

This application is a national application of the international application number PCT/CN2003/000214 which was filed on Mar. 1, 2013 and which claimed priority of international application PCT/CN2012/071872 having a filing day of Mar. 2, 2012. This application claims priority of both of these applications and the contents of both of them are incorporated herein by reference in their entirety.

FIELD OF THE INVENTION

The present invention relates to certain pyridinyl and pyrimidinyl sulfoxide and sulfone compounds, pharmaceutical compositions comprising such compounds, and methods of treating cancer, including leukemias and solid tumors, inflammatory diseases, osteoporosis, atherosclerosis, irritable bowel syndrome, and other diseases and medical conditions, with such compounds and pharmaceutical compositions. The present invention also relates to certain pyridinyl and pyrimidinyl sulfone compounds for use in inhibiting nicotinamide phosphoribosyltransferase ("NAMPT").

BACKGROUND OF THE INVENTION

Nicotinamide adenine dinucleotide (NAD) plays a fundamental role in both cellular energy metabolism and cellular signaling. NAD plays an important role in energy metabolism, as the pyridine ring in the NAD molecule readily accepts and donates electrons in hydride transfer reactions catalyzed by numerous dehydrogenases. The enzyme nicotinamide phosphoribosyltransferase (NAMPT, NMPRT, NMPRTase, or NAmPRTase, International nomenclature: E.C. 2.4.2.12), promotes the condensation of nicotinamide with 5-phosphoribosyl-1-pyrophosphate to generate nicotinamide mononucleotide, which is a precursor in the biosynthesis of NAD.

NAMPT is implicated in a variety of functions, including the promotion of vascular smooth muscle cell maturation, inhibition of neutrophil apoptosis, activation of insulin receptors, development of T and B lymphocytes, and reduction of blood glucose. Thus, small molecule NAMPT inhibitors have potential uses as therapies in a variety of diseases or conditions, including cancers involving solid and liquid tumors, non-small cell lung cancer, leukemia, lymphoma, ovarian cancer, glioma, breast cancer, uterine cancer, colon cancer, cervical cancer, lung cancer, prostate cancer, skin cancer, rhino-gastric tumors, colorectal cancer, central nervous system (CNS) cancer, bladder cancer, pancreatic cancer and Hodgkin's disease. NAMPT inhibitors also have potential uses as therapies for diseases or conditions such as cancer, rheumatoid arthritis, diabetes, atherosclerosis, sepsis, or aging.

Rongvaux et al. have demonstrated that NAMPT is implicated in the regulation of cell viability during genotoxic or oxidative stress, and NAMPT inhibitors may therefore be useful as treatments for inflammation. Rongvaux, A., et al. *J. Immunol.* 2008, 181, 4685-4695. NAMPT may also have effects on the reaction of endothelial cells to high glucose levels, oxidative stress, and aging. Thus, NAMPT inbhitors may enable proliferating endothelial cells to resist the oxidative stress of aging and of high glucose, and to productively use excess glucose to support replicative longevity and angiogenic activity.

In particular, NAMPT inhibitors have been shown to interfere with NAD biosynthesis and to induce apoptotic cell death without any DNA damaging effects or primary effects on cellular energy metabolism, and thus have important anti-tumor effects. For example, the NAMPT inhibitor FK866 has these biochemical effects, and has also been shown to reduce NAD levels, induce a delay in tumor growth and enhance tumor radiosensitivity in a mouse mammary carcinoma model. See, e.g., Hasmann M. and I. Schemainda, "FK866, a Highly Specific Noncompetitive Inhibitor of Nicotinamide Phosphoribosyltransferase, Represents a Novel Mechanism for Induction of Tumor Cell Apoptosis," *Cancer Res.* 2003, 63, 7436-7442: Drevs, J. et al., "Antiangiogenic potency of FK866/K22.175, a new inhibitor of intracellular NAD biosynthesis, in murine renal cell carcinoma," *Anticancer Res.* 2003, 23, 4853-4858.

More recently, another NAMPT inhibitor, CHS-828, has been shown to potently inhibit cell growth in a broad range of tumor cell lines. See Olesen, U. H. et al., "Anticancer agent CHS-828 inhibits cellular synthesis of NAD," *Biochem. Biophys. Res. Commun.* 2008, 367, 799-804; Ravaud, A. et al, "Phase I study and guanidine kinetics of CHS-828, a guanidine-containing compound, administered orally as a single dose every 3 weeks in solid tumors: an ECSG/EORTC study," *Eur. J. Cancer* 2005, 41, 702-707. Both FK866 and CHS-828 are currently in clinical trials as cancer treatments.

There remains a need for potent NAMPT inhibitors with desirable pharmaceutical properties. Certain pyridinyl and pyrimidinyl sulfoxide and sulfone derivatives have been found in the context of this invention to have NAMPT-modulating activity.

SUMMARY OF THE INVENTION

In one aspect, the invention is directed to compounds of Formula I:

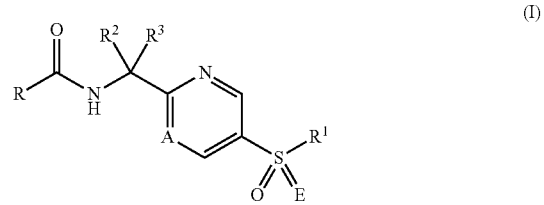

wherein:
A is CH or N;
E is O or is absent;
R is (a) a bicyclic heteroaryl comprising one or more heteroatom ring members independently selected from N, S or O, wherein said bicyclic heteroaryl is unsubstituted or is substituted with one or more substituents selected from the group consisting of deuterium, amino, alkylamino, dialkylamino, alkyl, halo, cyano, haloalkyl, hydroxy, hydroxyalkyl, and alkoxy; and wherein one or more N ring members of said bicyclic heteroaryl is optionally an N-oxide; or
(b) a five- or six-membered nitrogen-linked heterocycloalkyl ring fused to a phenyl or monocyclic heteroaryl, wherein said phenyl or heteroaryl is unsubstituted or is substituted with one or more substituent selected from the group consisting of deuterium, amino, alkylamino, dialkylamino, alkyl, halo, cyano, haloalkyl, hydroxy, hydroxyalkyl, and alkoxy;

$R^1$ is (1) $R^m$ or -alkylenyl-$R^m$ where $R^m$ is cycloalkyl, heterocycloalkyl, phenyl, or monocyclic heteroaryl, wherein each of said cycloalkyl, heterocycloalkyl, phenyl, and heteroaryl is unsubstituted or is substituted with one or more substituents $R^x$;

wherein each $R^x$ substituent is independently selected from the group consisting of deuterium, halo, hydroxy, hydroxyalkyl, cyano, —$NR^aR^b$, -alkylenyl-$NR^aR^b$, oxo, alkyl, cyanoalkyl, haloalkyl, alkoxy, —S-alkyl, haloalkoxy, alkoxyalkyl-, alkenyl, alkynyl, —C(O)alkyl, —C(O)alkyl-O-alkyl, —$CO_2$alkyl, —$CO_2H$, —$CONH_2$, C(O)NH(alkyl), —C(O)NH(haloalkyl), —C(O)N(alkyl)$_2$, —C(O)NH(cycloalkyl), arylalkyl-, arylalkoxy-, aryloxy-, cycloalkyl, cycloalkyloxy, (cycloalkyl)alkyl, heterocycloalkyl, aryl, (heterocycloalkyl)alkyl-, (heterocycloalkyl)alkoxy-, —C(O)cycloalkyl, —C(O)heterocycloalkyl, heteroaryl, (heteroaryl)alkyl-, —S(O)-alkyl, —$SO_2$-alkyl, —$SO_2$-aryl, —$SO_2$-fluoroalkyl, —$N(R^c)$—C(O)-alkyl, —$N(R^c)$—C(O)-aryl, —$N(R^c)$—$CO_2$-alkyl, —$SO_2NH_2$, —$SO_2NH$(alkyl), —$SO_2N$(alkyl)$_2$, —$SO_2NH$(cycloalkyl), and —N(H)($SO_2$alkyl), or two adjacent $R^x$ substituents on a phenyl or heteroaryl $R^m$ groups taken together form methylenedioxy, wherein each of said cycloalkyl, heterocycloalkyl, aryl, and heteroaryl within $R^x$ is unsubstituted or is substituted with one or more substituents independently selected from the group consisting of deuterium, alkyl, halo, hydroxy, cyano, alkoxy, amino, —C(O)alkyl, and —$CO_2$alkyl;

wherein $R^a$ and $R^b$ are each independently H, alkyl, alkoxy, alkoxyalkyl, cyanoalkyl, or haloalkyl; and $R^c$ is H, alkyl or arylalkyl-;

(2) alkyl unsubstituted or substituted with one or more substituents selected from the group consisting of deuterium, halo, hydroxy, cyano, alkoxy, haloalkoxy, —$NR^sR^t$, —C(O)alkyl, $CO_2$alkyl, —$CO_2H$, —$CONR^sR^t$, —SOalkyl, —$SO_2$alkyl, and —$SO_2NR^sR^t$;

where $R^s$ and $R^t$ are each independently H, alkyl, alkoxyalkyl, haloalkyl, —C(O)alkyl, or —$CO_2$alkyl; or (3) —$N(R^n)R^o$;

wherein $R^n$ is H, $R^m$, -alkylenyl-$R^m$, hydroxyalkyl, cyanoalkyl, alkoxyalkyl, haloalkyl, —$CONR^hR^i$, or —$C(O)R^j$;

where $R^m$ is as defined in (1) above;

$R^h$ and $R^i$ are each independently H or alkyl, or $R^h$ and $R^i$ taken together with the nitrogen to which they are attached form a monocyclic heterocycloalkyl; and $R^j$ is an alkyl unsubstituted or substituted with one or more substituents selected from the group consisting of: deuterium, halo, amino, hydroxy, alkoxy, cycloalkyl, heteroaryl, phenyl, and heterocycloalkyl; or a cycloalkyl, heterocycloalkyl, phenyl, or heteroaryl, each unsubstituted or substituted with one or more substituents selected from the group consisting of deuterium, alkyl, halo, amino, hydroxy, and alkoxy; and $R^o$ is H or $R^j$;

$R^2$ and $R^3$ are each independently selected from the group consisting of H and deuterium;

and pharmaceutically acceptable salts of compounds of Formula I;

wherein the compound of Formula I is not 1H-pyrrolo[3,2-c]pyridine-2-carboxylic acid (5-benzenesulfonyl-pyridin-2-ylmethyl)-amide.

In a further aspect, the invention relates to pharmaceutical compositions each comprising an effective amount of at least one compound of Formula I or a pharmaceutically acceptable salt of a compound of Formula I. Pharmaceutical compositions according to the invention may further comprise at least one pharmaceutically acceptable excipient.

In another aspect, the invention is directed to a method of treating a subject suffering from a disease or medical condition mediated by NAMPT activity, comprising administering to the subject in need of such treatment an effective amount of at least one compound of Formula I or a pharmaceutically acceptable salt of a compound of Formula I, or comprising administering to the subject in need of such treatment an effective amount of a pharmaceutical composition comprising an effective amount of at least one compound of Formula I or a pharmaceutically acceptable salt of a compound of Formula I.

An aspect of the present invention concerns the use of compound of Formula I for the preparation of a medicament used in the treatment, prevention, inhibition or elimination of cancer.

An aspect of the present invention concerns the use of a compound of Formula I for the preparation of a medicament used in the treatment, prevention, inhibition or elimination of cancer, where the cancer can be selected from leukemia, lymphoma, ovarian cancer, breast cancer, uterine cancer, colon cancer, cervical cancer, lung cancer, prostate cancer, skin cancer, central nervous system (CNS) cancer, bladder cancer, pancreatic cancer and Hodgkin's disease.

An aspect of the present invention concerns the use of a compound of Formula I for the preparation of a medicament used in the treatment, prevention, inhibition or elimination of cancer, where the cancer can be selected from cancers with solid and liquid tumors, non-small cell lung cancer, leukemia, lymphoma, ovarian cancer, glioma, breast cancer, uterine cancer, colon cancer, cervical cancer, lung cancer, prostate cancer, skin cancer, rhino-gastric tumors, colorectal cancer, CNS cancer, bladder cancer, pancreatic cancer and Hodgkin's disease.

In another aspect, the compounds of Formula I and pharmaceutically acceptable salts thereof are useful as NAMPT modulators. Thus, the invention is directed to a method for modulating NAMPT activity, including when NAMPT is in a subject, comprising exposing NAMPT to an effective amount of at least one compound of Formula I or a pharmaceutically acceptable salt of a compound of Formula I.

In yet another aspect, the present invention is directed to methods of making compounds of Formula I and pharmaceutically acceptable salts thereof. In certain embodiments of the compounds, pharmaceutical compositions, and methods of the invention, the compound of Formula I is a compound selected from those species described or exemplified in the detailed description below, or is a pharmaceutically acceptable salt of such a compound.

Additional embodiments, features, and advantages of the invention will be apparent from the following detailed description and through practice of the invention.

DETAILED DESCRIPTION AND PARTICULAR EMBODIMENTS

For the sake of brevity, the disclosures of the publications cited in this specification, including patents and patent applications, are herein incorporated by reference in their entirety.

Most chemical names were generated using IUPAC nomenclature herein. Some chemical names were generated using different nomenclatures or alternative or commercial names known in the art. In the case of conflict between names and structures, the structures prevail.

General Definitions

As used above, and throughout this disclosure, the following terms, unless otherwise indicated, shall be understood to have the following meanings. If a definition is missing, the conventional definition as known to one skilled in the art controls. If a definition provided herein conflicts or is different from a definition provided in any cited publication, the definition provided herein controls.

As used herein, the terms "including", "containing", and "comprising" are used in their open, non-limiting sense.

As used herein, the singular forms "a", "an", and "the" include plural referents unless the context clearly dictates otherwise.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Chemical Definitions

As used herein, "alkyl" refers to a saturated, straight- or branched-chain hydrocarbon group having from 1 to 10 carbon atoms. Representative alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, n-hexyl, and the like, and longer alkyl groups, such as heptyl, octyl, and the like. As used herein, "lower alkyl" means an alkyl having from 1 to 6 carbon atoms.

The term "alkylamino" as used herein denotes an amino group as defined herein wherein one hydrogen atom of the amino group is replaced by an alkyl group as defined herein. Aminoalkyl groups can be defined by the following general formula —NH-alkyl. This general formula includes groups of the following general formulae: —NH—$C_1$-$C_{10}$-alkyl and —NH—$C_1$-$C_6$-alkyl. Examples of aminoalkyl groups include, but are not limited to aminomethyl, aminoethyl, aminopropyl, aminobutyl.

The term "dialkylamino" as used herein denotes an amino group as defined herein wherein two hydrogen atoms of the amino group are replaced by alkyl groups as defined herein. Diaminoalkyl groups can be defined by the following general formula —N(alkyl)$_2$, wherein the alkyl groups can be the same or can be different and can be selected from alkyls as defined herein, for example $C_1$-$C_{10}$-alkyl or $C_1$-$C_6$-alkyl.

The term "alkylenyl" refers to a divalent alkyl group.

The term "alkoxy" as used herein includes —O-(alkyl), wherein alkyl is defined above.

As used herein, "alkoxyalkyl" means -(alkylenyl)-O-(alkyl), wherein each "alkyl" is independently an alkyl group defined above.

As used herein, an "alkenyl" refers to a straight- or branched-chain hydrocarbon group having one or more double bonds therein and having from 2 to 10 carbon atoms. Illustrative alkenyl groups include, but are not limited to, ethylenyl, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, and the like. As used herein, "lower alkenyl" means an alkenyl having from 2 to 6 carbon atoms.

As used herein, "alkynyl" refers to a straight- or branched-chain hydrocarbon group having one or more triple bonds therein and having from 2 to 10 carbon atoms Exemplary alkynyl groups include, but are not limited to, ethynyl, propynyl, butynyl, pentynyl, hexynyl, methylpropynyl, 4-methyl-1-butynyl, 4-propyl-2-pentynyl, 4-butyl-2-hexynyl, and the like.

The term "amino" as used herein refers to an —$NH_2$ group.

"Aryl" means a mono-, bi-, or tricyclic aromatic group, wherein all rings of the group are aromatic. For bi- or tricyclic systems, the individual aromatic rings are fused to one another. Exemplary aryl groups include, but are not limited to, phenyl, naphthalene, and anthracene.

"Aryloxy" as used herein refers to an —O-(aryl) group, wherein aryl is defined as above.

"Arylalkyl" as used herein refers to an -(alkylenyl)-(aryl) group, wherein alkylenyl and aryl are as defined above. Exemplary arylalkyls comprise a lower alkyl group. Non-limiting examples of suitable arylalkyl groups include benzyl, 2-phenethyl, and naphthalenylmethyl.

"Arylalkoxy" as used herein refers to an —O-(alkylenyl)-aryl group wherein alkylenyl and aryl are as defined above.

The term "cyano" as used herein means a substituent having a carbon atom joined to a nitrogen atom by a triple bond.

The term "cyanoalkyl" denotes an alkyl group as defined above wherein a hydrogen atom of the alkyl group is replaced by a cyano (—CN) group. The alkyl portion of the cyanoalkyl group provides the connection point to the remainder of the molecule.

The term "deuterium" as used herein means a stable isotope of hydrogen having one proton and one neutron.

The term "halo" represents chloro, fluoro, bromo, or iodo. In some embodiments, halo is chloro, fluoro, or bromo. The term "halogen" as used herein refers to fluorine, chlorine, bromine, or iodine.

The term "haloalkyl" denotes an alkyl group as defined above wherein one or more, for example one, two, or three of the hydrogen atoms of the alkyl group are replaced by a halogen atom, for example fluoro, bromo, or chloro, in particular fluoro. Examples of haloalkyl include, but are not limited to, monofluoro-, difluoro-, or trifluoro-methyl, -ethyl or -propyl, for example, 3,3,3-trifluoropropyl, 2-fluoroethyl, 2,2,2-trifluoroethyl, fluoromethyl, difluoromethyl, or trifluoromethyl, or bromoethyl or chloroethyl. Similarly, the term "fluoroalkyl" refers to an alkyl group as defined above substituted with one or more, for example one, two, or three fluorine atoms.

The term "haloalkoxy" as used herein refers to an —O—(haloalkyl) group wherein haloalkyl is defined as above. Exemplary haloalkoxy groups are bromoethoxy, chloroethoxy, trifluoromethoxy and 2,2,2-trifluoroethoxy.

The term "hydroxy" means an —OH group.

The term "hydroxyalkyl" denotes an alkyl group that is substituted by at least one hydroxy group, for example, one, two or three hydroxy group(s). The alkyl portion of the hydroxyalkyl group provides the connection point to the remainder of a molecule. Examples of hydroxyalkyl groups include, but are not limited to, hydroxymethyl, hydroxyethyl, 1-hydroxypropyl, 2-hydroxyisopropyl, 1,4-dihydroxybutyl, and the like.

The term "methylenedioxy" as used herein means a functional group with the structural formula —O—CH$_2$—O— which is connected to the molecule by two chemical bonds via the oxygens.

The term "oxo" means an =O group and may be attached to a carbon atom or a sulfur atom. The term "N-oxide" refers to the oxidized form of a nitrogen atom.

As used herein, the term "cycloalkyl" refers to a saturated or partially saturated, monocyclic, fused polycyclic, bridged polycyclic, or spiro polycyclic carbocycle having from 3 to 15 ring carbon atoms. A non limiting category of cycloalkyl groups are saturated or partially saturated, monocyclic carbocycles having from 3 to 6 carbon atoms. Illustrative examples of cycloalkyl groups include, but are not limited to, the following moieties:

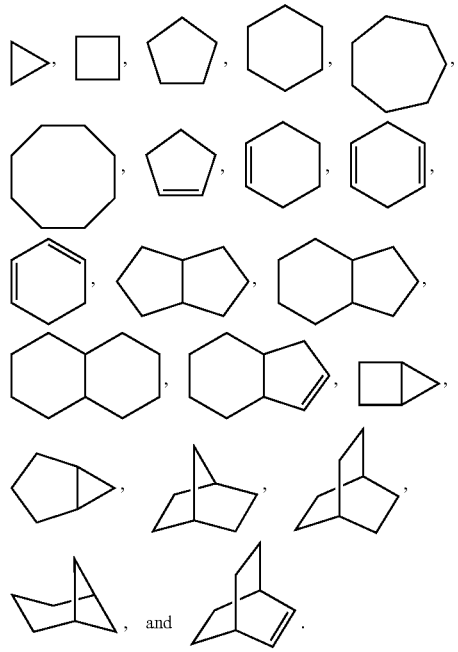

"Heterocycloalkyl" as used herein refers to a monocyclic, or fused, bridged, or spiro polycyclic ring structure that is saturated or partially saturated and has from 3 to 12 ring atoms selected from carbon atoms and up to three heteroatoms selected from nitrogen, oxygen, and sulfur. The ring structure may optionally contain up to two oxo groups on carbon or sulfur ring members. Heterocycloalkyl groups also include monocyclic rings having 5 to 6 atoms as ring members, of which 1, 2 or 3 ring members are selected from N, S or O and the rest are carbon atoms. A "nitrogen-linked" heterocycloalkyl is attached to the parent moiety via a nitrogen ring atom. A "carbon-linked" heterocycloalkyl is attached to the parent moiety via a carbon ring atom. Illustrative heterocycloalkyl entities include, but are not limited to:

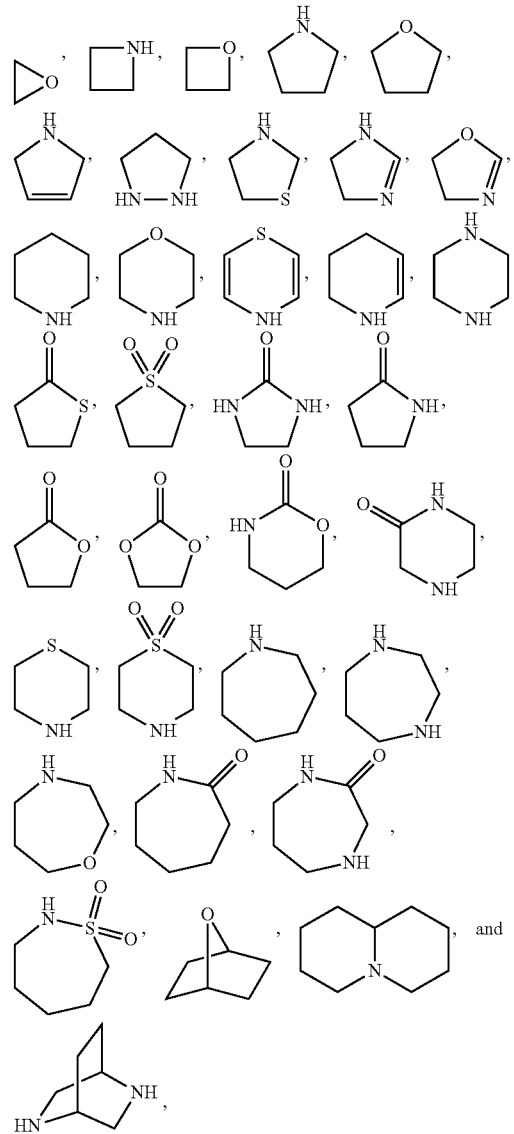

"(Heterocycloalkyl)alkyl-" refers to a heterocycloalkyl group as defined above, substituted with an alkylenyl group as defined above, wherein the alkylenyl group provides for the attachment to the parent moiety.

The term "(heterocycloalkyl)alkoxy-" refers to a (heterocycloalkyl)-(alkylenyl)-O— group, wherein heterocycloalkyl and alkylenyl are as defined above.

As used herein, the term "heteroaryl" refers to a monocyclic, or fused polycyclic, aromatic heterocycle having from three to 15 ring atoms that are selected from carbon, oxygen, nitrogen, and sulfur. Suitable heteroaryl groups do not include ring systems that must be charged to be aromatic, such as pyrylium. Certain suitable 5-membered heteroaryl rings (as a monocyclic heteroaryl or as part of a polycyclic heteroaryl) have one oxygen, sulfur, or nitrogen atom, or one nitrogen plus one oxygen or sulfur, or 2, 3, or 4 nitrogen atoms. Certain suitable 6-membered heteroaryl rings (as a monocyclic heteroaryl or as part of a polycyclic heteroaryl) have 1, 2, or 3 nitrogen atoms. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The term "bicyclic heteroaryl" refers to a heteroaryl as defined above, having two constituent aromatic rings, wherein the two rings are fused to one another and at least one of the rings is a heteroaryl as defined above. Bicyclic heteroaryls include bicyclic heteroaryl groups comprising 1, 2, 3, or 4 heteroatom ring members, and that are unsubstituted or substituted with one or more substituents selected from the group consisting of amino and halo; and wherein one or more N ring members of said heteroaryl is optionally an N-oxide. Bicyclic heteroaryls also include 8-, 9-, or 10-membered bicyclic heteroaryl groups. Bicyclic heteroaryls also include 8-, 9-, or 10-membered bicyclic heteroaryl groups that have 1, 2, 3, or 4 heteroatom ring members, and that are unsubstituted or substituted by with one or more substituents selected from the group consisting of amino and halo; and wherein one or more N ring members of said heteroaryl is optionally an N-oxide. Illustrative examples of bicyclic heteroaryls include, but are not limited to:

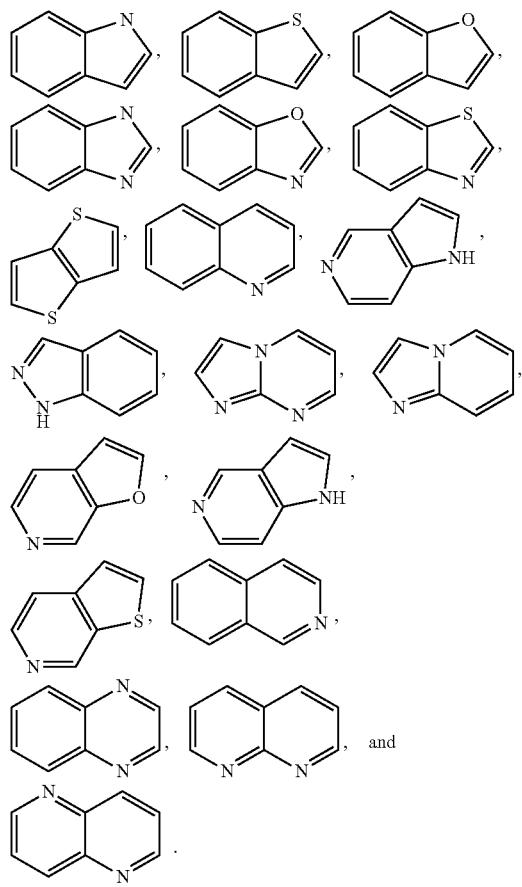

The term "five- or six-membered nitrogen-linked heterocycloalkyl ring fused to a phenyl or monocyclic heteroaryl, wherein said phenyl or heteroaryl is unsubstituted or is substituted with amino" include, but are not limited to, the following groups

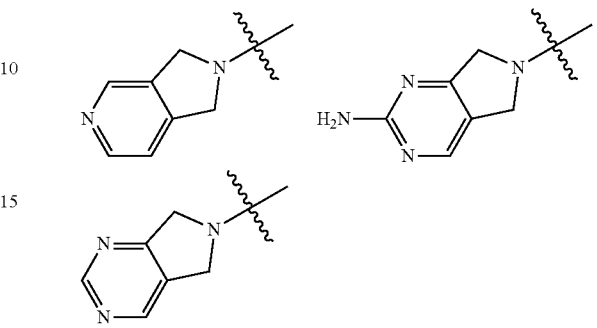

Those skilled in the art will recognize that the species of heteroaryl cycloalkyl, and heterocycloalkyl groups listed or illustrated above are not exhaustive, and that additional species within the scope of these defined terms may also be selected.

As used herein, the term "substituted" means that the specified group or moiety bears one or more suitable substituents. As used herein, the term "unsubstituted" means that the specified group bears no substituents. As used herein, the term "optionally substituted" means that the specified group is unsubstituted or substituted by the specified number of substituents. Where the term "substituted" is used to describe a structural system, the substitution is meant to occur at any valency-allowed position on the system.

As used herein, the expression "one or more substituents" denotes one to maximum possible number of substitution(s) that can occur at any valency-allowed position on the system. In a certain embodiment, one or more substituent means 1, 2, 3, 4, or 5 substituents. In another embodiment, one or more substituent means 1, 2, or 3 substituents.

Any atom that is represented herein with an unsatisfied valence is assumed to have the sufficient number of hydrogen atoms to satisfy the atom's valence.

When any variable (e.g., alkyl, alkylenyl, heteroaryl, $R^1$, $R^2$, or $R^a$) appears in more than one place in any formula or description provided herein, the definition of that variable on each occurrence is independent of its definition at every other occurrence.

Numerical ranges, as used herein, are intended to include sequential whole numbers. For example, a range expressed as "from 0 to 4" or "0-4" includes 0, 1, 2, 3 and 4.

When a multifunctional moiety is shown, the point of attachment to the core is indicated by a line or hyphen. For example, aryloxy- refers to a moiety in which an oxygen atom is the point of attachment to the core molecule while aryl is attached to the oxygen atom.

Additional Definitions

As used herein, the term "subject" encompasses mammals and non-mammals. Examples of mammals include, but are not limited to, any member of the Mammalian class: humans; non-human primates such as chimpanzees, and other apes and monkey species; farm animals such as cattle, horses, sheep, goats, swine; domestic animals such as rabbits, dogs, and cats; and laboratory animals including rodents, such as rats, mice and guinea pigs, and the like. Examples of non-mammals include, but are not limited to, birds, fish and the like. In one embodiment of the present invention, the mammal is a human.

"Patient" includes both human and animals.

The term "inhibitor" refers to a molecule such as a compound, a drug, an enzyme activator, or a hormone that blocks or otherwise interferes with a particular biologic activity.

The term "modulator" refers to a molecule, such as a compound of the present invention, that increases or decreases, or otherwise affects the activity of a given enzyme or protein.

The terms "effective amount" or "therapeutically effective amount" refer to a sufficient amount of the agent to provide the desired biological result. That result can be reduction and/or alleviation of the signs, symptoms, or causes of a disease or medical condition, or any other desired alteration of a biological system. For example, an "effective amount" for therapeutic use is the amount of a compound, or of a composition comprising the compound, that is required to provide a clinically relevant change in a disease state, symptom, or medical condition. An appropriate "effective" amount in any individual case may be determined by one of ordinary skill in the art using routine experimentation. Thus, the expression "effective amount" generally refers to the quantity for which the active substance has a therapeutically desired effect.

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying metabolic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

Additional Chemical Descriptions

Any formula given herein is intended to represent compounds having structures depicted by the structural formula as well as certain variations or forms. For example, compounds of any formula given herein may have asymmetric or chiral centers and therefore exist in different stereoisomeric forms. All stereoisomers, including optical isomers, enantiomers, and diastereomers, of the compounds of the general formula, and mixtures thereof, are considered to fall within the scope of the formula. Furthermore, certain structures may exist as geometric isomers (i.e., cis and trans isomers), as tautomers, or as atropisomers. All such isomeric forms, and mixtures thereof, are contemplated herein as part of the present invention. Thus, any formula given herein is intended to represent a racemate, one or more enantiomeric forms, one or more diastereomeric forms, one or more tautomeric or atropisomeric forms, and mixtures thereof.

Diastereomeric mixtures may be separated into their individual diastereomers on the basis of their physical chemical differences by methods well known to those skilled in the art, such as, for example, by chromatography and/or fractional crystallization. Enantiomers may be separated by converting the enantiomeric mixture into a diastereomeric mixture by reaction with an appropriate optically active compound (e.g., chiral auxiliary such as a chiral alcohol or Mosher's acid chloride, or formation of a mixture of diastereomeric salts), separating the diastereomers and converting (e.g., hydrolyzing or de-salting) the individual diastereomers to the corresponding pure enantiomers. Enantiomers may also be separated by use of chiral HPLC column. The chiral centers of compounds of the present invention may be designated as "R" or "S" as defined by the IUPAC 1974 Recommendations.

The compounds of the invention can form pharmaceutically acceptable salts, which are also within the scope of this invention. A "pharmaceutically acceptable salt" refers to a salt of a free acid or base of a compound of Formula I that is non-toxic, is physiologically tolerable, is compatible with the pharmaceutical composition in which it is formulated, and is otherwise suitable for formulation and/or administration to a subject. Reference to a compound herein is understood to include reference to a pharmaceutically acceptable salt of said compound unless otherwise indicated.

Compound salts include acidic salts formed with inorganic and/or organic acids, as well as basic salts formed with inorganic and/or organic bases. In addition, where a given compound contains both a basic moiety, such as, but not limited to, a pyridine or imidazole, and an acidic moiety, such as, but not limited to, a carboxylic acid, one of skill in the art will recognize that the compound may exist as a zwitterion ("inner salt"); such salts are included within the term "salt" as used herein. Salts of the compounds of the invention may be prepared, for example, by reacting a compound with an amount of a suitable acid or base, such as an equivalent amount, in a medium such as one in which the salt precipitates or in an aqueous medium followed by lyophilization.

Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate ("mesylate"), ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counterions. Hence, a pharmaceutically acceptable salt can have one or more charged atoms and/or one or more counter ion.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

Additionally, acids and bases which are generally considered suitable for the formation of pharmaceutically useful salts from pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, MD, available from FDA). These disclosures are incorporated herein by reference thereto.

Additionally, any compound described herein is intended to refer also to any unsolvated form, or a hydrate, solvate, or polymorph of such a compound, and mixtures thereof, even if such forms are not listed explicitly. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of a crystalline solid. "Solvate" encompasses both solution-phase and isolatable solvates. Suitable solvates include those formed with pharmaceutically acceptable solvents such as water, ethanol, and the like. In some embodiments, the solvent is water and the solvates are hydrates.

One or more compounds of the invention may optionally be converted to a solvate. Methods for the preparation of solvates are generally known. Thus, for example, M. Caira et al., J. Pharmaceutical Sci., 93(3), 601-611 (2004), describes the preparation of the solvates of the antifungal fluconazole in ethyl acetate as well as from water. Similar preparations of solvates, hemisolvate, hydrates, and the like are described by E. C. van Tonder et al, AAPS PharmSciTech., 5(1), article 12 (2004); and A. L. Bingham et al, Chem. Commun., 603-604 (2001). A typical, non-limiting process involves dissolving the inventive compound in a suitable amounts of the solvent (organic solvent or water or a mixture thereof) at a higher than ambient temperature, and cooling the solution at a rate sufficient to form crystals which are then isolated by standard methods. Analytical techniques such as, for example, infrared spectroscopy, show the presence of the solvent (or water) in the crystals as a solvate (or hydrate).

The invention also relates to pharmaceutically acceptable prodrugs of the compounds of Formula I, and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula I). A "pharmaceutically acceptable prodrug" is a prodrug that is non-toxic, biologically tolerable, and otherwise suitable for formulation and/or administration to the subject. Illustrative procedures for the selection and preparation of suitable prodrug derivatives are described, for example, in "Design of Prodrugs", ed. H. Bundgaard, Elsevier, 1985.

Examples of prodrugs include pharmaceutically acceptable esters of the compounds of the invention, which are also considered to be part of the invention. Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol. Additional discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press.

For example, if a compound of Formula I contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholine ($C_2$-$C_3$)alkyl, and the like.

Similarly, if a compound of Formula I contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of Formula I incorporates an amine functional group, a prodrug can be formed by the replacement of a hydrogen atom in the amine group with a group such as, for example, R"-carbonyl, R"O-carbonyl, NR"R'-carbonyl where R" and R' are each independently ($C_1$-$C_{10}$) alkyl, ($C_3$-$C_7$) cycloalkyl, benzyl, or R"-carbonyl is a natural α-aminoacyl or natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl, carboxy ($C_1$-$C_6$)alkyl, amino($C_1$-$C_4$)alkyl or mono-N- or di-N,N—($C_1$-$C_6$)alkylaminoalkyl, —C(Y$^4$)Y$^5$ wherein Y$^4$ is H or methyl and $Y^5$ is mono-N- or di-N,N—($C_1$-$C_6$)alkylamino morpholino, piperidin-1-yl or pyrrolidin-1-yl, and the like.

The present invention also relates to pharmaceutically active metabolites of compounds of Formula I, and uses of such metabolites in the methods of the invention. A "pharmaceutically active metabolite" means a pharmacologically active product of metabolism in the body of a compound of Formula I or salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number Examples of isotopes that can be incorporated into compounds of the invention include isotopes of hydrogen, carbon, nitrogen, oxygen, phosphorous, fluorine, chlorine, and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labelled compounds are useful in metabolic studies (for example with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly suitable for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

The use of the terms "salt," "solvate," "polymorph," "prodrug," and the like, with respect to the compounds described herein is intended to apply equally to the salt, solvate, polymorph, and prodrug forms of enantiomers, stereoisomers, rotamers, tautomers, atropisomers, and racemates of the inventive compounds.

Compounds of the Invention

In some embodiments of Formula I, A is CH. In other embodiments, A is N.

In some embodiments of Formula I, E is O. In other embodiments, E is absent.

In some embodiments, R is an unsubstituted or substituted bicyclic heteroaryl as defined for Formula I. In some embodiments, the bicyclic heteroaryl has 1, 2, or 3 nitrogen ring atoms. In other embodiments, the bicyclic heteroaryl is a 9- or 10-membered bicyclic heteroaryl, unsubstituted or substituted as described for Formula I. In other embodiments, the bicyclic heteroaryl is a 8- or 9-membered heteroaryl, unsubstituted or substituted as described for Formula I. In other embodiments, R is:

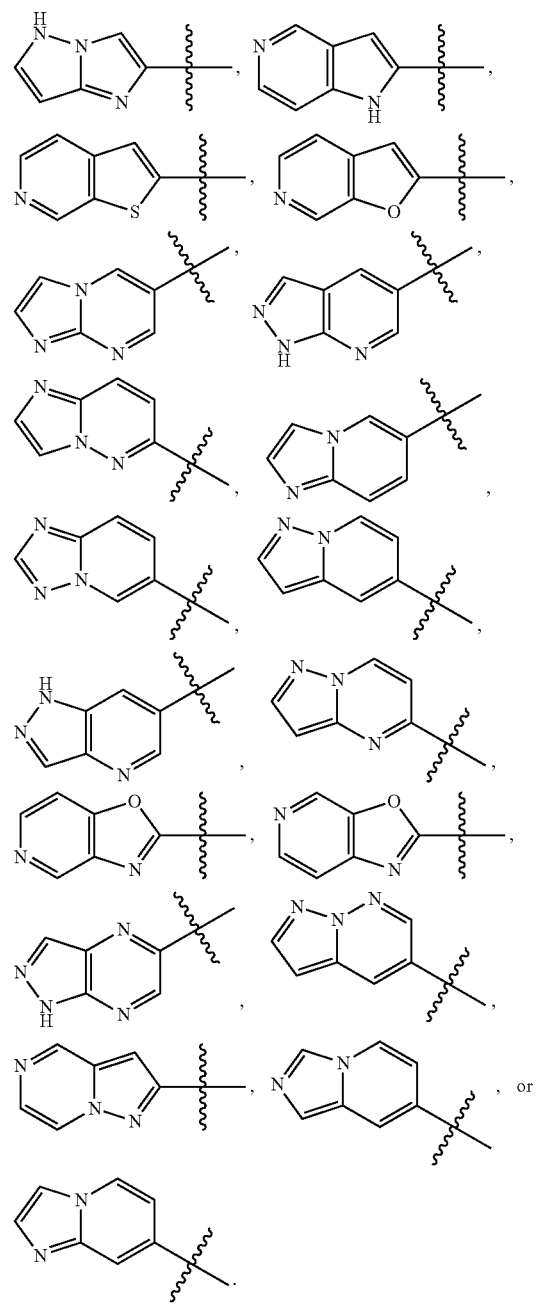

each unsubstituted or substituted as described for Formula I.

In other embodiments, R is a bicyclic heteroaryl selected from the group consisting of:

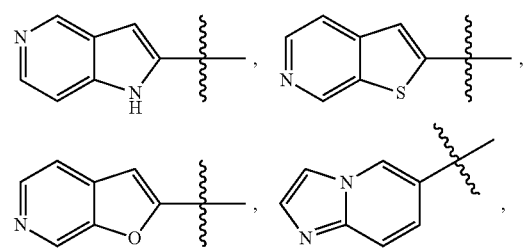

-continued

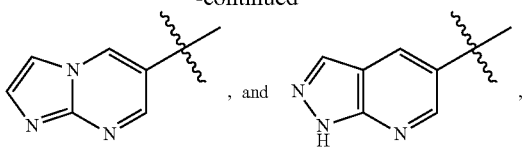

each unsubstituted or substituted as described for Formula I. In further embodiments, R is selected from the group consisting of:

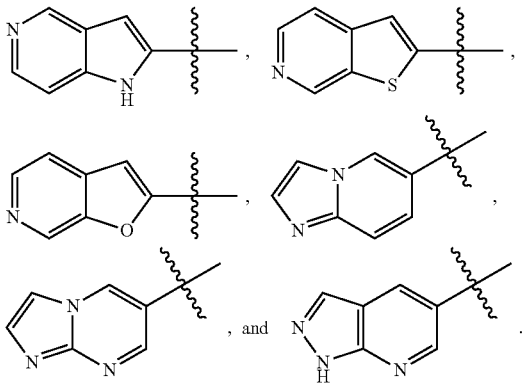

In further embodiments R is

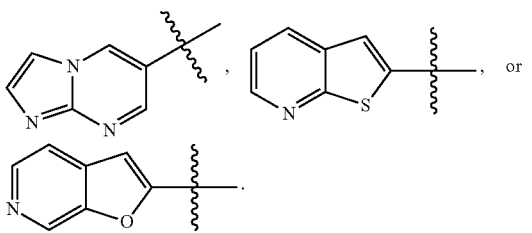

In other embodiments, R is a five- or six-membered nitrogen-linked heterocycloalkyl ring fused to an unsubstituted or substituted phenyl or monocyclic heteroaryl, for examples a 6 membered heteroaryl, as defined in Formula I. In further embodiments, R is

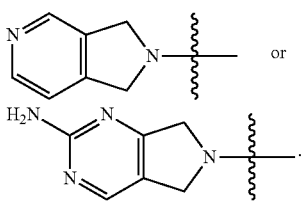

In still other embodiments, R is

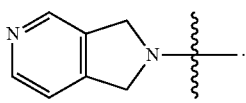

In other embodiments, R is substituted with one or more substituents selected from the group consisting of amino and halo.

In some embodiments, $R^1$ is $R'''$. In other embodiments, $R^1$ is -alkylenyl-$R'''$.

In some embodiments, $R'''$ is cycloalkyl, unsubstituted or substituted as indicated for Formula I. In some embodiments, the cycloalkyl is cyclopropyl, cyclobutyl, cyclopentyl, or cyclohexyl. In other embodiments, the cycloalkyl is cyclohexyl.

In some embodiments, $R'''$ is a heterocycloalkyl, unsubstituted or substituted as indicated for Formula I. In some embodiments, the heterocycloalkyl is azetidinyl, pyrrolidinyl, piperidinyl, morpholinyl, piperazinyl, oxetanyl, tetrahydrofuranyl, or tetrahydropyranyl. In other embodiments, the heterocycloalkyl is 1-piperidinyl, 4-piperidinyl, or piperazinyl. In still other embodiments, the heterocycloalkyl is 4-piperidinyl. In certain embodiments, the heterocycloalkyl is unsubstituted. In other embodiments, the heterocycloalkyl is substituted with an alkyl, —C(O)alkyl, —C(O)alkyl-O-alkyl, —CO$_2$alkyl, haloalkyl, or monocyclic heterocycloalkyl group. In other embodiments, $R'''$ is heterocycloalkyl substituted with an oxetanyl, tetrahydrofuranyl, tetrahydropyranyl, or pyrrolidinyl group.

In other embodiments, $R'''$ is phenyl or a monocyclic heteroaryl, each unsubstituted or substituted as described for Formula I. In other embodiments, $R'''$ is phenyl, pyridinyl, pyrazolyl, pyrimidinyl, thiazolyl, or pyrazinyl, each unsubstituted or substituted as indicated for Formula I. In other embodiments, $R'''$ is pyrazolyl or pyridinyl, each unsubstituted or substituted as indicated for Formula I, In still other embodiments, $R'''$ is phenyl, unsubstituted or substituted as described for Formula I.

In some embodiments, the $R'''$ group is substituted with one or more $R^x$ substituents each independently selected from the group consisting of: fluoro, chloro, bromo, hydroxy, hydroxymethyl, hydroxyethyl, cyano, amino, di(alkyl)amino, alkylamino, monofluoroalkyl, trifluoroalkyl, methoxy, ethoxy, trifluoromethoxy, acetyl, propionyl, butyryl, methoxycarbonyl, ethoxycarbonyl, tert-butoxycarbonyl, carboxyl, methylsulfonyl, ethylsulfonyl, trifluoromethylsulfonyl, methylamido, ethylamido, oxetanyl, pyrrolidinyl, tetrahydrofuranyl, piperidinyl, tetrahydropyranyl, morpholinyl, piperazinyl, pyridinyl, imidazolyl, pyrrolyl, pyrimidinyl, and phenyl, each substituted or unsubstituted as indicated in Formula I. In still further embodiments, the $R'''$ group is substituted with 1, 2, or 3 $R^x$ substituents each independently selected from the group consisting of: fluoro, trifluoromethyl, trifluoromethoxy, morpholinyl, 4-methyl-piperazinyl, piperidinyl, methoxy, cyano, acetyl, ethylamido, methylsulfonyl, ethylsulfonyl, cyano, chloro, dimethylamino, methyl, ethyl, propyl, isopropyl, isobutyl, butyryl, oxetanyl, tetrahydropyranyl, pyrrolidinyl, and 1-(3-oxetanyl)-piperidin-4-yl.

In further embodiments, $R'''$ is phenyl, unsubstituted or substituted with 1 or 2 $R^x$ substituents independently selected from the group consisting of: fluoro, trifluoromethyl, trifluoromethoxy, morpholinyl, 4-methyl-piperazinyl, methoxy, cyano, ethylamido, methylsulfonyl, or ethylsulfonyl. In further embodiments, $R'''$ is phenyl, unsubstituted or substituted with 1 or 2 $R^x$ substituents independently selected from the group consisting of: fluoro, trifluoromethyl, methoxy, trifluoromethoxy, morpholinyl, and 4-methyl-piperazinyl.

In other embodiments, $R^1$ is an alkyl, unsubstituted or substituted as described for Formula I. In some embodiments, $R^1$ is an alkyl substituted with one or more substituents selected from the group consisting of halo, hydroxy, cyano, alkoxy, trifluoroalkyl, trifluoroalkoxy, amino, methylamino, dimethylamino, acetyl, methoxycarbonyl, amido, and methylsulfonyl.

In other embodiments, $R^1$ is —N(R″)R°. In such embodiments, R″ is R‴ or -alkylenyl-R‴, where R‴ is as described above. In other embodiments, R″ is hydroxyalkyl, cyanoalkyl, alkoxyalkyl, haloalkyl, —CONR$^h$R$^i$, or —C(O)R$^j$, where R$^h$ and R$^i$ are each independently H or alkyl, and R$^j$ is hydroxymethyl, cycloalkyl, piperidinyl, or phenyl. In some embodiments, R° is H or alkyl.

In some embodiments, one of $R^2$ and $R^3$ is deuterium and the other is H. In other embodiments, both $R^2$ and $R^3$ are H.

In some embodiments, each alkyl or alkylene described above is independently a $C_{1-10}$alkyl. In other embodiments, each alkyl or alkylene in Formula I is independently a $C_{1-6}$alkyl. In still other embodiments, each alkyl or alkylene in Formula I is independently a $C_{1-4}$alkyl.

In certain embodiments, the compound of Formula I is chosen from the following table:

| Ex. | Structure | Name |
|---|---|---|
| 1 | 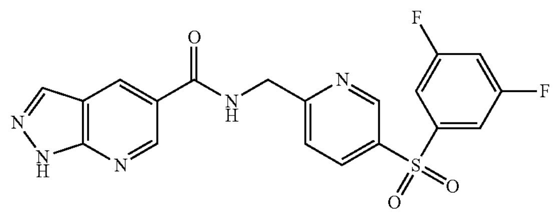 [SMILES: O=C(NCc1ccc(S(=O)(=O)c2cc(F)cc(F)c2)cn1)c1cnc2[nH]ncc2c1] | 1H-Pyrazolo[3,4-b]pyridine-5-carboxylic acid [5-(3,5-difluoro-benzenesulfonyl)-pyridin-2-ylmethyl]-amide |
| 2 | 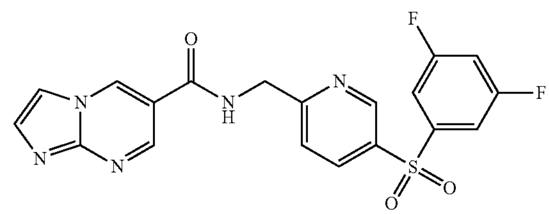 [SMILES: O=C(NCc1ccc(S(=O)(=O)c2cc(F)cc(F)c2)cn1)c1cnc2nccn2c1] | Imidazo[1,2-a]pyrimidine-6-carboxylic acid [5-(3,5-difluoro-benzenesulfonyl)-pyridin-2-ylmethyl]-amide |
| 3 | 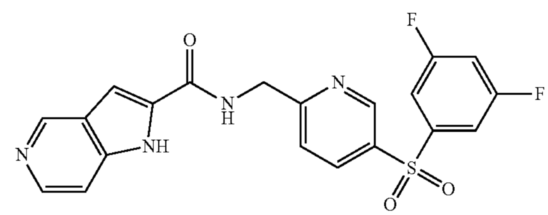 [SMILES: O=C(NCc1ccc(S(=O)(=O)c2cc(F)cc(F)c2)cn1)c1cc2cnccc2[nH]1] | 1H-Pyrrolo[3,2-c]pyridine-2-carboxylic acid [5-(3,5-difluoro-benzenesulfonyl)-pyridin-2-ylmethyl]-amide |
| 4 | 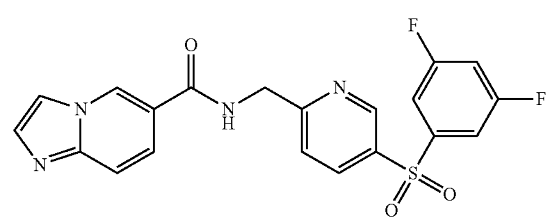 [SMILES: O=C(NCc1ccc(S(=O)(=O)c2cc(F)cc(F)c2)cn1)c1ccc2nccn2c1] | Imidazo[1,2-a]pyridine-6-carboxylic acid [5-(3,5-difluoro-benzenesulfonyl)-pyridin-2-ylmethyl]-amide |
| 5 | 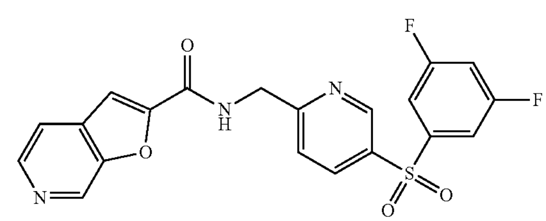 [SMILES: O=C(NCc1ccc(S(=O)(=O)c2cc(F)cc(F)c2)cn1)c1cc2ccncc2o1] | Furo[2,3-c]pyridine-2-carboxylic acid [5-(3,5-difluoro-benzenesulfonyl)-pyridin-2-ylmethyl]-amide |
| 6 | 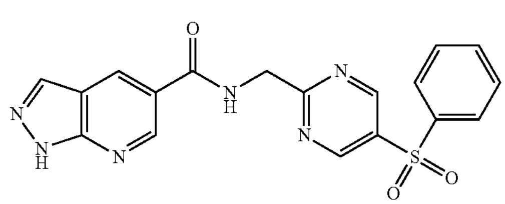 [SMILES: O=C(NCc1ncc(S(=O)(=O)c2ccccc2)cn1)c1cnc2[nH]ncc2c1] | 1H-Pyrazolo[3,4-b]pyridine-5-carboxylic acid (5-benzenesulfonyl-pyrimidin-2-ylmethyl)-amide |

| Ex. | Structure | Name |
|---|---|---|
| 7 | 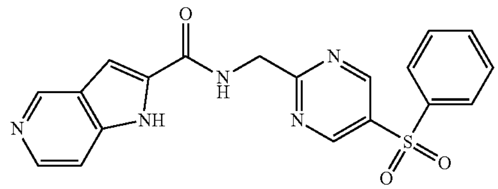 [SMILES: O=C(NCc1ncc(S(=O)(=O)c2ccccc2)cn1)c1cc2cnccc2[nH]1] | 1H-Pyrrolo[3,2-c]pyridine-2-carboxylic acid (5-benzenesulfonyl-pyrimidin-2-ylmethyl)-amide |
| 8 | 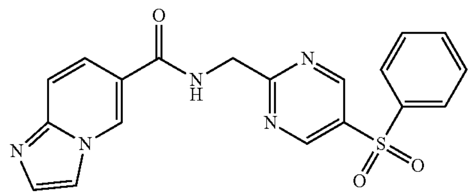 [SMILES: O=C(NCc1ncc(S(=O)(=O)c2ccccc2)cn1)c1ccc2nccn2c1] | Imidazo[1,2-a]pyridine-6-carboxylic acid (5-benzenesulfonyl-pyrimidin-2-ylmethyl)-amide |
| 9 | 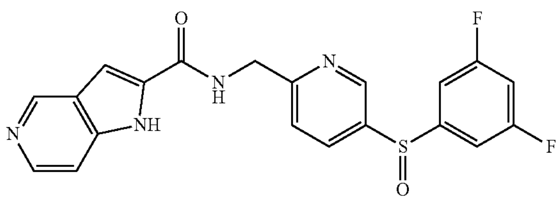 [SMILES: O=C(NCc1ccc(S(=O)c2cc(F)cc(F)c2)cn1)c1cc2cnccc2[nH]1] | 1H-Pyrrolo[3,2-c]pyridine-2-carboxylic acid [5-(3,5-difluoro-benzenesulfinyl)-pyridin-2-ylmethyl]-amide (racemic) |
| 10 | 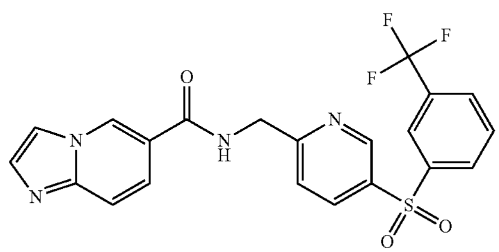 [SMILES: O=C(NCc1ccc(S(=O)(=O)c2cccc(C(F)(F)F)c2)cn1)c1ccc2nccn2c1] | Imidazo[1,2-a]pyridine-6-carboxylic acid [5-(3-trifluoromethyl-benzenesulfonyl)-pyridin-2-ylmethyl]-amide |
| 11 | 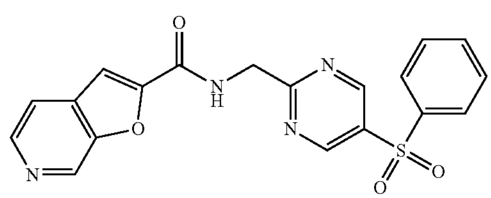 [SMILES: O=C(NCc1ncc(S(=O)(=O)c2ccccc2)cn1)c1cc2ccncc2o1] | Furo[2,3-c]pyridine-2-carboxylic acid (5-benzenesulfonyl-pyrimidin-2-ylmethyl)-amide |
| 12 | 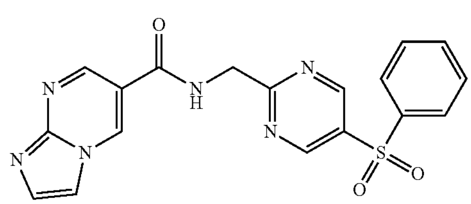 [SMILES: O=C(NCc1ncc(S(=O)(=O)c2ccccc2)cn1)c1cnc2nccn2c1] | Imidazo[1,2-a]pyrimidine-6-carboxylic acid (5-benzenesulfonyl-pyrimidin-2-ylmethyl)-amide |
| 13 | 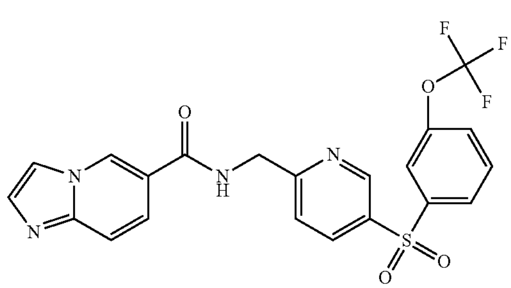 [SMILES: O=C(NCc1ccc(S(=O)(=O)c2cccc(OC(F)(F)F)c2)cn1)c1ccc2nccn2c1] | Imidazo[1,2-a]pyridine-6-carboxylic acid [5-(3-trifluoromethoxy-benzenesulfonyl)-pyridin-2-ylmethyl]-amide |

-continued

| Ex. | Structure | Name |
|---|---|---|
| 14 | 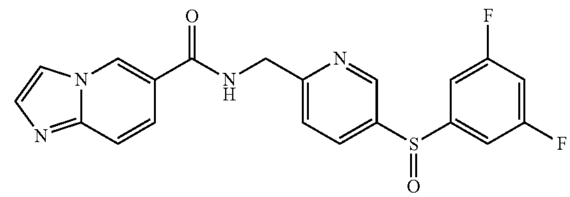 [SMILES: O=C(NCc1ccc(S(=O)c2cc(F)cc(F)c2)cn1)c1ccc2nccn2c1] | Imidazo[1,2-a]pyridine-6-carboxylic acid [5-(3,5-difluoro-benzenesulfinyl)-pyridin-2-ylmethyl]-amide (racemic) |
| 15 | 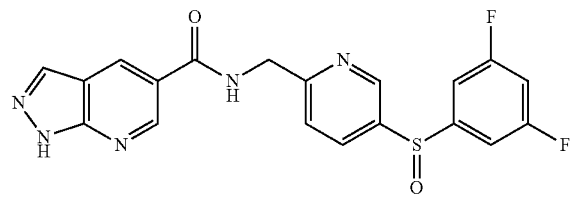 [SMILES: O=C(NCc1ccc(S(=O)c2cc(F)cc(F)c2)cn1)c1cnc2[nH]ncc2c1] | 1H-Pyrazolo[3,4-b]pyridine-5-carboxylic acid [5-(3,5-difluoro-benzenesulfinyl)-pyridin-2-ylmethyl]-amide (racemic) |
| 16 | 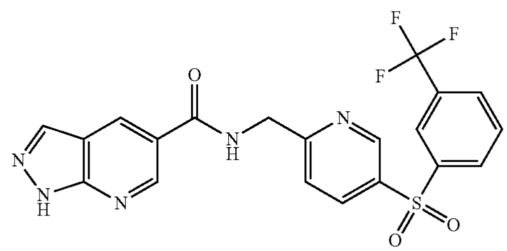 [SMILES: O=C(NCc1ccc(S(=O)(=O)c2cccc(C(F)(F)F)c2)cn1)c1cnc2[nH]ncc2c1] | 1H-Pyrazolo[3,4-b]pyridine-5-carboxylic acid [5-(3-trifluoromethyl-benzenesulfonyl)-pyridin-2-ylmethyl]-amide |
| 17 | 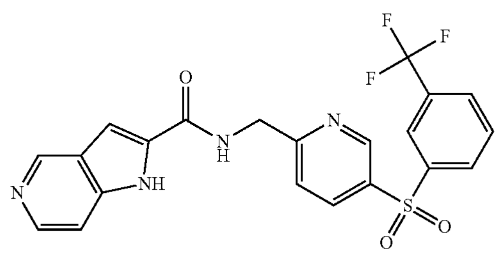 [SMILES: O=C(NCc1ccc(S(=O)(=O)c2cccc(C(F)(F)F)c2)cn1)c1cc2cnccc2[nH]1] | 1H-Pyrrolo[3,2-c]pyridine-2-carboxylic acid [5-(3-trifluoromethyl-benzenesulfonyl)-pyridin-2-ylmethyl]-amide |
| 18 | 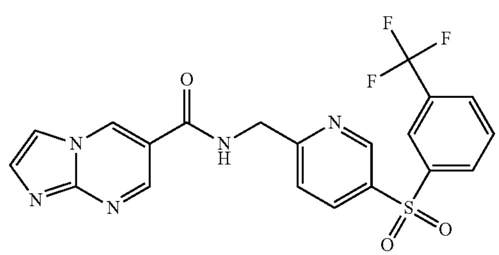 [SMILES: O=C(NCc1ccc(S(=O)(=O)c2cccc(C(F)(F)F)c2)cn1)c1cnc2nccn2c1] | Imidazo[1,2-a]pyrimidine-6-carboxylic acid (5-(3-trifluoromethyl-benzenesulfonyl)-pyridin-2-ylmethyl]-amide |
| 19 | 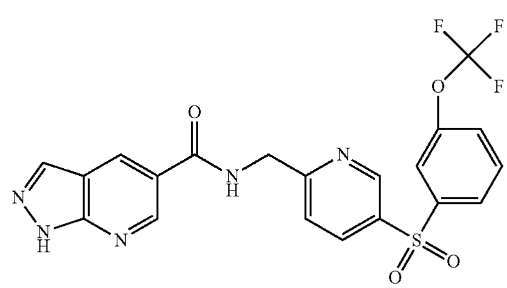 [SMILES: O=C(NCc1ccc(S(=O)(=O)c2cccc(OC(F)(F)F)c2)cn1)c1cnc2[nH]ncc2c1] | 1H-Pyrazolo[3,4-b]pyridine-5-carboxylic acid [5-(3-trifluoromethoxy-benzenesulfonyl)-pyridin-2-ylmethyl]-amide |

-continued

| Ex. | Structure | Name |
|---|---|---|
| 20 | 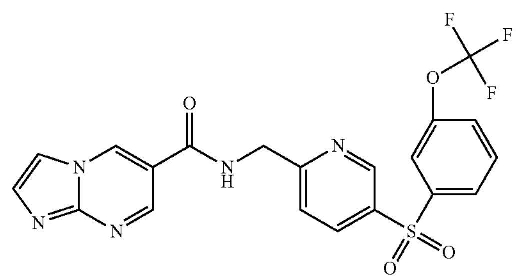 [SMILES: O=C(NCc1ccc(S(=O)(=O)c2cccc(OC(F)(F)F)c2)cn1)c1cnc2nccn2c1] | Imidazo[1,2-a]pyrimidine-6-carboxylic acid [5-(3-trifluoromethoxy-benzenesulfonyl)-pyridin-2-ylmethyl]-amide |
| 21 | 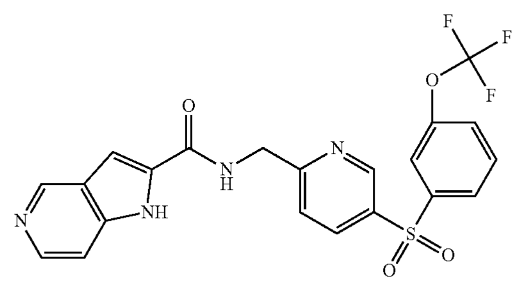 [SMILES: O=C(NCc1ccc(S(=O)(=O)c2cccc(OC(F)(F)F)c2)cn1)c1cc2cnccc2[nH]1] | 1H-Pyrrolo[3,2-c]pyridine-2-carboxylic acid [5-(3-trifluoromethoxy-benzenesulfonyl)-pyridin-2-ylmethyl]-amide |
| 22 | 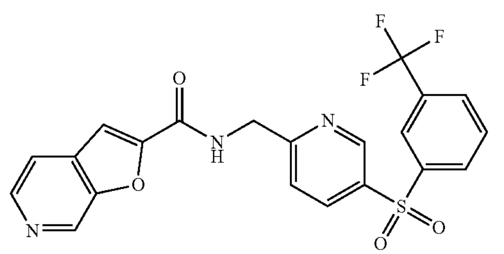 [SMILES: O=C(NCc1ccc(S(=O)(=O)c2cccc(C(F)(F)F)c2)cn1)c1cc2ccncc2o1] | Furo[2,3-c]pyridine-2-carboxylic acid [5-(3-trifluoromethyl-benzenesulfonyl)-pyridin-2-ylmethyl]-amide |
| 23 | 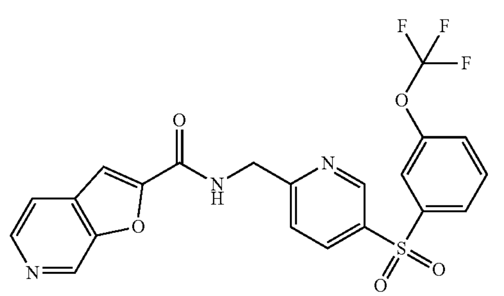 [SMILES: O=C(NCc1ccc(S(=O)(=O)c2cccc(OC(F)(F)F)c2)cn1)c1cc2ccncc2o1] | Furo[2,3-c]pyridine-2-carboxylic acid [5-(3-trifluoromethoxy-benzenesulfonyl)-pyridin-2-ylmethyl]-amide |
| 24 | 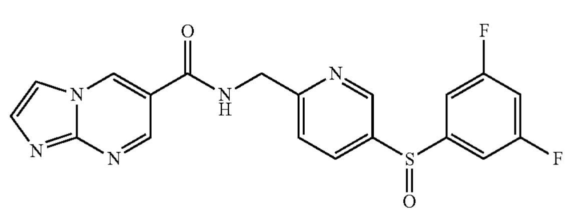 [SMILES: O=C(NCc1ccc(S(=O)c2cc(F)cc(F)c2)cn1)c1cnc2nccn2c1] | Imidazo[1,2-a]pyrimidine-6-carboxylic acid [5-(3,5-difluoro-benzenesulfinyl)-pyridin-2-ylmethyl]-amide (racemic) |
| 25 | 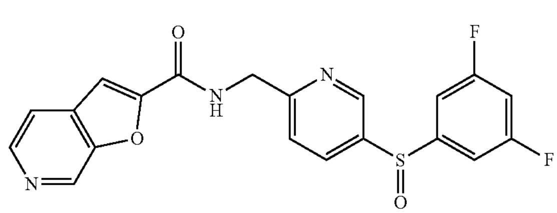 [SMILES: O=C(NCc1ccc(S(=O)c2cc(F)cc(F)c2)cn1)c1cc2ccncc2o1] | Furo[2,3-c]pyridine-2-carboxylic acid [5-(3,5-difluoro-benzenesulfinyl)-pyridin-2-ylmethyl]-amide (racemic) |

-continued

| Ex. | Structure | Name |
|---|---|---|
| 26 | 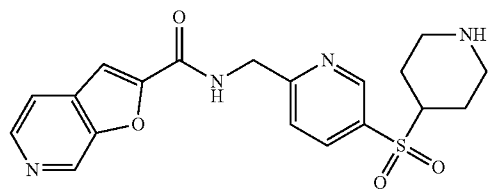 [SMILES: O=C(NCc1ccc(S(=O)(=O)C2CCNCC2)cn1)c1cc2ccncc2o1] | Furo[2,3-c]pyridine-2-carboxylic acid [5-(piperidine-4-sulfonyl)-pyridin-2-ylmethyl]-amide |
| 27 | 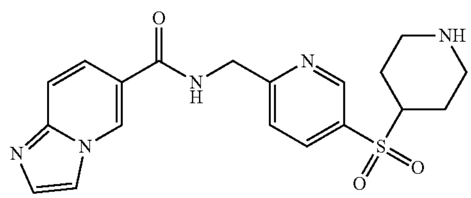 [SMILES: O=C(NCc1ccc(S(=O)(=O)C2CCNCC2)cn1)c1ccc2nccn2c1] | Imidazo[1,2-a]pyridine-6-carboxylic acid [5-(piperidine-4-sulfonyl)-pyridin-2-ylmethyl]-amide |
| 28 | 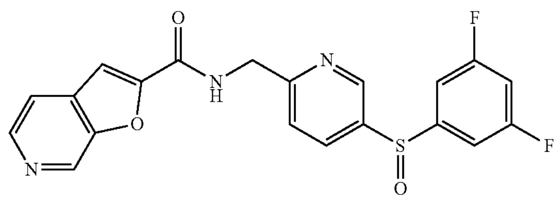 [SMILES: O=C(NCc1ccc(S(=O)c2cc(F)cc(F)c2)cn1)c1cc2ccncc2o1] | Furo[2,3-c]pyridine-2-carboxylic acid [5-(3,5-difluoro-benzenesulfinyl)-pyridin-2-ylmethyl]-amide (stereoisomer 1) |
| 29 | 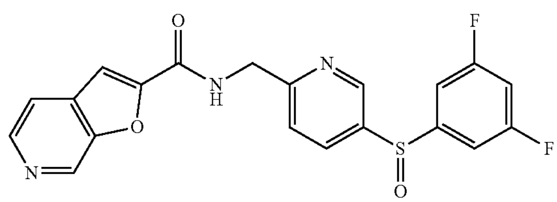 [SMILES: O=C(NCc1ccc(S(=O)c2cc(F)cc(F)c2)cn1)c1cc2ccncc2o1] | Furo[2,3-c]pyridine-2-carboxylic acid [5-(3,5-difluoro-benzenesulfinyl)pyridin-2-ylmethyl]-amide (stereoisomer 2) |
| 30 | 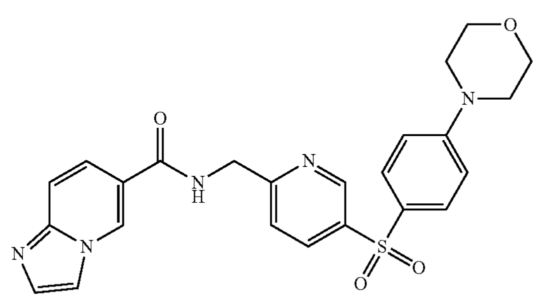 [SMILES: O=C(NCc1ccc(S(=O)(=O)c2ccc(N3CCOCC3)cc2)cn1)c1ccc2nccn2c1] | Imidazo[1,2-a]pyridine-6-carboxylic acid (5-(4-morpholin-4-yl-benzenesulfonyl)-pyridin-2-ylmethyl]-amide |
| 31 | 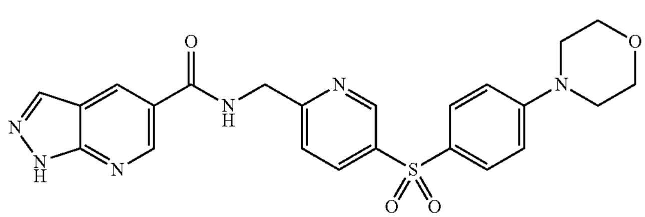 [SMILES: O=C(NCc1ccc(S(=O)(=O)c2ccc(N3CCOCC3)cc2)cn1)c1cnc2[nH]ncc2c1] | 1H-Pyrazolo[3,4-b]pyridine-5-carboxylic acid [5-(4-morpholin-4-yl-benzenesulfonyl)-pyridin-2-ylmethyl]-amide |
| 32 | 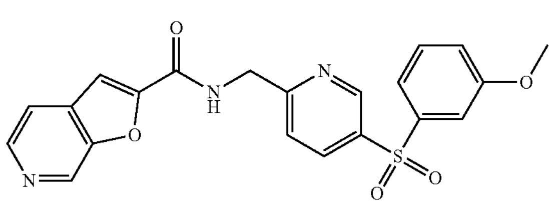 [SMILES: COc1cccc(S(=O)(=O)c2ccc(CNC(=O)c3cc4ccncc4o3)nc2)c1] | Furo[2,3-c]pyridine-2-carboxylic acid methoxy-benzenesulfonyl)-pyridin-2-ylmethyl)-amide |

-continued

| Ex. | Structure | Name |
|---|---|---|
| 33 | 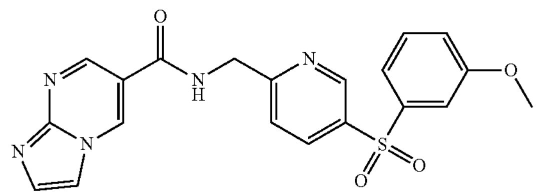 [SMILES: COc1cccc(S(=O)(=O)c2ccc(CNC(=O)c3cnc4nccn4c3)nc2)c1] | Imidazo[1,2-a]pyrimidine-6-carboxylic acid [5-(3-methoxy-benzenesulfonyl)-pyridin-2-ylmethyl]-amide |
| 34 | 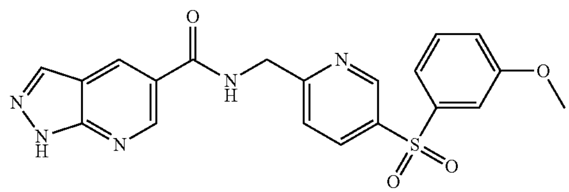 [SMILES: COc1cccc(S(=O)(=O)c2ccc(CNC(=O)c3cnc4[nH]ncc4c3)nc2)c1] | 1H-Pyrazolo[3,4-b]pyridine-5-carboxylic acid [5-(3-methoxy-benzenesulfonyl)-pyridin-2-ylmethyl]-amide |
| 35 | 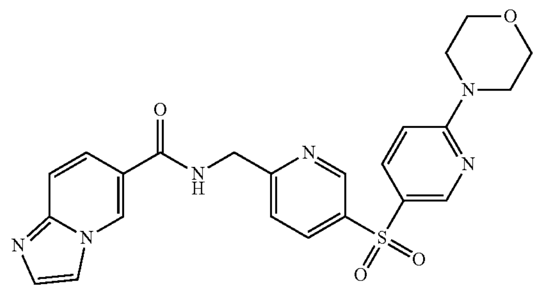 | Imidazo[1,2-a]pyridine-6-carboxylic acid [5-(6-morpholin-4-yl-pyridine-3-sulfonyl)-pyridin-2-ylmethyl]-amide |
| 36 | 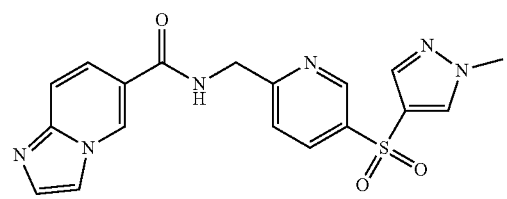 [SMILES: Cn1cc(S(=O)(=O)c2ccc(CNC(=O)c3ccc4nccn4c3)nc2)cn1] | Imidazo[1,2-a]pyridine-6-carboxylic acid [5-(1-methyl-1H-pyrazole-4-sulfonyl)-pyridin-2-ylmethyl]-amide |
| 37 | 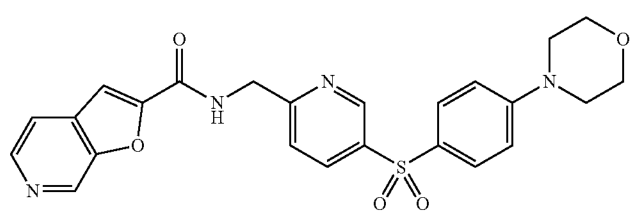 [SMILES: O=C(NCc1ccc(S(=O)(=O)c2ccc(N3CCOCC3)cc2)cn1)c1cc2ccncc2o1] | Furo[2,3-c]pyridine-2-carboxylic acid [5-(4-morpholin-4-yl-benzenesulfonyl)-pyridin-2-ylmethyl]-amide |
| 38 | 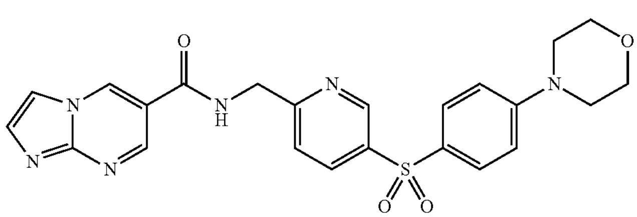 [SMILES: O=C(NCc1ccc(S(=O)(=O)c2ccc(N3CCOCC3)cc2)cn1)c1cnc2nccn2c1] | Imidazo[1,2-a]pyrimidine-6-carboxylic acid [5-(4-morpholin-4-yl-benzenesulfonyl)-pyridin-2-ylmethyl]-amide |
| 39 | 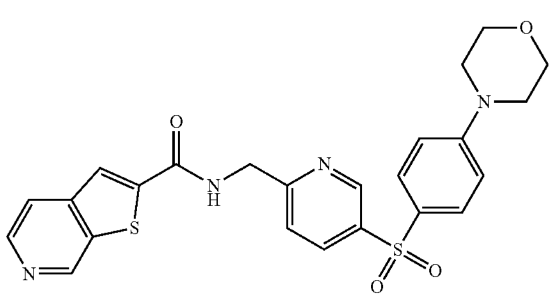 [SMILES: O=C(NCc1ccc(S(=O)(=O)c2ccc(N3CCOCC3)cc2)cn1)c1cc2ccncc2s1] | Thieno[2,3-c]pyridine-2-carboxylic acid [5-(4-morpholin-4-yl-benzenesulfonyl)-pyridin-2-ylmethyl]-amide |

-continued

| Ex. | Structure | Name |
|---|---|---|
| 40 | 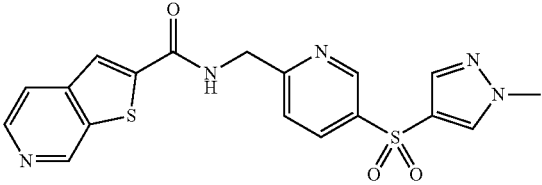 | Thieno[2,3-c]pyridine-2-carboxylic acid [5-(1-methyl-1H-pyrazole-4-sulfonyl)-pyridin-2-ylmethyl]-amide |
| 41 | 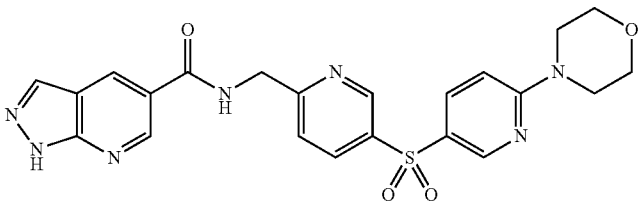 [SMILES: O=C(NCc1ccc(S(=O)(=O)c2ccc(N3CCOCC3)nc2)cn1)c1cnc2[nH]ncc2c1] | 1H-Pyrazolo[3,4-b]pyridine-5-carboxylic acid (5-(6-morpholin-4-yl-pyridine-3-sulfonyl)-pyridin-2-ylmethyl]-amide |
| 42 | 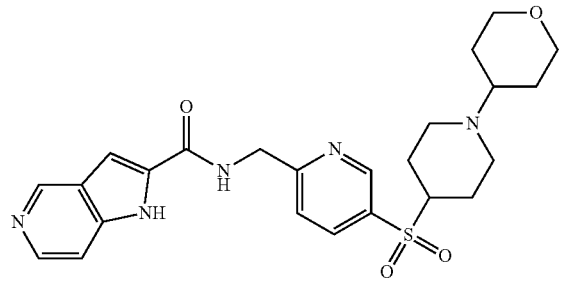 [SMILES: O=C(NCc1ccc(S(=O)(=O)C2CCN(C3CCOCC3)CC2)cn1)c1cc2cnccc2[nH]1] | 1H-Pyrrolo[3,2-c]pyridine-2-carboxylic acid {5-[1-(tetrahydro-pyran-4-yl)-piperidine-4-sulfonyl]-pyridin-2-ylmethyl)-amide |
| 43 | 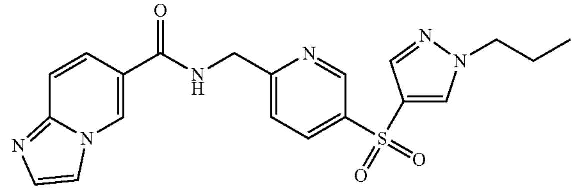 [SMILES: CCCn1cc(S(=O)(=O)c2ccc(CNC(=O)c3ccc4nccn4c3)nc2)cn1] | Imidazo[1,2-a]pyridine-6-carboxylic acid [5-(1-propyl-1H-pyrazole-4-sulfonyl)-pyridin-2-ylmethyl]-amide |
| 44 | 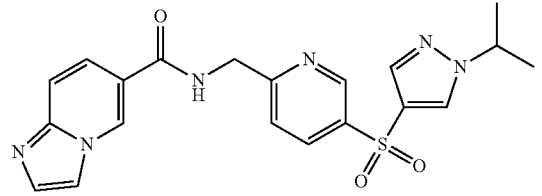 [SMILES: CC(C)n1cc(S(=O)(=O)c2ccc(CNC(=O)c3ccc4nccn4c3)nc2)cn1] | Imidazo[1,2-a]pyridine-6-carboxylic acid isopropyl-1H-pyrazole-4-sulfonyl)-pyridin-2-ylmethyl)-amide |
| 45 | 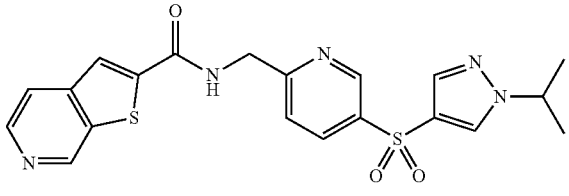 [SMILES: CC(C)n1cc(S(=O)(=O)c2ccc(CNC(=O)c3cc4ccncc4s3)nc2)cn1] | Thieno[2,3-c]pyridine-2-carboxylic acid [5-(1-isopropyl-1H-pyrazole-4-sulfonyl)-pyridin-2-ylmethyl]-amide |

| Ex. | Structure | Name |
|---|---|---|
| 46 | 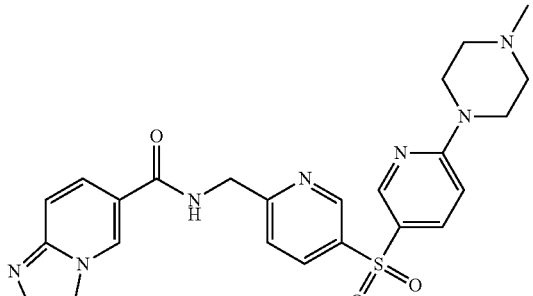 | Imidazo[1,2-a]pyridine-6-carboxylic acid {5-[6-(4-methyl-piperazin-1-yl)-pyridine-3-sulfonyl]-pyridin-2-ylmethyl}-amide |
| 47 | 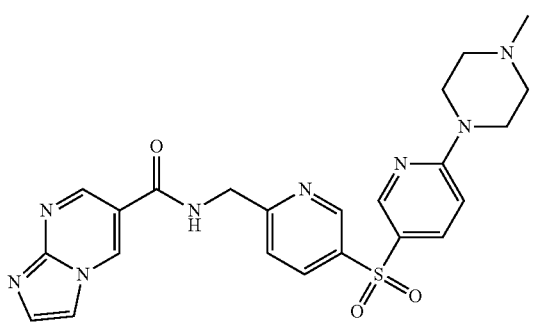 [SMILES: CN1CCN(c2ccc(S(=O)(=O)c3ccc(CNC(=O)c4cnc5nccn5c4)nc3)cn2)CC1] | Imidazo[1,2-a]pyrimidine-6-carboxylic acid {5-[6-(4-methyl-piperazin-1-yl)-pyridine-3-sulfonyl]-pyridin-2-ylmethyl}-amide |
| 48 | 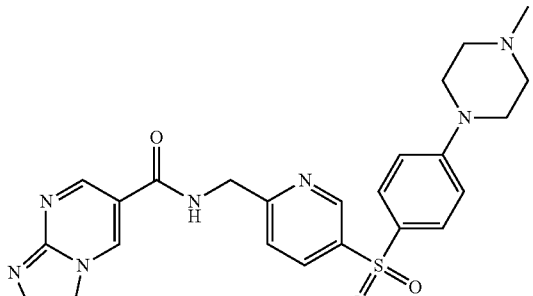 | Imidazo[1,2-a]pyrimidine-6-carboxylic acid {5-[4-(4-methyl-piperazin-1-yl)-benzenesulfonyl]-pyridin-2-ylmethyl)-amide |
| 49 | 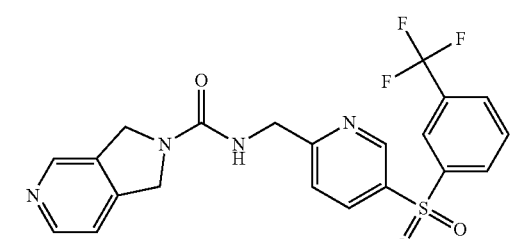 | 1,3-Dihydro-pyrrolo[3,4-c]pyridine-2-carboxylic acid [5-(3-trifluoromethyl-benzenesulfonyl)-pyridin-2-ylmethyl]-amide |
| 50 | 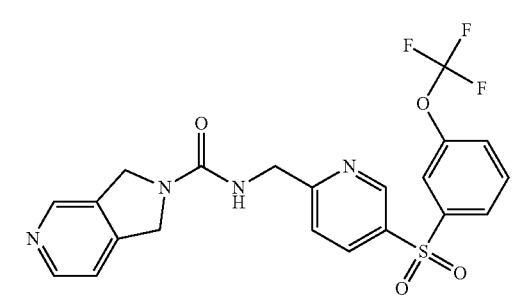 [SMILES: O=C(NCc1ccc(S(=O)(=O)c2cccc(OC(F)(F)F)c2)cn1)N1Cc2ccncc2C1] | 1,3-Dihydro-pyrrolo[3,4-c]pyridine-2-carboxylic acid [5-(3-trifluoromethoxy-benzenesulfonyl)-pyridin-2-ylmethyl]-amide |

| Ex. | Structure | Name |
|---|---|---|
| 51 | 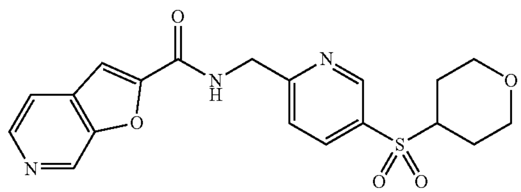 [SMILES: O=C(NCc1ccc(S(=O)(=O)C2CCOCC2)cn1)c1cc2ccncc2o1] | Furo[2,3-c]pyridine-2-carboxylic acid [5-(tetrahydro-pyran-4-sulfonyl)-pyridin-2-ylmethyl]-amide |
| 52 | 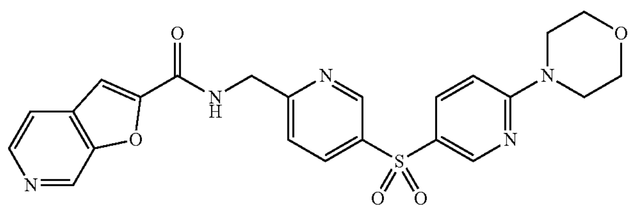 | Furo[2,3-c]pyridine-2-carboxylic acid [5-(6-morpholin-4-yl-pyridine-3-sulfonyl)-pyridin-2-ylmethyl]-amide |
| 53 | 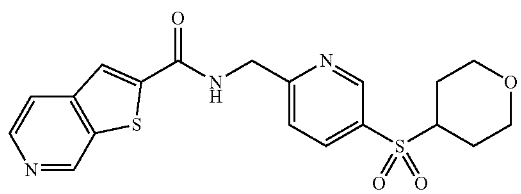 | Thieno[2,3-c]pyridine-2-carboxylic acid [5-(tetrahydro-pyran-4-sulfonyl)-pyridin-2-ylmethyl]-amide |
| 54 | 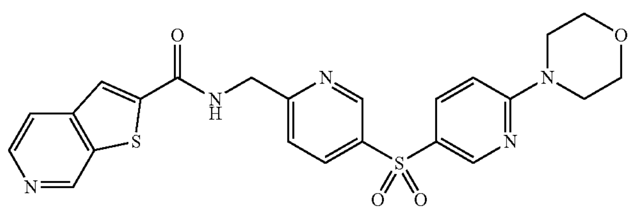 [SMILES: O=C(NCc1ccc(S(=O)(=O)c2ccc(N3CCOCC3)nc2)cn1)c1cc2ccncc2o1] | Thieno[2,3-c]pyridine-2-carboxylic acid [5-(6-morpholin-4-yl-pyridine-3-sulfonyl)-pyridin-2-ylmethyl]-amide |
| 55 | 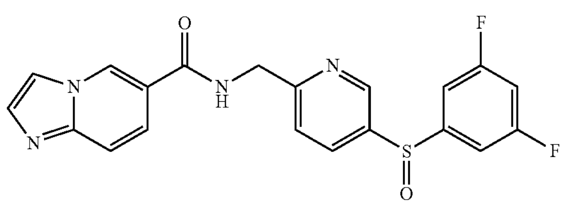 [SMILES: O=C(NCc1ccc(S(=O)c2cc(F)cc(F)c2)cn1)c1ccc2nccn2c1] | Imidazo[1,2-a]pyridine-6-carboxylic acid [5-(3,5-difluoro-benzenesulfinyl)-pyridin-2-ylmethyl]-amide (racemic) |
| 56 | 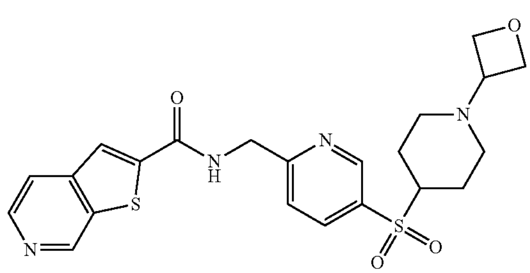 [SMILES: O=C(NCc1ccc(S(=O)(=O)C2CCN(C3COC3)CC2)cn1)c1cc2ccncc2s1] | Thieno[2,3-c]pyridine-2-carboxylic acid [5-(1-oxetan-3-yl-piperidine-4-sulfonyl)-pyridin-2-ylmethyl]-amide |
| 57 | 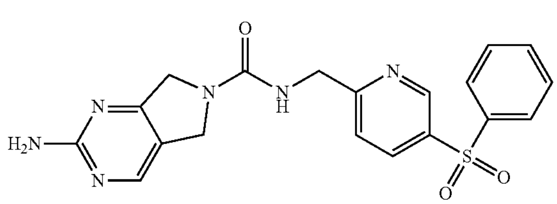 [SMILES: Nc1ncc2c(n1)CN(C(=O)NCc1ccc(S(=O)(=O)c3ccccc3)cn1)C2] | 2-Amino-5,7-dihydro-pyrrolo[3,4-d]pyrimidine-6-carboxylic acid (5-benzenesulfonyl-pyridin-2-ylmethyl)-amide |

-continued

| Ex. | Structure | Name |
|---|---|---|
| 58 | 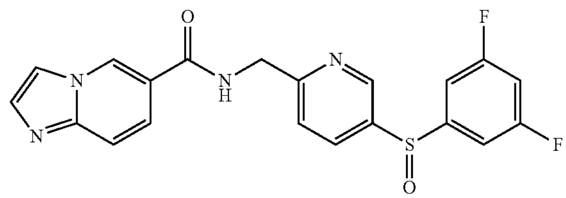 [SMILES: O=C(NCc1ccc(S(=O)c2cc(F)cc(F)c2)cn1)c1ccc2nccn2c1] | Imidazo[1,2-a]pyridine-6-carboxylic acid [5-(3,5-difluoro-benzenesulfinyl)-pyridin-2-ylmethyl]-amide (racemic) |
| 59 | 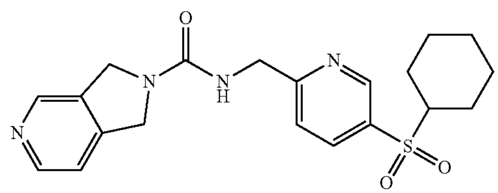 [SMILES: O=C(NCc1ccc(S(=O)(=O)C2CCCCC2)cn1)N1Cc2ccncc2C1] | 1,3-Dihydro-pyrrolo[3,4-c]pyridine-2-carboxylic acid (5-cyclohexanesulfonyl-pyridin-2-ylmethyl)-amide |
| 60 | 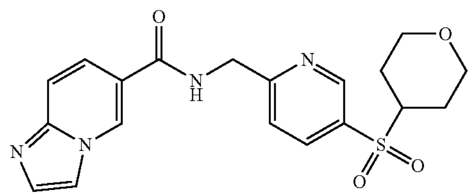 [SMILES: O=C(NCc1ccc(S(=O)(=O)C2CCOCC2)cn1)c1ccc2nccn2c1] | Imidazo[1,2-a]pyridine-6-carboxylic acid [5-(tetrahydro-pyran-4-sulfonyl)-pyridin-2-ylmethyl]-amide |
| 61 | 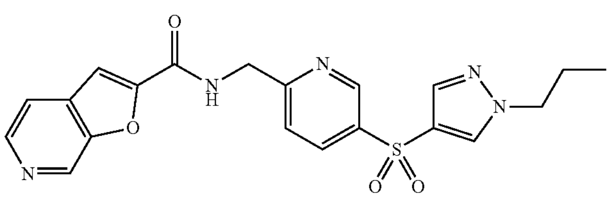 [SMILES: CCCn1cc(S(=O)(=O)c2ccc(CNC(=O)c3cc4ccncc4o3)nc2)cn1] | Furo[2,3-c]pyridine-2-carboxylic acid [5-(1-propyl-1H-pyrazole-4-sulfonyl)-pyridin-2-ylmethyl]-amide |
| 62 | 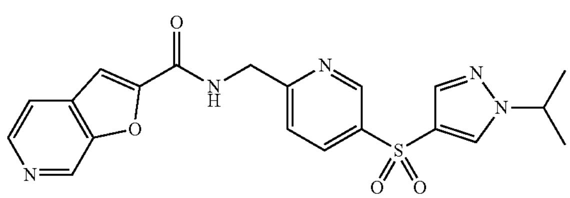 [SMILES: CC(C)n1cc(S(=O)(=O)c2ccc(CNC(=O)c3cc4ccncc4o3)nc2)cn1] | Furo[2,3-c]pyridine-2-carboxylic acid [5-(1-isopropyl-1H-pyrazole-4-sulfonyl)-pyridin-2-ylmethyl]-amide |
| 63 | 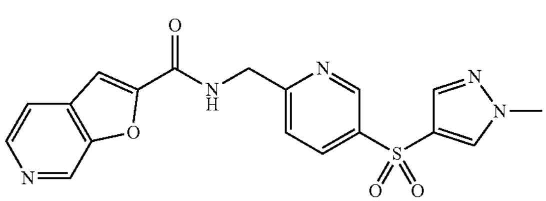 | Furo[2,3-c]pyridine-2-carboxylic acid [5-(1-methyl-1H-pyrazole-4-sulfonyl)-pyridin-2-ylmethyl]-amide |
| 64 | 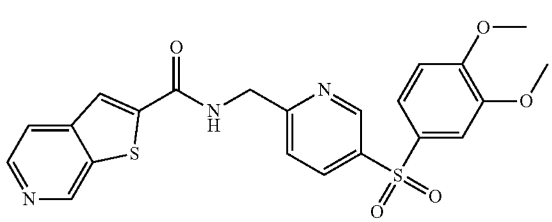 [SMILES: COc1ccc(S(=O)(=O)c2ccc(CNC(=O)c3cc4ccncc4s3)nc2)cc1OC] | Thieno[2,3-c]pyridine-2-carboxylic acid [5-(3,4-dimethoxy-benzenesulfonyl)-pyridin-2-ylmethyl]-amide |

-continued

| Ex. | Structure | Name |
|---|---|---|
| 65 | 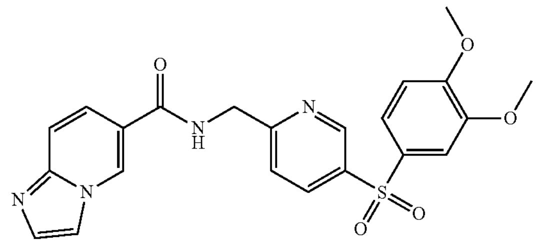 [SMILES: COc1ccc(S(=O)(=O)c2ccc(CNC(=O)c3ccc4nccn4c3)nc2)cc1OC] | Imidazo[1,2-a]pyridine-6-carboxylic acid [5-(3,4-dimethoxy-benzenesulfonyl)-pyridin-2-ylmethyl]-amide |
| 66 | 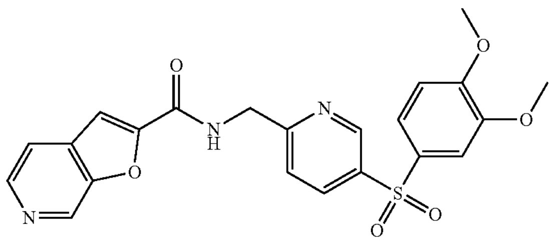 [SMILES: COc1ccc(S(=O)(=O)c2ccc(CNC(=O)c3cc4ccncc4o3)nc2)cc1OC] | Furo[2,3-c]pyridine-2-carboxylic acid [5-(3,4-dimethoxy-benzenesulfonyl)-pyridin-2-ylmethyl]-amide |
| 67 | 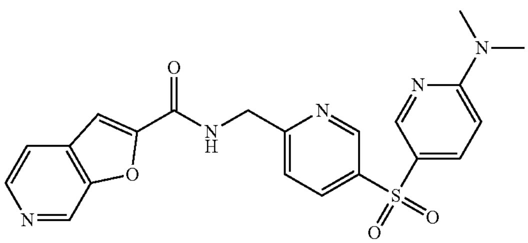 [SMILES: CN(C)c1ccc(S(=O)(=O)c2ccc(CNC(=O)c3cc4ccncc4o3)nc2)cn1] | Furo[2,3-c]pyridine-2-carboxylic acid [5-(6-dimethylamino-pyridine-3-sulfonyl)-pyridin-2-ylmethyl]-amide |
| 68 | 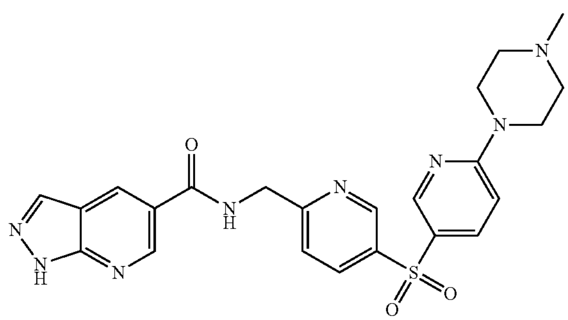 [SMILES: CN1CCN(c2ccc(S(=O)(=O)c3ccc(CNC(=O)c4cnc5[nH]ncc5c4)nc3)cn2)CC1] | 1H-Pyrazolo[3,4-b]pyridine-5-carboxylic acid {5-[6-(4-methyl-piperazin-1-yl)-pyridine-3-sulfonyl]-pyridin-2-ylmethyl}-amide |
| 69 | 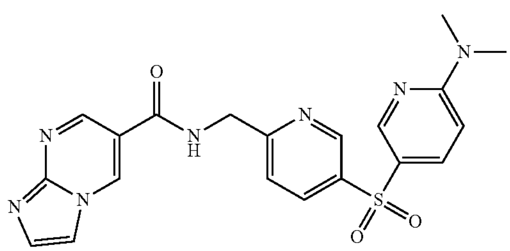 [SMILES: CN(C)c1ccc(S(=O)(=O)c2ccc(CNC(=O)c3cnc4nccn4c3)nc2)cn1] | Imidazo[1,2-a]pyrimidine-6-carboxylic acid [5-(6-dimethylamino-pyridine-3-sulfonyl)-pyridin-2-ylmethyl]-amide |
| 70 | 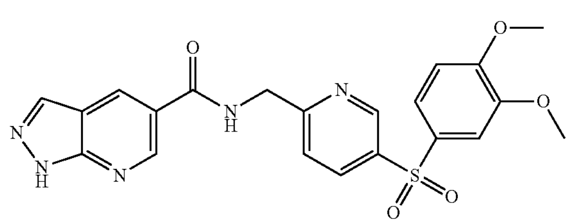 [SMILES: COc1ccc(S(=O)(=O)c2ccc(CNC(=O)c3cnc4[nH]ncc4c3)nc2)cc1OC] | 1H-Pyrazolo[3,4-b]pyridine-5-carboxylic acid [5-(3,4-dimethoxy-benzenesulfonyl)-pyridin-2-ylmethyl]-amide |

| Ex. | Structure | Name |
|---|---|---|
| 71 | 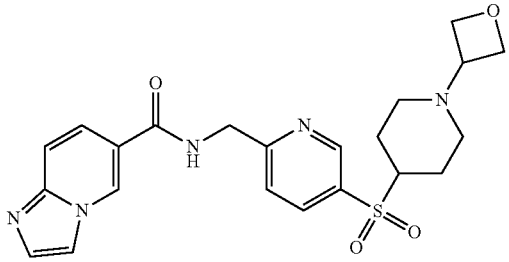 [SMILES: O=C(NCc1ccc(S(=O)(=O)C2CCN(C3COC3)CC2)cn1)c1ccc2nccn2c1] | Imidazo[1,2-a]pyridine-6-carboxylic acid [5-(1-oxetan-3-yl-piperidine-4-sulfonyl)-pyridin-2-ylmethyl]-amide |
| 72 | 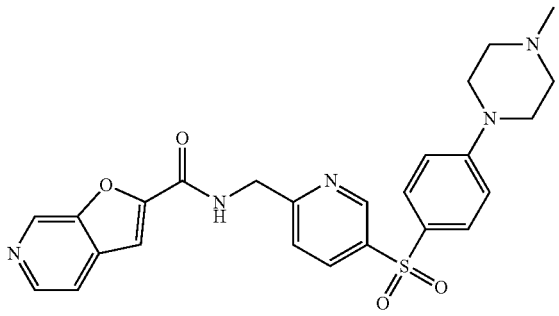 [SMILES: CN1CCN(c2ccc(S(=O)(=O)c3ccc(CNC(=O)c4cc5ccncc5o4)nc3)cc2)CC1] | Furo[2,3-c]pyridine-2-carboxylic acid {5-[4-(4-methyl-piperazin-1-yl)-benzenesulfonyl)-pyridin-2-ylmethyl}-amide |
| 73 | 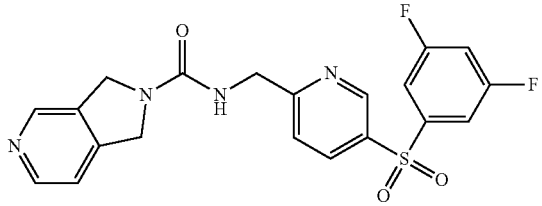 [SMILES: O=C(NCc1ccc(S(=O)(=O)c2cc(F)cc(F)c2)cn1)N1Cc2ccncc2C1] | 1,3-Dihydro-pyrrolo[3,4-c]pyridine-2-carboxylic acid [5-(3,5-difluoro-benzenesulfonyl)-pyridin-2-ylmethyl]-amide |
| 74 | 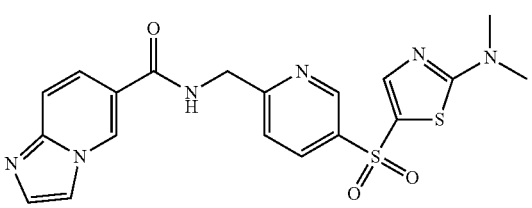 [SMILES: CN(C)c1ncc(S(=O)(=O)c2ccc(CNC(=O)c3ccc4nccn4c3)nc2)s1] | Imidazo[1,2-a]pyridine-6-carboxylic acid [5-(2-dimethylamino-thiazole-5-sulfonyl)-pyridin-2-ylmethyl]-amide |
| 75 | 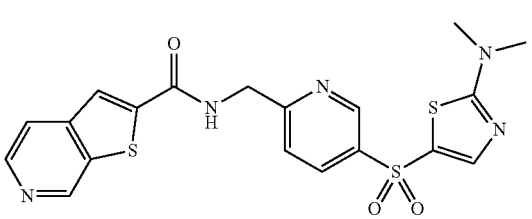 [SMILES: CN(C)c1ncc(S(=O)(=O)c2ccc(CNC(=O)c3cc4ccncc4s3)nc2)s1] | Thieno[2,3-c]pyridine-2-carboxylic acid [5-(2-dimethylamino-thiazole-5-sulfonyl)-pyridin-2-ylmethyl]-amide |
| 76 | 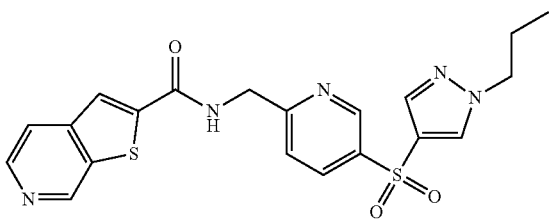 [SMILES: CCCn1cc(S(=O)(=O)c2ccc(CNC(=O)c3cc4ccncc4s3)nc2)cn1] | Thieno[2,3-c]pyridine-2-carboxylic acid [5-(1-propyl-1H-pyrazole-4-sulfonyl)-pyridin-2-ylmethyl]-amide |

| Ex. | Structure | Name |
|---|---|---|
| 77 | 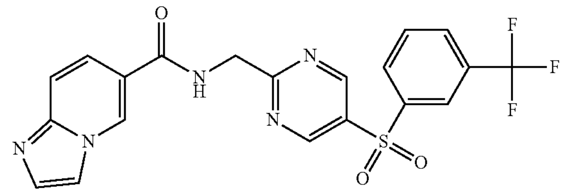 [SMILES: O=C(NCc1ncc(S(=O)(=O)c2cccc(C(F)(F)F)c2)cn1)c1ccc2nccn2c1] | Imidazo[1,2-a]pyridine-6-carboxylic acid [5-(3-trifluoromethyl-benzenesulfonyl)-pyrimidin-2-ylmethyl]-amide |
| 78 | 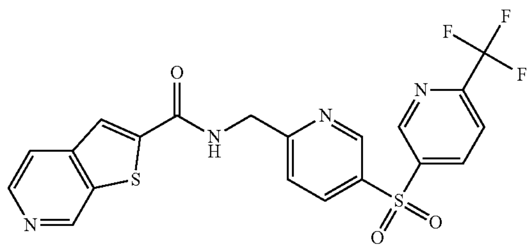 | Thieno[2,3-c]pyridine-2-carboxylic acid [5-(6-trifluoromethyl-pyridine-3-sulfonyl)-pyridin-2-ylmethyl]-amide |
| 79 | 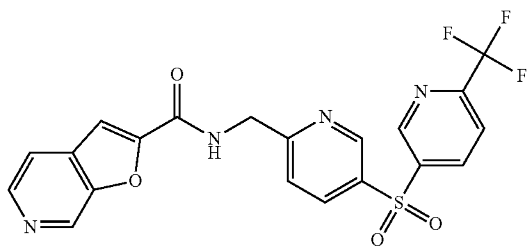 [SMILES: O=C(NCc1ccc(S(=O)(=O)c2ccc(C(F)(F)F)nc2)cn1)c1cc2ccncc2o1] | Furo[2,3-c]pyridine-2-carboxylic acid [5-(6-trifluoromethyl-pyridine-3-sulfonyl)-pyridin-2-ylmethyl]-amide |
| 80 | 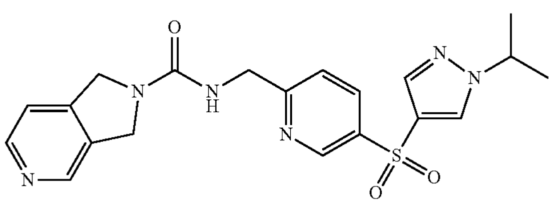 [SMILES: CC(C)n1cc(S(=O)(=O)c2ccc(CNC(=O)N3Cc4ccncc4C3)nc2)cn1] | 1,3-Dihydro-pyrrolo[3,4-c]pyridine-2-carboxylic acid [5-(1-isopropyl-1H-pyrazole-4-sulfonyl)-pyridin-2-ylmethyl]-amide |
| 81 | 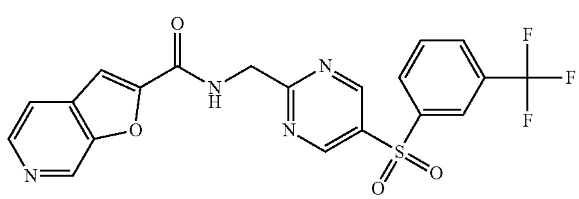 [SMILES: O=C(NCc1ncc(S(=O)(=O)c2cccc(C(F)(F)F)c2)cn1)c1cc2ccncc2o1] | Furo[2,3-c]pyridine-2-carboxylic acid [5-(3-trifluoromethyl-benzenesulfonyl)-pyrimidin-2-ylmethyl]-amide |
| 82 | 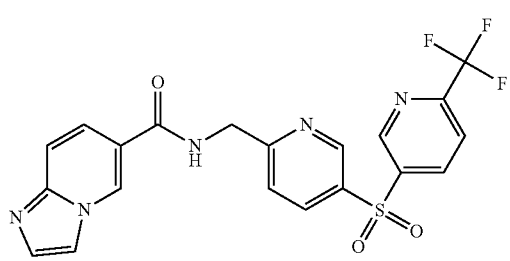 [SMILES: O=C(NCc1ccc(S(=O)(=O)c2ccc(C(F)(F)F)nc2)cn1)c1ccc2nccn2c1] | Imidazo[1,2-a]pyridine-6-carboxylic acid [5-(6-trifluoromethyl-pyridine-3-sulfonyl)-pyridin-2-ylmethyl]-amide |

| Ex. | Structure | Name |
|---|---|---|
| 83 | 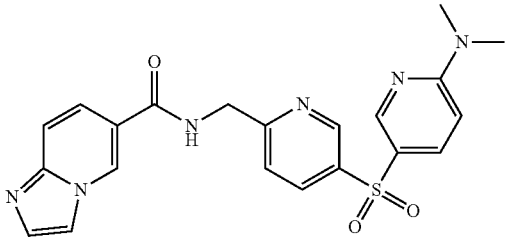 [SMILES: CN(C)c1ccc(S(=O)(=O)c2ccc(CNC(=O)c3ccc4nccn4c3)nc2)cn1] | Imidazo[1,2-a]pyridine-6-carboxylic acid [5-(6-dimethylamino-pyridine-3-sulfonyl)-pyridin-2-ylmethyl]-amide |
| 84 | 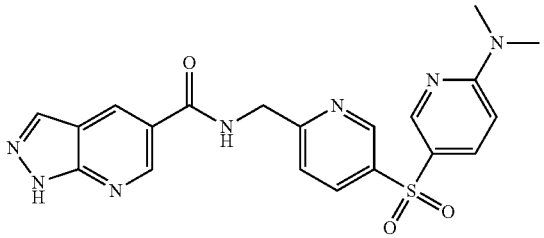 [SMILES: CN(C)c1ccc(S(=O)(=O)c2ccc(CNC(=O)c3cnc4[nH]ncc4c3)nc2)cn1] | 1H-Pyrazolo[3,4-b]pyridine-5-carboxylic acid [5-(6-dimethylamino-pyridine-3-sulfonyl)-pyridin-2-ylmethyl]-amide |
| 85 | 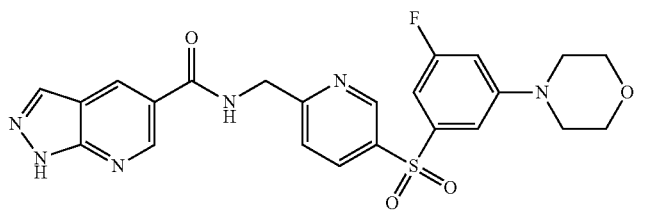 [SMILES: O=C(NCc1ccc(S(=O)(=O)c2cc(F)cc(N3CCOCC3)c2)cn1)c1cnc2[nH]ncc2c1] | 1H-Pyrazolo[3,4-b]pyridine-5-carboxylic acid [5-(3-fluoro-5-morpholin-4-yl-benzenesulfonyl)-pyridin-2-ylmethyl]-amide |
| 86 | 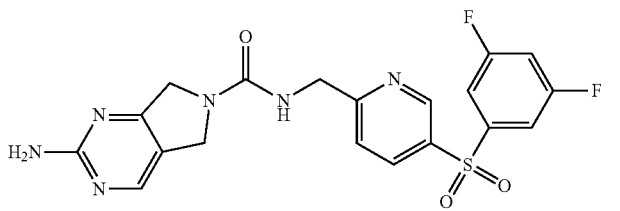 [SMILES: Nc1ncc2c(n1)CN(C(=O)NCc1ccc(S(=O)(=O)c3cc(F)cc(F)c3)cn1)C2] | 2-Amino-5,7-dihydro-pyrrolo[3,4-d]pyrimidine-6-carboxylic acid [5-(3,5-difluoro-benzenesulfonyl)-pyridin-2-ylmethyl]-amide |
| 87 | 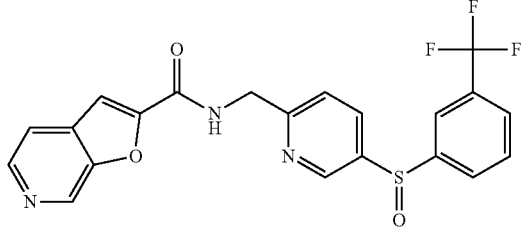 [SMILES: O=C(NCc1ccc(S(=O)c2cccc(C(F)(F)F)c2)cn1)c1cc2ccncc2o1] | Furo[2,3-c]pyridine-2-carboxylic acid [5-(3-trifluoromethyl-benzenesulfinyl)-pyridin-2-ylmethyl]-amide (racemic) |
| 88 | 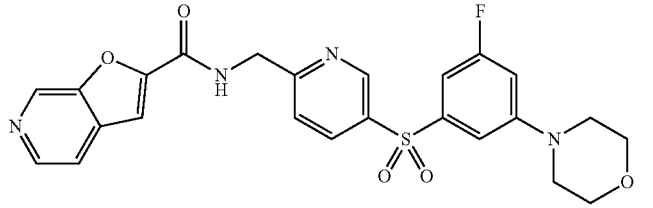 [SMILES: O=C(NCc1ccc(S(=O)(=O)c2cc(F)cc(N3CCOCC3)c2)cn1)c1cc2ccncc2o1] | Furo[2,3-c]pyridine-2-carboxylic acid [5-(3-fluoro-5-morpholin-4-yl-benzenesulfonyl)-pyridin-2-ylmethyl]-amide |

-continued

| Ex. | Structure | Name |
|---|---|---|
| 89 | 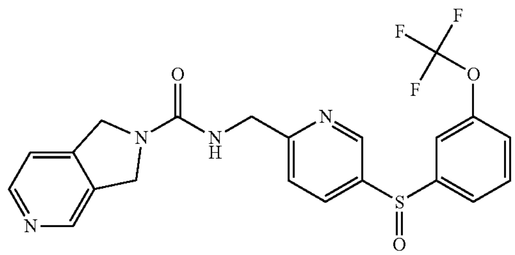 [SMILES: O=C(NCc1ccc(S(=O)c2cccc(OC(F)(F)F)c2)cn1)N1Cc2ccncc2C1] | 1,3-Dihydro-pyrrolo[3,4-c]pyridine-2-carboxylic acid [5-(3-trifluoromethoxy-benzenesulfinyl)-pyridin-2-ylmethyl]-amide (racemic) |
| 90 | 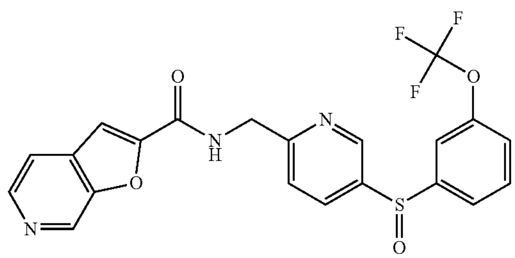 [SMILES: O=C(NCc1ccc(S(=O)c2cccc(OC(F)(F)F)c2)cn1)c1cc2ccncc2o1] | Furo[2,3-c]pyridine-2-carboxylic acid [5-(3-trifluoromethoxy-benzenesulfinyl)-pyridin-2-ylmethyl]-amide (racemic) |
| 91 | 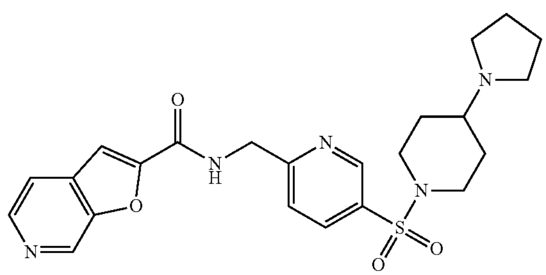 [SMILES: O=C(NCc1ccc(S(=O)(=O)N2CCC(N3CCCC3)CC2)cn1)c1cc2ccncc2o1] | Furo[2,3-c]pyridine-2-carboxylic acid [5-(4-pyrrolidin-1-yl-piperidine-1-sulfonyl)-pyridin-2-ylmethyl]-amide |
| 92 | 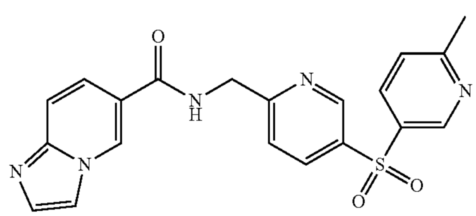 [SMILES: Cc1ccc(S(=O)(=O)c2ccc(CNC(=O)c3ccc4nccn4c3)nc2)cn1] | Imidazo[1,2-a]pyridine-6-carboxylic acid [5-(6-methyl-pyridine-3-sulfonyl)-pyridin-2-ylmethyl]-amide |
| 93 | 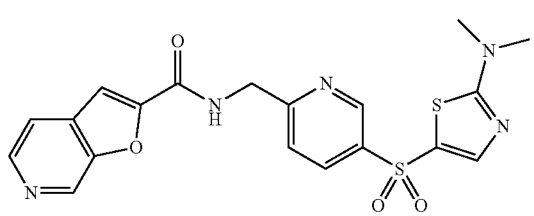 [SMILES: CN(C)c1ncc(S(=O)(=O)c2ccc(CNC(=O)c3cc4ccncc4o3)nc2)s1] | Furo[2,3-c]pyridine-2-carboxylic acid [5-(2-dimethylamino-thiazole-5-sulfonyl)-pyridin-2-ylmethyl]-amide |
| 94 | 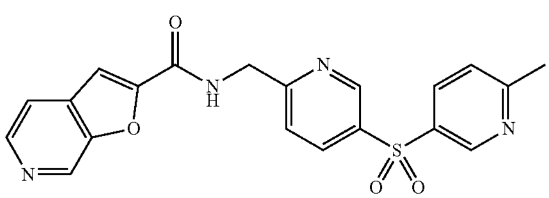 | Furo[2,3-c]pyridine-2-carboxylic acid [5-(6-methyl-pyridine-3-sulfonyl)-pyridin-2-ylmethyl]-amide |

-continued

| Ex. | Structure | Name |
|---|---|---|
| 95 | 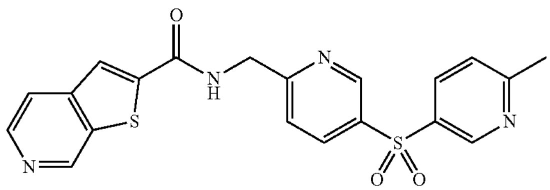 [SMILES: Cc1ccc(S(=O)(=O)c2ccc(CNC(=O)c3cc4ccncc4o3)nc2)cn1] | Thieno[2,3-c]pyridine-2-carboxylic acid [5-(6-methyl-pyridine-3-sulfonyl)-pyridin-2-ylmethyl]-amide |
| 96 | 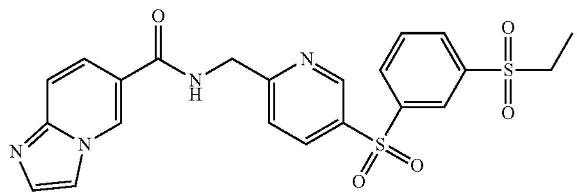 [SMILES: CCS(=O)(=O)c1cccc(S(=O)(=O)c2ccc(CNC(=O)c3ccc4nccn4c3)nc2)c1] | Imidazo[1,2-a]pyridine-6-carboxylic acid [5-(3-ethanesulfonyl-benzenesulfonyl)-pyridin-2-ylmethyl]-amide |
| 97 | 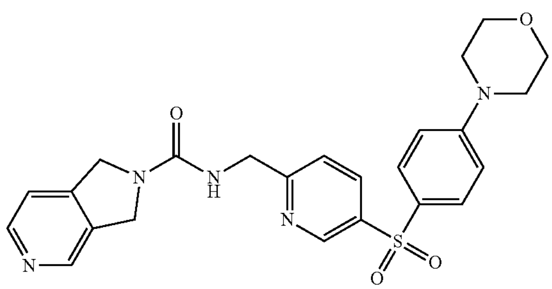 [SMILES: O=C(NCc1ccc(S(=O)(=O)c2ccc(N3CCOCC3)cc2)cn1)N1Cc2ccncc2C1] | 1,3-Dihydro-pyrrolo[3,4-c]pyridine-2-carboxylic acid [5-(4-morpholin-4-yl-benzenesulfonyl)-pyridin-2-ylmethyl]-amide |
| 98 | 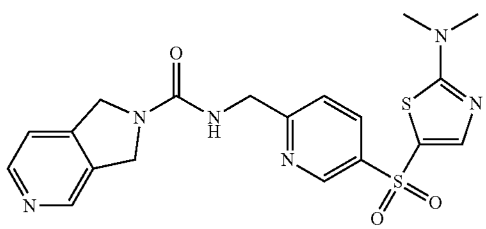 [SMILES: CN(C)c1ncc(S(=O)(=O)c2ccc(CNC(=O)N3Cc4ccncc4C3)nc2)s1] | 1,3-Dihydro-pyrrolo[3,4-c]pyridine-2-carboxylic acid [5-(2-dimethylamino-thiazole-5-sulfonyl)-pyridin-2-ylmethyl]-amide |
| 99 | 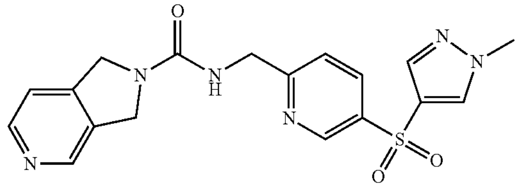 [SMILES: Cn1cc(S(=O)(=O)c2ccc(CNC(=O)N3Cc4ccncc4C3)nc2)cn1] | 1,3-Dihydro-pyrrolo[3,4-c]pyridine-2-carboxylic acid [5-(1-methyl-1H-pyrazole-4-sulfonyl)-pyridin-2-ylmethyl]-amide |
| 100 | 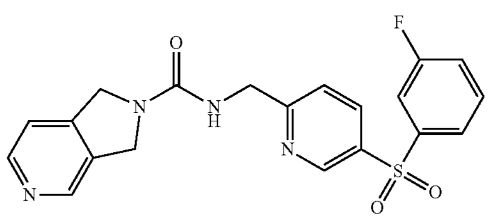 [SMILES: O=C(NCc1ccc(S(=O)(=O)c2cccc(F)c2)cn1)N1Cc2ccncc2C1] | 1,3-Dihydro-pyrrolo[3,4-c]pyridine-2-carboxylic acid [5-(3-fluoro-benzenesulfonyl)-pyridin-2-ylmethyl]-amide |
| 101 | 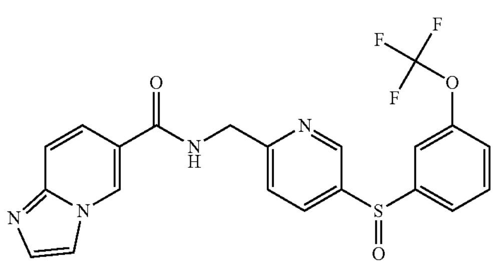 [SMILES: O=C(NCc1ccc(S(=O)c2cccc(OC(F)(F)F)c2)cn1)c1ccc2nccn2c1] | Imidazo[1,2-a]pyridine-6-carboxylic acid [5-(3-trifluoromethoxy-benzenesulfinyl)-pyridin-2-ylmethyl]-amide (racemic) |

| Ex. | Structure | Name |
|---|---|---|
| 102 | 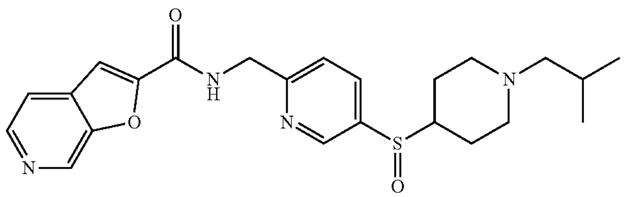 [SMILES: CC(C)CN1CCC(S(=O)c2ccc(CNC(=O)c3cc4ccncc4o3)nc2)CC1] | Furo[2,3-c]pyridine-2-carboxylic acid [5-(1-isobutyl-piperidine-4-sulfinyl)-pyridin-2-ylmethyl]-amide (racemic) |
| 103 | 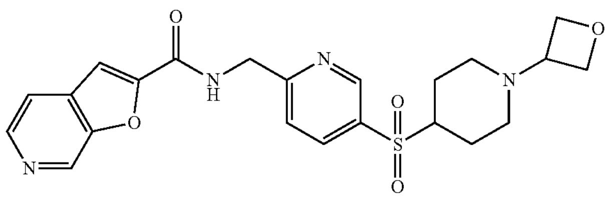 [SMILES: O=C(NCc1ccc(S(=O)(=O)C2CCN(C3COC3)CC2)cn1)c1cc2ccncc2o1] | Furo[2,3-c]pyridine-2-carboxylic acid [5-(1-oxetan-3-yl-piperidine-4-sulfonyl)-pyridin-2-ylmethyl]-amide |
| 104 | 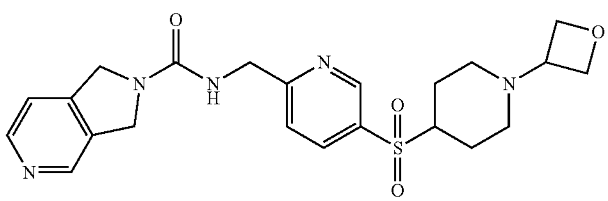 [SMILES: O=C(NCc1ccc(S(=O)(=O)C2CCN(C3COC3)CC2)cn1)N1Cc2ccncc2C1] | 1,3-Dihydro-pyrrolo[3,4-c]pyridine-2-carboxylic acid [5-(1-oxetan-3-yl-piperidine-4-sulfonyl)-pyridin-2-ylmethyl]-amide |
| 105 | 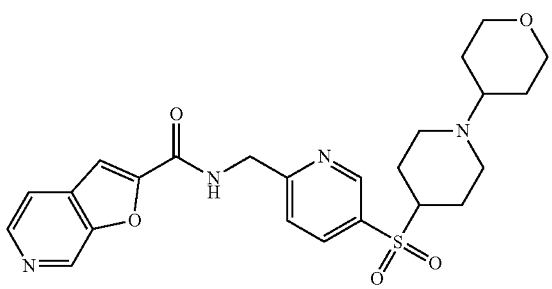 [SMILES: O=C(NCc1ccc(S(=O)(=O)C2CCN(C3CCOCC3)CC2)cn1)c1cc2ccncc2o1] | Furo[2,3-c]pyridine-2-carboxylic acid {5-[1-(tetrahydro-pyran-4-yl)-piperidine-4-sulfonyl]-pyridin-2-ylmethyl)-amide |
| 106 | 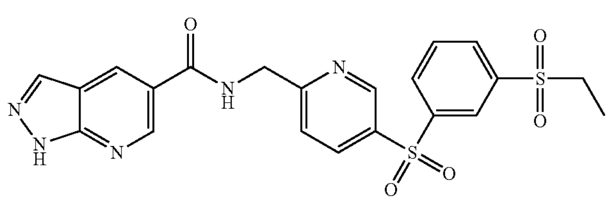 [SMILES: CCS(=O)(=O)c1cccc(S(=O)(=O)c2ccc(CNC(=O)c3cnc4[nH]ncc4c3)nc2)c1] | 1H-Pyrazolo[3,4-b]pyridine-5-carboxylic acid [5-(3-ethanesulfonyl-benzenesulfonyl)-pyridin-2-ylmethyl]-amide |
| 107 | 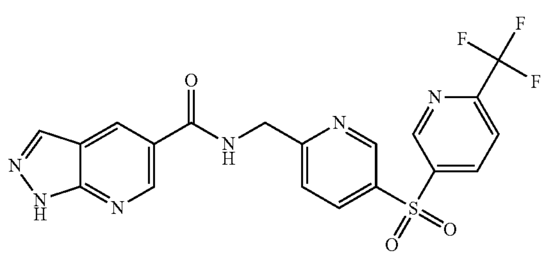 [SMILES: O=C(NCc1ccc(S(=O)(=O)c2ccc(C(F)(F)F)nc2)cn1)c1cnc2[nH]ncc2c1] | 1H-Pyrazolo[3,4-b]pyridine-5-carboxylic acid [5-(6-trifluoromethyl-pyridine-3-sulfonyl)-pyridin-2-ylmethyl]-amide |

| Ex. | Structure | Name |
|---|---|---|
| 108 | 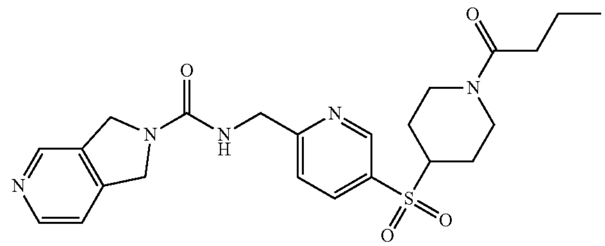 | 1,3-Dihydro-pyrrolo[3,4-c]pyridine-2-carboxylic acid [5-(1-butyryl-piperidine-4-sulfonyl)-pyridin-2-ylmethyl]-amide |
| 109 | 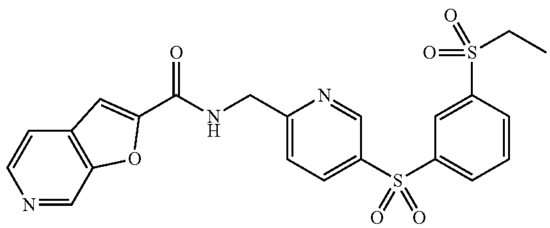 [SMILES: CCS(=O)(=O)c1cccc(S(=O)(=O)c2ccc(CNC(=O)c3cc4ccncc4o3)nc2)c1] | N-[[5-(3-ethylsulfonylphenyl)sulfonyl-2-pyridyl]methyl]furo[2,3-c]pyridine-2-carboxamide |
| 110 | 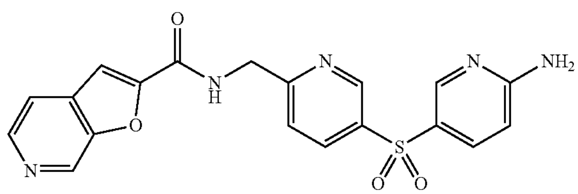 [SMILES: Nc1ccc(S(=O)(=O)c2ccc(CNC(=O)c3cc4ccncc4o3)nc2)cn1] | N-[[5-[(6-amino-3-pyridyl)sulfonyl]-2-pyridyl]methyl]furo[2,3-c]pyridine-2-carboxamide |
| 111 | 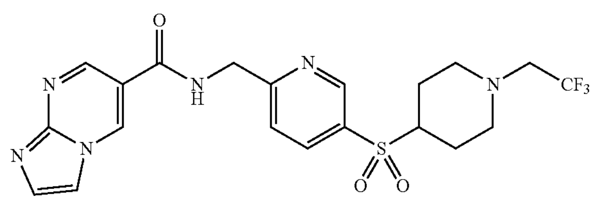 [SMILES: O=C(NCc1ccc(S(=O)(=O)C2CCN(CC(F)(F)F)CC2)cn1)c1cnc2nccn2c1] | N-[[5-[[1-(2,2,2-trifluoroethyl)-4-piperidyl]sulfonyl]-2-pyridyl]methyl]imidazo[1,2-a]pyrimidine-6-carboxamide |
| 112 | 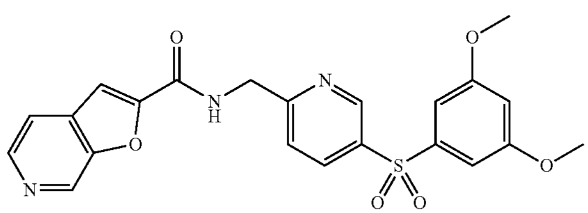 [SMILES: COc1cc(OC)cc(S(=O)(=O)c2ccc(CNC(=O)c3cc4ccncc4o3)nc2)c1] | N-[[5-(3,5-dimethoxyphenyl)sulfonyl-2-pyridyl]methyl]furo[2,3-c]pyridine-2-carboxamide |
| 113 | 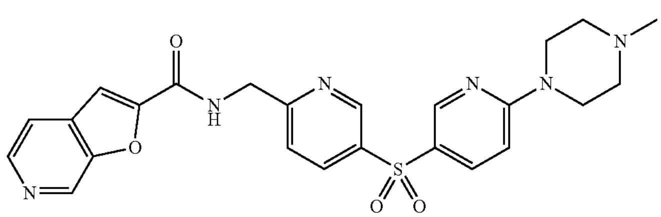 [SMILES: CN1CCN(c2ccc(S(=O)(=O)c3ccc(CNC(=O)c4cc5ccncc5o4)nc3)cn2)CC1] | N-[[5-[[6-(4-methylpiperazin-1-yl)-1-pyridyl]sulfonyl]-2-pyridyl]methyl]furo[2,3-c]pyridine-2-carboxamide or |
| 114 | | N-[[5-(3-ethylsulfonylphenyl)sulfonyl-2-pyridyl]methyl]-1,3-dihydropyrrolo(3,4-c]pyridine-2-carboxamide | or a pharmaceutically acceptable salt thereof, or a stereoisomer or a pharmaceutically acceptable salt of a stereoisomer thereof.

In certain other embodiments, the compound of Formula I is chosen from the following table.

| Ex. | Structure | Name |
|---|---|---|
| 115 | 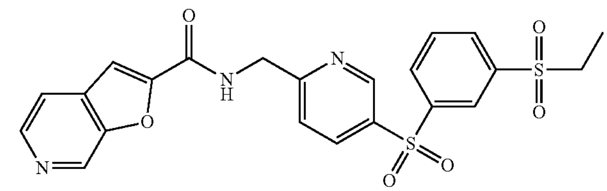 [SMILES: CCS(=O)(=O)c1cccc(S(=O)(=O)c2ccc(CNC(=O)c3cc4ccncc4o3)nc2)c1] | N-[[5-(3-ethylsulfonylphenyl)sulfonyl-2-pyridyl]methyl]furo[2,3-c]pyridine-2-carboxamide |
| 116 | 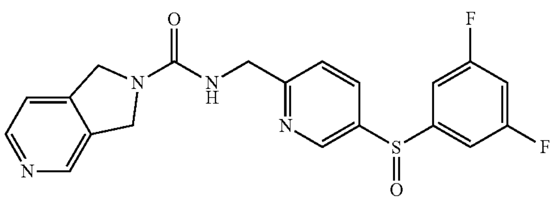 [SMILES: O=C(NCc1ccc(S(=O)c2cc(F)cc(F)c2)cn1)N1Cc2ccncc2C1] | N-[[5-(3,5-difluorophenyl)sulfinyl-2-pyridyl]methyl]-1,3-dihydropyrrolo[3,4-c]pyridine-2-carboxamide |
| 117 | 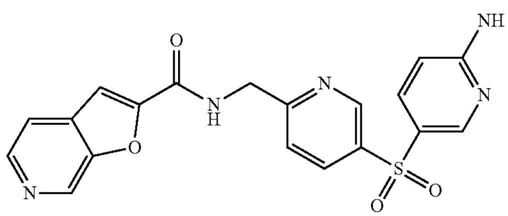 [SMILES: Nc1ccc(S(=O)(=O)c2ccc(CNC(=O)c3cc4ccncc4o3)nc2)cn1] | N-[[5-[(6-amino-3-pyridyl)sulfonyl]-2-pyridyl]methyl]furo[2,3-c]pyridine-2-carboxamide |
| 118 | 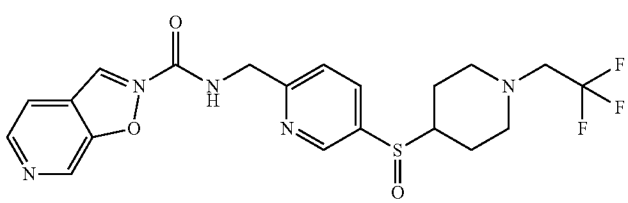 | N-[[5-[[1-(2,2,2-trifluoroethyl)-4-piperidyl]sulfinyl]-2-pyridyl]methyl]furo[2,3-c]pyridine-2-carboxamide |
| 119 | 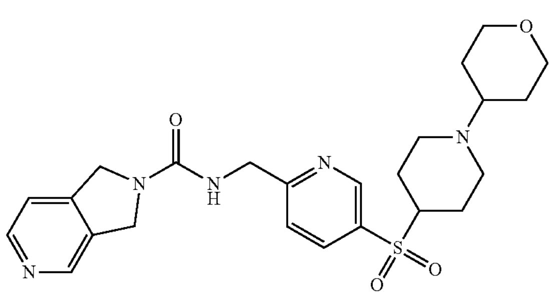 [SMILES: O=C(NCc1ccc(S(=O)(=O)C2CCN(C3CCOCC3)CC2)cn1)N1Cc2ccncc2C1] | N-[[5-[(1-tetrahydropyran-4-yl-4-piperidyl)sulfonyl]-2-pyridyl]methyl]-1,3-dihydropyrrolo[3,4-c]pyridine-2-carboxamide |
| 120 | 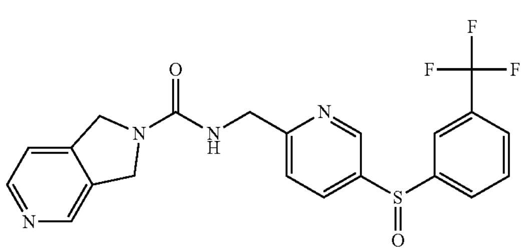 [SMILES: O=C(NCc1ccc(S(=O)c2cccc(C(F)(F)F)c2)cn1)N1Cc2ccncc2C1] | N-[[5-[3-(trifluoromethyl)phenyl]sulfinyl-2-pyridyl]methyl]-1,3-dihydropyrrolo[3,4-c]pyridine-2-carboxamide |

| Ex. | Structure | Name |
|---|---|---|
| 121 | 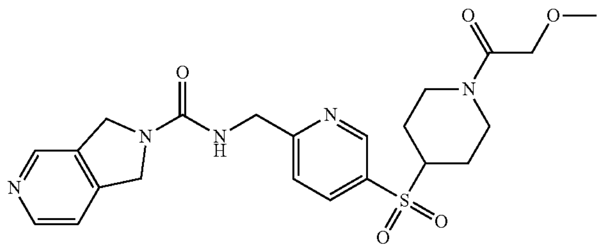 [SMILES: COCC(=O)N1CCC(S(=O)(=O)c2ccc(CNC(=O)N3Cc4ccncc4C3)nc2)CC1] | N-[[5-[[1-(2-methoxyacetyl)-4-piperidyl]sulfonyl]-2-pyridyl]methyl]-1,3-dihydropyrrolo[3,4-c]pyridine-2-carboxamide |
| 122 | 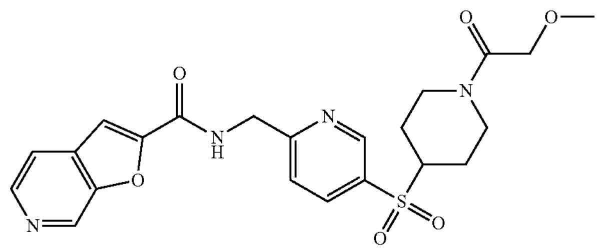 [SMILES: COCC(=O)N1CCC(S(=O)(=O)c2ccc(CNC(=O)c3cc4ccncc4o3)nc2)CC1] | N-[[5-[[1-(2-methoxyacetyl)-4-piperidyl]sulfonyl]-2-pyridyl]methyl]furo[2,3-c]pyridine-2-carboxamide |
| 123 | 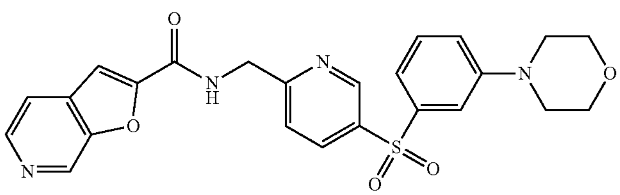 [SMILES: O=C(NCc1ccc(S(=O)(=O)c2cccc(N3CCOCC3)c2)cn1)c1cc2ccncc2o1] | N-[[5-(3-morpholinophenyl)sulfonyl-2-pyridyl]methyl]furo[2,3-c]pyridine-2-carboxamide |
| 124 | 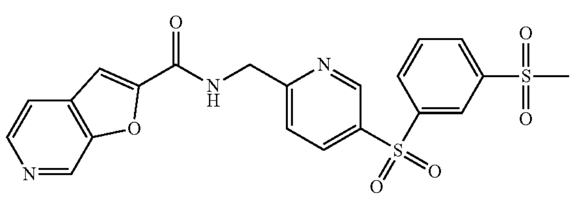 [SMILES: CS(=O)(=O)c1cccc(S(=O)(=O)c2ccc(CNC(=O)c3cc4ccncc4o3)nc2)c1] | N-[[5-(3-methylsulfonylphenyl)sulfonyl-2-pyridyl]methyl]furo[2,3-c]pyridine-2-carboxamide |
| 125 | 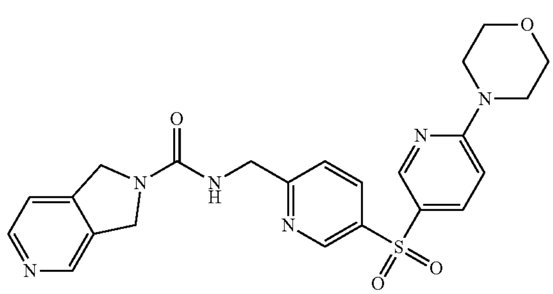 [SMILES: O=C(NCc1ccc(S(=O)(=O)c2ccc(N3CCOCC3)nc2)cn1)N1Cc2ccncc2C1] | N-[[5-[(6-morpholino-3-pyridyl)sulfonyl]-2-pyridyl]methyl]-1,3-dihydropyrrolo[3,4-c]pyridine-2-carboxamide |
| 126 | 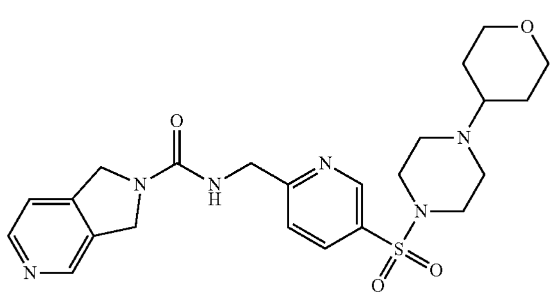 | N-[[5-(4-tetrahydropyran-4-ylpiperazin-1-yl)sulfonyl-2-pyridyl]methyl]-1,3-dihydropyrrolo[3,4-c]pyridine-2-carboxamide |

-continued

| Ex. | Structure | Name |
|---|---|---|
| 127 | 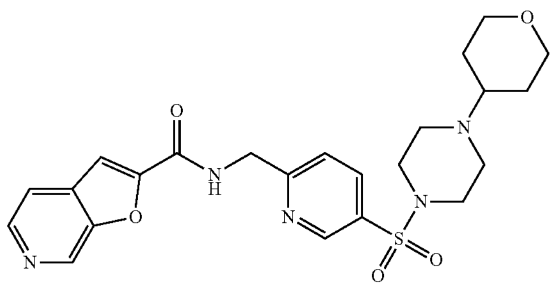 [SMILES: O=C(NCc1ccc(S(=O)(=O)N2CCN(C3CCOCC3)CC2)cn1)c1cc2ccncc2o1] | N-[[5-(4-tetrahydropyran-4-ylpiperazin-1-yl)sulfonyl-2-pyridyl]methyl]furo[2,3-c]pyridine-2-carboxamide |
| 128 | 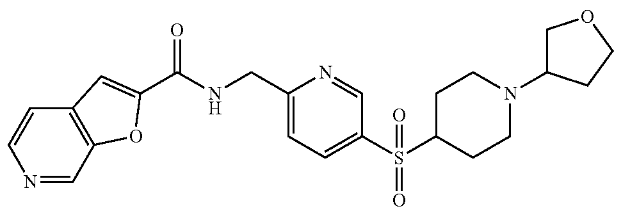 [SMILES: O=C(NCc1ccc(S(=O)(=O)C2CCN(C3CCOC3)CC2)cn1)c1cc2ccncc2o1] | N-[[5-[(1-tetrahydrofuran-3-yl-4-piperidyl)sulfonyl]-2-pyridyl]methyl]furo[2,3-c]pyridine-2-carboxamide |
| 129 | 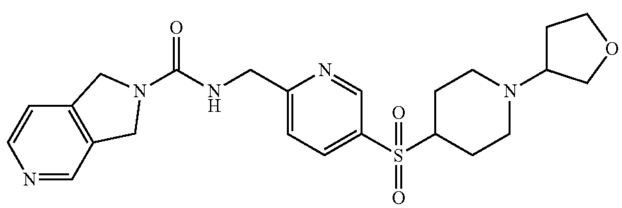 [SMILES: O=C(NCc1ccc(S(=O)(=O)C2CCN(C3CCOC3)CC2)cn1)N1Cc2ccncc2C1] | N-[[5-[(1-tetrahydrofuran-3-yl-4-piperidyl)sulfonyl]-2-pyridyl]methyl]-1,3-dihydropyrrolo[3,4-c]pyridine-2-carboxamide |
| 130 | 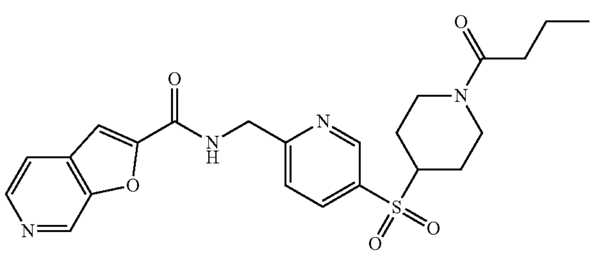 [SMILES: CCCC(=O)N1CCC(S(=O)(=O)c2ccc(CNC(=O)c3cc4ccncc4o3)nc2)CC1] | N-[[5-[(1-butanoyl-4-piperidyl)sulfonyl]-2-pyridyl]methyl]furo[2,3-c]pyridine-2-carboxamide |
| 131 | 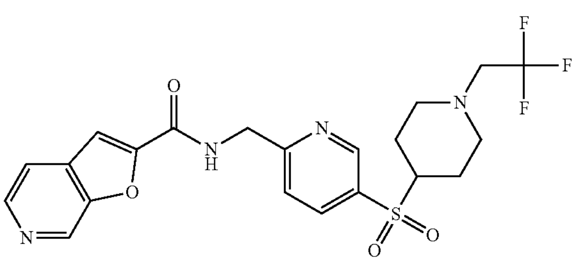 [SMILES: O=C(NCc1ccc(S(=O)(=O)C2CCN(CC(F)(F)F)CC2)cn1)c1cc2ccncc2o1] | N-[[5-[[1-(2,2,2-trifluoroethyl)-4-piperidyl]sulfonyl]-2-pyridyl]methyl]furo[2,3-c]pyridine-2-carboxamide |
| 132 | 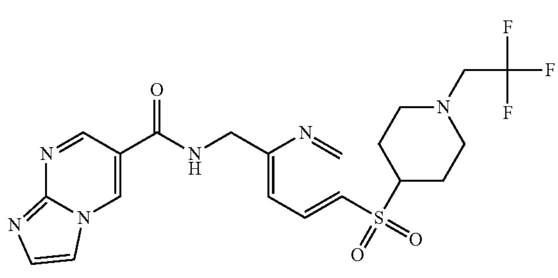 [SMILES: C=N/C(=C\C=C\S(=O)(=O)C1CCN(CC(F)(F)F)CC1)CNC(=O)c1cnc2nccn2c1] | N-[[5-[[1-(2,2,2-trifluoroethyl)-4-piperidyl]sulfonyl]-2-pyridyl]methyl]imidazo[1,2-a]pyrimidine-6-carboxamide |

| Ex. | Structure | Name |
|---|---|---|
| 133 | 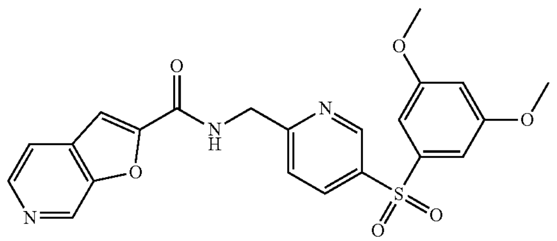 [SMILES: COc1cc(OC)cc(S(=O)(=O)c2ccc(CNC(=O)c3cc4ccncc4o3)nc2)c1] | N-[[5-(3,5-dimethoxyphenyl)sulfonyl-2-pyridyl]methyl]furo[2,3-c]pyridine-2-carboxamide |
| 134 | 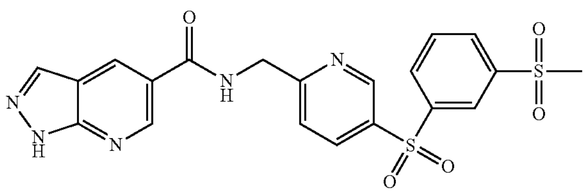 [SMILES: CS(=O)(=O)c1cccc(S(=O)(=O)c2ccc(CNC(=O)c3cnc4[nH]ncc4c3)nc2)c1] | N-[[5-(3-methylsulfonylphenyl)sulfonyl-2-pyridyl]methyl]-1H-pyrazolo[3,4-b]pyridine-5-carboxamide |
| 135 | 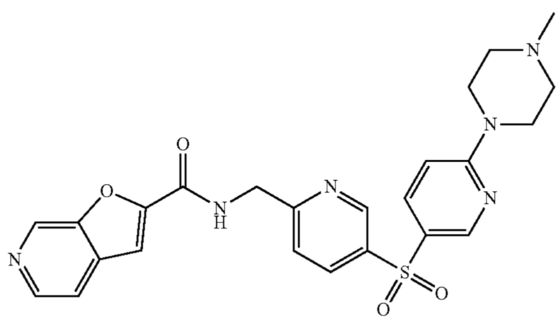 | N-[[5-[[6-(4-methylpiperazin-1-yl)-3-pyridyl]sulfonyl]-2-pyridyl]methyl]furo[2,3-c]pyridine-2-carboxamide |
| 136 | 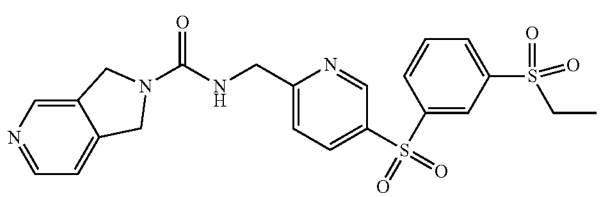 [SMILES: CCS(=O)(=O)c1cccc(S(=O)(=O)c2ccc(CNC(=O)N3Cc4ccncc4C3)nc2)c1] | N-[[5-(3-ethylsulfonylphenyl)sulfonyl-2-pyridyl]methyl]-1,3-dihydropyrrolo[3,4-c]pyridine-2-carboxamide |
| 137 | 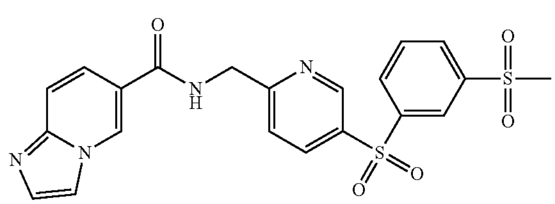 [SMILES: CS(=O)(=O)c1cccc(S(=O)(=O)c2ccc(CNC(=O)c3ccc4nccn4c3)nc2)c1] | N-[[5-(3-methylsulfonylphenyl)sulfonyl-2-pyridyl]methyl]imidazo[1,2-a]pyridine-6-carboxamide |
| 138 | 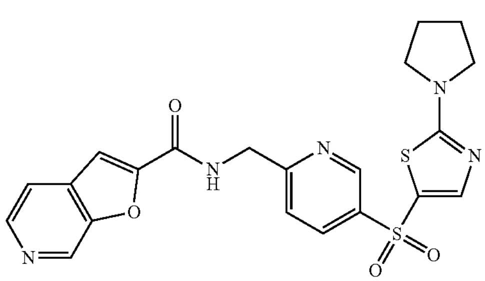 [SMILES: O=C(NCc1ccc(S(=O)(=O)c2cnc(N3CCCC3)s2)cn1)c1cc2ccncc2o1] | N-[[5-(2-pyrrolidin-1-ylthiazol-5-yl)sulfonyl-2-pyridyl]methyl]furo[2,3-c]pyridine-2-carboxamide |

| Ex. | Structure | Name |
| --- | --- | --- |
| 139 | 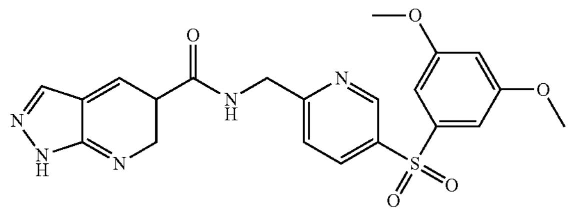 [SMILES: COc1cc(OC)cc(S(=O)(=O)c2ccc(CNC(=O)C3C=c4cn[nH]c4=NC3)nc2)c1] | N-[[5-(3,5-dimethoxyphenyl)sulfonyl-2-pyridyl]methyl]-1H-pyrazolo[3,4-b]pyridine-5-carboxamide |
| 140 | 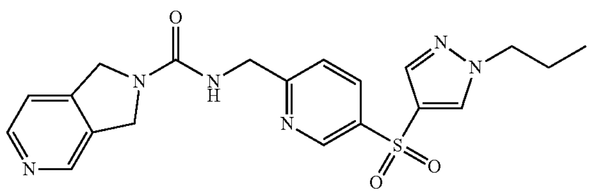 [SMILES: CCCn1cc(S(=O)(=O)c2ccc(CNC(=O)N3Cc4ccncc4C3)nc2)cn1] | N-[[5-(1-propylpyrazol-4-yl)sulfonyl-2-pyridyl]methyl]-1,3-dihydropyrrolo[3,4-c]pyridine-2-carboxamide |
| 141 | 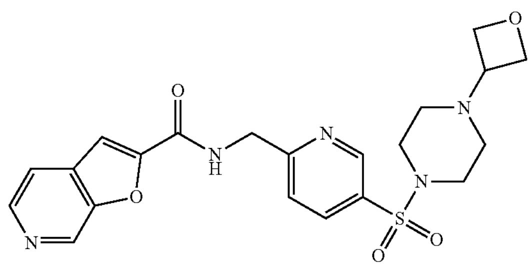 | N-[[5-[4-(oxetan-3-yl)piperazin-1-yl]sulfonyl-2-pyridyl]methyl]furo[2,3-c]pyridine-2-carboxamide |
| 142 | 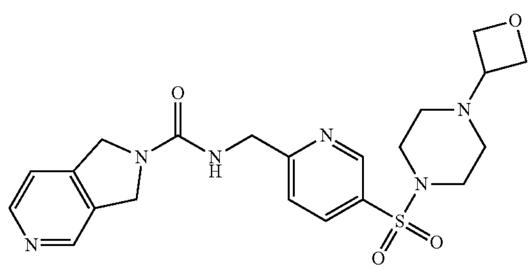 [SMILES: O=C(NCc1ccc(S(=O)(=O)N2CCN(C3COC3)CC2)cn1)N1Cc2ccncc2C1] | N-[[5-[4-(oxetan-3-yl)piperazin-1-yl]sulfonyl-2-pyridyl]methyl]-1,3-dihydropyrrolo[3,4-c]pyridine-2-carboxamide |
| 143 | 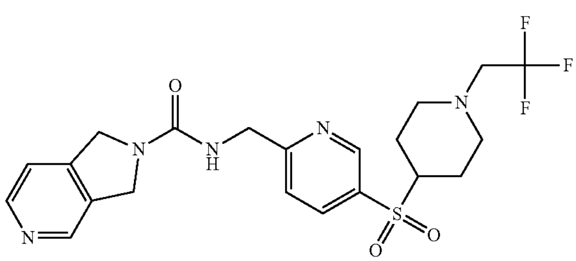 [SMILES: O=C(NCc1ccc(S(=O)(=O)C2CCN(CC(F)(F)F)CC2)cn1)N1Cc2ccncc2C1] | N-[[5-[[1-(2,2,2-trifluoroethyl)-4-piperidyl]sulfonyl]-2-pyridyl)methyl]-1,3-dihydropyrrolo[3,4-c]pyridine-2-carboxamide |
| 144 | 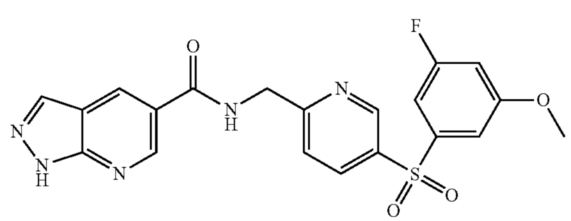 [SMILES: COc1cc(F)cc(S(=O)(=O)c2ccc(CNC(=O)c3cnc4[nH]ncc4c3)nc2)c1] | N-[[5-(3-fluoro-5-methoxy-phenyl)sulfonyl-2-pyridyl]methyl]-1H-pyrazolo[3,4-b]pyridine-5-carboxamide |

-continued

| Ex. | Structure | Name |
|---|---|---|
| 145 | 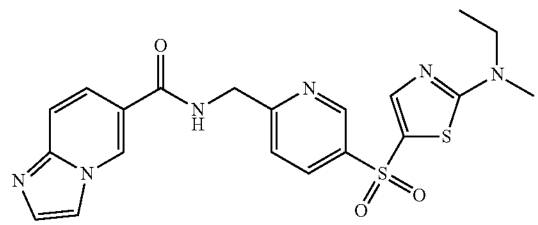 [SMILES: CCN(C)c1ncc(S(=O)(=O)c2ccc(CNC(=O)c3ccc4nccn4c3)nc2)s1] | N-[[5-[2-[ethyl(methyl)amino]thiazol-5-yl]sulfonyl-2-pyridyl]methyl]imidazo[1,2-a]pyridine-6-carboxamide |
| 146 | 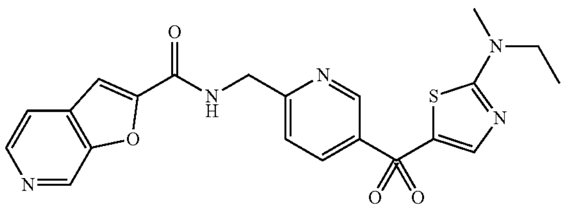 | N-[[5-[2-[ethyl(methyl)amino]thiazol-5-yl]sulfonyl-2-pyridyl]methyl]furo[2,3-c]pyridine-2-carboxamide |
| 147 | 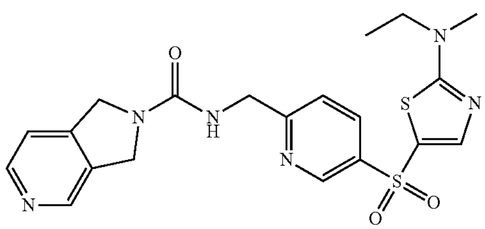 [SMILES: CCN(C)c1ncc(S(=O)(=O)c2ccc(CNC(=O)N3Cc4ccncc4C3)nc2)s1] | N-[[5-[2-[ethyl(methyl)amino]thiazol-5-yl]sulfonyl-2-pyridyl]methyl]-1,3-dihydropyrrolo[3,4-c]pyridine-2-carboxamide |
| 148 | 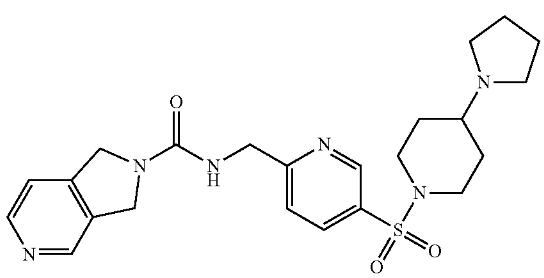 [SMILES: O=C(NCc1ccc(S(=O)(=O)N2CCC(N3CCCC3)CC2)cn1)N1Cc2ccncc2C1] | N-[[5-[(4-pyrrolidin-1-yl-1-piperidyl)sulfonyl]-2-pyridyl]methyl]-1,3-dihydropyrrolo[3,4-c]pyridine-2-carboxamide |
| 149 | 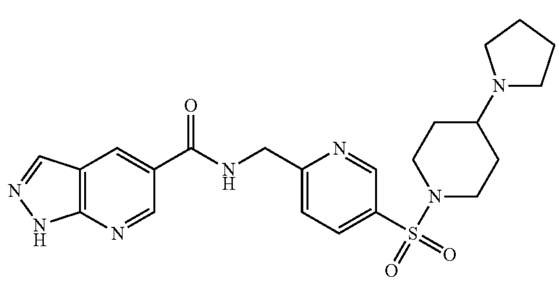 [SMILES: O=C(NCc1ccc(S(=O)(=O)N2CCC(N3CCCC3)CC2)cn1)c1cnc2[nH]ncc2c1] | N-[[5-[(4-pyrrolidin-1-yl-1-piperidyl)sulfonyl]-2-pyridyl]methyl]-1H-pyrazolo[3,4-b]pyridine-5-carboxamide |
| 150 | 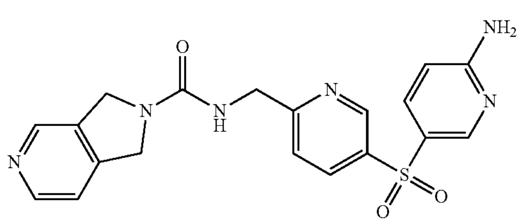 [SMILES: Nc1ccc(S(=O)(=O)c2ccc(CNC(=O)N3Cc4ccncc4C3)nc2)cn1] | N-[[5-[(6-amino-3-pyridyl)sulfonyl]-2-pyridyl]methyl]-1,3-dihydropyrrolo[3,4-c]pyridine-2-carboxamide |

| Ex. | Structure | Name |
| --- | --- | --- |
| 151 | 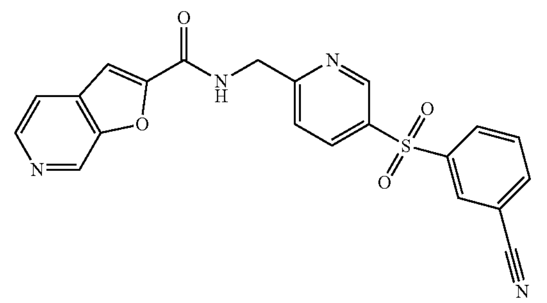 [SMILES: N#Cc1cccc(S(=O)(=O)c2ccc(CNC(=O)c3cc4ccncc4o3)nc2)c1] | N-[[5-(3-cyanophenyl)sulfonyl-2-pyridyl]methyl]furo[2,3-c]pyridine-2-carboxamide |
| 152 | 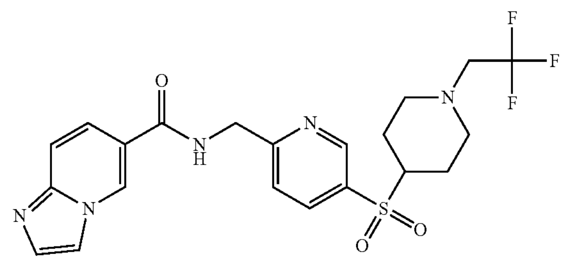 [SMILES: O=C(NCc1ccc(S(=O)(=O)C2CCN(CC(F)(F)F)CC2)cn1)c1ccc2nccn2c1] | N-[[5-[[1-(2,2,2-trifluoroethyl)-4-piperidyl]sulfonyl]-2-pyridyl]methyl]imidazo[1,2-a]pyridine-6-carboxamide |
| 153 | 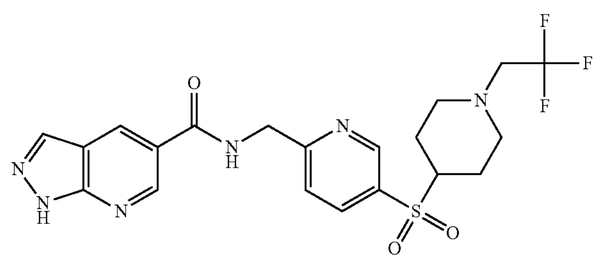 [SMILES: O=C(NCc1ccc(S(=O)(=O)C2CCN(CC(F)(F)F)CC2)cn1)c1cnc2[nH]ncc2c1] | N-[[5-[[1-(2,2,2-trifluoroethyl)-4-piperidyl]sulfonyl]-2-pyridyl]methyl]-1H-pyrazolo[3,4-b]pyridine-5-carboxamide |
| 154 | 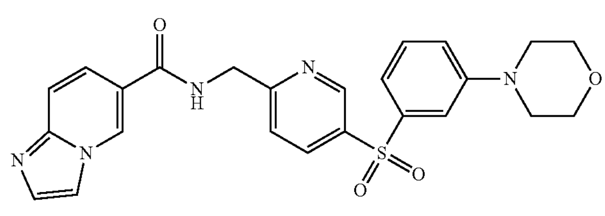 [SMILES: O=C(NCc1ccc(S(=O)(=O)c2cccc(N3CCOCC3)c2)cn1)c1ccc2nccn2c1] | N-[[5-(3-morpholinophenyl)sulfonyl-2-pyridyl]methyl]imidazo[1,2-a]pyridine-6-carboxamide |
| 155 | 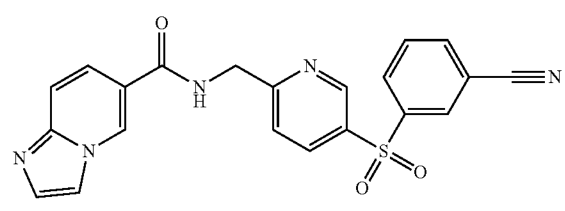 [SMILES: N#Cc1cccc(S(=O)(=O)c2ccc(CNC(=O)c3ccc4nccn4c3)nc2)c1] | N-[[5-(3-cyanophenyl)sulfonyl-2-pyridyl]methyl]imidazo[1,2-a]pyridine-6-carboxamide |
| 156 | 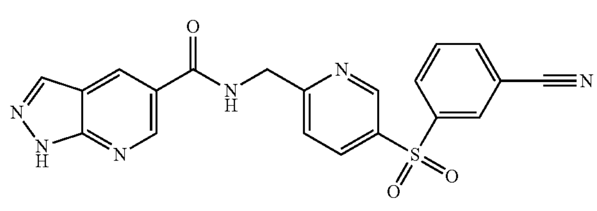 [SMILES: N#Cc1cccc(S(=O)(=O)c2ccc(CNC(=O)c3cnc4[nH]ncc4c3)nc2)c1] | N-[[5-(3-cyanophenyl)sulfonyl-2-pyridyl]methyl]-1H-pyrazolo[3,4-b]pyridine-5-carboxamide |

| Ex. | Structure | Name |
|---|---|---|
| 157 | 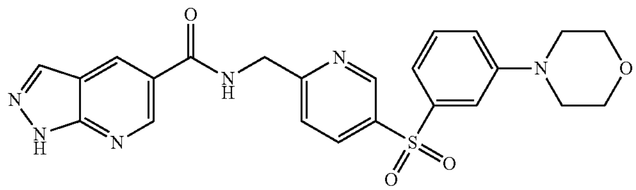 [SMILES: O=C(NCc1ccc(S(=O)(=O)c2cccc(N3CCOCC3)c2)cn1)c1cnc2[nH]ncc2c1] | N-[[5-(3-morpholinophenyl)sulfonyl-2-pyridyl]methyl]-1H-pyrazolo[3,4-b]pyridine-5-carboxamide |
| 158 | 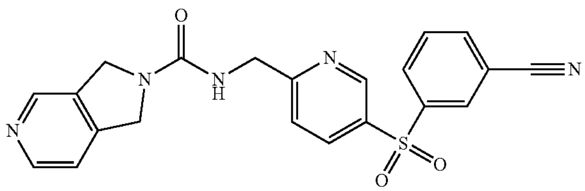 [SMILES: N#Cc1cccc(S(=O)(=O)c2ccc(CNC(=O)N3Cc4ccncc4C3)nc2)c1] | N-[[5-(3-cyanophenyl)sulfonyl-2-pyridyl]methyl]-1,3-dihydropyrrolo[3,4-c]pyridine-2-carboxamide |
| 159 | 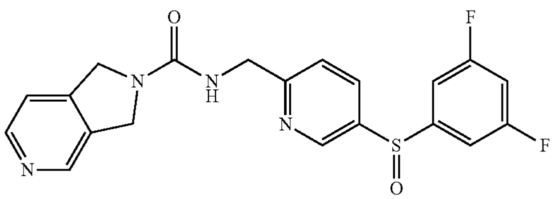 [SMILES: O=C(NCc1ccc(S(=O)c2cc(F)cc(F)c2)cn1)N1Cc2ccncc2C1] | N-[[5-(3,5-difluorophenyl)sulfinyl-2-pyridyl]methyl]-1,3-dihydropyrrolo[3,4-c]pyridine-2-carboxamide (enantiomer 1) |
| 160 | 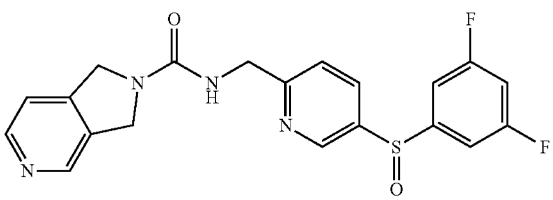 [SMILES: O=C(NCc1ccc(S(=O)c2cc(F)cc(F)c2)cn1)N1Cc2ccncc2C1] | N-[[5-(3,5-difluorophenyl)sulfinyl-2-pyridyl]methyl]-1,3-dihydropyrrolo[3,4-c]pyridine-2-carboxamide (enantiomer 2) |
| 161 | 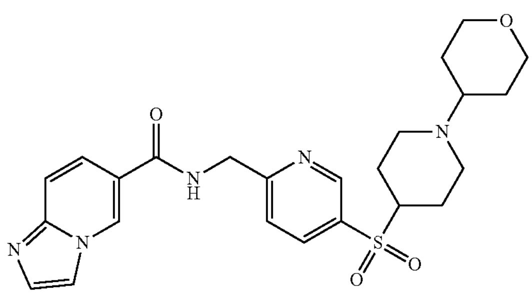 [SMILES: O=C(NCc1ccc(S(=O)(=O)C2CCN(C3CCOCC3)CC2)cn1)c1ccc2nccn2c1] | N-[[5-[(1-tetrahydropyran-4-yl-4-piperidyl)sulfonyl]-2-pyridyl]methyl]imidazo[1,2-a]pyridine-6-carboxamide |
| 162 | 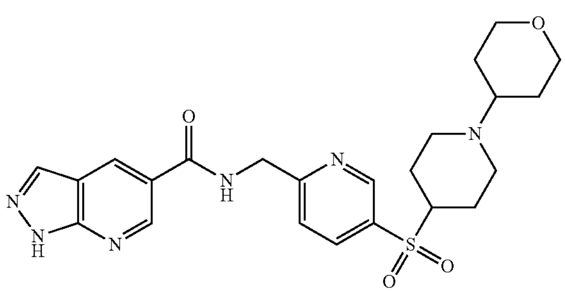 [SMILES: O=C(NCc1ccc(S(=O)(=O)C2CCN(C3CCOCC3)CC2)cn1)c1cnc2[nH]ncc2c1] | N-[[5-[(1-tetrahydropyran-4-yl-4-piperidyl)sulfonyl]-2-pyridyl]methyl]-1H-pyrazolo[3,4-b]pyridine-5-carboxamide |
| 163 | 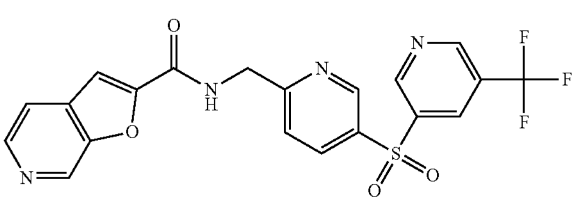 | N-[[5-[[5-(trifluoromethyl)-3-pyridyl]sulfonyl]-2-pyridyl]methyl]furo[2,3-c]pyridine-2-carboxamide |

-continued

| Ex. | Structure | Name |
|---|---|---|
| 164 | 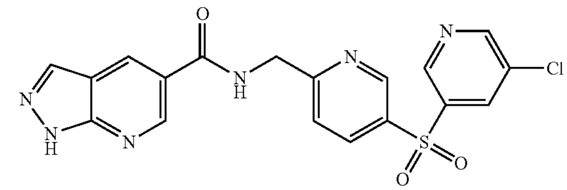 [SMILES: O=C(NCc1ccc(S(=O)(=O)c2cncc(Cl)c2)cn1)c1cnc2[nH]ncc2c1] | N-[[5-[(5-chloro-3-pyridyl)sulfonyl]-2-pyridyl]methyl]-1H-pyrazolo[3,4-b]pyridine-5-carboxamide |
| 165 | 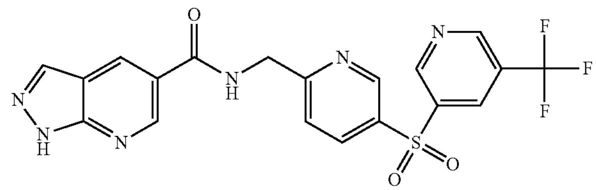 [SMILES: O=C(NCc1ccc(S(=O)(=O)c2cncc(C(F)(F)F)c2)cn1)c1cnc2[nH]ncc2c1] | N-[[5-[[5-(trifluoromethyl)-3-pyridyl]sulfonyl]-2-pyridyl]methyl]-1H-pyrazolo[3,4-b]pyridine-5-carboxamide |
| 166 | 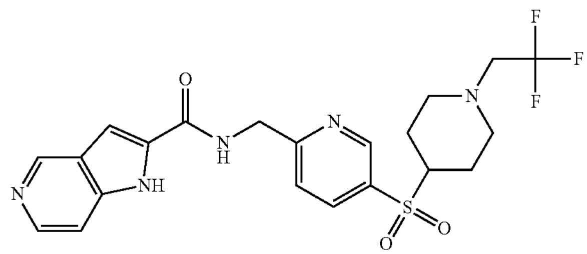 [SMILES: O=C(NCc1ccc(S(=O)(=O)C2CCN(CC(F)(F)F)CC2)cn1)c1cc2cnccc2[nH]1] | N-[[5-[[1-(2,2,2-trifluoroethyl)-4-piperidyl]sulfonyl]-2-pyridyl]methyl]-1H-pyrrolo[3,2-c]pyridine-2-carboxamide |
| 167 | 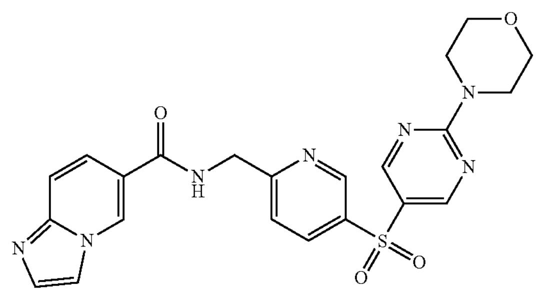 | N-[[5-(2-morpholinopyrimidin-5-yl)sulfonyl-2-pyridyl]methyl]imidazo[1,2-a]pyridine-6-carboxamide |
| 168 | 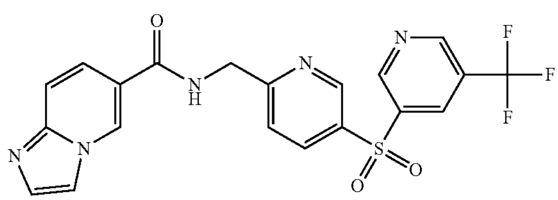 | N-[[5-[[5-(trifluoromethyl)-3-pyridyl]sulfonyl]-2-pyridyl]methyl]imidazo[1,2-a]pyridine-6-carboxamide |
| 169 | 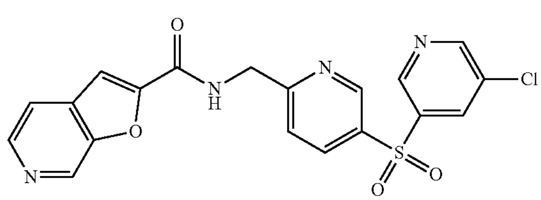 [SMILES: O=C(NCc1ccc(S(=O)(=O)c2cncc(Cl)c2)cn1)c1cc2ccncc2o1] | N-[[5-[(5-chloro-3-pyridyl)sulfonyl]-2-pyridyl]methyl]furo[2,3-c]pyridine-2-carboxamide |
| 170 | 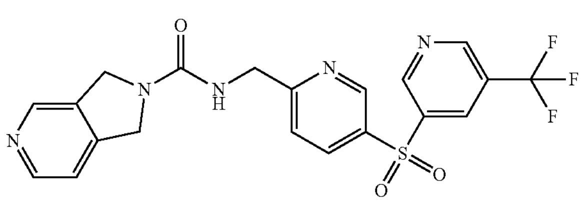 [SMILES: O=C(NCc1ccc(S(=O)(=O)c2cncc(C(F)(F)F)c2)cn1)N1Cc2ccncc2C1] | N-[[5-[[5-(trifluoromethyl)-3-pyridyl]sulfonyl]-2-pyridyl]methyl]-1,3-dihydropyrrolo[3,4-c]pyridine-2-carboxamide |

| Ex. | Structure | Name |
|---|---|---|
| 171 | 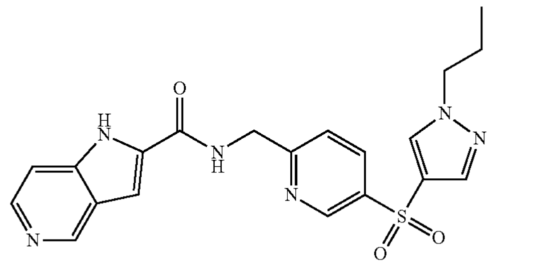 [SMILES: CCCn1cc(S(=O)(=O)c2ccc(CNC(=O)c3cc4cnccc4[nH]3)nc2)cn1] | N-[[5-(1-propylpyrazol-4-yl)sulfonyl-2-pyridyl]methyl]-1H-pyrrolo[3,2-c]pyridine-2-carboxamide |
| 172 | 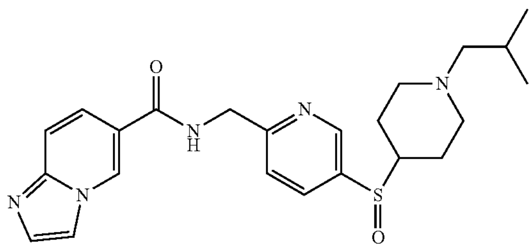 [SMILES: CC(C)CN1CCC(S(=O)c2ccc(CNC(=O)c3ccc4nccn4c3)nc2)CC1] | N-[[5-[(1-isobutyl-4-piperidyl)sulfinyl]-2-pyridyl]methyl]imidazo[1,2-a]pyridine-6-carboxamide |
| 173 | 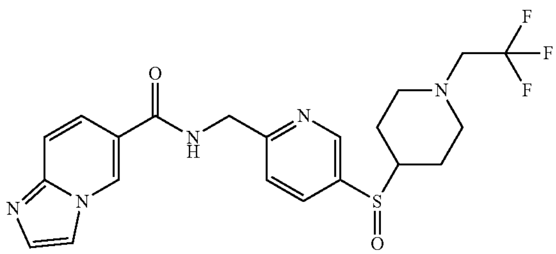 [SMILES: O=C(NCc1ccc(S(=O)C2CCN(CC(F)(F)F)CC2)cn1)c1ccc2nccn2c1] | N-[[5-[[1-(2,2,2-trifluoroethyl)-4-piperidyl]sulfinyl]-2-pyridyl]methyl]imidazo[1,2-a]pyridine-6-carboxamide |
| 174 | 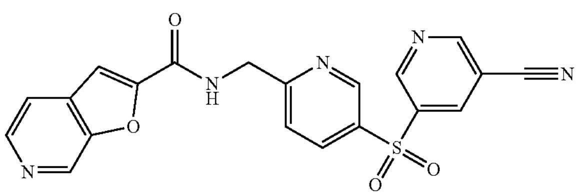 [SMILES: N#Cc1cncc(S(=O)(=O)c2ccc(CNC(=O)c3cc4ccncc4o3)nc2)c1] | N-[[5-[(5-cyano-3-pyridyl)sulfonyl]-2-pyridyl]methyl]furo[2,3-c]pyridine-2-carboxamide |
| 175 | 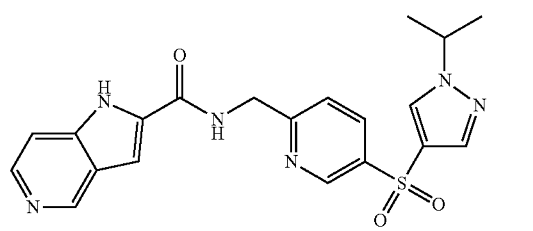 [SMILES: CC(C)n1cc(S(=O)(=O)c2ccc(CNC(=O)c3cc4cnccc4[nH]3)nc2)cn1] | N-[[5-(1-isopropylpyrazol-4-yl)sulfonyl-2-pyridyl]methyl]-1H-pyrrolo[3,2-c]pyridine-2-carboxamide |
| 176 | 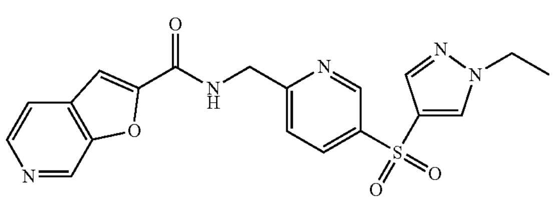 [SMILES: CCn1cc(S(=O)(=O)c2ccc(CNC(=O)c3cc4ccncc4o3)nc2)cn1] | N-[[5-(l-ethylpyrazol-4-yl)sulfonyl-2-pyridyl]methyl]furo[2,3-c]pyridine-2-carboxamide |
| 177 | 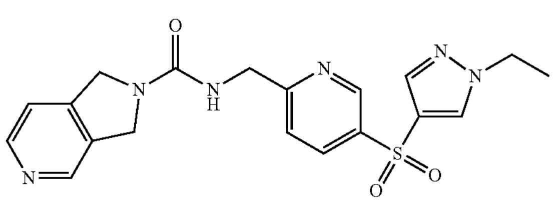 [SMILES: CCn1cc(S(=O)(=O)c2ccc(CNC(=O)N3Cc4ccncc4C3)nc2)cn1] | N-[[5-(1-ethylpyrazol-4-yl)sulfonyl-2-pyridyl]methyl]-1,3-dihydropyrrolo[3,4-c]pyridine-2-carboxamide |

| Ex. | Structure | Name |
|---|---|---|
| 178 | 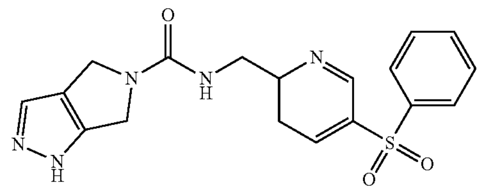 [SMILES: O=C(NCC1CC=C(S(=O)(=O)c2ccccc2)C=N1)N1Cc2cn[nH]c2C1] | N-[[5-(benzenesulfonyl)-2-pyridyl]methyl]-4,6-dihydro-1H-pyrrolo[3,4-c]pyrazole-5-carboxamide |
| 179 | 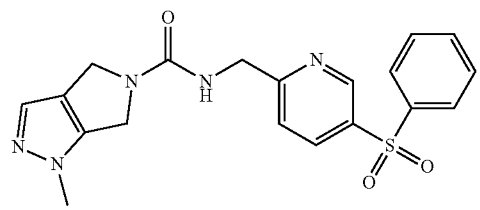 [SMILES: Cn1ncc2c1CN(C(=O)NCc1ccc(S(=O)(=O)c3ccccc3)cn1)C2] | N-[[5-(benzenesulfonyl)-2-pyridyl]methyl]-1-methyl-4,6-dihydropyrrolo[3,4-c]pyrazole-5-carboxamide |
| 180 | 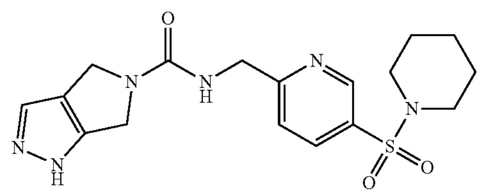 [SMILES: O=C(NCc1ccc(S(=O)(=O)N2CCCCC2)cn1)N1Cc2cn[nH]c2C1] | N-[[5-(1-piperidylsulfonyl)-2-pyridyl]methyl]-4,6-dihydro-1H-pyrrolo[3,4-c]pyrazole-5-carboxamide |
| 181 | 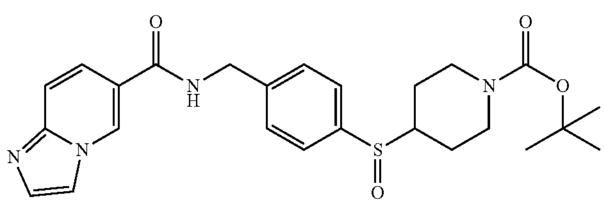 [SMILES: CC(C)(C)OC(=O)N1CCC(S(=O)c2ccc(CNC(=O)c3ccc4nccn4c3)cc2)CC1] | tert-butyl 4-[[6-[(imidazo[1,2-a]pyridine-6-carbonylamino)methyl]-3-pyridyl]sulfinyl]piperidine-1-carboxylate |
| 182 | 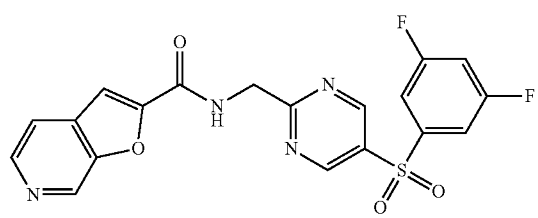 [SMILES: O=C(NCc1ncc(S(=O)(=O)c2cc(F)cc(F)c2)cn1)c1cc2ccncc2o1] | N-[[5-(3,5-difluorophenyl)sulfonyl-pyrimidin-2-yl]methyl]furo[2,3-c]pyridine-2-carboxamide |
| 183 | 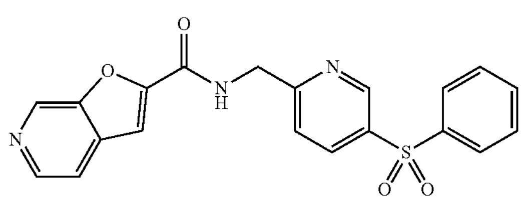 [SMILES: O=C(NCc1ccc(S(=O)(=O)c2ccccc2)cn1)c1cc2ccncc2o1] | N-[[5-(benzenesulfonyl)-2-pyridyl]methyl]furo[2,3-c]pyridine-2-carboxamide |
| 184 | 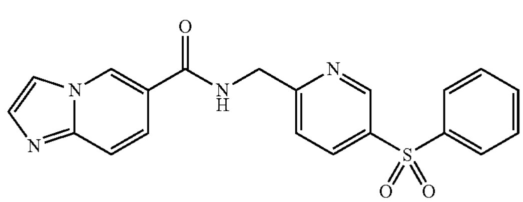 [SMILES: O=C(NCc1ccc(S(=O)(=O)c2ccccc2)cn1)c1ccc2nccn2c1] | N-[[5-(benzenesulfonyl)-2-pyridyl]methyl]imidazo[1,2-a]pyridine-6-carboxamide |

| Ex. | Structure | Name |
|---|---|---|
| 185 | 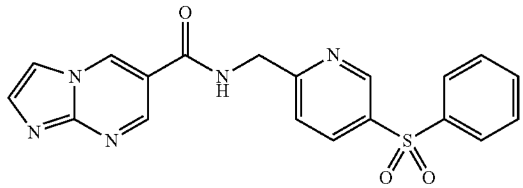 [SMILES: O=C(NCc1ccc(S(=O)(=O)c2ccccc2)cn1)c1cnc2nccn2c1] | N-[[5-(benzenesulfonyl)-2-pyridyl]methyl]imidazo[1,2-a]pyrimidine-6-carboxamide |
| 186 | 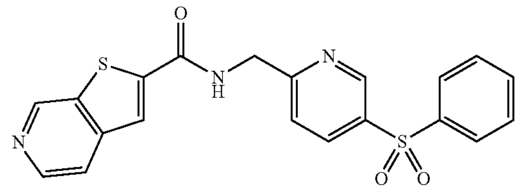 [SMILES: O=C(NCc1ccc(S(=O)(=O)c2ccccc2)cn1)c1cc2ccncc2s1] | N-[[5-(benzenesulfonyl)-2-pyridyl]methyl]thieno[2,3-c]pyridine-2-carboxamide |
| 187 | | N-[[5-(benzenesulfonyl)pyrimidin-2-yl]methyl]thieno[2,3-c]pyridine-2-carboxamide | or a pharmaceutically acceptable salt thereof, or a stereoisomer or a pharmaceutically acceptable salt of a stereoisomer thereof.

Pharmaceutical Description

The dosage forms of the present invention may contain a mixture of one or more compounds of this invention, and may include additional materials known to those skilled in the art as pharmaceutical excipients. "Excipient" includes any excipient commonly used in pharmaceutics and should be selected on the basis of compatibility and the release profile properties of the desired dosage form. Exemplary excipients include, e.g., binders, suspending agents, disintegration agents, filling agents, surfactants, solubilizers, stabilizers, lubricants, wetting agents, diluents, and the like. Exemplary exipients include, e.g., acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, and the like. See, e.g., Hoover, John E., *Remington's Pharmaceutical Sciences*, Mack Publishing Co., Easton, Pa. 1975.

Exemplary excipients include: stabilizing additives such as gum acacia, gelatin, methyl cellulose, polyethylene glycol, carboxylic acids and salts thereof, and polylysine; acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); aerosol propellants (butane, dichlorodifluoro-methane, dichlorotetrafluoroethane, isobutane, propane, trichloromonofluoromethane); air displacements (carbon dioxide, nitrogen); alcohol denaturants (denatonium benzoate, methyl isobutyl ketone, sucrose octacetate); alkalizing agents (strong ammonia solution, ammonium carbonate, diethanolamine, diisopropanolamine, potassium hydroxide, sodium bicarbonate, sodium borate, sodium carbonate, sodium hydroxide, trolamine); anticaking agents (see "glidant" below); antifoaming agents (dimethicone, simethicone); antimicrobial preservatives (benzalkonium chloride, benzalkonium chloride solution, benzelthonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); antioxidants (ascorbic acid, acorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); capsule lubricants (see "tablet and capsule lubricant" below); chelating agents (edetate disodium, ethylenediaminetetraacetic acid and salts, edetic acid); coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcystalline wax, zein); colorants (caramel, red, yellow, black or blends, ferric oxide): complexing agents (ethylenediaminetetraacetic acid and salts (EDTA), edetic acid, gentisic acid ethanolmaide, oxyquinoline sulfate); desiccants (calcium chloride, calcium sulfate, silicon dioxide); emulsifying and/or solubilizing agents (acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, soritan monooleate, sorbitan monopalmitate, sorbitan monostearate, stearic acid, trolamine, emulsifying wax); filtering aids (powdered cellulose, purified siliceous earth); flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); glidants and/or anticaking agents (calcium silicate, magnesium silicate, colloidal silicon dioxide, talc); humectants (glycerin, hexylene glycol, propylene glycol, sorbitol); plasticizers (castor oil, diacetylated monoglycerides, diethyl phthalate, glycerin, mono- and di-acetylated monoglycerides, polyethylene glycol, propylene glycol, triacetin, triethyl citrate); polymers (e.g., cellulose acetate, alkyl celloloses, hydroxyalkylcelloloses, acrylic polymers and copolymers); solvents (acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water); sorbents (powdered cellulose, charcoal, purified siliceous earth); carbon dioxide sorbents (barium hydroxide lime, soda lime); stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); suspending and/or viscosity-increasing agents (acacia, agar, alginic acid, aluminum monostearate, bentonite, purified bentonite, magma bentonite, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum); sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); tablet binders (acacia, alginic acid, sodium carboxymethylcellulose, microcrystalline cellulose, dextrin, ethylcellulose, gelatin, liquid glucose, guar gum, hydroxypropyl methylcellulose, methycellulose, polyethylene oxide, povidone, pregelatinized starch, syrup); tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); tablet disintegrants (alginic acid, microcrystalline cellulose, croscarmellose sodium, corspovidone, polacrilin potassium, sodium starch glycolate, starch, pregelatinized starch); tablet and/or capsule lubricants (calcium stearate, glyceryl behenate, magnesium stearate, light mineral oil, polyethylene glycol, sodium stearyl fumarate, stearic acid, purified stearic acid, talc, hydrogenated vegetable oil, zinc stearate); tonicity agent (dextrose, glycerin, mannitol, potassium chloride, sodium chloride); vehicle: flavored and/or sweetened (aromatic elixir, compound benzaldehyde elixir, iso-alcoholic elixir, peppermint water, sorbitol solution, syrup, tolu balsam syrup); vehicle: oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, seame oil, soybean oil, squalane); vehicle: solid carrier (sugar spheres); vehicle: sterile (bacteriostatic water for injection, bacteriostatic sodium chloride injection); viscosity-increasing (see "suspending agent" below); water repelling agent (cyclomethicone, dimethicone, simethicone); and wetting and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaureate, sorbitan monooleate, sorbitan monopalmitate, sorbitan monostearate, tyloxapol). This list is not meant to be exclusive, but instead merely representative of the classes of excipients and the particular excipients which may be used in dosage forms of the present invention.

In certain aspects, the invention relates to methods of treating diseases or conditions mediated by elevated levels of NAMPT, or which are generally mediated by NAMPT activity. Such disease or condition is one or more selected from the group consisting of cancer, ovarian cancer, breast cancer, uterine cancer, colon cancer, cervical cancer, lung cancer, prostate cancer, skin cancer, bladder cancer, pancreatic cancer, leukemia, lymphoma, Hodgkin's disease, viral infections, Human Immunodeficiency Virus, hepatitis virus, herpes virus, herpes simplex, inflammatory disorders, irritable bowel syndrome, inflammatory bowel disease, rheumatoid arthritis, asthma, chronic obstructive pulmonary disease, osteoarthritis, osteoporosis, dermatitis, atoptic dermatitis, psoriasis, systemic lupus erythematosis, multiple sclerosis, psoriatic arthritis, ankylosing spodylitis, graft-versus-host disease, Alzheimer's disease, cerebrovascular accident, atherosclerosis, diabetes, glomerulonephiritis, metabolic syndrome, non-small cell lung cancer, small cell lung cancer, multiple myeloma, leukemias, lymphomas, squamous cell cancers, kidney cancer, uretral and bladder cancers, cancers of head and neck, and cancers of the brain and central nervous system (CNS).

The inventive compounds can be useful in the therapy of proliferative diseases such as, but not limited to cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease.

More specifically, the compounds can be useful in the treatment of a variety of cancers, including (but not limited to) the following: carcinoma, including that of the bladder, breast, colon, kidney, liver, lung, including small cell lung cancer, non-small cell lung cancer, head and neck, esophagus, gall bladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

The compounds of the invention may induce or inhibit apoptosis.

The compounds of the invention may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

A further aspect of the invention is a method of inhibiting a NAMPT pathway in a subject, said method comprising administering to said subject a pharmaceutically acceptable amount of a compound of the invention to a subject in need thereof.

Another embodiment of the invention comprises a pharmaceutical formulation of the invention, wherein the pharmaceutical formulation, upon administration to a subject (e.g., a human), results in a decrease in tumor burden.

Still another embodiment of the invention is a pharmaceutical formulation comprising at least one compound of Formula I and a pharmaceutically acceptable excipient, and further comprising one or more adjunctive active agent.

The pharmaceutical formulations of the invention may further comprise a therapeutic effective amount of an adjunctive active agent.

The compounds of the present invention are also useful in combination therapies with at least one adjunctive active agent. Such methods include regimes in which the compound of the invention and the at least one adjunctive active agent are administered simultaneously or sequentially. Also useful are pharmaceutical compositions in which at least one compound of the present invention and at least one adjunctive active agent are combined in a single formulation.

The expression "adjunctive active agent" generally refers to agents which targets the same or a different disease, symptom, or medical condition as the primary therapeutic agent. Adjunctive active agents may treat, alleviate, relieve, or ameliorate side effects caused by administration of the primary therapeutic agents. Examples of adjunctive active agents include, but are not limited to, antineoplastic agents, filgrastim, and erythropoietin. Such agents include those which modify blood cell growth and maturation. Non-limiting examples of adjunctive active agent are filgrastim, pegfilgrastim and erythropoietin. Other such adjunctive active agents include those which inhibit nausea associated with administration of chemotherapeutic agents, such as a 5-$HT_3$ receptor inhibitor (e.g., dolansetron, granisetron, or ondansetron), with or without dexamethasone. The invention also describes one or more uses of the compounds of the present invention with an adjunctive active agent such as TNF, GCSF, or other chemotherapeutic agents. Additional adjunctive active agents include those that mediate cytotoxicity of NAMPT inhibitors, such as nicotinic acid rescue agents, or other compounds that play a role in the NAMPT pathway, such as niacin (nicotinic acid), nicotinamide, or related compounds, or modified release formulations of such compounds, for example, NIASPAN®.

The terms "chemotherapeutic agent" and "antineoplastic agent" generally refer to agents, which treat, prevent, cure, heal, alleviate, relieve, alter, remedy, ameliorate, improve, or affect malignancies and their metastasis. Examples of such agents include, but are not limited to, prednisone, fluorouracil (e.g., 5-fluorouracil (5-FU)), anastrozole, bicalutamide, carboplatin, cisplatin, chlorambucil, docetaxel, doxorubicin, flutamide, interferon-alpha, letrozole, leuprolide, megestrol, mitomycin, oxaliplatin, paclitaxel, plicamycin (Mithracin™), tamoxifen, thiotepa, topotecan, valrubicin, vinblastine, vincristine, and any combination of any of the foregoing.

The invention is also directed to a method of treating or preventing a disorder associated with excessive rate of growth of cells in a subject (e.g., a mammal) comprising administering to the subject an effective amount of the pharmaceutical 10 formulation of the invention. Non-limiting examples of disorder include cancer or metastasis from malignant tumors.

Another aspect of the invention is a method of inhibiting tumor cell growth and rate of division in a subject (e.g., a mammal) with cancer, or other disorder associated with abnormally dividing cells comprising administering to the subject an effective amount of the pharmaceutical formulation of this invention.

Another embodiment of the invention is a method of treating bone pain due to excessive growth of a tumor or metastasis to bone in a subject (e.g., a mammal) in need thereof comprising administering to the subject an effective amount of the pharmaceutical formulation of this invention.

A further embodiment of the invention is a method of preparing a pharmaceutical formulation comprising mixing at least one compound of the present invention, and, optionally, one or more pharmaceutically acceptable excipients.

The invention is also directed to methods of synthesizing compounds of the present invention.

Still another aspect of this invention is to provide a method for treating, preventing, inhibiting or eliminating a disease or condition in a patient by inhibiting NAMPT in said patient by administering a therapeutically effective amount of at least one compound of this disclosure, wherein said disease or condition is selected from the group consisting of cancer, ovarian cancer, breast cancer, uterine cancer, colon cancer, cervical cancer, lung cancer, prostate cancer, skin cancer, bladder cancer, pancreatic cancer, leukemia, lymphoma, Hodgkin's disease, viral infections. Human Immunodeficiency Virus, hepatitis virus, herpes virus, herpes simplex, inflammatory disorders, irritable bowel syndrome, inflammatory bowel disease, rheumatoid arthritis, asthma, chronic obstructive pulmonary disease, osteoarthritis, osteoporosis, dermatitis, atoptic dermatitis, psoriasis, systemic lupus erythematosis, multiple sclerosis, psoriatic arthritis, ankylosing spodylitis, graft-versus-host disease, Alzheimer's disease, cerebrovascular accident, atherosclerosis, diabetes, glomerulonephiritis, metabolic syndrome, non-small cell lung cancer, small cell lung cancer, multiple myeloma, leukemias, lymphomas, squamous cell cancers, kidney cancer, uretral and bladder cancers, cancers of head and neck, cancers of the brain and central nervous system.

In a certain embodiment, the compounds of formula I can be used in the treatment of solid and liquid tumors, non-small cell lung cancer, leukemia, lymphoma, ovarian cancer, glioma, breast cancer, uterine cancer, colon cancer, cervical cancer, lung cancer, prostate cancer, skin cancer, rhinogastric tumors, colorectal cancer, CNS cancer, bladder cancer, pancreatic cancer and Hodgkin's disease.

In a certain embodiment, the compounds of formula I can be used in the treatment of solid and liquid tumors, non-small cell lung cancer, leukemia, lymphoma, ovarian cancer, breast cancer, uterine cancer, colon cancer, cervical cancer, lung cancer, prostate cancer, skin cancer, rhino-gastric tumors, colorectal cancer, bladder cancer, pancreatic cancer and Hodgkin's disease.

Another embodiment is a pharmaceutical formulation comprising a pharmaceutically acceptable compound of the present invention, which provides, upon administration to a subject (e.g., a human), a decrease in tumor burden and/or metastases. The pharmaceutical formulation can be administered by oral means or other suitable means.

Yet another embodiment is a method of treating ovarian cancer in a subject (e.g., a human) in need thereof by administering to the subject an effective amount of the compound or the pharmaceutical formulation of the present invention.

Yet another embodiment is a method of treating non-small cell lung cancer (NSCLC) in a subject (e.g., a human) in need thereof by administering to the subject an effective amount of the compound or of a pharmaceutical composition comprising the compound as described herein.

Yet another embodiment is a method of treating colon cancer in a subject (e.g., a human) in need thereof by administering to the subject an effective amount of the compound or the pharmaceutical formulation of the present invention.

Yet another embodiment is a method of treating breast cancer in a subject (e.g., a human) in need thereof by administering to the subject an effective amount of the pharmaceutical formulation of the present invention.

Yet another embodiment is a method of treating leukemia in a subject (e.g., a human) in need thereof by administering to the subject an effective amount of the compound or the pharmaceutical formulation of the present invention.

Yet another embodiment is a method of treating colon cancer before or after surgical resection and/or radiation therapy, in a subject (e.g., a human) in need thereof by administering to the subject an effective amount of the compound or the pharmaceutical formulation of the present invention.

Yet another embodiment is a method of treating cancer before or after surgical resection and/or radiation therapy, in a subject (e.g., a human) in need thereof by administering to the subject an effective amount of the compound or the pharmaceutical formulation of the present invention, including adjunctive therapy to treat nausea, with or without dexamethasone.

Yet another embodiment is a method of treating cancer before or after surgical resection and or radiation therapy, in a subject (e.g., a human) in need thereof by administering to the subject an effective amount of the compound or the pharmaceutical formulation of the present invention, including adjunctive therapy with one or more additional therapeutic agents, or their pharmaceutically acceptable salts. Non-limiting examples of such additional therapeutic agents include cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil or 5-FU); anti-metabolites (such as methoxtrexate); alkylating agents (such as temozolomide, cyclophosphamide); Farnesyl protein transferase inhibitors (such as, SARASAR™ (4-[2-[4-[(11R)-3,10-dibromo-8-chloro-6,11-dihydro-5H-benzo[5,-6]cyclohepta[1,2-b]pyridin-11-yl-]-1-piperidinyl]-2-oxoehtyl]-1-piperidine-carboxamide, or SCH 66336), tipifarnib (Zamestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa® (from Astra Zeneca Pharmaceuticals, England), Tarceva® (EGFR kinase inhibitors), antibodies to EGFR (e.g., C225), GLEEVEC® (C-abl kinase inhibitor from Novartis Pharmaceuticals, East Hanover, N.J.); interferons such as, for example, Intron® (from Merck & Company), Peg-Intron® (from Merck & Company); hormonal therapy combinations; aromatase combinations; ara-C, adriamycin, cytoxan, and gemcitabine.

Other anti-cancer (also known as anti-neoplastic) agents include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN® from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade®, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Ifosfomide, Rituximab, C225, and Campath, 5-fluorouracil and leucovorin, with or without a 5-HT$_3$ receptor inhibitor (e.g., dolansetron, granisetron, ondansetron) with or without dexamethasone.

Additionally, according to the present invention, the compounds of the invention described herein may be administered and/or formulated in combination with an adjunctive active agent. In certain embodiments, the adjunctive active agent is niacin, nicotinamide, nicotinic acid, nicotinamide mononucleotide (NMN), or variations thereof, including modified release formulations of niacin, such as NIASPAN®. Niacin, nicotinamide, nicotinic acid, nicotinamide mononucleotide (NMN), or variations thereof have also been described in the literature as "rescue agents" or "rescuing agents" and these terms have been used herein. The role of nicotinamide and/or nicotinic acid as a rescuing or rescue agent has for example been described by Beauparlant et al. in Anti-Cancer Drugs 2009, 20:346-354 and by Rongvaux et al. in The Journal of Immunology, 2008, 181: 4685-4695. These two references describe the role of a rescuing or rescue agent with regards to ameliorating possible toxic effects of NAMPT inhibitors.

If formulated as a fixed dose, such combination products employ the compounds of this invention within the dosage range described herein (or as known to those skilled in the art) and the other pharmaceutically active agents or treatments within its dosage range. For example, the CDC2 inhibitor olomucine has been found to act synergistically with known cytotoxic agents in inducing apoptosis (J. Cell Sci, (1995) 108, 2897). The compounds of the invention may also be administered sequentially with known anticancer or cytotoxic agents when a combination formulation is inappropriate. In any combination treatment, the invention is not limited in the sequence of administration; compounds of the disclosed Formulas may be administered either prior to or after administration of the known anticancer or cytotoxic agent. For example, the cytotoxic activity of the cyclin-dependent kinase inhibitor flavopiridol is affected by the sequence of administration with anticancer agents. Cancer Research, (1997) 57, 3375. Such techniques are within the skills of persons skilled in the art as well as attending physicians.

Any of the aforementioned methods may be augmented by administration of fluids (such as water), loop diuretics, one or more adjunctive active agents, such as a chemotherapeutic or antineoplastic agent, such as leucovorin and fluorouracil, or an adjunctive chemotherapeutic agent (such as filgrastim and erythropoietin), or any combination of the foregoing.

Yet another embodiment is a method for administering a compound of the instant invention to a subject (e.g., a human) in need thereof by administering to the subject the pharmaceutical formulation of the present invention.

Yet another embodiment is a method of preparing a pharmaceutical formulation of the present invention by mixing at least one pharmaceutically acceptable compound of the present invention, and, optionally, one or more pharmaceutically acceptable additives or excipients.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

The compositions and formulations of the invention can be administered as sterile compositions and sterile formulations. Sterile pharmaceutical formulations are compounded or manufactured according to pharmaceutical-grade sterilization standards (e.g., United States Pharmacopeia Chapters 797, 1072, and 1211; California Business & Professions Code 4127.7; 16 California Code of Regulations 1751, 21 Code of Federal Regulations 21, or ex-U.S. counterparts to such regulations) known to those of skill in the art.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

The compound can be administered orally or intravenously.

The pharmaceutical preparation can be in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, for example from about 1 mg to about 500 mg, in particular from about 1 mg to about 250 mg, or from about 1 mg to about 25 mg, according to the particular application.

The actual dosage employed may be varied depending upon the requirements of the patient and the severity of the condition being treated Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Schemes and Examples

Exemplary, non-limiting, chemical entities and methods useful in preparing compounds of the invention will now be described by reference to illustrative synthetic schemes for their general preparation below and the specific examples that follow. Those skilled in the art will appreciate that other synthetic routes may be used to synthesize the compounds according to the invention. Although specific starting materials and reagents are depicted and discussed herein, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Each of the reactions depicted in the reaction schemes is preferably run at a temperature from about 0° C. to the reflux temperature of the solvent used. Unless otherwise specified, the variables shown in the schemes below are as defined above in reference to Formula I.

Compounds according to the invention may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Sigma-Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-23, Wiley, N.Y. (1967-2006 ed.), or Beilsteins Handbuch der organischen Chemie, 4, Aufl. ed. Springer-Verlag, Berlin, including supplements (also available via the Beilstein online database).

Synthetic chemistry transformations and protecting group methodologies (protection and deprotection) useful in synthesizing compounds according to the invention and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, 3rd Ed., John Wiley and Sons (1999); and L. Paquette, ed., Encyclopedia of Reagents for Organic Synthesis, John Wiley and Sons (1995) and subsequent editions thereof. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenyl-methyleneoxycarbonyl (Fmoc). The need for such protection is readily determined by one skilled in the art.

Compounds according to the invention may be prepared singly or as compound libraries comprising, for example, at least two, or 5 to 1,000 compounds, or 10 to 100 compounds. Libraries of compounds of Formula I may be prepared by a combinatorial "split and mix" approach or by multiple parallel syntheses using either solution phase or solid phase chemistry, by procedures known to those skilled in the art. Thus, according to a further aspect of the invention there is provided a compound library comprising at least two compounds of Formula I, or pharmaceutically acceptable salts thereof.

In the methods of preparing compounds according to the invention, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., J. Chromatogr. 1975, 113(3), 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, a-methyl-b-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. L and Wilen, S. "Stereochemistry of Organic Compounds," John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, a-methoxy-a-(trifluoromethyl)phenyl acetate of the racemic mixture and analyzing the $^1$H NMR spectrum for the presence of the two atropisomeric enantiomers or diastereomers (Jacob, et al. J. Org. Chem. 1982, 47, 4165). Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, *J. Chromatogr.*, 1990) 513:375-378). Enriched or purified enantiomers can be distinguished by methods used to distinguish other chiral molecules with asymmetric carbon atoms, such as optical rotation and circular dichroism.

Abbreviations and acronyms used in the following Schemes and elsewhere herein are defined as follows:

CDCl₃ deuterated chloroform
CD₃OD deuterated methanol
δ chemical shift (ppm)
DCM dichloromethane
DMF N,N-dimethylformamide
DMSO dimethylsulfoxide
DMSO-d₆ deuterated dimethylsulfoxide
EDCI  1-(3-dimethylaminopropyl)-3-ethylcarbodiimide hydrochloride
ELSD Evaporative Light Scattering Detector
ESI electrospray ionization
EtOH ethanol
HATU O-(7-Azabenzotriazol-1-yl)-N,N,N'N'-tetramethyl uronium hexafluorophosphate
h hour(s)
¹H NMR proton nuclear magnetic resonance
HOBt 1H-benzo[d][1,2,3]triazol-1-ol hydrate
HPLC high pressure liquid chromatography
LC/MS liquid chromatography/mass spectrometry
MeOH methanol
min minutes
MHz megahertz
NMP N-methylpyrrolidinone
PDA photo diode array detector
rt room temperature
RT retention time
TFA trifluoroacetic acid
THF tetrahydrofuran
TLC thin layer chromatography Exemplary general reaction schemes that are useful in preparing compounds of the invention are described below.

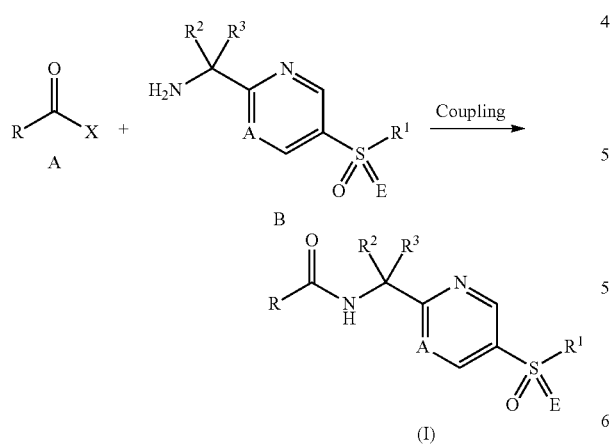

Compounds of Formula I may be prepared as shown above in Scheme A. Compounds of Formula A, in which X is, for example, OH, chloro, or bromo, are reacted with amines B to produce compounds of Formula I Where X is OH, coupling reactions may occur in the presence of a coupling reagent such as EDCI, HATU, or HOBt, and a base (e.g., K₂CO₃, Cs₂CO₃, trialkylamine, sodium or potassium alkoxide) in an inert solvent such as dichloromethane, N,N-dialkylformamide (such as DMF), N,N-dialkylacetamide, dialkylethers, cyclic ethers, DMSO, or NMP, or a mixture thereof, at temperatures ranging from −78° C. to 200° C. Such coupling reactions between amines and acids are well-known in the art. Alternatively, compounds A where X is bromo or chloro may be reacted with amines B in the presence of a suitable base, such as triethylamine, K₂CO₃, or Cs₂CO₃, to form compounds of Formula I.

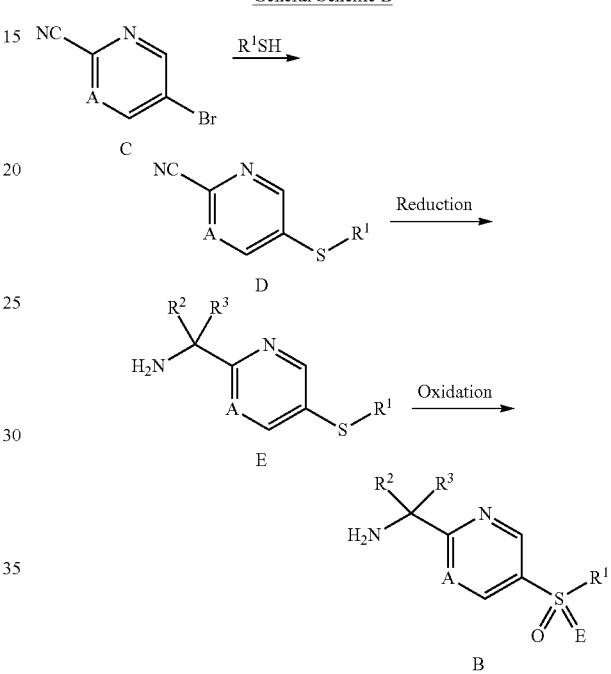

Amines B, in which R² and R³ are both H, may be prepared according to General Scheme B. Cyano-bromo pyridines and pyrimidines of formula C are commercially available or may be prepared by reacting the analogous 2-chloro compound with potassium cyanide. Compounds C are reacted with suitably substituted thiols R¹—SH in the presence of a base such as K₂CO₃ or Cs₂CO₃ in a solvent such as DMSO, DMF, or NMP, preferably at elevated temperature, to form thioethers D. The nitrile group of compounds D is then reduced under hydrogenation conditions using a hydrogen source such as hydrogen gas or the like, in the presence of a suitable metal catalyst such as Raney nickel, in a solvent such as methanol or ethanol, to form amines E. The thiol group of compounds E is then oxidized to the sulfone or sulfoxide oxidation state using a suitable oxidant such as m-chloroperbenzoic acid in a solvent such as chloroform.

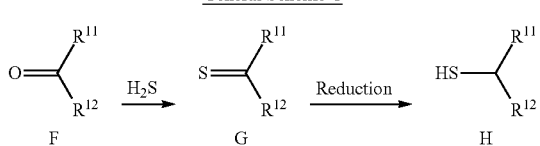

Certain thiols useful in preparing compounds of Formula I may be prepared according to General Scheme C. Ketones or aldehydes F, where $R^{11}$ and $R^{12}$ are chosen as needed to produce compounds of Formula I, are reacted with hydrogen sulfide to form the analogous thiones G, which are then reduced with a suitable reducing agent such as sodium borohydride, to produce thiols H. Thiols H may then be used in methods such as those shown in General Scheme B.

General Scheme D

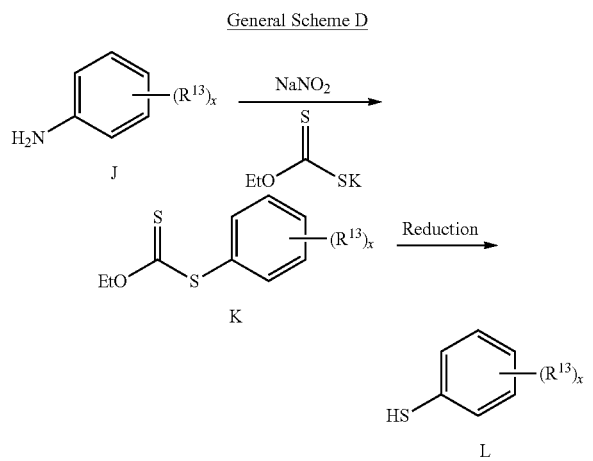

Aromatic thiols useful in preparing compounds of the invention may be prepared according to General Scheme D. Anilines J are reacted with sodium nitrite and a sulfur source such as a dithioate analog, to form compounds of formula K, which are then reduced with, for example, zinc, to form aromatic thiols L. Thiols L may then be used in methods such as those shown in General Scheme B.

General Scheme E

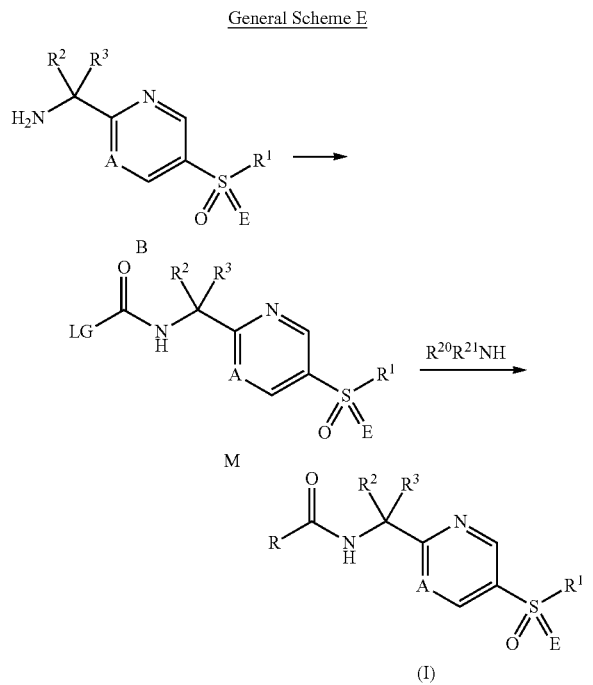

Certain compounds of Formula I, wherein the R group is connected to the carbonyl carbon via a nitrogen atom within the R group (forming a urea) may be prepared according to General Scheme E. Amines B are activated using methods known to one of skill in the art, wherein LG is a suitable leaving group such as an alkoxy or halo group, and the activated compounds M are then reacted, either in situ or in a separate reaction step, with a suitably substituted amine $R^{20}R^{21}NH$ in the presence of a base such as a trialkylamine, to form compounds of Formula I.

Those having skill in the art will recognize that the starting materials, reagents, and conditions described in the above general schemes may be varied and additional steps employed to produce compounds encompassed by the present inventions.

Methods of Chemical Analysis

Unless otherwise indicated, $^1H$ NMR spectra were recorded at ambient temperature using one of the following machines: Varian Unity Inova (400 MHz) spectrometer with a triple resonance 5 mm probe, Bruker Avance DRX400 (400 MHz) spectrometer with a triple resonance 5 mm probe, a Bruker Avance DPX 300 (300 MHz) equipped with a standard 5 mm dual frequency probe for detection of $^1H$ and $^{13}C$, a Bruker AVIII (400 MHz) using a BBI Broad Band Inverse 5 mm probe, or a Bruker AVIII (500 MHz) using a QNP (Quad Nucleus detect) 5 mm probe. Chemical shifts are expressed in ppm relative to an internal standard; tetramethylsilane (ppm=0.00). The following abbreviations have been used: br=broad signal, s=singlet, d=doublet, dd=double doublet, t=triplet, q=quartet, m=multiplet.

High Pressure Liquid Chromatography-Mass Spectrometry (LC/MS) experiments to determine retention times (RT) and associated mass ions (e.g., $[M+H]^+$, $[M+Na]^+$, $[M-H]^-$) were performed using one of the following methods:

Method A

Instrument: SHIMADZU LC/MS-2010EV
LC Parameters: Column: Shim-pack XR-ODS, 2.2 um, 3.0*50 mm; Mobile Phase A: Water/0.05% TFA; Mobile Phase B: Acetonitrile; Gradient: 5% to 100% B in 2.0 min, 100% B for 1.1 min, 100% to 5% B in 0.2 min, then stop; Flow Rate: 1.0 mL/min; Column Temperature: 40° C.; Detector: 254 nm and ELSD; Sample Preparation: 1 mg/mL in Methanol; Injection Volume: 1 µL.
MS Parameters: Interface: ESI (Positive); Interface Voltage: 4.5 kv; Heat Block: 250° C.; Nebulizing Gas: 1.50 L/min; Scan Range: 90-900 (m/z); Detector voltage: 1.7 kv.

Method B

Instrument: SHIMADZU LC/MS-2010EV
LC Parameters: Column: Waters XBridge C18, 3.0×50 mm, 3.5µ; Mobile Phase A: Water/5 mM Ammonium Acetate; Mobile Phase B: Methanol; Gradient: 10% to 100% B in 1.8 min, 100% B for 1.3 min, 100% to 10% B in 0.1 min, then stop; Flow Rate: 0.9 mL/min; Column Temperature: 40° C.; Detector: PDA and ELSD; Sample Preparation: 1 mg/mL in Methanol; Injection Volume: 1 µL.
MS Parameters: Interface: ESI (Positive & Negative); Interface Voltage: 4.0 kv; Heat Block: 250° C.; Nebulizing Gas: 1.50 L/min; Scan Range: 90-900 (m/z): Detector voltage: 1.5 kv.

Method C

Instrument: SHIMADZU LC/MS-2010EV
LC Parameters: Column: Shim-pack XR-ODS, 2.2 µm, 3.0*50 mm; Mobile Phase A: Water/0.05% TFA; Mobile Phase B: Acetonitrile/0.05% TFA; Gradient: 5% to 100% B in 2.0 min, 100% B for 1.1 min, 100% to 5% B in 0.2 min, then stop; Flow Rate: 1.0 mL/min; Column Temperature: 40° C.; Detector: 254 nm and ELSD; Sample Preparation: 1 mg/mL in Methanol; Injection Volume; 1 µL.

MS Parameters: Interface: ESI (Positive); Interface Voltage: 4.5 kv; Heat Block: 250° C.; Nebulizing Gas: 1.50 L/min; Scan Range: 90-900 (m/z); Detector voltage: 1.5 kv.

Method D

Instrument: SHIMADZU LC/MS-2010EV
LC Parameters: Column: Waters Xselect C18, 3.0×50 mm, 3.5 µm; Mobile Phase A: Water/0.1% formic acid; Mobile Phase B: Acetonitrile/0.05% formic acid; Gradient: 5% to 100% B in 2.0 min, 100% B for 1.2 min, 100% to 5% B in 0.1 min, then stop; Flow Rate: 0.9 mL/min; Column Temperature: 35° C.; Detector: 254 nm and ELSD; Sample Preparation: 1 mg/mL in Methanol; Injection Volume: 1 µL.

MS Parameters: Interface: ESI (Positive & Negative); Interface Voltage: 4.5 kv; Heat Block: 250° C.; Nebulizing Gas: 1.50 L/min; Scan Range: 90-900 (m/z); Detector voltage: 1.5 kv.

Method E

Instrument: SHIMADZU LC/MS-2010EV
LC Parameters: Column: Shim-pack XR-ODS, 3.0×50 mm, 2.2 µm; Mobile Phase A: Water/005% TFA; Mobile Phase B: Acetonitrile; Gradient: 5% to 100% B in 2.0 min, 100% B for 1 min, 100% to 5% B in 0.3 min, then stop; Flow Rate: 1.0 mL/min; Column Temperature: 40° C.; Detector: 254 nm and ELSD; Sample; Preparation: 1 mg/mL in Methanol; Injection Volume: 1 µL.

MS Parameters: Interface: ESI (Positive); Interface Voltage: 4.5 kv; Heat Block: 250° C.; Nebulizing Gas: 1.50 L/min; Scan Range: 90-900 (m/z); Detector voltage: 1.3 kv.

Method F

Instrument: SHIMADZU LC/MS-2020
LC Parameters: Column: Shim-pack XR-ODS, 2.2 um, 3.0*50 mm; Mobile Phase A Water/0.05% TFA; Mobile Phase B: Acetonitrile; Gradient: 5% B to 100% B for 2.0 min, 100% B for 1.2 min, 100% B to 5% in 0.1 min, then stop; Flow Rate: 1.0 mL/min; Column Temperature: 40° C.; Detector: UV and ELSD; Sample Preparation: 1 mg/mL in Methanol; Injection Volume: 1 µL.

MS Parameters: Interface: ESI (Positive); Interface Voltage: 4.5 kv; Heat Block: 250° C.; Nebulizing Gas: 1.50 L/min; Scan Range: 70-900 (m/z); Detector voltage: 1.1 kv.

Method G

Instrument: SHIMADZU LC/MS-2020EV
LC Parameters: Column: Shim-pack XR-ODS, 50 mm*3.0 mm, 2.2 um; Mobile Phase A: Water/0.05% TFA; Mobile Phase B: Acetonitrile; Gradient: 5% to 100% B in 2.1 min, 100% B for 0.8 min, 100% to 5% B in 0.1 min, then stop; Flow Rate: 1.0 mL/min; Column Temperature: 40° C.; Detector: 254 nm and ELSD; Sample Preparation: 1 mg/mL in Acetonitrile; Injection Volume: 1 µL.

MS Parameters: Interface: ESI (Positive); Interface Voltage: 4.5 kv; Heat Block: 250° C.; Nebulizing Gas: 1.50 L/min; Scan Range: 90-900 (m/z); Detector voltage: 1.05 kv.

Method H

Instrument: SHIMADZU LC/MS-2020
LC Parameters: Column: Shim-pack XR-ODS, 2.2 um, 3.0*50 mm; Mobile Phase A. Water/0.05% TFA; Mobile Phase B: Acetonitrile/0.05% TFA; Gradient: 5% to 100% B in 2.0 min, 100% B for 1.2 min, 100% to 5% B in 0.1 min, then stop; Flow Rate: 1.0 mL/min; Column Temperature: 40° C.; Detector: 254 nm and ELSD; Sample Preparation: 1 mg/mL in Methanol; Injection Volume: 1 µL.

MS Parameters: Interface: ESI (Positive); Interface Voltage: 4.5 kv; Heat Block: 250° C.; Nebulizing Gas: 1.50 L/min; Scan Range: 90-900 (m/z); Detector voltage: 1.1 kv.

Method I

Instrument: SHIMADZU LC/MS-2020
LC Parameters: Column: Shim-pack XR-ODS, 50*3.0 mm, 2.2 um; Mobile Phase A. Water/0.05% TFA; Mobile Phase B: Acetonitrile/0.05% TFA; Gradient: 5% B to 100% B for 2.0 min, 100% B for 1.2 min, 100% B to 5% B in 0.1 mm, then stop; Flow Rate: 1.0 mL/min; Column Temperature: 40° C.; Detector: 254 nm and ELSD; Sample Preparation: 1 mg/mL in Methanol; Injection Volume: 1 µL.

MS Parameters: Interface: ESI (Positive); Interface Voltage: 4.5 kv; Heat Block: 250° C.; Nebulizing Gas: 1.50 L/min; Scan Range: 70-900 (m/z); Detector voltage: 1.05 kv.

Method J

Instrument: SHIMADZU LC/MS-2020
LC Parameters: Column: Shim-pack XR-ODS, 3.0×50 mm, 2.2µ; Mobile Phase A: Water/0.05% TFA; Mobile Phase B: Acetonitrile; Gradient: 5% to 100% B in 2.0 min, 100% B for 1.2 min, 100% to 5% B in 0.2 min, then stop; Flow Rate: 1.0 mL/min; Column Temperature: 40° C.; Detector: 254 nm and ELSD; Sample Preparation: 1 mg/mL in Acetonitrile; Injection Volume: 1 µL.

MS Parameters: Interface: ESI (Positive); Interface Voltage: 4.5 kv; Heat Block: 200° C.; Nebulizing Gas: 1.50 L/min; Scan Range: 90-900 (m/z); Detector voltage: 1.05 kv.

Method K

Instrument: SHIMADZU LC/MS-2020
LC Parameters: Column: Gemini-NX 3u C18 110A; Mobile Phase A: Water/0.04% Ammonia; Mobile Phase B: Acetonitrile; Gradient: 5% to 100% B in 2.0 min, 100% B for 1.1 min, 100% to 5% B in 0.1 min, then stop; Flow Rate: 1.0 mL/min; Column Temperature: 35° C.; Detector: 254 nm and ELSD; Sample Preparation: 1 mg/mL in Methanol; Injection Volume: 1 µL.

MS Parameters: Interface: ESI (Positive & Negative); Interface Voltage: 4.5 kv; Heat Block: 200° C.; Nebulizing Gas: 1.50 L/min; Scan Range: 90-900 (m/z): Detector voltage: 0.75 kv.

Method L

Instrument: SHIMADZU LC/MS-2020EV
LC Parameters: Column: Halo C18, 2.7 um, 3.0×50 mm; Mobile Phase A: Water/5 mM Ammonium Acetate; Mobile Phase B: Methanol; Gradient: 10% to 100% B in 1.8 min, 100% B for 1.2 min, 100% to 10% B in 0.1 min, then stop; Flow Rate: 0.9 mL/min; Column Temperature:

40° C.; Detector: PDA and ELSD; Sample Preparation: 1 mg/mL in Methanol; Injection Volume: 1 µL.

MS Parameters: Interface: ESI (Positive & Negative); Interface Voltage: 4.5 kv; Heat Block: 200° C.; Nebulizing Gas: 1.50 L/min; Scan Range: 90-900 (m/z); Detector voltage: 0.9 kv.

Method M

| Instrument | Berger SFC-MS |
|---|---|
| Mobile phase A | Carbon Dioxide |
| Mobile phase B | Methanol w/0.1% Ammonium Hydroxide |
| Column | Phenomenex Cellulose-1, 3 µm, 4.6*50 mm |
| Column temperature | 40° C. |
| LC gradient | 5-60% B in 1.8 min |
| LC Flowrate | 5 mL/min |
| UV wavelength | 254 nm |
| Mass Spectrometer | Waters Micromass ZQ |
| Ionization | ESI+ |

Method N

Instrument: SHIMADZU LC/MS-2020
LC Parameters: Column: Shim-pack XR-ODS, 2.2 um, 3.0*50 mm; Mobile Phase A: Water/0.05% TFA; Mobile Phase B: Acetonitrile; Gradient: 5% B to 100% B for 2.0 min, 100% B for 1.2 min, 100% B to 5% in 0.1 min, then stop; Flow Rate: 1.0 mL/min; Column Temperature: 40° C.; Detector: UV and ELSD; Sample Preparation: 1 mg/mL in Methanol; Injection Volume: 1 µL.
MS Parameters: Interface: ESI (Positive); Interface Voltage: 4.5 kv; Heat Block: 250° C.; Nebulizing Gas: 1.50 L/min; Scan Range: 70-900 (m/z); Detector voltage: 1.1 kv.

Method O

Instrument: SHIMADZU LC/MS-2020EV
LC Parameters: Column: Shim-pack XR-ODS, 2.2 um, 3.0*50 mm; Mobile Phase A: Water/0.05% TFA; Mobile Phase B: Acetonitrile/0.05% TFA; Gradient: 5% B to 100% B for 1.2 min, 100% B for 0.9 min, 100% B to 5% in 0.2 min, then stop; Flow Rate: 1.0 mL/min; Column Temperature: 40° C.; Detector: PDA and ELSD; Sample Preparation: 1 mg/mL in acetonitrile; Injection Volume: 1 L.
MS Parameters: Interface: ESI (Positive); Interface Voltage: tuning file: Heat Block: 250° C.; Nebulizing Gas: 1.50 L/min; Scan Range: 90-900 (m/z); Detector voltage: 1.1 kv.

Method P

Instrument: SHIMADZU UHPLCMS-2020EV (LC-30AD pump, binary solvent manager, SIL-30AC auto sampler, SPDM20A detector, Alltech 3300 ELSD detector)
LC Parameters: Column: Shim-pack XR-ODS, 1.6 um, 2.0*50 mm; Mobile Phase A: Water/0.1% formic acid; Mobile Phase B: Acetonitrile/0.05% formic acid; Gradient: 5% B to 100% B for 2.0 min, 100% B for 1.1 min, 100% B to 5% in 0.1 min, then stop; Flow Rate: 0.7 mL/min; Column Temperature: 40° C.; Detector: diode array detection (DAD) and ELSD; Injection Volume: 1 µL.
MS Parameters: Interface: ESI (Positive); Interface Voltage: 4.0 kv; Heat Block: 200° C.; Nebulizing Gas: 1.50 L/min; Scan Range: 90-900 (m/z); Detector voltage: 0.9 kv.

Method Q

Instrument: SHIMADZU LC/MS-2020EV
LC Parameters: Column: Shim-pack XR-ODS, 2.2 um, 3.0*50 mm; Mobile Phase A: Water/0.1% formic acid; Mobile Phase B: Acetonitrile/0.05% formic acid; Gradient: 5% B to 100% B for 2.0 min, 100% B for 1.1 min, 100% B to 5% in 0.1 min, then stop; Flow Rate: 1.0 mL/min; Column Temperature: 40° C.; Detector: PDA and ELSD; Sample Preparation: 1 mg/mL in acetonitrile; Injection Volume: 1 µL.
MS Parameters: Interface: ESI (Positive); Interface Voltage: tuning file: Heat Block: 250° C.; Nebulizing Gas: 1.50 L/min; Scan Range: 90-900 (m/z); Detector voltage: 0.9 kv.

Method R

Instrument: SHIMADZU LC/MS-2020
LC Parameters: Column: Shim-pack XR-ODS, 2.2 um, 3.0*50 mm; Mobile Phase A: Water/0.1% formic acid; Mobile Phase B: Acetonitrile/0.05% formic acid; Gradient: 5% B to 100% B for 2.0 min, 100% B for 1.2 min, 100% B to 5% in 0.2 min, then stop; Flow Rate: 1.0 mL/min; Column Temperature: 40° C.; Detector UV and ELSD; Sample Preparation: 1 mg/mL in acetonitrile; Injection Volume: 1 µL.
MS Parameters: Interface: ESI (Positive); Interface Voltage: 4.5 kv; Heat Block: 200° C.; Nebulizing Gas: 1.50 L/min; Scan Range: 90-900 (m/z); Detector voltage: 0.95 kv.

The following examples illustrate the preparation of representative compounds of the invention. Unless otherwise specified, all reagents and solvents were of standard commercial grade and were used without further purification.

I. PREPARATION OF INTERMEDIATES

Intermediate 1

Furo[2,3-c]pyridine-2-carboxylic acid

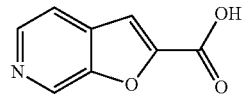 [SMILES: O=C(O)c1cc2ccncc2o1]

Step 1. Ethyl 3-hydroxyisonicotinate. A solution of 3-hydroxyisonicotinic acid (495 g, 3.56 mol) in EtOH (7 L) and concentrated $H_2SO_4$ (250 mL) was heated under reflux for 72 h and then cooled to rt and concentrated under reduced pressure to remove the solvent. The residue was dissolved in water (3 L) and the pH was adjusted to 4 by addition of saturated aqueous $NaHCO_3$ solution. The resulting precipitate was removed by filtration and the filtrate was extracted with DCM (2 L×3). The combined organic phase was washed with brine, dried over anhydrous $Na_2SO_4$, and then concentrated under reduced pressure to give ethyl 3-hydroxyisonicotinate (414 g, 70%) as yellow oil.

Step 2. Ethyl 3-(2-ethoxy-2-oxoethoxy)isonicotinate. To a solution of triphenylphosphine (780 g, 2.97 mol) in THF (6 L) at −10° C. was added dropwise diisopropyl azodicarboxylate (600 mL, 2.97 mol). The reaction mixture was stirred at −10° C. for 30 min and then ethyl 3-hydroxyisonicotinate (414 g, 2.48 mol) in THF (1 L) solution was added dropwise. The resulting mixture was stirred at rt for 16 h and then concentrated under reduced pressure. The residue was partitioned between ethyl acetate (4 L) and 1 N HCl (2 L) The aqueous layer was separated and the organic phase was extracted by 1 N HCl (1 L×2). The combined aqueous layers were slowly adjusted to pH 8 by addition of solid NaHCO$_3$ and then extracted with ethyl acetate (2 L×2). The combined organic layers were dried over anhydrous Na$_2$SO$_4$ and then concentrated under reduced pressure to give the title compound (380 g, 61%) as a brown oil.

Step 3. Ethyl 3-hydroxyfuro[2,3-c]pyridine-2-carboxylate. To a suspension of NaH (72 g, 1.8 mol, 60% suspension in mineral oil) in anhydrous THF (2 L) at 0° C. was added dropwise a solution of ethyl 3-(2-ethoxy-2-oxoethoxy)isonicotinate (380 g, 1.5 mol) in THF (I L) under argon. The reaction mixture was stirred at rt for 16 h and then carefully quenched with ice water (1 L). The resulting mixture was concentrated to a volume of 1.2 L and then diluted with saturated aqueous NaHCO$_3$ solution (2.5 L), and stirred for an additional 30 min. The precipitated solid was collected by filtration and washed with ethyl acetate (1 L) The filtrate was washed with ethyl acetate (1 L×2) and the aqueous layer was combined with the solid and carefully acidified to a pH of 5 with acetic acid. The resulting solid was collected by filtration and dried under vacuum to give the title compound (210 g, 68%) as a yellow solid.

Step 4. Ethyl 3-(((trifluoromethyl)sulfonyl)oxy)furo[2,3-c]pyridine-2-carboxylate. To a solution of ethyl 3-hydroxyfuro[2,3-c]pyridine-2-carboxylate (210 g, 1.01 mol) and pyridine (107 mL, 1.3 mol) in anhydrous DCM (3 L) at 0° C. was added dropwise triflic anhydride (203 g, 1.2 mol). The reaction mixture was stirred at rt for 16 h and then quenched with ice water (1 L). The aqueous layer was extracted with DCM (1 L×2) and the combined organic layer was dried over anhydrous Na$_2$SO$_4$ and then concentrated under reduced pressure. The residue was purified by silica gel column chromatography eluting with 10% ethyl acetate/ petroleum ether to give the title compound (298 g, 87%) as a white solid.

Step 5. Ethyl furo[2,3-c]pyridine-2-carboxylate. To a solution of ethyl 3-(((trifluoromethyl)sulfonyl)oxy)furo[2,3-c]pyridine-2-carboxylate (298 g, 0.88 mol) in ethanol (3 L) was added 10% Pd/C (30 g) and triethylamine (281 mL, 2.02 mol). The reaction mixture was stirred under an atmosphere of hydrogen for 16 h and then filtered through a pad of diatomaceous earth. The filtrate was concentrated under reduced pressure and the residue was purified by silica gel column chromatography eluting with 20% ethyl acetate/ petroleum ether to give the title compound (158 g, 94%) as a pale yellow solid.

Step 6. To a solution of ethyl furo[2,3-c]pyridine-2-carboxylate (158 g, 0.83 mol) in water:THF:MeOH (1:1:1, 2.4 L) was added KOH (139 g, 2.49 mol). The reaction mixture was stirred at rt for 16 h and then concentrated to a volume of 750 mL. To this residue was added acetic acid until pH~4. The resulting solids were collected by filtration, washed with water (300 mL×2) and dried in a vacuum oven overnight to give the title compound (101 g, 75%) as a pale yellow solid. $^1$H NMR (400 MHz, DMSO-d$_6$) δ 9.07 (s, 1H), 8.47 (d, J=5.6 Hz, 1H), 7.80 (d, J=5.2 Hz, 1H), 7.61 (s, 1H). MS (ESI+) m/z: 164 [M+H]$^+$.

Intermediate 2

Imidazo[1,2-a]pyridine-6-carboxylic acid

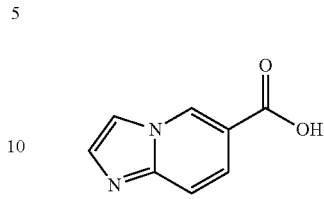

Step 1. Imidazo[1,2-a]pyridine-6-carboxylic acid hydrochloride salt. A mixture of 2-chloroacetaldehyde (277 g, 40%) and 6-aminonicotinic acid (150 g) in EtOH (330 mL) was heated to reflux and stirred for 8 h. After cooling, a solid precipitated and was isolated by vacuum filtration, then washed with ethanol and dried under vacuum to give the title compound as a light yellow solid (1.78 g, 82%).

Step 2. Imidazo[1,2-a]pyridine-6-carboxylic acid hydrochloride salt (170 g) was diluted with water (600 mL) and heated until a clear solution resulted, then an aqueous solution of NaOH (2 M) was added slowly to adjust the pH=5-6. The reaction mixture was cooled to 0° C. using an ice-H$_2$O bath. The resulting precipitate was collected by vacuum filtration, then washed with ethanol and dried under vacuum to give the title product (107.2 g, 77%) as a light yellow powder. $^1$H NMR (400 MHz, DMSO-d$_6$) δ 13.76-12.82 (br, 1H), 9.28 (s, 1H), 8.10 (s, 1H), 7.68 (s, 1H), 7.64-7.56 (m, 2H). MS (ESI+) m/z: 163 [M+H]$^-$.

Intermediate 3

Imidazo[1,2-a]pyrimidine-6-carboxylic acid

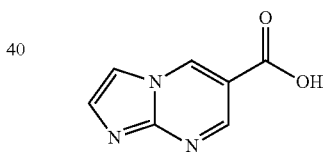

Step 1. Sodium (Z)-2-(dimethoxymethyl)-3-methoxy-3-oxoprop-en-1-olate. Methyl 3,3-dimethoxypropanoate (100 g, 675 mmol) and methyl formate (81 g, 1350 mmol) were dissolved in anhydrous THF (450 mL). Sodium hydride (60% dispersion; 32.4 g, 810 mmol, 1.2 eq.) was then added slowly in portions at 0° C. The reaction mixture was stirred at rt for 1 h, then was heated at 50° C. for 3 h. During this period, H$_2$ evolution was observed. After cooling to rt, the solvent was then removed under reduced pressure to give the crude product which was directly used in the next step without further purification.

Step 2. Methyl 2-aminopyrimidine-5-carboxylate. The crude enolate from step 1 was dissolved in DMF (200 mL), and guanidine hydrochloride (64 g, 670 mmol) was added. The mixture was heated at 100° C. under N$_2$ for 3 h. After cooling to rt, water was added and the mixture was cooled with an ice-water bath. The resulting precipitate was collected by vacuum filtration and dried under vacuum to give the desired product (63 g, 61% yield for 2 steps).

Step 3. Methyl imidazo[1,2-a]pyrimidine-6-carboxylate. To a mixture of 2-bromo-1,1-diethoxyethane (100.6 g, 0.51 mol) and methyl 2-aminopyrimidine-5-carboxylate (63 g, 0.41 mol) in ethanol (300 mL) was added concentrated HBr (40%) (55 g). The reaction mixture was heated to reflux for 3 h under $N_2$. After cooling to rt, the mixture was further cooled with an ice-water bath. The resulting precipitate was collected by vacuum filtration and dried under vacuum overnight to give the desired product (92 g, 87%).

Step 4. Into a round bottom flask containing methyl imidazo[1,2-a]pyrimidine-6-carboxylate (92 g, 356.5 mmol), was added water (200 mL). NaOH (6 N in $H_2O$, 2.5 eq.) was then added dropwise with stirring at rt. After stirring at rt for 1 h, the mixture was cooled with an ice-water bath and concentrated HCl was added (pH=5-6). The resulting mixture was concentrated under reduced pressure to approximately 150 mL (¾ volume) and cooled with an ice-water bath. The resulting precipitate was collected by vacuum filtration, washed with cold water (50 mL) and dried to give the title compound as an off-white solid (46 g, 79%). $^1$H NMR (DMSO-$d_6$, 400 MHz) δ 9.29 (d, J=2.0 Hz, 1H), 8.89 (d, J=2.0 Hz, 1H), 7.94 (s, 1H), 7.70 (s, 1H). MS (m/z, ES$^-$): 164.1 [M+H]$^+$, 186.1 [M+Na]$^+$.

Intermediate 4

1H-Pyrazolo[3,4-b]pyridine-5-carboxylic acid

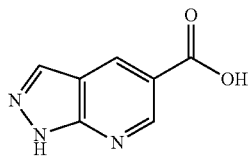 [SMILES: O=C(O)c1cnc2[nH]ncc2c1]

Step 1. 1-(4-Methoxybenzyl)-1H-pyrazol-5-amine. To a solution of acrylonitrile (30 mL, 455 mmol) in THF (250 mL), $NH_2NH_2.H_2O$ (23.19 mL, 478 mmol) was added drop-wise at 0° C. After addition was complete, the mixture was stirred at rt for 2 h, then 4-methoxybenzaldehyde (55.4 mL, 455 mmol) was added drop-wise. The mixture was stirred at rt overnight, then at reflux for 2 h. After cooling to rt the mixture was quenched by addition of 300 mL of ice water. The mixture was extracted with ethyl acetate (3×), then the combined organic layers were extracted with 1 N HCl. The aqueous layer was neutralized with aqueous 10 N NaOH solution, then extracted with ethyl acetate. The organic layer was washed with $H_2O$ and brine, then dried over $Na_2SO_4$. Filtration, concentration, and recrystrallization with $Et_2O$ gave the target compound as a white solid (50 g, 60%).

Step 2. Ethyl 4-hydroxy-(4-methoxybenzyl)-1H-pyrazolo[3,4-b]pyridine-5-carboxylate. 1-(4-Methoxybenzyl)-1H-pyrazol-5-amine (3.94 g, 19.39 mmol), followed by diethyl 2-(ethoxymethylene)malonate (4 mL, 20 mmol) was added to a 200 mL round bottom flask fitted with a distillation head to remove ethanol. The mixture was heated to 130° C. for 45 min, then 10 mL of diphenyl ether was added and the temperature was raised to 240° C. for 2 h. The reaction mixture was then cooled to rt and $Et_2O$ (100 mL) was added. The resulting precipitate was collected by vacuum filtration and dried under vacuum to afford the target compound as a white solid (4 g, 62%).

Step 3. Ethyl 4-chloro-1-(4-methoxybenzyl)-1H-pyrazolo[3,4-b]pyridine-5-carboxylate. $POCl_3$ (10 mL) was added to ethyl 4-hydroxy-1-(4-methoxybenzyl)-1H-pyrazolo[3,4-b]pyridine-5-carboxylate (7.5 g, 19.39 mmol). The mixture was stirred at 60° C. for 3 h. The mixture was poured into ice water and the resulting precipitate was collected by vacuum filtration and dried under vacuum to afford the target compound a light yellow solid (6.4 g, 80%).

Step 4. Ethyl 1-(4-methoxybenzyl)-1H-pyrazolo[3,4-b]pyridine-5-carboxylate. To a solution of ethyl 4-chloro-1-(4-methoxybenzyl)-1H-pyrazolo[3,4-b]pyridine-5-carboxylate (5.9 g, 17 mmol) in THF (50 mL), triethylamine (1.7 g, 17 mmol), followed by Pd(OH)$_2$/C (300 mg) was added. The mixture was stirred at rt for 3 h under $H_2$. The mixture was filtered and concentrated. The residue was dissolved in ethyl acetate and washed with saturated aqueous $NaHCO_3$ solution and brine, then dried over $Na_2SO_4$. Filtration and concentration gave target compound as a light gray solid (5.3 g, 100%).

Step 5. Ethyl 1-(4-methoxybenzyl)-1H-pyrazolo[3,4-b]pyridine-5-carboxylate (4.4 g, 14 mmol) was dissolved in TFA (158 mL) and heated to 80° C. The mixture was stirred at 80° C. for 4 h, then was concentrated to dryness. The residue was poured into ice water, then aqueous NaOH solution (2 M) was added until the pH was approximately 14. The solid formed was removed by filtration, and the aqueous layer was washed with ethyl acetate. To the aqueous layer was added concentrated HCl was added until the pH was approximately 7. The resulting precipitate was collected by vacuum filtration and dried under vacuum to afford the title compound as a white solid (2.1 g, 80%). $^1$H NMR (400 MHz, DMSO-$d_6$) δ 14.38-13.62 (br, 1H), 9.07 (d, J=1.6 Hz, 1H), 8.81 (d, J=1.6 Hz, 1H), 8.32 (s, 1H). MS (m/z, ESI+): 164 [M+H]$^+$.

Intermediate 5

1H-Pyrrolo[3,2-c]pyridine-2-carboxylic acid

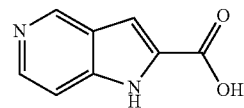 [SMILES: O=C(O)c1cc2cnccc2[nH]1]

Step 1. 3-Iodopyridin-4-amine. To a 2 L 3-necked flask was added a solution of 38 mL of concentrated sulfuric acid in 200 mL water. The solution was cooled with an ice-water bath, then 4-aminopyridine (200 g, 2.12 mol) and acetic acid (700 mL) were added in batches. The mixture was then heated to reflux. Iodine (189 g, 0.745 mol) and periodic acid dihydrate (97 g, 0.424 mol) were both equally divided into four parts. One batch of iodine was added and then one batch of periodic acid dihydrate was added 15 min later. After 30 min, a new batch of iodine and periodic acid dihydrate were added in the same way. When all four batches of iodine and periodic acid dehydrate were added, the mixture was kept refluxing for an additional 3 h, After cooling to rt the reaction mixture was slowly poured into water while stirring, then a 40% solution of NaOH in water was added until pH>9 $Na_2SO_3$ was added to destroy the unreacted iodine. After cooling to rt, a filtration was performed. The collected solid was further purified by recrystallization in chloroform to give the desired product (184 g, 39%).

Step 2. To a 2 L 3-necked flask was added DMF (700 mL), triethylene diamine (168 g, 1.5 mol), and 4-amino-3-iodopyridine (24, 110 g, 0.5 mol). The mixture was cooled with an ice-water bath and pyruvic acid (132 g, 1.5 mol) was slowly added, followed by palladium acetate (4.49 g, 0.02 mol). Under nitrogen atmosphere, the mixture was heated to 115° C. The reaction generated effervescence. The reaction mixture was kept at 115-120° C. for 11 h. The mixture was concentrated under reduced pressure. The residue was poured into water (500 mL), and concentrated HCl was added to adjust pH to <1. The mixture was cooled by adding ice and a filtration was performed. The cake thus obtained was a brownish black solid.

The above cake was added into 500 mL of water. Concentrated HCl was added (to ensure complete protonation) followed by 5 g of active carbon. The mixture was heated to reflux for 20 min and then filtration was performed while hot. The solid was discarded and the hot filtrate was placed in a refrigerator to allow the HCl salt of the desired product to precipitate. Upon cooling, filtration was performed which afforded a dark brown solid with a wet weight of 48 g as the HCl salt of the desired product.

The solid was then added to 250 mL of water and the mixture was heated until a clear solution resulted. Solid NaOH was slowly added to adjust pH to 5-6, then active carbon and an additional 500 mL of water was added. The mixture was heated to reflux for 30 min, then filtration was performed while hot. The resulting cake was added to 750 mL of water, heated to reflux, and filtered again. The cake thus obtained was discarded. The two batches of filtrate were combined and cooled in a refrigerator. The resulting precipitate was collected by vacuum filtration, then washed with ethanol to give the title compound as a slightly yellow solid (25 g, 31%). MS (m/z, ES−): 161.1 [M−1], 323.1 [2M−1]. $^1$H NMR (DMSO-$d_6$, 400 MHz) δ 12.20 (br s, 1H), 8.97 (s, 1H), 8.27 (d, J=5.6 Hz, 1H), 7.41 (d, J=6.0 Hz, 1H), 7.23 (s, 1H).

Intermediate 6

Thieno[2,3-c]pyridine-2-carboxylic acid

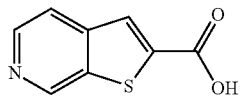 [SMILES: O=C(O)c1cc2ccncc2s1]

Step 1. 3,5-Dibromoisonicotinaldehyde. Lithium diisopropylamide (507 mmol, 1.2 eq.) was added to 200 mL of dry THF at −78° C. under $N_2$. A solution of 3,5-dibromopyridine (100 g, 424 mmol) in 537 mL of dry THF was then added drop-wise over 30 min. The reaction mixture was stirred at −78° C. for 1 h. Ethyl formate (34.4 g, 465 mmol) was added drop-wise and stirred at −78° C. for 30 min, then the reaction mixture was poured into ice-cold saturated aqueous $NaHCO_3$ solution. The mixture was extracted with 3×500 mL of EtOAc. The organic layer was concentrated to provide a brown solid, which was filtered through a pad of silica gel (eluted with dichloromethane) to give the title compound as a yellow powder (70 g, 63%).

Step 2: Methyl 4-bromothieno[2,3-c]pyridine-2-carboxylate. 3,5-Dibromoisonicotinaldehyde (80 g, 303 mmol), followed by cesium carbonate (98 g, 302 mmol) was added to a 2 L round bottom flask containing THF (1.3 L) under $N_2$. Methyl mercaptoacetate (32 g, 302 mmol) was added and the mixture was heated at 60° C. overnight. After cooling to rt, ethyl acetate was added and the organic layer was washed with water, aqueous saturated $NaHCO_3$ solution, and brine, then dried over $Na_2SO_4$, and filtered to give a white solid. The crude product was purified by recrystallization from ethyl acetate to give the desired product (60 g, 73%).

Step 3. Methyl thieno[2,3-c]pyridine-2-carboxylate. Methyl 4-bromothieno[2,3-c]pyridine-2-carboxylate (115 g, 423 mmol), TEA (42.7 g, 423 mmol), THF (1.5 L), and MeOH (500 mL) were mixed and degassed. Under nitrogen, palladium on carbon (10%, 14.7 g, 13.9 mmol) was added. The mixture was hydrogenated with a Parr apparatus at 45 psi $H_2$ for 3 days. The catalyst was filtered off and the filtrate was concentrated to give the desired compound as a white solid (65 g, 80%).

Step 4. A three necked 2 L round bottom flask equipped with an overhead stirrer and thermocouple was charged with methyl thieno[2,3-c]pyridine-2-carboxylate (130 g, 674 mmol) and water (650 mL). Aqueous sodium hydroxide solution (10 N) was added with stirring at 20° C. Over the next 20 min, the temperature rose to 25° C. and the solid dissolved. After 1 h, concentrated HCl (1.5 eq.) was slowly added to the reaction mixture with rapid stirring, generating a thick slurry. After stirring for 1 h, the slurry was filtered and the solid was dried under vacuum to give the title compound as a white solid (105.5 g, 88%) MS (m/z, ES−): 178.0 [M−1]. $^1$H-NMR (DMSO-$d_6$, 400 MHz) δ 12.24 (br s, 1H), 8.97 (s, 1H), 8.27 (d, J=6.0 Hz, 1H), 7.40 (d, J=5.6 Hz, 1H), 7.23 (s, 1H).

Intermediate 7

Imidazo[1,2-b]pyridazine-6-carboxylic acid

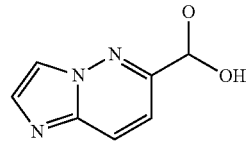 [SMILES: OC(O)c1ccc2nccn2n1]

Step 1. 6-Chloro-imidazo[1,2-b]pyridazine. A solution of 6-chloro-1,2-diazinan-3-amine (10 g, 73.75 mmol, 1.00 equiv), 2-bromo-1,1-dimethoxyethane (50 g, 295.83 mmol, 4.01 equiv), and HBr (40%, 45 mL) in ethanol (100 mL) was stirred overnight at 90° C. The majority of the ethanol was removed under reduced pressure then the pH value of the solution was adjusted to 10 with 5% aqueous potassium carbonate solution. The resulting mixture was extracted with 6×500 mL of ethyl acetate. The combined organic layers were dried over anhydrous sodium sulfate and concentrated under vacuum. The residue was purified on a silica gel column eluted with ethyl acetate/petroleum ether (1/2~1/1) to give 6.5 g (57%) of the title compound as a yellow solid. $^1$H NMR (300 MHz, $CDCl_3$) δ 7.95 (s, 1H), 7.91 (s, 1H), 7.80 (s, 1H), 7.05 (d, J=9.3 Hz, 1H).

Step 2. Imidazo[1,2-b]pyridazine-6-carboxylic acid methyl ester. A mixture of 6-chloro-imidazo[1,2-b]pyridazine (200 mg, 1.30 mmol, 1.00 equiv), bis(triphenylphosphine)palladium(II) dichloride (200 mg, 0.28 mmol, 0.22 equiv), and triethylamine (0.5 mL) in methanol (4 mL) was stirred under carbon monoxide (10 atm) in a 50-mL pressure reactor overnight at 110° C. The solid material was removed by filtration. The filtrate was concentrated under vacuum and the residue was purified on a silica gel column eluted with ethyl acetate/petroleum ether (1/1) to give 100 mg (43%) of the title compound as a yellow solid. $^1$H NMR (300 MHz, $CDCl_3$) δ 8.16 (s, 1H), 8.08 (d, J=9.6 Hz, 1H), 7.94 (s, 1H), 7.77 (d, J=9.6 Hz, 1H), 4.09 (s, 3H).

Step 3. A mixture of imidazo[1,2-b]pyridazine-6-carboxylic acid methyl ester (900 mg, 5.08 mmol, 1.00 equiv) and 5% aqueous sodium hydroxide solution (15 mL, 3.75 equiv) in THF (3 mL) was stirred overnight at rt. The pH value of the solution was adjusted to 2 with 1 M HCl. The resulting mixture was concentrated under vacuum to give 3 g of crude title product as a yellow solid. The crude product was used without further purification. LC/MS (Method A, ESI): RT=0.43 min, m/z=164.0 [M+H]+.

Intermediate 8

Pyrazolo[1,5-a]pyridine-5-carboxylic acid

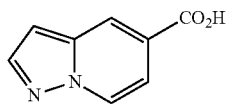

Step 1. 1-Amino-4-methoxypyridinium iodide. A solution of aminooxysulfonic acid (11.4 g, 100.80 mmol, 0.50 equiv) and 4-methoxypyridine (22 g, 201.60 mmol, 1.00 equiv) in water (200 mL) was stirred under nitrogen for 0.5 h at 90° C. Potassium carbonate (14 g, 101.30 mmol, 0.50 equiv) was added at rt. The resulting mixture was concentrated under vacuum then ethanol (150 mL) was added to dissolve the residue. The insoluble material was removed by filtration. The filtrate was cooled to −20° C. and then hydroiodic acid (16 g, 40%) was added. The resulting solution was stirred for 1 h at −20° C. The precipitated product was collected by filtration and washed with cold ethanol to give 9.3 g (46%) of the title compound as a white solid. TLC: 1:5 MeOH/DCM, $R_f$=0.02.

Step 2. 5-Methoxy-pyrazolo[1,5-a]pyridine-3-carboxylic acid methyl ester. A mixture of 1-amino-4-methoxypyridinium iodide (6 g, 23.80 mmol, 1.00 equiv), potassium carbonate (5 g, 36.18 mmol, 1.50 equiv), and methyl propiolate (2 g, 23.79 mmol, 1.00 equiv) in DMF (50 mL) was stirred under nitrogen for 4 h at rt. After the reaction completed, the mixture was concentrated under vacuum. The residue was dissolved in 150 mL of dichloromethane and then washed with 1×20 mL of saturated aqueous sodium bicarbonate solution. The organic layer was concentrated under vacuum and the residue was purified on a silica gel column eluted with ethyl acetate/hexane (1:3) to give 1.5 g (31%) of title product as a solid. LC/MS (Method D, ESI): RT=1.30 min, m/z=207.0 [M+H]+.

Step 3. Pyrazolo[1,5-a]pyridin-5-ol. A mixture of methyl 5-methoxypyrazolo[1,5-a]pyridine-3-carboxylate (100 mg, 0.48 mmol, 1.00 equiv) in 40% HBr (5 mL) was stirred for 16 h at 100° C. The reaction mixture was cooled to rt and the pH value of the solution was adjusted to 8 with 5 M potassium hydroxide solution. The resulting solution was extracted with 2×50 mL of ether. The organic layers were combined and concentrated under vacuum. The residue was purified on a silica gel column eluted with ethyl acetate/petroleum ether (1:3 to 1:1) to yield 20 mg (31%) of the title compound as a white solid. LC/MS (Method D, ESI): RT=0.41 min, m/z=135.0 [M+H]−.

Step 4. Trifluoro-methanesulfonic acid pyrazolo[1,5-a]pyridin-5-yl ester. A mixture of pyrazolo[1,5-a]pyridin-5-ol (300 mg, 2.24 mmol, 1.00 equiv) and trifluoromethanesulfonic anhydride (0.5 mL) in pyridine (5 mL) was stirred for 10 h at rt. The resulting mixture was concentrated under vacuum and the residue was dissolved in 100 mL of dichloromethane. The mixture was washed with 1×10 mL of sodium bicarbonate solution. The organic layer was dried over anhydrous sodium sulfate and concentrated under vacuum. The residue was purified on a silica gel column eluted with ethyl acetate/petroleum ether (1:3) to yield 200 mg (34%) of the title compound as a solid. LC/MS (Method B, ESI): RT=2.13 min, m/z=267.0 [M+H]+.

Step 5. Pyrazolo[1,5-a]pyridine-5-carboxylic acid methyl ester. A mixture of trifluoro-methanesulfonic acid pyrazolo[1,5-a]pyridin-5-yl ester (200 mg, 0.75 mmol, 1.00 equiv), triethylamine (227 mg, 2.24 mmol, 3.00 equiv), DMSO (98 mg, 1.25 mmol, 1.67 equiv), and bis(triphenylphosphine)palladium(II) dichloride (53 mg, 0.08 mmol, 0.10 equiv) in methanol (20 mL) was stirred under carbon monoxide (10 atm) for 16 h at 100° C. in a 50-mL pressure reactor. After the reaction completed, the reaction mixture was cooled to rt and the mixture was concentrated under vacuum. The residue was purified on a silica gel column eluted with ethyl acetate/petroleum ether (1:3) to afford 130 mg of the title compound as a solid. LC/MS (Method H, ESI): RT=1.36 min, m/z=177.0 [M+H]+.

Step 6. A mixture of pyrazolo[1,5-a]pyridine-5-carboxylic acid methyl ester (130 mg, 0.74 mmol, 1.00 equiv) and potassium hydroxide (1 g, 17.82 mmol, 24.15 equiv) in methanol (2 mL), THF (2 mL), and water (5 mL) was stirred for 12 h at rt. The reaction mixture was washed with 2×50 mL of ethyl acetate. The aqueous layer was collected and the pH value of the solution was adjusted to 6 with 1 N HCl. The solution was extracted with 5×50 mL of ethyl acetate. The combined organic layers were dried over anhydrous sodium sulfate and concentrated under vacuum to give 100 mg (84%) the title compound as a yellow solid. LC/MS (Method G, ESI): RT=1.32 m, in, m/z=163.0 [M+H]+.

Intermediate 9

1H-Pyrazolo[4,3-b]pyridine-6-carboxylic acid

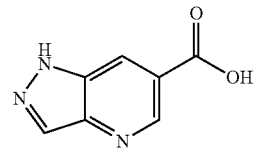 [SMILES: O=C(O)c1cnc2cn[nH]c2c1]

Step 1. 5-Bromo-2-methyl-pyridin-3-ylamine. To a stirred mixture of iron filings (5 g, 89.29 mmol, 3.88 equiv) and ammonium chloride (1 g, 18.70 mmol, 0.81 equiv) in ethanol (66 mL) and water (33 mL) was added a solution of 5-bromo-2-methyl-3-nitropyridine (5 g, 23.04 mmol, 1.00 equiv) in ethanol (50 mL) dropwise at 90° C. The reaction mixture was stirred for 10 min at 90° C. and then cooled to rt. The solid material was removed by filtration. The filtrate was concentrated under vacuum and the residue was purified on a silica gel column eluted with ethyl acetate/petroleum ether (1:2) to yield 1.6 g (37%) of the title compound as a yellow solid. LC/MS (Method I, ESI): RT=0.81 min, m/z=187.0; 189.0 [M+H]+.

Step 2. N-(5-Bromo-2-methyl-pyridin-3-yl)-acetamide. A solution of 5-bromo-2-methyl-pyridin-3-ylamine (3 g, 16.04 mmol, 1.00 equiv) in acetic anhydride (20 mL) and acetic acid (10 mL) was stirred overnight at rt. The resulting mixture was concentrated under vacuum to give 2.6 g (71%)

of the title compound as a light yellow solid. LC/MS (Method I, ESI): RT=1.05 min, m/z=229.0; 231.0 [M+H]$^+$.

Step 3. 1-(6-Bromo-pyrazolo[4,3-b]pyridin-1-yl)-ethanone. A mixture of N-(5-bromo-2-methyl-pyridin-3-yl)-acetamide (3.5 g, 15.28 mmol, 1.00 equiv), isopentyl nitrite (4 g, 34.73 mmol, 2.27 equiv), potassium acetate (20 g), and acetic anhydride (30 mL) in toluene (150 mL) was stirred under nitrogen overnight at 90° C. The reaction mixture was cooled to rt and the solid material was removed by filtration. The filtrate was concentrated under vacuum and the residue was purified on a silica gel column eluted with ethyl acetate/petroleum ether (1:5) to give in 2 g (55%) of the title compound as a light yellow solid. LC/MS (Method I, ESI): RT=1.44 min, m/z=240.0; 242.0 [M+H]$^+$.

Step 4. 1H-Pyrazolo[4,3-b]pyridine-6-carboxylic acid methyl ester. A mixture of 1-(6-bromo-pyrazolo[4,3-b]pyridin-1-yl)-ethanone (2 g, 8.33 mmol, 1.00 equiv), bis(triphenylphosphine)palladium(II) dichloride (1 g, 1.42 mmol, 0.17 equiv), and triethylamine (2.5 mL) in methanol (70 mL) was stirred overnight under carbon monoxide (10 atmospheres) at 100° C. in a 100 mL pressure reactor. The reaction mixture was cooled to rt and the solid material was removed by filtration. The filtrate was concentrated under vacuum and the residue was purified on a silica gel column eluted with ethyl acetate/petroleum ether (1:5) to afford 0.8 g (54%) of the title compound as a light yellow solid. TLC: 1:1 ethyl acetate/petroleum ether, $R_f$=0.2.

Step 5. A solution 1H-pyrazolo[4,3-b]pyridine-6-carboxylic acid methyl ester (200 mg, 1.13 mmol, 1.00 equiv) and sodium hydroxide (200 mg, 5.00 mmol, 4.43 equiv) in water (10 mL) was stirred overnight at rt. After the reaction was complete, the pH value of the solution was adjusted to 3 with concentrated HCl. The resulting mixture was concentrated under vacuum to give 1 g of crude title product as a light yellow solid. LC/MS (Method I, ESI): RT=0.91 min, m/z=164.0; 242.0 [M+H]$^+$.

Intermediate 10

[1,2,4]Triazolo[1,5-a]pyridine-6-carboxylic acid

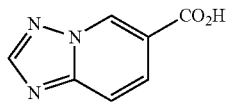 [SMILES: O=C(O)c1ccc2ncnn2c1]

Step 1. N'-(5-Bromo-pyridin-2-yl-N,N-dimethyl-formamidine. A solution of 5-bromopyridin-2-amine (4 g, 23.12 mmol, 1.00 equiv) and N,N-dimethylformamide dimethyl acetal (9.6 mL, 3.00 equiv) in DMF (30 mL) was stirred under nitrogen for 12 h at 130° C. The reaction mixture was cooled to rt and then concentrated under vacuum to give 4 g (76%) of the title compound as an oil. TLC: 1:5 MeOH/DCM, $R_f$=0.6.

Step 2. 6-Bromo-[1,2,4]triazolo[1,5-a]pyridine. To a solution of N'-(5-bromo-pyridin-2-yl)-N,N-dimethyl-formamidine (4 g, 17.54 mmol, 1.00 equiv) in methanol (40 mL) maintained under nitrogen at 0° C. was added pyridine (4 mL, 2.00 equiv) and (aminooxy)sulfonic acid (3.6 g, 31.83 mmol, 1.30 equiv). The resulting solution was stirred for 12 h at rt. After the reaction completed, the mixture was concentrated under vacuum. The residue was diluted with 150 mL of ethyl acetate then washed with 1×50 mL of saturated aqueous sodium carbonate solution and 2×50 mL of water. The organic layer was dried over anhydrous sodium sulfate then concentrated under vacuum. The residue was purified on a silica gel column eluted with ethyl acetate/hexane (1:1) to give 2.5 g (72%) title compound as a solid. LC/MS (Method D, ESI): RT=1.15 min, m/z=198.0 [M+H]$^-$.

Step 3. [1,2,4]Triazolo[1,5-a]pyridine-6-carboxylic acid methyl ester. A mixture of 6-bromo-[1,2,4]triazolo[1,5-a]pyridine (2.4 g, 12.12 mmol, 1.00 equiv), bis(triphenylphosphine)palladium(II) dichloride (800 mg, 1.14 mmol, 0.10 equiv) and triethylamine (4 g, 39.53 mmol, 3.00 equiv) in DMSO (1.6 g, 20.48 mmol, 1.67 equiv) and methanol (50 mL) was stirred under carbon monoxide (10 atm) for 20 h at 100° C. The reaction mixture was cooled to rt and quenched with brine (50 mL). The resulting solution was extracted with ethyl acetate (3×40 mL). The combined organic layers were dried over anhydrous sodium sulfate then concentrated under vacuum. The residue was purified on a silica gel column eluted with ethyl acetate/hexane (1:1) to give 0.98 g (46%) of the title compound as a crude solid. LC/MS (Method C, ESI): RT=1.04 min, m/z=178.0 [M+H]$^+$.

Step 4. A solution of [1,2,4]triazolo[1,5-a]pyridine-6-carboxylic acid methyl ester (200 mg, 1.13 mmol, 1.00 equiv) in TH-IF (2 mL) was added to a solution of potassium hydroxide (1 g, 17.82 mmol, 15.79 equiv) in water (10 mL) The resulting mixture was stirred for 10 h at rt After the reaction completed, the pH value of the solution was adjusted to 5-6 with 1 N HCl. The mixture was extracted with 3×50 mL of ethyl acetate. The combined organic layers were dried over anhydrous sodium sulfate and concentrated under vacuum to give 112 mg (61%) of the title compound 15 as a solid. LC/MS (Method C, ESI): RT=0.9 min, m/z=164.0 [M+H]$^+$.

Intermediate 11

Pyrazolo[1,5-a]pyrimidine-5-carboxylic acid

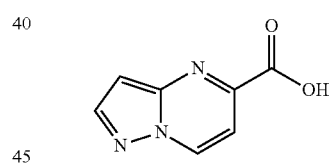

Step 1. 4H-Pyrazolo[1,5-a]pyrimidin-5-one. A solution of 1H-pyrazol-3-ylamine (7 g, 84.24 mmol, 1.00 equiv) and ethyl prop-2-ynoate (50 mL) in dioxane (10 g, 1.21 equiv) was stirred under nitrogen overnight at 110° C. The reaction mixture was cooled to rt and the precipitated product was collected by filtration to give 4 g (36%) of the title compound as a light brown solid. $^1$H NMR (300 MHz, DMSO-$d_6$) δ 12.04 (s, 1H), 8.41-8.44 (m, 1H), 7.71 (d, J=1.8 Hz, 1H), 5.88 (d, J=8.1 Hz, 1H), 5.77 (m, 1H).

Step 2. 5-Chloro-pyrazolo[1,5-a]pyrimidine. A solution of 4H-pyrazolo[1,5-a]pyrimidin-5-one (1 g, 7.40 mmol, 1.00 equiv) in phosphorus oxychloride (15 mL) was stirred under nitrogen for 2 h at 120° C. The reaction mixture was cooled to rt then concentrated under vacuum. The residue was purified on a silica gel column eluted with ethyl acetate/petroleum ether (1:2) to give 0.6 g (53%) of the title compound as a light yellow solid. LC/MS (Method I, ESI): RT=1.21 min, m/z=154.0 [M+H]$^+$.

Step 3. Pyrazolo[1,5-a]pyrimidine-5-carboxylic acid methyl ester. A mixture of 5-chloro-pyrazolo[1,5-a]pyrimidine (2 g, 13.02 mmol, 1.00 equiv), triethylamine (4 mL), methanol (80 mL), and bis(triphenylphosphine)palladium (II) dichloride (1 g, 1.42 mmol, 0.11 equiv) was stirred in a 100-mL pressure reactor overnight at 100° C. under 10 atmospheres of carbon monoxide. The reaction mixture was cooled to rt then concentrated under vacuum. The residue was purified on a silica gel column eluted with ethyl acetate/petroleum ether (1:5) to yield 1.2 g (52%) of the title compound as a light yellow solid. LC/MS (Method I, ESI): RT=1.09 min, m/z=178.0 [M+H]⁺.

Step 4. To a solution of methyl pyrazolo[1,5-a]pyrimidine-5-carboxylic acid methyl ester (100 mg, 0.56 mmol, 1.00 equiv) in acetic acid (5 mL) was added concentrated HCl (37%, 5 mL). The resulting solution was stirred for 3 h at 120° C., then concentrated under vacuum. The residue was dissolved in 3 mL of water and then adjusted to pH 5 with saturated aqueous sodium carbonate solution. The precipitated product was collected by filtration then air-dried to give 0.08 g (87%) of pyrazolo[1,5-a]pyrimidine-5-carboxylic acid as a light yellow solid. LC/MS (Method I, ESI): RT=0.95 min, m/z=164.0 [M+H]⁺.

Intermediate 12

3-tert-Butylamino-imidazo[1,2-a]pyridine-6-carboxylic acid

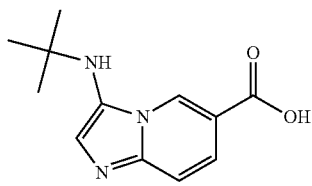 [SMILES: CC(C)(C)Nc1cnc2ccc(C(=O)O)cn12]

Step 1. 3-tert-Butylamino-imidazo[1,2-a]pyridine-6-carboxylic acid methyl ester. To a solution of methyl 6-aminopyridine-3-carboxylate (3.8 g, 24.98 mmol, 1.00 equiv) and 2-oxoacetic acid hydrate (3.9 g, 42.39 mmol, 1.70 equiv) in methanol (120 mL) was added perchloric acid (250 mg, 2.50 mmol, 0.10 equiv). The reaction mixture was stirred for 30 min and 2-isocyano-2-methylpropane (2.08 g, 25.02 mmol, 1.00 equiv) was then added. The reaction mixture was stirred for 12 h at rt and then concentrated under vacuum. The residue was purified on a silica gel column eluted with dichloromethane/ethyl acetate (2:1) to give 850 mg (14%) of the title compound as a yellow solid. ¹H NMR (300 MHz, CDCl₃) δ 8.97-8.96 (dd, J=0.9, 1.5 Hz, 1H), 7.69-7.65 (dd, J=4.2, 9.6 Hz, 1H), 7.53-7.50 (dd, J=4.2, 9.6 Hz, 1H), 7.39 (s, 1H), 3.96 (s, 3H), 1.23(s, 9H).

Step 2. Sodium 3-tert-Butylamino-imidazo[1,2-a]pyridine-6-carboxylate. To a solution of 3-tert-butylamino-imidazo[1,2-a]pyridine-6-carboxylic acid methyl ester (300 mg, 1.21 mmol, 1.00 equiv) in methanol (5 mL) was added a solution of sodium hydroxide (97 mg, 2.42 mmol, 2.00 equiv) in water (5 mL). The resulting solution was stirred for 1.5 h at 46° C. The reaction mixture was cooled to rt and then quenched by the addition of 0.15 mL of HCl. The resulting mixture was concentrated under vacuum to give 345.6 mg (crude) of the title product as a yellow solid. LC/MS (Method I, ESI) RT=1.02 min, m/z=234.0 [M+H–22]⁺.

Step 3. Sodium 3-tert-butylamino-imidazo[1,2-a]pyridine-6-carboxylate (300 mg, 1.17 mmol, 1.00 equiv) was dissolved in acetic acid (10 mL) and then concentrated under vacuum. The residue was purified on a silica gel column eluted with dichloromethane/methanol (20:1) to give 150 mg (54%) of the title compound as a yellow solid LC/MS (Method F, ESI): RT=0.94 min, m/z=234.0 [M+H]⁺.

Intermediate 13

2,3-Dihydro-1H-pyrrolo[3,4-c]pyridine

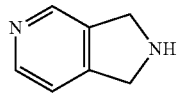

Step 1. Ethyl N-(prop-2-yn-1-yl)carbamate. To a solution of prop-2-yn-1-amine (11.5 g, 208.79 mmol, 1.00 equiv) and sodium hydroxide (9.1 g, 227.50 mmol, 1.09 equiv) in water (40 mL) and toluene (110 mL) maintained under nitrogen was added ethyl chloroformate (23.9 g, 220.23 mmol, 1.05 equiv) dropwise in 20 min with stirring at 10° C. The resulting solution was stirred overnight at rt then extracted with 3×100 mL of toluene. The combined organic layers were dried over anhydrous sodium sulfate then concentrated under vacuum to give 15 g (57%) of ethyl N-(prop-2-yn-1-yl)carbamate as a light yellow oil. TLC ethyl acetate/petroleum ether (1:2), R_f=0.5.

Step 2. Pyrimidine-5-carboxaldehyde. To a solution of 5-bromopyrimidine (2 g, 12.58 mmol, 1.00 equiv) in THF (20 mL) placed in a 50-mL 3-necked round-bottom flask purged and maintained with an inert atmosphere of nitrogen was added n-butyllithium (1.1 mL) at −78° C. The reaction mixture was stirred at −78° C. for another 2 h. Ethyl formate (5.2 mL) was then added and the resulting solution was stirred for 2 h at −78° C. The resulting mixture was warmed to 0° C. and washed with 50 mL of brine. The organic layer was dried with anhydrous sodium carbonate and concentrated. The residue was purified on a silica gel column eluted with ethyl acetate/petroleum ether (1:1) to give 11 g of crude pyrimidine-5-carboxaldehyde as a yellow oil. TLC: ethyl acetate/petroleum ether (1/1), R_f=0.2.

Step 3. Pyrimidin-5-ylmethanol. A mixture of pyrimidine-5-carboxaldehyde (2 g, 18.50 mmol, 1.00 equiv) and sodium borohydride (2 g) in methanol (100 mL) was stirred at 0-10° C. for 30 min. The reaction mixture was concentrated under vacuum and the residue was purified on a silica gel column eluted with dichloromethane/methanol (50:1) to yield 1.2 g (59%) of pyrimidin-5-ylmethanol (commercially available, CAS 25193-95-7) as a light yellow solid. LC/MS (Method N ESI): RT=0.74 min, m/z=111.0 [M+H]⁺.

Step 4. 5-(Chloromethyl)pyrimidine. To a solution of pyrimidin-5-ylmethanol (1.1 g, 10 mmol, 1.00 equiv) in dichloromethane (30 mL) was added thionyl chloride (2 mL) dropwise with stirring. The resulting solution was stirred at rt for 2 h then concentrated in vacuum to give 1.1 g of crude 5-(chloromethyl)pyrimidine as a yellow oil. TLC: ethyl acetate/petroleum ether (1:1), R_f=0.4.

Step 5. Ethyl N-(prop-2-yn-1-yl)-N-(pyrimidin-5-ylmethyl)carbamate. A mixture of ethyl N-(prop-2-yn-1-yl)carbamate (1.27 g, 9.99 mmol, 1.00 equiv) benzyltriethylammonium chloride (500 mg, 2.60 mmol, 0.26 equiv), 5-(chloromethyl)pyrimidine (1.28 g, 9.96 mmol, 1.00 equiv) and potassium hydroxide (3 g, 53.47 mmol, 5.37 equiv) in toluene (30 mL) was stirred overnight under nitrogen at rt.

The resulting mixture was concentrated under vacuum and the residue was purified on a silica gel column eluted with ethyl acetate/petroleum ether (1:1) to afford 0.3 g (14%) of ethyl N-(prop-2-yn-1-yl)-N-(pyrimidin-5-ylmethyl)carbamate as a light yellow oil. $^1$H NMR (300 MHz, CDCl$_3$) δ 9.16 (s, 1H), 8.73 (s, 2H), 4.59 (s, 2H), 4.11-4.26 (m, 4H), 2.28 (t, J=2.4 Hz, 1H), 1.30 (t, J=7.2 Hz, 3H).

Step 6. Ethyl 1H,2H,3H-Pyrrolo[3,4-c]pyridine-2-carboxylate. A mixture of ethyl N-(prop-2-yn-1-yl)-N-(pyrimidin-5-ylmethyl)carbamate (I g, 4.56 mmol, 1.00 equiv) in xylene (30 mL) was stirred under nitrogen at 150° C. for 2 days. The resulting mixture was concentrated under vacuum and the residue was purified on a silica gel column eluted with ethyl acetate/petroleum ether (1/2) to give 0.4 g (46%) of ethyl 1H,2H,3H-pyrrolo[3,4-c]pyridine-2-carboxylate as a light brown crude solid. $^1$H NMR (300 MHz, CDCl$_3$) δ 8.53-8.93 (m, 2H), 7.24 (d, J=5.1 Hz, 1H), 4.73-4.80 (m, 4H), 4.22-4.33 (m, 2H), 1.33-1.49 (m, 3H).

Step 7. 23-Dihydro-1H-pyrrolo[3,4-c]pyridine. A mixture of ethyl 1H,2H,3H-pyrrolo[3,4-c]pyridine-2(3H)-carboxylate (400 mg, 2.4 mmol, 1.00 equiv) and barium hydroxide (0.8 g) in water (100 mL) was stirred overnight at 120° C. The reaction mixture was cooled to rt and the solid material was collected by filtration. The residue was stirred in hot ethyl acetate (150 mL) and then filtered to remove solid material. The filtrate was concentrated under vacuum to give 0.18 g (72%) of 2,3-dihydro-1H-pyrrolo[3,4-c]pyridine as a light yellow oil. $^1$H NMR (300 MHz, CDCl$_3$) δ 8.51 (s, 1H), 8.41-8.45 (t, J=4.8 Hz, 1H), 7.13-7.20 (m, 1H), 4.25 (s, 2H), 4.22 (s, 2H).

Intermediate 14

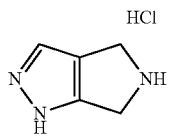

Step 1. tert-Butyl 2H,4H,5H,6H-pyrrolo[3,4-c]pyrazole-5-carboxylate. A solution of tert-butyl 3-[(dimethylamino)methylidene]-4-oxopyrrolidine-1-carboxylate (1 g, 4.16 mmol, 1.00 equiv) and hydrazine hydrate (340 mg, 6.79 mmol, 1.63 equiv) in ethanol (10 mL) was stirred for 5 h at rt. The resulting mixture was concentrated under vacuum and the residue was purified on a silica gel column eluted with ethyl acetate/petroleum ether (1:5 to 1:2) to give 250 mg (29%) of tert-butyl 2H,4H,5H,6H-pyrrolo[3,4-c]pyrazole-5-carboxylate as a yellow solid LC/MS (Method C, ESI): RT=1.30 min, m/z=210.0 [M+H]$^+$.

Step 2. A solution of tert-butyl 2H,4H,5H,6H-pyrrolo[3,4-c]pyrazole-5-carboxylate (250 mg, 1.19 mmol, 1.00 equiv) in DCM (5 mL) and TFA (5 mL) was stirred at rt overnight. The reaction mixture was concentrated under vacuum and the residue was redissolved in 20 mL of concentrated HCl and then concentrated under vacuum again to yield 200 mg of crude 2H,4H,5H,6H-pyrrolo[3,4-c]pyrazole hydrochloride as a dark red solid. LC/MS (Method C, ESI): RT=0.46 min, m/z=110.0 [M−H]$^+$.

II. PREPARATION OF EXAMPLE COMPOUNDS

Example 8

Imidazo[1,2-a]pyridine-6-carboxylic acid 5-benzenesulfonyl-pyrimidin-2-ylmethyl)-amide

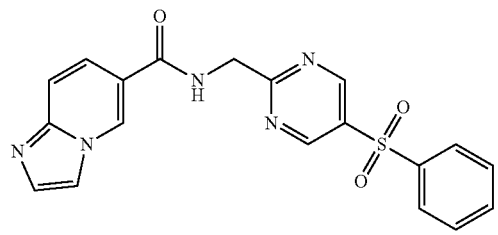 [SMILES: O=C(NCc1ncc(S(=O)(=O)c2ccccc2)cn1)c1ccc2nccn2c1]

Step 1. 5-Bromopyrimidine-2-carbonitrile. A mixture of 5-bromo-2-chloropyrimidine (20 g, 103.40 mmol, 1.00 equiv), 1,4-diaza-bicyclo[2.2.2]octane (2.32 g), and potassium carbonitrile (6.72 g, 103.20 mmol, 1.00 equiv) in water (54.2 mL) and DMSO (80 mL) was stirred overnight at rt. Water (50 mL) was then added and the resulting solution was extracted with 3×00 mL of ether. The combined organic layers were dried over anhydrous sodium sulfate and concentrated under vacuum to afford 16 g (84%) of 5-bromopyrimidine-2-carbonitrile as a yellow solid. $^1$H NMR (300 MHz, CDCl$_3$) δ 8.94 (s, 2H).

Step 2. 5-(Phenylsulfanyl)pyrimidine-2-carbonitrile. A mixture of 5-bromopyrimidine-2-carbonitrile (2.0 g, 10.87 mmol, 1.00 equiv), benzenethiol (1.1 g, 9.98 mmol, 0.92 equiv), and cesium carbonate (7.08 g, 21.73 mmol, 2.00 equiv) in 1-methylpyrrolidin-2-one (10 mL) was stirred for 2 h at 100° C. The resulting solution was diluted with 50 mL of water and extracted with 3×50 mL of ether. The organic layers were combined was washed with 3×50 mL of brine, dried over anhydrous sodium sulfate, and concentrated under vacuum. The residue was purified on a silica gel column eluted with ethyl acetate/petroleum ether (1:30) to give 1.1 g (47%) of 5-(phenylsulfanyl) pyrimidine-2-carbonitrile as an off-white solid. $^1$H NMR (300 MHz, CDCl$_3$) δ 8.74 (s, 2H), 7.64-7.58 (m, 2H), 7.56-7.49 (m, 3H).

Step 3: [5-(Phenylsulfanyl)pyrimidin-2-yl]methanamine. A mixture of 5-(phenylsulfanyl)pyrimidine-2-carbonitrile (1.1 g, 5.16 mmol, 1.00 equiv), Raney-Ni (0.2 g), and ammonium hydroxide (2 mL, 28-30% aqueous solution) in methanol (10 mL) was stirred under 1 atmosphere of hydrogen for 4 h at rt. The catalyst was then removed by filtration. The filtrate was concentrated under vacuum to give 2.1 g of [5-(phenylsulfanyl)pyrimidin-2-yl]methanamine as a brown solid. LC/MS (Method A, ESI): RT=1.19 min, m/z=218.0 [M+H]$^+$.

Step 4: tert-Butyl N-[[5-(phenylsulfanyl)pyrimidin-2-yl]methyl]carbamate. To a solution of [5-(phenylsulfanyl)pyrimidin-2-yl]methanamine (2.1 g, 9.66 mmol, 1.00 equiv) and triethylamine (1.49 g, 14.72 mmol, 1.52 equiv) in dichloromethane (20 mL) was added a solution of di-tert-butyl dicarbonate (2.32 g, 10.63 mmol, 1.10 equiv) in dichloromethane (10 mL) dropwise within 15 min. The reaction mixture was stirred for 2 h at rt and then diluted with 20 mL of water. The resulting solution was extracted with 3×50 mL of ethyl acetate. The combined organic layers was washed with 3×50 mL of brine, dried over anhydrous sodium sulfate and concentrated in vacuum. The residue was purified on a silica gel column eluted with ethyl acetate/petroleum ether (1:50) to give 1.1 g (36%) of tert-butyl N-[[5-(phenylsulfanyl)pyrimidin-2-yl]methyl]carbamate as brown oil. LC/MS (Method A, ESI): RT=1.72 min, m/z=318.0 [M–H]+.

Step 5: tert-Butyl N-[[5-(benzenesulfonyl)pyrimidin-2-yl]methyl]carbamate. To a solution of tert-butyl N-[[5-(phenylsulfanyl)pyrimidin-2-yl]methyl]carbamate (1.1 g, 3.47 mmol, 1.00 equiv) in chloroform (10 mL) was added dropwise a solution of 3-chloroperbenzoic acid (3 g, 17.38 mmol, 5.02 equiv) in chloroform (15 mL). The resulting solution was stirred for 1 h at rt and then quenched by the addition of saturated aqueous sodium sulfite solution (20 mL). The pH value of the solution was adjusted to 9 with 3 N potassium hydroxide solution. The mixture was washed with 3×20 mL of brine. The organic layer was dried over anhydrous sodium sulfate and concentrated under vacuum to give 0.5 g (41%) of tert-butyl N-[[5-(benzenesulfonyl)pyrimidin-2-yl]methyl]carbamate as brown oil. LC/MS (Method H, ESI): RT=1.46 min, m/z=350.0 [M+H]+.

Step 6: [5-(Benzenesulfonyl) pyrimidin-2-yl]methanamine. Hydrogen chloride gas was bubbled into a solution of tert-butyl N-[[5-(benzenesulfonyl)pyrimidin-2-yl]methyl] carbamate (500 mg, 1.43 mmol, 1.00 equiv) in dichloromethane (20 mL). The resulting solution was stirred for 2 h at rt. The pH value of the solution was adjusted to 9 with 1N sodium hydroxide. The resulting mixture was extracted by 2×20 mL of dichloromethane. The combined organic layers was dried over anhydrous sodium sulfate then concentrated under vacuum to give 360 mg of [5-(benzenesulfonyl)pyrimidin-2-yl]methanamine as a brown oil LC/MS (Method A, ESI): RT=1.13 min, m/z=250.0 [M+H]+.

Step 7: N-[[5-(Benzenesulfonyl) pyrimidin-2-yl]methyl] imidazo[1,2-a]pyridine-6-carboxamide. A solution of [5-(benzenesulfonyl)pyrimidin-2-yl]methanamine (100 mg, 0.40 mmol, 1.00 equiv), imidazo[1,2-a]pyridine-6-carboxylic acid (78 mg, 0.48 mmol, 1.20 equiv), EDCI (230 mg, 1.48 mmol, 3.69 equiv), triethylamine (120 mg, 1.19 mmol, 2.96 equiv), and HOBt (80 mg, 0.59 mmol, 1.48 equiv) in DMF (2 mL) was stirred overnight at rt. The reaction mixture was quenched by the addition of 30 mL of water/ice. The resulting solution was extracted with 3×30 mL of ethyl acetate. The organic layers were combined, washed with 3×30 mL of brine and then dried over anhydrous sodium sulfate. The crude product was purified by Preparative HPLC with the following conditions (2#-Waters 2767-2 (HPLC-08)): Column, Xbridge Prep Phenyl, 5 um, 19*150 mm, mobile phase, water with 50 mmol ammonium bicarbonate and acetonitrile (10.0% acetonitrile up to 33.0% in 2 min, up to 53.0% in 8 min, up to 100.0% in 1 min, down to 10.0% in 1 min); Detector, UV 220 nm to give 30.8 mg (20%) of the title compound as a white solid. 1H NMR (300 MHz, CD3OD) δ 9.24 (s, 2H), 9.05 (s, 1H), 8.08-8.06 (d, J=7.5 Hz, 2 H), 7.96 (s, 1H), 7.75-7.70 (t, J=8.1 Hz, 2H), 7.67-7.60 (m, 4H), 4.90-4.87 (m, 2H). LC/MS (Method J, ESI): RT=1.25 min, m/z=393.9 [M+H]−.

Example 22

Furo[2,3-c]pyridine-2-carboxylic acid [5-(3-trifluoromethyl-benzenesulfonyl)-pyridin-2-ylmethyl]-amide

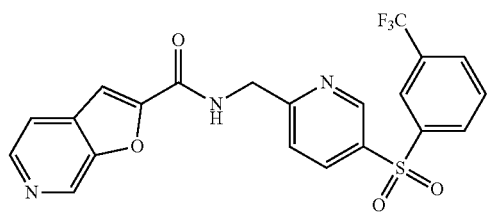 [SMILES: O=C(NCc1ccc(S(=O)(=O)c2cccc(C(F)(F)F)c2)cn1)c1cc2ccncc2o1]

Step 1: 5-[[3-(Trifluoromethylphenyl]sulfanyl]pyridine-2-carbonitrile. A mixture of 5-bromopyridine-2-carbonitrile (2.1 g, 11.48 mmol, 1.02 equiv), 3-(trifluoromethyl)benzene-1-thiol (2 g, 11.22 mmol, 1.00 equiv), and potassium carbonate (3.1 g, 22.43 mmol, 2.00 equiv) in DMF (40 mL) was stirred overnight at 120° C. The reaction was quenched by the addition of 60 mL of ice-water. The resulting solution was extracted with 4×50 mL of ethyl acetate. The organic layers were combined, dried over anhydrous sodium sulfate, and concentrated under vacuum. The residue was purified on a silica gel column with ethyl acetate/petroleum ether (1/50) to give 2.2 g (70%) of 5-[[3-(trifluoromethyl)phenyl]sulfanyl]pyridine-2-carbonitrile as yellow oil. 1H NMR (300 MHz, CDCl3) δ 8.48-8.49 (m, 1H), 7.78 (s, 1H), 7.55 (m, 2H), 7.49-7.53 (m, 3H).

Step 2: 5-(3-(Trifluoromethyl)phenylsulfonyl)-picolinonitrile. To a solution of 5-(3-(trifluoromethyl)phenylthio) picolinonitrile (900 mg, 3.21 mmol, 1.00 equiv) in dichloromethane (30 mL) was added m-chloroperbenzoic acid (4.1 g, 23.84 mmol, 7.42 equiv) in small portions at 0° C. The resulting solution was stirred at rt for 2 h then quenched with saturated sodium bisulfite solution. The resulting mixture was extracted with 4×50 mL of dichloromethane. The organic layers were combined, dried over anhydrous sodium sulfate, and concentrated under vacuum. The residue was purified on a silica gel column eluted with ethyl acetate/petroleum ether (1/2) to give 800 mg (80%) of 5-(3-(trifluoromethyl)phenylsulfonyl)-picolinonitrile as a white solid. TLC: 1:1 ethyl acetate/petroleum ether, Rf=0.6.

Step 3: (5-[[3-(Trifluoromethyl)benzene]sulfonyl]pyridin-2-yl) Methanamine. To a mixture of Raney Ni (15 g) and 5-(3-(trifluoromethyl)phenylsulfonyl) picolinonitrile (2.2 g, 7.05 mmol, 1.00 equiv) in methanol (150 mL) was added hydrazine hydrate (15 mL) dropwise with stirring at 0° C. The reaction mixture was stirred for 10 min at rt. The nickel catalyst was removed by filtration and the filtrate was concentrated under vacuum. The residue was diluted with water (100 mL) and the resulting solution was extracted with 3×300 mL of ethyl acetate. The organic layers were combined and concentrated under vacuum to give 1.6 g (72%) of (5-[[3-(trifluoromethyl)benzene]sulfonyl]pyridin-2-yl) methanamine as a yellow solid. 1H NMR (400 MHz, CDCl3) δ 9.17 (s, 1H), 8.12 (m, 3H), 7.78 (m, 1H), 7.70 (m, 1H), 7.52 (m, 1H), 4.09 (s, 2H).

Step 4. A solution of furo[2,3-c]pyridine-2-carboxylic acid (60 mg, 0.37 mmol, 1.16 equiv) EDCI (70 mg, 0.37 mmol, 1.15 equiv), HOBt (45 mg, 0.33 mmol, 1.05 equiv), and triethylamine (0.5 mL) in DMF (4 mL) was stirred for 10 min at rt. (5-[[3-(Trifluoromethyl)benzene]sulfonyl]pyridin-2-yl)methanamine (100 mg, 0.32 mmol, 1.00 equiv) was then added and the reaction mixture was stirred overnight at rt. The resulting solution was diluted with 120 mL of ethyl acetate and washed with 2×100 mL of water. The organic layer was dried over anhydrous sodium sulfate and concentrated under vacuum. The residue was purified on a silica gel column with ethyl acetate/petroleum ether (1:1-1:9) to give 46.4 mg (32%) of the title compound as a light yellow solid. $^1$H NMR (300 MHz, DMSO-$d_6$) δ 9.59 (t, J=6.0 Hz, 1H), 9.15 (d, J=1.8 Hz, 1H), 9.03 (s, 1H), 8.38 (m, 2H), 8.31 (m, 2H), 8.07 (d, J=8.1 Hz, 1H), 7.79 (m, 2H), 7.57 (m, 2H), 4.62 (d, J=6.0 Hz, 2H). LC/MS (Method F, ESI): RT=1.44 min, m/z=462.0 [M+H]$^+$.

Example 26

Furo[2,3-c]pyridine-2-carboxylic acid [5-(piperidine-4-sulfonyl)-pyridin-2-ylmethyl]-amide

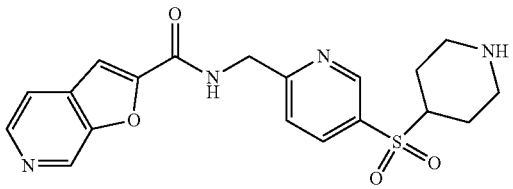 [SMILES: O=C(NCc1ccc(S(=O)(=O)C2CCNCC2)cn1)c1cc2ccncc2o1]

Step 1: tert-Butyl 4-sulfanylidenepiperidine-1-carboxylate. Hydrogen sulfide 25 gas was bubbled into a solution of tert-butyl 4-oxopiperidine-1-carboxylate (30 g, 150.57 mmol, 1.00 equiv) in isopropanol (300 mL). The reaction mixture was stirred for 4 h at 0-10° C. The resulting mixture was concentrated under vacuum to half the volume and then used in the next step without further purification. TLC (5:1 petroleum ether/ethyl acetate): $R_f$=0.4.

Step 2: tert-Butyl 4-sulfanylpiperidine-1-carboxylate. The solution of tert-butyl 4-sulfanylidenepiperidine-1-carboxylate (32 g, 148.62 mmol, 1.00 equiv) obtained in the previous step was diluted with ethanol (300 mL) and kept under nitrogen. Sodium borohydride (23 g, 624.58 mmol, 4.20 equiv) was then added to the reaction solution in portions within 20 min at 0-10° C. The reaction mixture was diluted with ethanol (40 mL) and stirred for 2 h at 80° C. then concentrated under vacuum. The residue was dissolved in 500 mL of water then extracted with 2×300 mL of ether. The organic layers were combined, washed with 2×200 mL of brine then dried over anhydrous sodium sulfate and concentrated under vacuum to give 17 g (53%) of tert-butyl 4-sulfanylpiperidine-1-carboxylate as a yellow oil. TLC (5:1 petroleum ether/ethyl acetate): $R_f$=0.35.

Step 3: tert-Butyl 4-[(6-cyanopyridin-3-yl)sulfanyl]piperidine-1-carboxylate. A mixture of 5-bromopyridine-2-carbonitrile (7.6 g, 40.70 mmol, 1.00 equiv, 98%), tert-butyl 4-sulfanylpiperidine-1-carboxylate (28 g, 83.74 mmol, 2.06 equiv), and potassium carbonate (11.6 g, 82.38 mmol, 2.02 equiv, 98%) in DMSO (150 mL) was stirred overnight at 120° C. After cooling to rt, the reaction mixture was quenched by the addition of 200 mL of water. The resulting solution was extracted with 3×200 mL of ethyl acetate. The combined organic layers were washed with 2×100 mL of water, dried over anhydrous sodium sulfate, and then concentrated under vacuum. The residue was purified on a silica gel column eluted with ethyl acetate/petroleum ether (1/10) to give 3.41 g (26%) of tert-butyl 4-[(6-cyanopyridin-3-yl) sulfanyl]piperidine-1-carboxylate as a yellow solid. LC/MS (Method C, ESI): RT=1.57 min, no MS signal.

Step 4: ten-Butyl 4-(6-cyanopyridine-3-sulfonyl)piperidine-1-carboxylate. To a solution of tert-butyl 4-[(6-cyanopyridin-3-yl)sulfanyl]piperidine-1-carboxylate (3.412 g, 10.47 mmol, 1.00 equiv) in chloroform (100 mL) was added 3-chloroperbenzoic acid (5.52 g, 31.35 mmol, 2.99 equiv) in small portions at rt. The reaction mixture was stirred for 50 min at rt and then diluted with 200 mL of dichloromethane. The resulting mixture was washed with saturated sodium sulfite solution (3×100 mL), 1 M sodium hydroxide solution (3×100 mL), and brine (3×100 mL). The organic layer was dried over anhydrous sodium sulfate and then concentrated under vacuum. The residue was purified on a silica gel column eluted with ethyl acetate/petroleum ether (1/20) to give 1.3 g (35%) of tert-butyl 4-(6-cyanopyridine-3-sulfonyl)piperidine-1-carboxylate as a white solid. $^1$H NMR (400 MHz, CDCl$_3$) δ 9.17-9.16 (d, J=2 Hz, 1H), 8.35-8.33 (dd, J=2.0, 8.0 MHz, 1H), 7.99-7.94 (dd, J=8.0, 14.0 Hz, 1H), 4.28 (br s, 2H), 3.18-3.10 (m, 1H), 2.70 (br s, 2H), 2.03-2.00 (d, 2H), 1.70-1.58 (m, 2H), 1.46 (s, 9H).

Step 5: tert-Butyl 4-[6-(aminomethyl) pyridine-3-sulfonyl]piperidine-1-carboxylate. To a solution of tert-butyl 4-(6-cyanopyridine-3-sulfonyl)piperidine-1-carboxylate (300 mg, 0.84 mmol) in methanol (20 mL) was added Raney Ni (100 mg) and ammonium hydroxide (1 mL, 28-30% aqueous solution). The resulting solution was stirred under 1 atmosphere of hydrogen for 1 h at rt. The catalyst was removed by filtration. The filtrate was concentrated under vacuum and the residue was purified on a silica gel column eluted with dichloromethane/methanol (20/1) to give 181 mg (61%) of tert-butyl 4-[6-(aminomethyl)pyridine-3-sulfonyl]piperidine-1-carboxylate as a green solid. LC/MS (Method K, ESI): RT=1.51 min, m/z=356.0 [M+H]$^+$.

Step 6: tert-Butyl 4-[6-([furo[2,3-c]pyridin-2-ylformamido]methyl)pyridine-3-sulfonyl]piperidine-1-carboxylate. A solution of tert-butyl 4-[6-(aminomethyl)pyridine-3-sulfonyl]piperidine-1-carboxylate (90 mg, 0.25 mmol), furo[2,3-c]pyridine-2-carboxylic acid (49.5 mg, 0.30 mmol, 1.20 equiv), EDCI (96 mg, 0.49 mmol), HOBt (51 mg, 0.37 mmol), and triethylamine (77 mg, 0.75 mmol, 3.01 equiv, 98%) in DMF (1 mL) was stirred overnight at rt. The reaction was then quenched by the addition of 10 mL of water and the resulting solution was extracted with 3×20 mL of ethyl acetate. The combined organic layers was washed with 2×20 mL of water, dried over anhydrous sodium sulfate, and concentrated under vacuum to give 104 mg (84%) of tert-butyl 4-[6-([furo[2,3-c]pyridin-2-ylformamido]methyl)pyridine-3-sulfonyl]piperidine-1-carboxylate as a yellow oil. LC/MS (Method F, ESI): RT=1.15 min, n z=501.0 [M+H]$^+$.

Step 7. A solution of tert-butyl 4-[6-([furo[2,3-c]pyridin-2-ylformamido]methyl)pyridine-3-sulfonyl]piperidine-1-carboxylate (104 mg, 0.20 mmol) in trifluoroacetic acid (2 mL) was stirred for 30 min at rt. The reaction mixture was concentrated under vacuum and the residue was dissolved in 20 mL of ethyl acetate. Saturated sodium bicarbonate solution was added to the organic solution to adjust its pH to 8. The mixture was extracted with 20 mL of ethyl acetate. The combined organic layers was dried over anhydrous sodium sulfate and then concentrated under vacuum. The crude product was purified by Preparative HPLC (Xbridge C18, 19×15 mm, mobile phase: CH$_3$CN/NH$_4$CO (10 mmol/L) in water, 12-25%, flow: 20 mL/min, 10 min, Detector, UV at 254 nm) to give 10.6 mg (13%) of the title compound as a yellow solid. $^1$H NMR (300 MHz, CDCl$_3$) δ 9.04-9.03 (d, J=3 Hz, 2H), 8.98 (s, 1H), 8.50-8.49 (d, J=3 Hz, 1H), 8.15-8.11 (m, 1H), 7.85 (s, 1H), 7.63-7.62 (d, J=3 Hz, 1H), 7.58-7.50 (m, 2H), 4.90-4.88 (d, 2H), 3.18-3.07 (t, 2H), 3.04-2.98 (m, 1H), 2.59-2.50 (m, 2H), 2.03-1.99 (d, 2H), 1.52 (s, 2H). LC/MS (Method H, ESI): RT=0.89 min, m/z=400.0 [M+H]⁻.

Examples 28 and 29

Furo[2,3-c]pyridine-2-carboxylic acid [5-(3,5-difluoro-benzenesulfinyl)-pyridin-2-ylmethyl]-amide (R and S isomers)

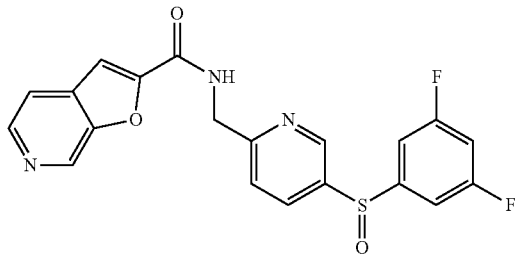 [SMILES: O=C(NCc1ccc(S(=O)c2cc(F)cc(F)c2)cn1)c1cc2ccncc2o1]

Step 1: [(3,5-Difluorophenyl)sulfanyl]methanethioate. To a solution of 3,5-difluoroaniline (20 g, 154.91 mmol, 1.00 equiv) in 6 N HCl (200 mL) at 0-5° C. was added a solution of sodium nitrite (11 g, 159.43 mmol, 1.03 equiv) in water (60 mL) dropwise with stirring in 20 min. The resulting solution was stirred for 1 h at 0-5° C. The solid material was removed by filtration. The filtrate was added to a solution of potassium ethyl sulfanylmethanethioate (50 g, 409.14 mmol, 2.64 equiv) in water (80 mL) dropwise with stirring under nitrogen at 70° C. in 1 h. The reaction mixture was stirred for 1 h at rt. The resulting solution was extracted with 3×200 mL of ethyl acetate. The combined organic layers was washed with 3×100 mL of brine, dried over anhydrous sodium sulfate, and concentrated under vacuum to give 36 g (99%) of ethyl[(3,5-difluorophenyl)sulfanyl]methanethioate as a brown oil. TLC (10:1 petroleum ether/ethyl acetate). $R_f$=0.5.

Step 2: 3,5-Difluorobenzene-1-thiol. To a solution of ethyl[(3,5-difluorophenyl)sulfanyl]methanethioate (10 g, 42.68 mmol, 1.00 equiv) in ethanol (100 mL) maintained under nitrogen was added a solution of potassium hydroxide (9.6 g, 171.11 mmol, 4.01 equiv) in water (10 mL) dropwise at rt with stirring in 5 min. The resulting solution was heated to reflux for 2.5 h. After cooling to rt, the mixture was concentrated under vacuum. The residue was diluted with 200 mL of water and the solution was washed with 3×50 mL of ethyl acetate. The aqueous layer was collected to which zinc powder (0.8 g) was then added. The pH of the solution was adjusted to 5 with concentrated hydrochloric acid at 0-10° C. The resulting solution was extracted with 3×100 mL of ethyl acetate. The combined organic layers was washed with 3×100 mL of brine, dried over anhydrous sodium sulfate, and concentrated under vacuum to give 5.0 g (80%) of 3,5-difluorobenzene-1-thiol as a brown oil. TLC (10:1 petroleum ether/ethyl acetate): $R_f$=0.45.

Step 3: 5-[(3,5-Difluorophenyl)sulfanyl]pyridine-2-carbonitrile. A mixture of 5-bromopyridine-2-carbonitrile (6.3 g, 34.43 mmol, 1.00 equiv), 3,5-difluorobenzene-1-thiol (5 g, 34.21 mmol, 0.99 equiv), and cesium carbonate (22.3 g, 68.23 mmol, 1.98 equiv) in 1-methylpyrrolidin-2-one (70 mL) was stirred under nitrogen at 100° C. for 1.5 h. The reaction was then quenched by the addition of 200 mL of water. The precipitated product (4.6 g) was collected by filtration. The filtrate was extracted with 3×200 mL of ethyl acetate. The combined organic layers was washed with 3×200 mL of brine, dried over anhydrous sodium sulfate, and concentrated under vacuum to give in total 7.6 g (89%) of 5-[(3,5-difluorophenyl)sulfanyl]pyridine-2-carbonitrile as a brown solid. LC/MS (Method J, ESI): RT=1.62 min, n z=249.0 [M+H]⁺.

Step 4: 5-[(3,5-Difluorobenzene)sulfinyl]pyridine-2-carbonitrile. To a solution of 5-[(3,5-difluorophenyl)sulfanyl]pyridine-2-carbonitrile (1.8 g, 7.25 mmol, 1.00 equiv) in chloroform (20 mL) was added 3-chloroperbenzoic acid (1.6 g, 9.27 mmol, 1.28 equiv) in portions at 0-5° C. within 30 min. The resulting solution was stirred at 0-5° C. for another 1.5 h. The resulting solution was diluted with 200 mL of dichloromethane then washed with 3×100 mL of saturated sodium bisulfite solution and then with 3×100 mL of 3 N sodium hydroxide. The organic layer was washed with 3×100 mL of brine then dried over anhydrous sodium sulfate and concentrated under vacuum. The residue was purified on a silica gel column eluted with dichloromethane/petroleum ether (10:1) followed by methanol to give 1.2 g (63%) of 5-[(3,5-difluorobenzene)sulfinyl]pyridine-2-carbonitrile as a yellow solid. ¹H NMR (300 MHz, CDCl₃) δ 9.21-9.20 (d, J=0.6 Hz, 1H), 8.42-8.39 (dd, J=2.4, 6.6 Hz, 1H), 7.89-7.86 (dd, J=0.6, 8.1 Hz, 1H), 7.53-7.51 (t, 2H), 7.15-7.08 (m, 1H).

Step 5: [5-[(3,5-Difluorobenzene)sulfinyl]pyridin-2-yl]methanamine. To a solution of 5-[(3,5-difluorobenzene)sulfinyl]pyridine-2-carbonitrile (1.2 g, 4.54 mmol, 1.00 equiv) in methanol (100 mL) was added Raney Ni (0.5 g). The reaction mixture was stirred under 1 atmosphere of hydrogen for 1 h at rt. The catalyst was removed by filtration and the filtrate was concentrated under vacuum. The residue was purified on a silica gel column eluted with ethyl acetate/petroleum ether (1:2)-dichloromethane/methanol (5:1) to give 0.8 g (66%) of [5-[(3,5-difluorobenzene)sulfinyl]pyridin-2-yl]methanamine as a green solid. IC/MS (Method I, ESI): RT=1.10 min, m/z=285.0 [M+H]⁺.

Step 6: N-([5-[(3,5-Difluorobenzene)sulfinyl]pyridin-2-yl]methyl)furo[2,3-c]pyridine-2-carboxamide. A solution of [5-[(3,5-difluorobenzene)sulfinyl]pyridin-2-yl]methanamine (150 mg, 0.56 mmol, 1.00 equiv), furo[2,3-c]pyridine-2-carboxylic acid (110 mg, 0.67 mmol, 1.21 equiv). HOBt (91 mg, 0.67 mmol, 1.20 equiv), EDCI (321 mg, 1.67 mmol, 3.00 equiv), and triethylamine (226 mg, 2.23 mmol, 4.00 equiv) in DMF (2 mL) was stirred for 2.5 h at rt. The reaction was then quenched by the addition of 50 mL of water and then extracted with 3×30 mL of ethyl acetate. The combined organic layers was washed with 3×50 mL of brine, dried over anhydrous sodium sulfate, and concentrated under vacuum. The residue was purified on a silica gel column eluted with dichloromethane/methanol (60:1 to 30:1) to give 26.7 mg (10%) of the title compound (racemic) as a white solid. ¹H NMR (300 MHz, DMSO-d₆) δ 9.63-9.59(t, J=6 Hz, 1H), 9.07 (s, 1H), 8.94-8.93(d, J=1.8 Hz, 1H), 8.49-8.48 (d, J=5.1 Hz, 1H), 8.15-8.12 (dd, J=2.1, 8.1 Hz, 1H), 7.84-7.83 (d, J=6 Hz, 1H), 7.66 (s, 1H), 7.60-7.45 (m, 3H), 7.44-7.42 (m, 1H), 4.64-4.62 (d, 2H). LC/MS (Method K, ESI): RT=1.51 min, m/z=414.1 [M+H]⁺. The enantiomers were separated by preparative chiral SFC (column: Phenomenex Cellulose-1, 21.2×150 mm, 5 µm; detection: UV 254 nm, mobile phase A: CO₂, mobile phase B: MeOH containing 0.1% NH₄OH; flow rate: 70 mL/min; gradient: isocratic, A:B=70:30). Isolation and concentration of the appropriate fractions afforded: Example 28: white solid (4.9 mg); analytical chiral SFC (Method M): RT=0.52 min; and Example 29: white solid (4.6 mg), analytical chiral SFC (Method M): RT=0.61 min.

Example 49

1,3-Dihydro-pyrrolo[3,4-c]pyridine-2-carboxylic acid [5-(3-trifluoromethyl-benzenesulfonyl)-pyridin-2-ylmethyl]-amide

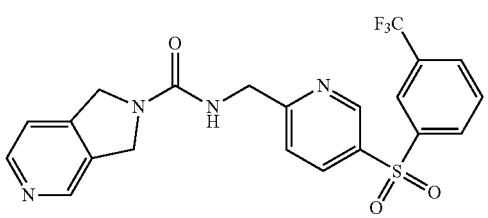 [SMILES: O=C(NCc1ccc(S(=O)(=O)c2cccc(C(F)(F)F)c2)cn1)N1Cc2ccncc2C1]

Step 1: 4-Nitrophenyl N-[(5-[[3-(trifluoromethyl)benzene]sulfonyl]pyridine-2-yl)methyl]carbamate. A solution of 4-nitrophenyl chloroformate (127 mg, 0.63 mmol, 1.00 equiv) and (5-[[3-(trifluoromethyl)benzene]sulfonyl]pyridin-2-yl)methanamine (200 mg, 0.63 mmol, 1.00 equiv) in toluene (50 mL) was refluxed for 3 h. The resulting mixture was concentrated under vacuum. The residue was purified on a silica gel column eluted with ethyl acetate/petroleum ether (1:2) to give 80 mg (26%) of 4-nitrophenyl N-[(5-[[3-(trifluoromethyl)benzene]sulfonyl]pyridine-2-yl)methyl]carbamate as a light yellow solid. LC/MS (Method C, ESI): RT=1.56 min, m/z=482.0 [M+H]$^+$.

Step 2. A solution of 2,3-dihydro-1H-pyrrolo[3,4-c]pyridine (10 mg, 0.08 mmol, 1.00 equiv) and 4-nitrophenyl N-[(5-[[3-(trifluoromethyl)benzene]sulfonyl]pyridin-2-yl)methyl]carbamate (40 mg, 0.08 mmol, 1.00 equiv) in ethanol (5 mL) was stirred for 2 h at rt. The resulting mixture was concentrated under vacuum. The residue was purified on a silica gel column eluted with dichloromethane/methanol (20:1) to give 20 mg (52%) of the title compound as a light yellow solid. $^1$H NMR (300 MHz, DMSO-$d_6$) δ 9.15 (d, J=1.8 Hz, 2H), 8.57 (s, 1H), 8.47 (d, J=5.1 Hz, 1H), 8.34 (m, 3H), 8.11 (d, J=7.5 Hz, 1H), 7.87 (m, 1H), 7.59 (d, J=8.4 Hz, 1H), 7.39 (d, J=4.8 Hz, 1H), 7.21 (m, 1H), 4.66 (d, 4H), 4.43 (d, J=5.7 Hz, 2H). LC/MS (Method I, ESI): RT=2.58 mm, m/z=463.0 [M+H]$^+$.

Example 51

Furo[2,3-c]pyridine-2-carboxylic acid [5-(tetrahydro-pyran-4-sulfonyl)-pyridin-2-ylmethyl]-amide

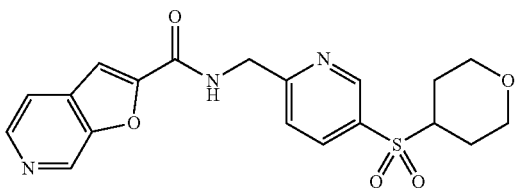 [SMILES: O=C(NCc1ccc(S(=O)(=O)C2CCOCC2)cn1)c1cc2ccncc2o1]

Step 1: Tetrahydropyran-4-thione. Hydrogen sulfide gas was bubbled into a solution of tetrahydropyran-4-one (10 g, 99.88 mmol, 1.00 equiv) in isopropanol (100 mL) at 0-5° C. The resulting solution was stirred at 0-5° C. for 5 h. The resulting mixture was concentrated under vacuum and the crude product was used in the next step without purification. TLC (5:1 petroleum ether/ethyl acetate): $R_f$=0.4.

Step 2: Tetrahydropyran-4-thiol. To a solution of tetrahydropyran-4-thione (11.6 g, 99.84 mmol, 1.00 equiv) in ethanol (100 mL) maintained under nitrogen was added sodium borohydride (5.7 g, 150.67 mmol, 1.51 equiv) in portions. The reaction mixture was stirred for 2 h at 80° C. After cooling to rt, the mixture was concentrated under vacuum. The residue was diluted with 200 mL of water and then extracted with 3×200 mL of ether. The combined organic layers was dried over anhydrous sodium sulfate and concentrated under vacuum to give 4.7 g (40%) of tetrahydropyran-4-thiol as a colorless oil. $^1$H NMR (300 MHz, CDCl$_3$) δ 3.93-3.83 (m, 2H), 3.81-3.74 (m, 1H), 3.42-3.31 (t, 2H), 2.07 (s, 1H), 1.91-1.80 (t, 2H), 1.59-1.44 (m, 2H).

Step 3: 5-(Oxan-4-ylsulfanyl)pyridine-2-carbonitrile. A mixture of 5-bromopyridine-2-carbonitrile (1.97 g, 10.76 mmol, 1.00 equiv), tetrahydropyran-4-thiol (1.4 g, 11.84 mmol, 1.10 equiv), and potassium carbonate (4.5 g, 32.56 mmol, 3.02 equiv) in DMF (30 mL) was stirred under nitrogen overnight at 120° C. The reaction mixture was cooled to rt and then diluted with 100 mL of water. The resulting solution was extracted with 3×50 mL of ethyl acetate. The combined organic layers was washed with 3×100 mL of brine, dried over anhydrous sodium sulfate, and concentrated under vacuum. The residue was purified on a silica gel column eluted with ethyl acetate/petroleum ether (1:20 to 1:5) to give 200 mg (8%) of 5-(oxan-4-ylsulfanyl) pyridine-2-carbonitrile as a yellow solid. $^1$H NMR (300 MHz, CDCl$_3$) δ 8.57 (1H, s), 7.71-7.67 (1H, d, J=8.4 Hz), 7.57-7.54 (1H, d, J=8.1 Hz), 3.99-3.98 (2H, m), 3.88-3.79 (1H, m), 3.53-3.46 (2H, m), 1.97-1.91 (2H, m), 1.77-1.68 (2H, m).

Step 4: 5-(Oxane-4-sulfonylpyridine-2-carbonitrile. To a solution of 5-(oxan-4-ylsulfanyl) pyridine-2-carbonitrile (200 mg, 0.91 mmol, 1.00 equiv) in chloroform (20 mL) was added m-chloroperbenzoic acid (782 mg, 4.53 mmol, 4.99 equiv) in portions at 0-5° C. The reaction mixture was stirred for 2 h at rt. The resulting solution was diluted with 100 mL of chloroform then washed sequentially with saturated sodium bisulfite solution (2×100 mL), saturated potassium carbonate solution (2×100 mL), and brine (2×100 mL). The organic layer was dried over anhydrous sodium sulfate and concentrated under vacuum to give 160 mg (70%) of 5-(oxane-4-sulfonyl)pyridine-2-carbonitrile as a white solid. TLC (2:1 petroleum ether/ethyl acetate): $R_f$=0.2.

Step 5: [5-(Oxane-4-sulfonyl)pyridin-2-yl]methanamine. To a solution of 5-(oxane-4-sulfonyl)pyridine-2-carbonitrile (160 mg, 0.63 mmol, 1.00 equiv) in methanol (20 mL) and ammonium hydroxide (0.5 mL) was added Raney-Ni (200 mg). The reaction mixture was stirred under 1 atmosphere of hydrogen for 10 min at rt. The catalyst was removed by filtration and the filtrate was concentrated under vacuum to give 100 mg (62%) of [5-(oxane-4-sulfonyl)pyridin-2-yl] methanamine as a blue solid. LC/MS (Method I, ESI): RT=0.88 min, m/z=257.0 [M+H]$^+$.

Step 6. A solution of furo[2,3-c]pyridine-2-carboxylic acid (35 mg, 0.21 mmol, 1.10 equiv), [5-(oxane-4-sulfonyl) pyridin-2-yl]methanamine (50 mg, 0.20 mmol, 1.00 equiv), EDCI (74.6 mg, 0.39 mmol, 1.99 equiv), triethylamine (59.2 mg, 0.59 mmol, 3.00 equiv), and HOBt (31.6 mg, 0.23 mmol, 1.20 equiv) in DMF (5 mL) was stirred overnight at rt. The reaction mixture was diluted with 50 mL of water. The resulting solution was extracted with 3×50 mL of ethyl acetate. The combined organic layers was washed with 3×100 mL of brine, dried over anhydrous sodium sulfate, and concentrated under vacuum. The residue was purified on a silica gel column eluted with dichloromethane/methanol (80:1 to 40:1) to give 3.3 mg (4%) of the title compound as an off-white solid. ¹H NMR (300 MHz, CD₃OD) δ 8.99-8.97 (m, 2H), 8.47-8.45 (d, J=5.4 Hz, 1H), 8.27-8.24 (dd, J=2.4, 8.4 Hz, 1H), 7.86-7.84 (dd, J=0.9, 5.4 Hz, 1H), 7.72-7.69 (d, J=8.4 Hz, 1H), 7.63 (s, 1H), 4.03-3.98 (m, 2H), 3.54-3.37 (m, 5H), 1.88-1.66 (m, 4H). LC/MS (Method A, ESI) RT=1.22 min, m/z=402.0 [M+H]⁺.

Example 57

2-Amino-5,7-dihydro-pyrrolo[3,4-d]pyrimidine-6-carboxylic acid 5-benzenesulfonyl-pyridin-2-ylmethyl)-amide

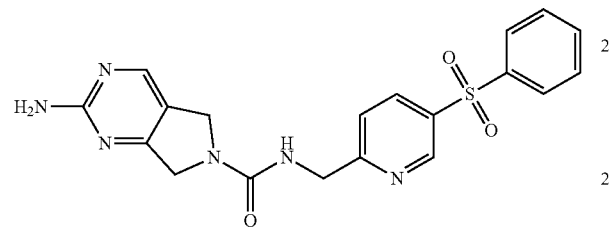

Step 1: 5-(Benzenesulfonyl) pyridine-2-carbonitrile. A mixture of 5-bromopyridine-2-carbonitrile (3 g, 16.39 mmol, 1.00 equiv), PhSO₂Na.2H₂O (3.96 g) and copper(I) iodide (310 mg, 1.63 mmol, 0.10 equiv) in DMSO (30 mL) was stirred under nitrogen for 2 h at 100° C. The reaction was quenched by the addition of 100 mL of water/ice. The crude product was collected by filtration and then dissolved in 50 mL of dichloromethane. The solid material was removed by filtration. The filtrate was concentrated under vacuum and the residue was purified on a silica gel column with ethyl acetate/petroleum ether (1:50) to give 2.5 g (62%) of 5-(benzenesulfonyl)pyridine-2-carbonitrile as a white solid. LC/MS (Method C, ESI): RT=1.37 min, m/z=245.0 [M+H]⁺.

Step 2: [5-(Benzenesulfonyl)pyridin-2-yl]methanamine. To a solution of 5-(benzenesulfonyl)pyridine-2-carbonitrile (500 mg, 2.05 mmol, 1.00 equiv) in ammonium hydroxide (1 mL) and methanol (10 mL) was added Raney-Ni (0.5 g). The reaction mixture was stirred under 1 atmosphere of hydrogen for 5 min at rt. The catalyst was removed by filtration. The filtrate was concentrated under vacuum and the residue was purified on a silica gel column with eluted chloroform/methanol (80:1 to 20:1) to give 0.3 g (59%) of [5-(benzenesulfonyl)pyridin-2-yl]methanamine as a green solid. LC/MS (Method H, ESI): RT 1.01 min, m/z=249.0 [M+H]⁺.

Step 3: N-[[5-(Benzenesulfonyl) pyridin-2-yl]methyl]carbamate. A solution of [5-(benzenesulfonyl)pyridin-2-yl]methanamine (100 mg, 0.40 mmol, 1.00 equiv) and 4-nitrophenyl chloroformate (81 mg, 0.40 mmol, 1.00 equiv) in toluene (20 mL) was refluxed for 2 h. The resulting mixture was concentrated under vacuum to give 0.18 g (crude) of 4-nitrophenyl N-[[5-(benzenesulfonyl)pyridin-2-yl]methyl]carbamate as a brown solid. LC/MS (Method C, ESI): RT=1.52 min, m/z=414.0 [M+H]⁺.

Step 4. A solution of 6,7-dihydro-5H-pyrrolo[3,4-d]pyrimidin-2-amine (commercially available, CAS Reg. No. 707539-41-1; see *Heterocycles* 2002, 56, 257-264) (180 mg, 1.32 mmol, 1.00 equiv) and 4-nitrophenyl N-[[5-(benzene-sulfonyl)pyridin-2-yl]methyl]carbamate (89 mg, 0.22 mmol, 0.16 equiv) in ethanol (25 mL) was stirred for 2 h at 80° C. The resulting mixture was concentrated under vacuum and the residue was purified on a silica gel column with dichloromethane/methanol (80:1) to give 10.2 mg (2%) of the title compound as an off-white solid. ¹H NMR (300 MHz, CD₃OD) δ 9.02-9.01 (d, J=2.1 Hz, 1H), 8.31-8.27 (dd, J=2.4, 8.1 Hz, 1H), 8.22 (s, 1H), 8.02-7.99 (m, 2H), 7.71-7.59 (m, 4H), 4.59-4.52 (m, 6H). LC/MS (Method H, ESI): RT=1.89 min, m/z=411.0 [M+H]⁺.

Example 91

Furo[2,3-c]pyridine-2-carboxylic acid [5-(4-pyrrolidin-1-yl-piperidine-1-sulfonyl)-pyridin-2-ylmethyl]-amide

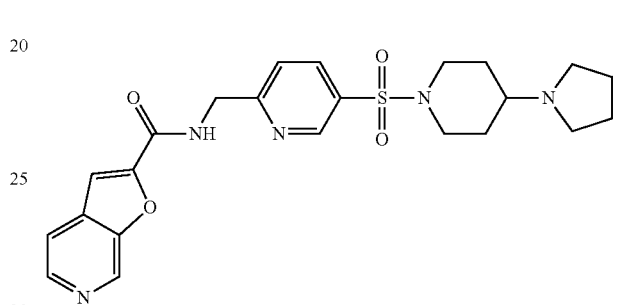

Step 1: 2-Chloro-5-[4-(pyrrolidin-1-yl)piperidine-1-sulfonyl]pyridine. To a stirred solution of 6-chloropyridine-3-sulfonyl chloride (1 g, 4.72 mmol, 1.00 equiv) and 4-(pyrrolidin-1-yl)piperidine (726.4 mg, 4.71 mmol, 1.00 equiv) in DMF (20 mL) at 0-5° C. was added triethylamine (1.43 g, 14.13 mmol, 3.00 equiv) dropwise. The reaction mixture was stirred overnight at rt. The resulting solution was diluted with dichloromethane (200 mL), then washed with 2×100 mL of water and 3×100 mL of brine. The organic layer was dried over anhydrous sodium sulfate and concentrated under vacuum to yield 1.5 g (96%) of 2-chloro-5-[4-(pyrrolidin-1-yl)piperidine-1-sulfonyl]pyridine as an off-white solid. LC/MS (Method B, ESI): RT=1.62 min, m/z=330.0 [M+H]⁺.

Step 2: 5-[4-(Pyrrolidin-1-yl)piperidine-1-sulfonyl]pyridine-2-carbonitrile. A solution of 2-chloro-5-[4-(pyrrolidin-1-yl)piperidine-1-sulfonyl]pyridine (1.5 g, 4.55 mmol, 1.00 equiv), zinc cyanide (800 mg, 6.81 mmol, 1.50 equiv), tetrakis(triphenylphosphine)palladium(0) (530 mg, 0.46 mmol, 0.10 equiv) in DMF (50 mL) was stirred under nitrogen for 4 h at 85° C. The reaction mixture was cooled to rt and then quenched by the addition of 150 mL of water. The precipitated crude product was collected by filtration. The solid was dissolved in a small quantity of dichloromethane and purified on a silica gel column eluted with dichloromethane/methanol (1:50 to 1:10) to give 330 mg (23%) of 5-[4-(pyrrolidin-1-yl)piperidine-1-sulfonyl]pyridine-2-carbonitrile as an off-white solid. LC/MS (Method C, ESI): RT=1.09 min, m/z=321.0 [M+H]⁺.

Step 3 [5-[4-(pyrrolidin-1-yl)piperidine-1-sulfonyl]pyridin-2-yl]methanamine. To a solution of 5-[4-(pyrrolidin-1-yl)piperidine-1-sulfonyl]pyridine-2-carbonitrile (330 mg, 1.03 mmol, 1.00 equiv) in methanol (150 mL) was added Raney-Ni (1 g) and ammonium hydroxide (3 mL, 28-30% aqueous solution). The reaction mixture was stirred under 1 atmosphere of hydrogen for 5 min at rt. The catalyst was removed by filtration. The filtrate was concentrated under vacuum to give 180 mg (54%) of [5-[4-(pyrrolidin-1-yl)piperidine-1-sulfonyl]pyridin-2-yl]methanamine as a blue solid. LC/MS (Method I, ESI): RT=0.85 min, m/z=325.0 [M+H]+.

Step 4: N-([5-[4-(Pyrrolidin-1-yl)piperidine-1-sulfonyl]pyridin-2-yl]methyl)furo[2,3-c]pyridine-2-carboxamide. A solution of [5-[4-(pyrrolidin-1-yl)piperidine-1-sulfonyl]pyridin-2-yl]methanamine (72 mg, 0.22 mmol, 1.00 equiv), furo[2,3-c]pyridine-2-carboxylic acid (40 mg, 0.25 mmol, 1.10 equiv), EDCI (85 mg, 0.44 mmol, 2.00 equiv), HOBt (36 mg, 0.27 mmol, 1.20 equiv), and triethylamine (67.3 mg, 0.67 mmol, 3.00 equiv) in DMF (10 mL) was stirred for 1.5 h at rt. The reaction was then quenched by the addition of 50 mL of water and the resulting solution was extracted with 3×50 mL of ethyl acetate. The combined organic layers were washed with 3×100 mL of brine, dried over anhydrous sodium sulfate, and then concentrated under vacuum. The residue was purified on a silica gel column eluted with dichloromethane/methanol (50:1 to 20:1) to give 14.3 mg (14%) of the title compound as a light yellow solid LC/MS (Method H, ESI): RT=1.01 min, z=470.0 [M+H]+. 1H NMR (400 MHz, DMSO-d6) δ 9.69-9.65 (t, J=6 Hz, 1H), 9.08 (s, 1H), 8.85-8.84 (d, J=2.1 Hz, 1H), 8.50-8.48 (d, J=5.1 Hz, 1H), 8.15-8.11 (dd, J=2.4, 8.4 Hz, 1H), 7.85-7.83 (d, J=5.1 Hz, 1H), 7.69-7.62 (d, J=8.1 Hz, 2H), 4.72-4.70 (d, J=6.0 Hz, 2H), 3.50-3.47 (d, J=9.6 Hz, 2H), 2.50-2.49 (m, 6H), 2.05-2.01 (m, 1H), 1.87-1.84 (d, J=10.8 Hz, 2H), 1.62 (s, 4H), 1.45-1.38 (m, 2H).

Example 105

Furo[2,3-c]pyridine-2-carboxylic acid {5-[1-(tetra-hydro-pyran-4-yl)-piperidine-4-sulfonyl]-pyridin-2-ylmethyl}-amide

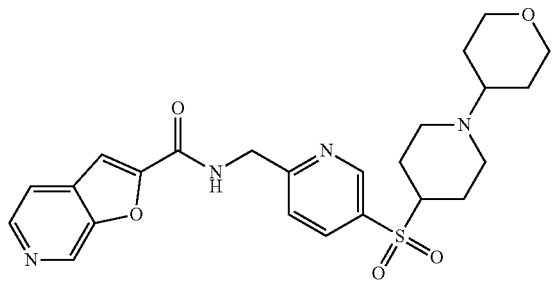 [SMILES: O=C(NCc1ccc(S(=O)(=O)C2CCN(C3CCOCC3)CC2)cn1)c1cc2ccncc2o1]

Step 1. N-[[5-(Piperidine-4-sulfonyl)pyridin-2-yl]methyl]furo[2,3-c]pyridine-2-carboxamide trifluoroacetic acid salt. A solution of tert-butyl 4-[6-([furo[2,3-c]pyridin-2-ylformamido]methyl)pyridine-3-sulfonyl]piperidine-1-carboxylate (500 mg, 1.00 mmol, 1.00 equiv) in dichloromethane (5 mL) and TFA (5 mL) was stirred for 1 h at rt. The resulting mixture was concentrated under vacuum to give 0.8 g of N-[[5-(piperidine-4-sulfonyl)pyridin-2-yl]methyl]furo[2,3-c]pyridine-2-carboxamide trifluoroacetic acid salt as a yellow oil. TLC (5:1 dichloromethane/methanol) Rf=0.2.

Step 2. A mixture of N-[[5-(piperidine-4-sulfonyl)pyridin-2-yl]methyl]furo[2,3-c]pyridine-2-carboxamide trifluoroacetic acid salt (320 mg, 0.62 mmol, 1.00 equiv), oxan-4-one (160 mg, 1.60 mmol, 2.57 equiv), sodium triacetoxyborohydride (160 mg, 0.75 mmol, 1.21 equiv), and 4 Å molecular sieves (1 g) in acetic acid (0.8 mL) and dichloromethane (10 mL) was stirred overnight at rt The solid material was removed by filtration. The filtrate was concentrated under vacuum and then redissolved in 50 mL of 0.1 M HCl. The pH of the solution was adjusted to 8 with 0.1 M NaOH. The solution was extracted with 3×50 mL of dichloromethane. The combined organic layers was washed with 3×50 mL of brine, dried over anhydrous sodium sulfate, and concentrated under vacuum. The residue was purified by preparative TLC eluted with dichloromethane/methanol (15:1) to give 60 mg (20%) of the title compound as a yellow solid. 1H NMR (300 MHz, CD3OD) δ 9.00 (s, 2H), 8.54 (s, 1H), 8.48-8.44 (d, J=12.9 Hz, 1H), 7.79 (s, 1H), 7.75-7.64 (m, 2H), 4.88 (s, 2H), 4.04-4.01 (d, 2H), 3.72-3.40 (m, 6H), 2.85-2.67 (m, 2H), 2.23-2.03 (m, 2H), 2.03-1.89 (m, 4H), 1.68-1.64 (m, 2H). LC/MS (Method H, ESI): RT=0.97 min, m/z=485.0 [M+H]−.

Example 110

N-[[5-(3-ethylsulfonylphenyl sulfonyl-2-pyridyl]methyl]furo[2,3-c]pyridine-2-carboxamide

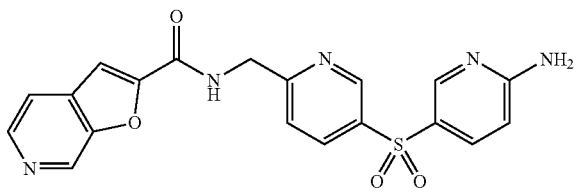 [SMILES: Nc1ccc(S(=O)(=O)c2ccc(CNC(=O)c3cc4ccncc4o3)nc2)cn1]

Step 1. tert-Butyl N-[5-[(lithiooxy)sulfinyl]pyridin-2-yl]carbamate. To a solution of tert-butyl N-(5-bromopyridin-2-yl)carbamate (3.0 g, 10.98 mmol, 1.00 equiv) in THF (30 mL) under nitrogen was added a 2.5 M solution of n-butyllithium (5.3 mL, 13.25 mmol, 1.21 equiv) in hexanes dropwise with stirring at −80° C. The reaction mixture was stirred at −80° C. for 30 min. Sulfur dioxide gas was bubbled into the mixture until all the starting material was consumed. The resulting solution was warmed to rt then diluted with 30 mL of ether. The precipitate was collected by filtration and then washed with ether (2×5 mL) to give 3.8 g of the title compound as a white solid. LCMS (Method J, ESI): RT=1.00 min, m/z=259.0 [M+2H−Li]+.

Step 2. 5-(6-Aminopyridine-3-sulfonyl)pyridine-2-carbonitrile. A solution of tert-butyl N-[5-[(lithiooxy)sulfinyl]pyridin-2-yl]carbamate (1.75 g, 6.62 mmol, 1.00 equiv) and 5-bromopyridine-2-carbonitrile (1 g, 5.46 mmol, 0.83 equiv) in DMSO (40 mL) was stirred for 2 h at 110° C. The reaction mixture was cooled to rt and then quenched with 40 mL of water. The resulting solution was extracted with 3×100 mL of dichloromethane. The combined organic layers was washed with 2×80 mL of brine, dried over anhydrous sodium sulfate and concentrated under vacuum. The residue was purified on a silica gel column eluted with dichloromethane/methanol (50:1) to give 0.9 g (52%) of the title compound as a white solid. LCMS (Method H, ESI): RT=1.13 min, m/z=261.0 [M+H]+.

Step 3. 5-[6-(Aminomethyl)pyridine-3-sulfonyl]pyridin-2-amine. To a solution of 5-(6-aminopyridine-3-sulfonyl)pyridine-2-carbonitrile (500 mg, 1.92 mmol, 1.00 equiv) in methanol (250 mL) was added Raney nickel (0.5 g). The reaction mixture was stirred under 1 atm of hydrogen at rt for 30 min. The catalyst was removed by filtration. The filtrate was concentrated under vacuum to yield 800 mg of as a blue solid. LCMS (Method I, ESI): RT=0.84 min, m/z=265.0 [M+H]+.

Step 4. A solution of furo[2,3-c]pyridine-2-carboxylic acid (277 mg, 1.70 mmol, 1.50 equiv), 5-[6-(aminomethyl)pyridine-3-sulfonyl]pyridin-2-amine (300 mg, 1.14 mmol, 1.00 equiv), EDCI (543 mg, 2.83 mmol, 2.50 equiv), HOBt (153 mg, 1.13 mmol, 1.00 equiv), and triethylamine (268 mg, 2.65 mmol, 2.33 equiv) in DMF (10 mL) was stirred for 3 h at rt. The reaction was quenched with 20 mL of water and then extracted with 3×50 mL of dichloromethane. The combined organic layers were washed with 2×20 mL of brine, dried over anhydrous sodium sulfate, and concentrated under vacuum. The crude product was purified by preparative HPLC (Waters 2767-2(HPLC-08); Column, Xbridge Shield RP 18, 5 um, 19*150 mm; mobile phase, water with 50 mmol $NH_4HCO_3$ and $CH_3CN$ (10.0% $CH_3CN$ up to 28.0% in 2 min, up to 46.0% in 10 min, up to 100.0% in 1 min, down to 10.0% in 1 min); Detector, UV 254 nm) to afford 8.5 mg of the title compound as a white solid. LCMS (Method H, ESI): RT=1.04 min, m/z=410.1 [M+H]$^+$. $^1$H NMR (400 MHz, DMSO-d$_6$) δ 9.64 (t, J=12.0 Hz, 1H), 9.07 (s, 1H), 9.01 (s, 1H), 8.50-8.47 (m, 2H), 8.26 (dd, J=2.4, 8.4 Hz, 1H), 7.84-7.80 (m, 2H), 7.67 (s, 1H), 7.58 (d, J=8.4 Hz, 1H), 7.16 (s, 1H), 6.49 (d, J=8.8 Hz, 1H), 4.66 (d, J=6.0 Hz, 2H), 2.54-2.50 (m, 1H).

Examples 159 and 160

N-[[5-(3,5-difluorophenyl)sulfinyl-2-pyridyl]methyl]-1,3-dihydropyrrolo[3,4-c]pyridine-2-carboxamide (enantiomers 1 and 2)

The title compounds were prepared according to Example 116 (see Table below) and the resulting mixture of enantiomers was separated by chiral chromatography. LC/MS data were comparable to those obtained for Example 116.

Example 178

N-[[5-(benzenesulfonyl)-2-pyridyl]methyl]-4,6-dihydro-1H-pyrrolo[3,4-c]pyrazole-5-carboxamide

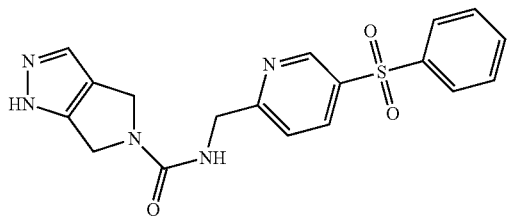 [SMILES: O=C(NCc1ccc(S(=O)(=O)c2ccccc2)cn1)N1Cc2cn[nH]c2C1]

Step 1. 5-(Benzenesulfonyl)pyridine-2-carbonitrile. A solution of 5-bromopyridine-2-carbonitrile (5 g, 27.32 mmol, 1.00 equiv) and sodium benzenesulfinate dehydrate (8.2 g, 41.00 mmol, 1.50 equiv) in DMSO (50 mL) was stirred for 4 h at 120° C. The reaction mixture was cooled to rt and the product was precipitated by the addition of an ice/water (1000 mL) mixture. The precipitate was collected by filtration and air-dried to give 6.1 g (91%) of 5-(benzenesulfonyl)pyridine-2-carbonitrile as a white solid LC/MS (Method O, ESI): RT=1.42 min, m/z=286.0 [M+CH$_3$CN+H]$^+$.

Step 2. [5-(Benzenesulfonyl)pyridin-2-yl]methanamine. A mixture of 5-(benzenesulfonyl)pyridine-2-carbonitrile (1.2 g, 4.91 mmol, 1.00 equiv), Raney-Ni (1 g) and conc. ammonium hydroxide (1.2 mL) in MeOH (400 mL) was stirred under 1 atmosphere of H$_2$ at rt for 10 min. The catalyst was removed by filtration. The filtrate was concentrated under vacuum and the residue was purified on a silica gel column eluted with DCM/MeOH (50.1) to yield 0.65 g (53%) of [5-(benzenesulfonyl)pyridin-2-yl]methanamine as a green solid. LC/MS (Method J, ESI): RT=1.05 min, m/z=249.0 [M+H]$^+$.

Step 3. 4-Nitrophenyl N-[[5-(benzenesulfonyl)pyridin-2-yl]methyl]carbamate. To a stirred solution of [5-(benzenesulfonyl)pyridin-2-yl]methanamine (200 mg, 0.81 mmol, 1.00 equiv) and 4-nitrophenyl chloroformate (163 mg, 0.81 mmol, 1.00 equiv) in DCM (5 mL) at rt was added triethylamine (244 mg, 2.41 mmol, 2.99 equiv) dropwise. The resulting solution was stirred for another 3 h at rt. Water (10 mL) was added to quench the reaction. The organic layer was collected and the aqueous layer was extracted with 10 mL of DCM. The combined organic layers were dried over anhydrous sodium sulfate and concentrated under vacuum to afford 0.3 g (90%) of 4-nitrophenyl N-[[5-(benzenesulfonyl)pyridin-2-yl]methyl]carbamate as a brown solid. TIC: petroleum ether:ethyl acetate=2:1, R$_f$=0.3.

Step 4. A solution of 4-nitrophenyl N-[[5-(benzenesulfonyl)pyridin-2-yl]methyl]carbamate (300 mg, 0.73 mmol, 1.00 equiv), 1H,4H,5H,6H-pyrrolo[3,4-c]pyrazole dihydrochloride (132 mg, 0.73 mmol, 1.00 equiv) and triethylamine (150 mg, 1.48 mmol, 2.04 equiv) in ethanol (10 mL) was stirred at 80° C. overnight. The reaction mixture was cooled to rt and 10 mL of H$_2$O was added. The resulting solution was extracted with 3×20 mL of ethyl acetate. The combined organic layers was washed with 3×20 mL of brine, dried over anhydrous sodium sulfate and concentrated under vacuum. The residue was purified by Prep-HPLC (1#-Pre-HPLC-016 (Waters): Column, SunFire Prep C18, 19*150 mm 5 um; mobile phase, water with 0.05% NH$_4$HCO, and CH$_3$CN (5% CH$_3$CN up to 45% in 7 min); Detector, UV 254 nm) to give 63.5 mg (23%) of N-[[5-(benzenesulfonyl)pyridin-2-yl]methyl]-1H,4H,5H,6H-pyrrolo[3,4-c]pyrazole-5-carboxamide as a light yellow solid. LC/MS (Method C, ESI): RT=2.56 min, m/z=383.8 [M+H]. $^1$H NMR (300 MHz, CD$_3$OD, ppm): δ 9.03 (d, J=2.4 Hz, 1H), 8.30 (dd, J=8.4, 2.4 Hz, 1H), 8.05 (t, 2H), 7.75-7.55 (m, 4H), 7.48 (s, 1H), 4.65-4.45 (m, 6H).

The following example compounds were prepared using methods analogous to those described for the referenced synthetic method.

| Ex. | Synthetic Method |
| --- | --- |
| 115 | Example 110 |
| 116 | Examples 28 and 29 |
| 117 | Example 110 |
| 118 | Example 26 |
| 119 | Example 105 |
| 120 | Example 49 |
| 121 | Example 105 |
| 122 | Example 105 |
| 123 | Example 110 |
| 124 | Example 110 |
| 125 | Example 110 |
| 126 | Example 91 |
| 127 | Example 91 |
| 128 | Example 105 |
| 129 | Example 105 |
| 130 | Example 105 |
| 131 | Example 105 |
| 132 | Example 105 |
| 133 | Example 8 |
| 134 | Example 110 |
| 135 | Example 110 |

| Ex. | Synthetic Method |
|---|---|
| 136 | Example 110 |
| 137 | Example 110 |
| 138 | Example 110 |
| 139 | Example 8 |
| 140 | Example 110 |
| 141 | Example 91 |
| 142 | Example 91 |
| 143 | Example 105 |
| 144 | Example 8 |
| 145 | Example 110 |
| 146 | Example 110 |
| 147 | Example 110 |
| 148 | Example 91 |
| 149 | Example 91 |
| 150 | Example 110 |
| 151 | Example 22 |
| 152 | Example 105 |
| 153 | Example 105 |
| 154 | Example 110 |
| 155 | Example 22 |
| 156 | Example 22 |
| 157 | Example 110 |
| 158 | Example 49 |
| 161 | Example 105 |
| 162 | Example 105 |
| 163 | Example 110 |
| 164 | Example 110 |
| 165 | Example 110 |
| 166 | Example 105 |
| 167 | Example 8 |
| 168 | Example 110 |
| 169 | Example 110 |
| 170 | Example 110 |
| 171 | Example 110 |
| 172 | Example 26 |
| 173 | Example 26 |
| 174 | Example 110 |
| 175 | Example 110 |
| 176 | Example 110 |
| 177 | Example 110 |
| 179 | Example 178 |
| 180 | Example 178 |
| 181 | Example 105 |
| 182 | Example 8 |
| 183 | Example 22 |
| 184 | Example 22 |
| 185 | Example 22 |
| 186 | Example 22 |
| 187 | Example 8 |

Additional examples were prepared using methods analogous to those described above.

Analytical Characterization:

Each of the specifically exemplified compounds described herein was prepared using the methods described above, and were analyzed by LC/MS. Data for each compound, along with the LC/MS method used to generate the data, is provided in Tables 1a and 1b.

TABLE 1a

LC/MS Data for Example Compounds.

| Ex. | LC/MS Method | RT (min); m z |
|---|---|---|
| 1 | Method I | 1.58; 430.0 |
| 2 | Method B | 2.00; 430.0 |
| 3 | Method A | 2.16; 429.0 |
| 4 | Method G | 2.60; 429.0 |
| 5 | Method C | 1.36; 429.9 |
| 6 | Method A | 2.08; 395.0 |
| 7 | Method C | 1.33; 394.2 |
| 8 | Method J | 1.25; 393.9 |
| 9 | Method G | 1.28; 413.0 |
| 10 | Method H | 3.77; 461.0 |
| 11 | Method J | 1.34; 394.9 |
| 12 | Method C | 1.19; 394.9 |
| 13 | Method F | 1.43; 477.1 |
| 14 | Method G | 1.25; 413.1 |
| 15 | Method C | 1.39; 413.9 |
| 16 | Method F | 1.63; 462.1 |
| 17 | Method F | 1.39; 461.1 |
| 18 | Method F | 1.41; 462.1 |
| 19 | Method C | 1.79; 478.2 |
| 20 | Method I | 1.50; 478.0 |
| 21 | Method C | 1.58; 477.2 |
| 22 | Method F | 1.44; 462.1 |
| 23 | Method C | 1.60; 478.2 |
| 24 | Method B | 2.68; 414.0 |
| 25 | Method B | 3.87; 414.0 |
| 26 | Method H | 0.93; 401.0 |
| 27 | Method H | 0.89; 400.0 |
| 28 | Method K | 1.51; 414.1 |
| 29 | Method K | 1.51; 414.1 |
| 30 | Method C | 1.39; 478.3 |
| 31 | Method B | 1.94; 479.1 |
| 32 | Method H | 1.35; 424.0 |
| 33 | Method C | 2.36; 424.1 |
| 34 | Method H | 1.54; 424.0 |
| 35 | Method C | 1.33; 479.2 |
| 36 | Method H | 1.36; 397.0 |
| 37 | Method C | 2.92; 479.2 |
| 38 | Method I | 2.21; 479.0 |
| 39 | Method I | 3.28; 495.0 |
| 40 | Method H | 1.50; 414.0 |
| 41 | Method C | 1.98; 479.9 |
| 42 | Method D | 4.63; 484.0 |
| 43 | Method I | 1.52; 425.0 |
| 44 | Method J | 1.24; 425.1 |
| 45 | Method J | 1.30; 442.1 |
| 46 | Method I | 1.07; 492.0 |
| 47 | Method H | 1.05; 493.0 |
| 48 | Method B | 2.77; 492.1 |
| 49 | Method I | 2.58; 463.0 |
| 50 | Method I | 2.56; 479.0 |
| 51 | Method A | 1.22; 402.0 |
| 52 | Method C | 2.01; 480.0 |
| 53 | Method C | 1.76; 417.9 |
| 54 | Method C | 1.76; 496.0 |
| 55 | Method G | 1.27; 413.1 |
| 56 | Method E | 1.32; 473.0 |
| 57 | Method H | 1.89; 411.0 |
| 58 | Method A | 1.38; 413.0 |
| 59 | Method I | 1.25; 401.0 |
| 60 | Method A | 1.20; 401.0 |
| 61 | Method J | 1.29; 426.2 |
| 62 | Method J | 1.28; 426.1 |
| 63 | Method J | 1.12; 398.1 |
| 64 | Method C | 2.35; 469.8 |
| 65 | Method C | 1.33; 452.9 |
| 66 | Method C | 1.37; 453.8 |
| 67 | Method H | 1.24; 438.0 |
| 68 | Method B | 1.83; 493.1 |
| 69 | Method H | 1.21; 438.0 |
| 70 | Method I | 4.46; 454.0 |
| 71 | Method E | 1.05; 456.0 |
| 72 | Method I | 1.05; 402.0 |
| 73 | Method C | 1.38; 430.9 |
| 74 | Method H | 1.22; 443.0 |
| 75 | Method H | 1.29; 460.0 |
| 76 | Method J | 1.32; 442.1 |
| 77 | Method H | 1.41; 462.0 |
| 78 | Method I | 2.25; 479.0 |
| 79 | Method A | 2.01; 463.0 |
| 80 | Method H | 1.18; 427.0 |
| 81 | Method I | 2.36; 463.0 |
| 82 | Method A | 1.40; 461.8 |
| 83 | Method G | 1.52; 437.2 |
| 84 | Method J | 1.38; 438.1 |
| 85 | Method L | 1.81; 497.1 |
| 86 | Method C | 1.94; 446.8 |

TABLE 1a-continued

LC/MS Data for Example Compounds.

| Ex. | LC/MS Method | RT (min); m z |
|---|---|---|
| 87 | Method H | 1.35; 446.0 |
| 88 | Method G | 1.93; 497.2 |
| 89 | Method E | 1.42; 463.0 |
| 90 | Method E | 1.49; 462.0 |
| 91 | Method H | 1.01; 470.0 |
| 92 | Method C | 1.22; 407.8 |
| 93 | Method J | 1.27; 444.0 |
| 94 | Method H | 1.20; 400.0 |
| 95 | Method C | 3.33; 428.4 |
| 96 | Method K | 1.44; 485.1 |
| 97 | Method C | 2.15; 479.9 |
| 98 | Method H | 1.18; 445.0 |
| 99 | Method J | 1.04; 399.1 |
| 100 | Method H | 1.27; 413.0 |
| 101 | Method K | 1.57; 461.0 |
| 102 | Method F | 4.69; 441.0 |
| 103 | Method C | 1.00; 457.0 |
| 104 | Method K | 1.14; 485.2 |
| 105 | Method H | 0.97; 485.0 |
| 106 | Method K | 1.87; 486.1 |
| 107 | Method A | 4.09; 463.0 |
| 108 | Method I | 1.14; 472.0 |
| 109 | Method C | 1.85; 485.9 |
| 110 | Method H | 1.04; 410.1 |
| 111 | Method A | 1.40; 483.0 |
| 112 | Method K | 2.42; 454.2 |
| 113 | Method G | 1.05; 493.2 |
| 114 | Method K | 1.04; 487.1 |

TABLE 1b

LC/MS Data for Example Compounds.

| Ex. | RT | m z | LC/MS Method |
|---|---|---|---|
| 115 | 1.85 | 485.9 | C |
| 116 | 1.43 | 415.1 | K |
| 117 | 1.07 | 410.1 | H |
| 118 | 1.30 | 466.8 | C |
| 119 | 2.32 | 486.3 | K |
| 120 | 1.91 | 447.0 | C |
| 121 | 1.26 | 474 | A |
| 122 | 1.09 | 473 | H |
| 123 | 1.80 | 479.0 | I |
| 124 | 1.46 | 472.1 | K |
| 125 | 1.32 | 481.0 | C |
| 126 | 1.68 | 487.1 | B |
| 127 | 1.73 | 486.1 | B |
| 128 | 1.65 | 471.2 | K |
| 129 | 1.37 | 472.0 | C |
| 130 | 1.47 | 471.0 | A |
| 131 | 1.38 | 483.1 | A |
| 132 | 1.43 | 483.0 | A |
| 133 | 2.42 | 454.1 | K |
| 134 | 1.33 | 472.1 | K |
| 135 | 2.21 | 493.2 | C |
| 136 | 1.40 | 487.1 | K |
| 137 | 5.19 | 471.1 | G |
| 138 | 1.37 | 470 | H |
| 139 | 2.34 | 454.1 | C |
| 140 | 2.60 | 427.0 | B |
| 141 | 1.23 | 479.9 | C |
| 142 | 1.83 | 459.1 | B |
| 143 | 1.95 | 484.1 | B |
| 144 | 2.30 | 442.1 | C |
| 145 | 1.55 | 457.1 | K |
| 146 | 1.62 | 458.1 | K |
| 147 | 1.52 | 459.1 | K |
| 148 | 1.62 | 471.2 | K |
| 149 | 1.32 | 470 | E |
| 150 | 2.20 | 411.1 | K |
| 151 | 2.53 | 419.1 | R |
| 152 | 1.43 | 482.1 | R |

TABLE 1b-continued

LC/MS Data for Example Compounds.

| Ex. | RT | m z | LC/MS Method |
|---|---|---|---|
| 153 | 2.12 | 483.1 | R |
| 154 | 1.40 | 477.8 | C |
| 155 | 2.17 | 417.8 | C |
| 156 | 1.53 | 418.8 | C |
| 157 | 2.81 | 478.9 | C |
| 158 | 2.57 | 419.8 | C |
| 161 | 1.05 | 483.9 | C |
| 162 | 0.97 | 485.0 | I |
| 163 | 1.34 | 463.0 | J |
| 164 | 1.19 | 429.0 | J |
| 165 | 1.24 | 463.0 | J |
| 166 | 1.88 | 482.0 | B |
| 167 | 2.76 | 480.0 | E |
| 168 | 1.93 | 461.9 | B |
| 169 | 1.39 | 428.8 | C |
| 170 | 2.28 | 463.8 | C |
| 171 | 1.50 | 425.1 | K |
| 172 | 1.13 | 440.3 | F |
| 173 | 1.48 | 425.2 | C |
| 174 | 2.25 | 419.8 | C |
| 175 | 1.27 | 425 | H |
| 176 | 1.73 | 412.1 | C |
| 177 | 1.51 | 413.1 | C |
| 179 | 1.47 | 398.2 | F |
| 180 | 1.17 | 391.2 | P |
| 181 | 1.09 | 440.3 | F |
| 182 | 1.94 | 431.2 | Q |
| 183 | 1.72 | 394.1 | F |
| 184 | 1.49 | 393.1 | K |
| 185 | 1.57 | 394.2 | Q |
| 186 | 1.80 | 410.2 | Q |
| 187 | 1.54 | 411.1 | Q |

It is understood that the person skilled in the art will be able to prepare the compounds of the present invention using methods known in the art along with the general method of synthesis described herein.

Assay 1: Biochemical Inhibition Assay

NAMPT protein purification. Recombinant His-tagged NAMPT was produced in *E. coli* cells, purified over a Ni column, and further purified over a size-exclusion column by XTAL Biostructures.

The NAMPT Enzymatic Reaction. The NAMPT enzymatic reactions were carried out in Buffer A (50 mM Hepes pH 7.5, 50 mM NaCl, 5 mM $MgCl_2$, and 1 mM THP) in 96-well V-bottom plates. The compound titrations were performed in a separate dilution plate by serially diluting the compounds in DMSO to make a 100× stock. Buffer A (89 μL) containing 33 nM of NAMPT protein was added to 1 μL of 100× compound plate containing controls (e.g. DMSO or blank). The compound and enzyme mixture was incubated for 15 min at rt, then 10 μL of 10× substrate and co-factors in Buffer A were added to the test well to make a final concentration of 1 μM NAM, 100 pM 5-Phospho-D-ribose 1-diphosphate (PRPP), and 2.5 mM Adenosine 5'-triphosphate (ATP). The reaction was allowed to proceed for 30 min at rt, then was quenched with the addition of 11 μL of a solution of formic acid and L-Cystathionine to make a final concentration of 1% formic acid and 10 μM L-Cystathionine. Background and signal strength was determined by addition (or non-addition) of a serial dilution of NMN to a pre-quenched enzyme and cofactor mix.

Quantification of NMN. A mass spectrometry-based assay was used to measure the NAMPT reaction product, β-nicotinamide mononucleotide (NMN), and the internal control (L-Cystathionine). NMN and L-Cystathionine were detected using the services of Biocius Lifesciences with the Rapid-Fire system. In short, the NMN and L-Cystathionine were bound to a graphitic carbon cartridge in 0.1% formic acid, eluted in 30% acetonitrile buffer, and injected into a Sciex 4000 mass spectrometer. The components of the sample were ionized with electrospray ionization and the positive ions were detected. The Q1 (parent ion) and Q3 (fragment ion) masses of NMN were 334.2 and 123.2, respectively. The Q1 and Q3 for L-Cystathionine were 223.1 and 134.1, respectively. The fragments are quantified and the analyzed by the following method.

Determination of $IC_{50}$ Values. First, the NMN signal was normalized to the L-Cystathionine signal by dividing the NMN signal by the L-Cystathionine signal for each well. The signal from the background wells were averaged and subtracted from the test plates. The compound treated cells were then assayed for percent inhibition by using this formula:

$$\%Inh=100-100*x/y$$

wherein x denotes the average signal of the compound treated wells and y denotes the average signal of the DMSO treated wells.

$IC_{50}$ values were then determined using the following formula:

$$IC_{50}=10\char`\^(LOG_{10}(X)+(((50-\%Inh \text{ at Cmpd Concentration } 1)/(XX-YY)*(LOG_{10}(X)-LOG_{10}(Y))))$$

wherein X denotes the compound concentration 1, Y denotes the compound concentration 2, XX denotes the % inhibition at compound concentration 1 (X), and YY denotes the % inhibition at compound concentration 2 (Y).

The compounds of this invention have $IC_{50}$ values that are preferably under 1 µM, more preferably under 0.1 µM, and most preferably under 0.01 µM. Results for the compounds tested in this assay are provided in Table 2 below.

Assay 2: In-Vitro Cell Proliferation Assay

Assay Method. A2780 cells were seeded in 96-well plates at $1\times10^3$ cells/well in 180 µL of culture medium (10% FBS, 1% Pen/Strep Amphotericin B, RPMI-1640) with and without the addition of either NMN or nicotinamide (NAM) After overnight incubation at 37° C. and 5% $CO_2$, the compound titrations were performed in a separate dilution plate by serially diluting the compounds in DMSO to make a 1000× stock. The compounds were then further diluted to 10 OX final concentration in culture media, whereupon 20 µL of each dilution was added to the plated cells with controls (e.g. DMSO and blank) to make a final volume of 200 µL. The final DMSO concentration in each well was 0.1%. The plates were then incubated for 72 h at 37° C. in a 5% $CO_2$ incubator. The number of viable cells was then assessed using sulforhodamine B (SRB) assay. Cells were fixed at 4° C. for 1 h with the addition of 50 µL 30% trichloroacetic acid (TCA) to make a final concentration of 6% TCA. The plates were washed four times with $H_2O$ and allowed to dry for at least 1 h, whereupon 100 µL of a 4% SRB in 1% acetic acid solution was added to each well and incubated at rt for at least 30 min. The plates were then washed three times with 1% acetic acid, dried, and treated with 100 µL of 10 mM Tris-Base solution. The plates were then read in a microplate reader at an absorbance of 570 nm. Background was generated on a separate plate with media only.

Determination of $IC_{50}$ Values. First, the signals from the background plate were averaged, then the background was subtracted from the test plates. The compound-treated cells were then assayed for % inhibition by using the following formula:

$$\%Inh=100-100*x/y$$

wherein x denotes the average signal of the compound-treated cells and y denotes the average signal of the DMSO-treated cells.

$IC_{50}$ values were then determined using the following formula:

$$IC_{50}=10\char`\^(LOG_{10}(X)+(((50-\%Inh \text{ at Cmpd Concentration } 1)/(XX-YY)*(LOG_{10}(X)-LOG_{10}(Y))))$$

wherein X denotes the compound concentration 1, Y denotes the compound concentration 2, XX denotes the % inhibition at compound concentration 1 (X), and YY denotes the % inhibition at compound concentration 2 (Y).

Specificity of Cytotoxicity. Inhibition of NAMPT could be reversed by the addition of NAM or NMN. The specificity of the compounds were determined via cell viability assay in the presence of the compound and either NAM or NMN Percent inhibitions were determined using the method given above.

The compounds of this invention have $IC_{50}$ values that are preferably under 1 µM, more preferably under 0.1 µM, and most preferably under 0.01 µM. Most preferable compounds of this invention are compounds that have $IC_{50}$ values in the enzymatic assay and the cell proliferation assay that are both under 1 µM, more preferably both of the values are under 0.1 µM, and most preferably both of the values are under 0.01 µM. Results for the compounds tested in this assay are provided in Table 2 (NT=not tested).

TABLE 2

Biochemical and Cell Proliferation Assay Results.

| Ex. | Biochemical ($IC_{50}$) [uM] | Cell Proliferation ($IC_{50}$) [uM] |
|---|---|---|
| 1 | 0.0563 | 0.0910 |
| 2 | 0.0065 | 0.0526 |
| 3 | 0.0199 | 0.0359 |
| 4 | 0.0071 | 0.0092 |
| 5 | 0.0056 | 0.0052 |
| 6 | 0.1080 | 2.0000 |
| 7 | 0.1500 | 0.1310 |
| 8 | 0.3520 | 0.4590 |
| 9 | 0.0553 | 0.2090 |
| 10 | 0.0127 | 0.0083 |
| 11 | 0.0461 | 0.3140 |
| 12 | 0.0191 | 0.8280 |
| 13 | 0.0085 | 0.0136 |
| 14 | 0.0365 | 0.0513 |
| 15 | 0.3570 | 0.3090 |
| 16 | 0.0394 | 0.0163 |
| 17 | 0.0191 | 0.0091 |
| 18 | 0.0047 | 0.0117 |
| 19 | 0.0537 | 0.0283 |
| 20 | 0.0034 | 0.0114 |
| 21 | 0.0118 | 0.0102 |
| 22 | 0.0066 | 0.0054 |
| 23 | 0.0061 | 0.0108 |
| 24 | 0.0162 | 0.2750 |
| 25 | 0.0211 | 0.0227 |
| 26 | 0.2040 | 2.0000 |
| 27 | 0.5720 | 0.9300 |
| 28 | 0.3400 | 2.0000 |
| 29 | 0.0048 | 0.0050 |
| 30 | 0.0072 | 0.0016 |
| 31 | 0.0193 | 0.0073 |
| 32 | 0.0061 | 0.0091 |
| 33 | 0.0046 | 0.0286 |
| 34 | 0.0599 | 0.1040 |
| 35 | 0.0086 | 0.0020 |
| 36 | 0.1010 | 0.4720 |
| 37 | 0.0035 | 0.0010 |
| 38 | 0.0021 | 0.0100 |
| 39 | 0.0028 | 0.0008 |
| 40 | 0.1340 | 2.0000 |

TABLE 2-continued

Biochemical and Cell Proliferation Assay Results.

| Ex. | Biochemical ($IC_{50}$) [uM] | Cell Proliferation ($IC_{50}$) [uM] |
| --- | --- | --- |
| 41 | 0.0190 | 0.0072 |
| 42 | 0.2490 | 0.0863 |
| 43 | 0.0273 | 0.0241 |
| 44 | 0.0299 | 0.0200 |
| 45 | 0.0072 | 0.0196 |
| 46 | 0.0069 | 0.0016 |
| 47 | 0.0022 | 0.0141 |
| 48 | 0.0023 | 0.0085 |
| 49 | 0.0037 | 0.0345 |
| 50 | 0.0034 | 0.0135 |
| 51 | 0.1700 | 0.3010 |
| 52 | 0.0020 | 0.0005 |
| 53 | 0.0921 | 0.5480 |
| 54 | 0.0017 | 0.0005 |
| 55 | 0.0159 | 0.0419 |
| 56 | 0.0259 | 0.0151 |
| 57 | NT | NT |
| 58 | 0.4070 | 0.9590 |
| 59 | 0.0275 | 0.2370 |
| 60 | 0.6930 | 1.3000 |
| 61 | 0.0065 | 0.0053 |
| 62 | 0.0555 | 0.0116 |
| 63 | NT | NT |
| 64 | NT | NT |
| 65 | 0.0307 | 0.0070 |
| 66 | 0.0028 | 0.0028 |
| 67 | 0.0026 | 0.0019 |
| 68 | NT | NT |
| 69 | 0.0054 | 0.0259 |
| 70 | 0.0485 | 0.0246 |
| 71 | NT | NT |
| 72 | NT | NT |
| 73 | 0.0173 | 0.0765 |
| 74 | 0.0078 | 0.0024 |
| 75 | 0.0022 | 0.0008 |
| 76 | 0.0031 | 0.0090 |
| 77 | 0.0176 | 0.0165 |
| 78 | 0.0594 | 0.5510 |
| 79 | 0.0205 | 0.1240 |
| 80 | 0.0227 | 0.0832 |
| 81 | 0.0123 | 0.0185 |
| 82 | 0.0723 | 0.3300 |
| 83 | 0.0091 | 0.0073 |
| 84 | 0.0278 | 0.0204 |
| 85 | 0.0329 | 0.0097 |
| 86 | 0.3540 | 2.0000 |
| 87 | 0.0177 | 0.0152 |
| 88 | 0.0059 | 0.0020 |
| 89 | 0.0080 | 0.0186 |
| 90 | 0.0162 | 0.0255 |
| 91 | 0.0474 | 0.0457 |
| 92 | 0.0339 | 0.0568 |
| 93 | 0.0049 | 0.00116 |
| 94 | 0.0113 | 0.0273 |
| 95 | 0.0377 | 0.234 |
| 96 | 0.0193 | 0.0381 |
| 97 | 0.0059 | 0.00423 |
| 98 | 0.0066 | 0.00497 |
| 99 | 0.0547 | 1.2 |
| 100 | 0.0111 | 0.0766 |
| 101 | 0.0315 | 0.0402 |
| 102 | 0.0693 | 0.0256 |
| 103 | 0.0552 | 0.0389 |
| 104 | 0.0679 | 0.116 |
| 105 | 0.0543 | 0.0286 |
| 106 | 0.1350 | 0.328 |
| 107 | 0.7310 | 1.3 |
| 108 | 0.0277 | 0.358 |
| 109 | 0.0068 | 0.0151 |
| 110 | 0.0133 | 0.0259 |
| 111 | 0.0030 | 0.101 |
| 112 | 0.00099 | 0.00106 |
| 113 | 0.000916 | 0.000488 |
| 114 | 0.00212 | 0.134 |
| 115 | 0.0068 | 0.0151 |
| 116 | 0.0155 | 0.00892 |
| 117 | 0.0133 | 0.0259 |
| 118 | 0.0761 | 0.0122 |
| 119 | 0.0375 | 0.0145 |
| 120 | 0.0117 | 0.00759 |
| 121 | 0.0682 | 2.0 |
| 122 | 0.103 | 0.0463 |
| 123 | 0.0218 | 0.0191 |
| 124 | 0.013 | 0.0189 |
| 125 | 0.014 | 0.0102 |
| 126 | 0.0684 | 0.056 |
| 127 | 0.0492 | 0.0313 |
| 128 | 0.073 | 0.0254 |
| 129 | 0.0327 | 0.0363 |
| 130 | 0.0398 | 0.0507 |
| 131 | 0.00524 | 0.0244 |
| 132 | 0.0030 | 0.101 |
| 133 | 0.00099 | 0.00106 |
| 134 | 0.0168 | 0.446 |
| 135 | 0.018 | 0.0344 |
| 136 | 0.00212 | 0.134 |
| 137 | 0.0568 | 0.0816 |
| 138 | 0.00945 | 0.00284 |
| 139 | 0.0147 | 0.00311 |
| 140 | 0.0118 | 0.0372 |
| 141 | 0.207 | 0.0717 |
| 142 | 0.22 | 0.255 |
| 143 | 0.111 | 0.0613 |
| 144 | 0.0262 | 0.0415 |
| 145 | 0.0101 | 0.00287 |
| 146 | 0.00565 | 0.00303 |
| 147 | 0.00683 | 0.00597 |
| 148 | 0.0757 | 0.0852 |
| 149 | 0.619 | 1.86 |
| 150 | 0.0992 | 0.678 |
| 151 | 0.0552 | 0.0546 |
| 152 | 0.247 | 0.106 |
| 153 | 1.74 | 1.34 |
| 154 | 0.0398 | 0.0465 |
| 155 | 0.074 | 0.0897 |
| 156 | 0.452 | 0.94 |
| 157 | 0.29 | 0.217 |
| 158 | 0.156 | 2.0 |
| 159 | 0.635 | 2.0 |
| 160 | 0.0201 | 0.0196 |
| 161 | 0.253 | 0.0528 |
| 162 | 1.83 | 0.295 |
| 163 | 0.0495 | 0.0253 |
| 164 | 0.143 | 0.0494 |
| 165 | 0.217 | 0.0644 |
| 166 | 0.224 | 0.091 |
| 167 | 0.023 | 0.0067 |
| 168 | 0.0608 | 0.0149 |
| 169 | 0.0664 | 0.0269 |
| 170 | 0.0491 | 0.0254 |
| 171 | 0.062 | 0.0512 |
| 172 | 0.249 | 0.106 |
| 173 | 0.202 | 0.0631 |
| 174 | 0.217 | 0.116 |
| 175 | 0.125 | 0.122 |
| 176 | 0.0542 | 0.0588 |
| 177 | 0.032 | 0.264 |
| 178 | 2.0 | 2.0 |
| 179 | 1.38 | 2.0 |
| 180 | 0.562 | 2.0 |
| 181 | NT | NT |
| 182 | 0.0251 | 0.0405 |
| 183 | 0.0381 | 0.139 |
| 184 | 0.0992 | 2.0 |
| 185 | 0.0202 | 0.495 |
| 186 | 0.125 | 0.918 |
| 187 | 0.433 | 2.0 |

While the present invention has been described in conjunction with the specific embodiments set forth above,

The invention claimed is:
1. A compound of Formula (I):

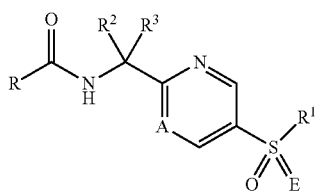

wherein:
A is CH or N;
E is O or is absent;
R is (a) a bicyclic heteroaryl comprising one or more heteroatom ring members independently selected from N, S or O, wherein said bicyclic heteroaryl is unsubstituted or is substituted with one or more substituents selected from the group consisting of deuterium, amino, alkylamino, dialkylamino, alkyl, halo, cyano, haloalkyl, hydroxy, hydroxyalkyl, and alkoxy; and wherein one or more N ring members of said bicyclic heteroaryl is optionally an N-oxide; or
(b) a five- or six-membered nitrogen-linked heterocycloalkyl ring fused to a phenyl or monocyclic heteroaryl, wherein said phenyl or heteroaryl is unsubstituted or is substituted with one or more substituent selected from the group consisting of deuterium, amino, alkylamino, dialkylamino, alkyl, halo, cyano, haloalkyl, hydroxy, hydroxyalkyl, and alkoxy;
$R^1$ is (1) $R^m$ or -alkylenyl-$R^m$, where $R^m$ is cycloalkyl, heterocycloalkyl, phenyl, or monocyclic heteroaryl;
wherein each of said cycloalkyl, heterocycloalkyl, phenyl, and heteroaryl is unsubstituted or is substituted with one or more substituents $R^x$;
wherein each $R^x$ substituent is independently selected from the group consisting of: deuterium, halo, hydroxy, hydroxyalkyl, cyano, —NR$^a$R$^b$, -alkylenyl-NR$^a$R$^b$, oxo, alkyl, cyanoalkyl, haloalkyl, alkoxy, —S-alkyl, haloalkoxy, alkoxyalkyl-, alkenyl, alkynyl, —C(O)alkyl, —C(O)alkyl-O-alkyl, —CO$_2$alkyl, —CO$_2$H, —CONH$_2$, —C(O)NH(alkyl), —C(O)NH(haloalkyl), —C(O)N(alkyl)$_2$, —C(O)NH(cycloalkyl), arylalkyl-, arylalkoxy-, aryloxy-, cycloalkyl, cycloalkyloxy, (cycloalkyl)alkyl, heterocycloalkyl, aryl, (heterocycloalkyl)alkyl-, (heterocycloalkyl)alkoxy-, —C(O)cycloalkyl, —C(O)heterocycloalkyl, heteroaryl, (heteroaryl)alkyl-, —S(O)-alkyl, —SO$_2$-alkyl, —SO$_2$-aryl, —SO$_2$-fluoroalkyl, —N(R$^c$)—C(O)-alkyl, —N(R$^c$)—C(O)-aryl, —N(R$^c$)—CO$_2$-alkyl, —SO$_2$NH$_2$, —SO$_2$NH(alkyl), —SO$_2$N(alkyl)$_2$, —SO$_2$NH(cycloalkyl), and —N(H)(SO$_2$alkyl), or two adjacent $R^x$ substituents on a phenyl or heteroaryl $R^m$ groups taken together form methylenedioxy,
wherein each of said cycloalkyl, heterocycloalkyl, aryl, and heteroaryl within $R^x$ is unsubstituted or is substituted with one or more substituents independently selected from the group consisting of deuterium, alkyl, halo, hydroxy, cyano, alkoxy, amino, —C(O)alkyl, and —CO$_2$alkyl;
wherein R$^a$ and R$^b$ are each independently H, alkyl, alkoxy, alkoxyalkyl, cyanoalkyl, or haloalkyl; and
R$^c$ is H, alkyl or arylalkyl-;
(2) alkyl unsubstituted or substituted with one or more substituents selected from the group consisting of deuterium, halo, hydroxy, cyano, alkoxy, haloalkoxy, —NR$^s$R$^t$, —C(O)alkyl, CO$_2$alkyl, —CO$_2$H, —CONR$^s$ R$^t$, —SOalkyl, —SO$_2$alkyl, and —SO$_2$NR$^s$R$^t$;
where R$^s$ and R$^t$ are each independently H, alkyl, alkoxyalkyl, haloalkyl, —C(O)alkyl, or —CO$_2$alkyl; or
(3) —N(R$^n$)R$^o$,
wherein R$^n$ is H, R$^m$, -alkylenyl-R$^m$, hydroxyalkyl, cyanoalkyl, alkoxyalkyl, haloalkyl, —CONR$^h$R$^i$, or —C(O)R$^j$;
where R$^m$ is as defined in (1) above;
R$^h$ and R$^i$ are each independently H or alkyl, or R$^h$ and R$^i$ taken together with the nitrogen to which they are attached form a monocyclic heterocycloalkyl; and
R$^j$ is an alkyl unsubstituted or substituted with one or more substituents selected from the group consisting of: deuterium, halo, amino, hydroxy, alkoxy, cycloalkyl, heteroaryl, phenyl, and heterocycloalkyl; or a cycloalkyl, heterocycloalkyl, phenyl, or heteroaryl, each unsubstituted or substituted with one or more substituents selected from the group consisting of: deuterium, alkyl, halo, amino, hydroxy, and alkoxy; and
R$^o$ is H or R$^j$;
$R^2$ and $R^3$ are each independently selected from the group consisting of H and deuterium;
wherein the compound of Formula I is not 1H-pyrrolo[3,2-c]pyridine-2-carboxylic acid (5-benzenesulfonyl-pyridin-2-ylmethyl)-amide;
or a pharmaceutically acceptable salt thereof.
2. The compound of claim 1, wherein R is an unsubstituted or substituted 8- or 9-membered heteroaryl.
3. The compound of claim 1, wherein R is:

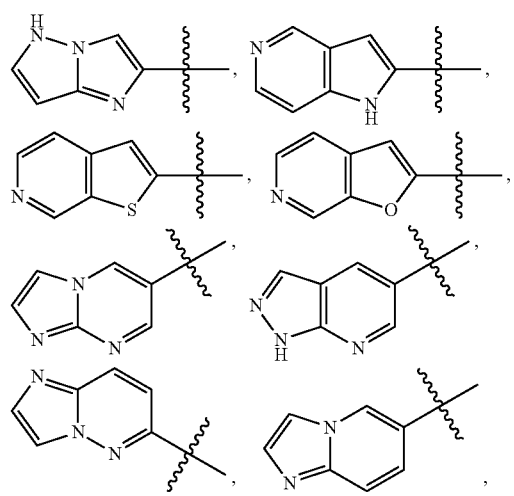

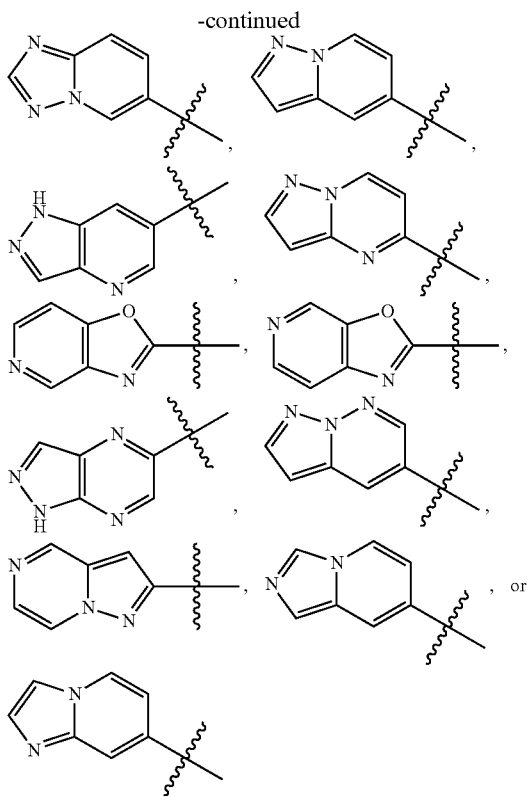

each unsubstituted or substituted as in claim 1.

4. The compound of claim 1, wherein R is a five- or six-membered nitrogen-linked heterocycloalkyl ring fused to an unsubstituted or substituted phenyl or monocyclic heteroaryl.

5. The compound of claim 1, wherein R is

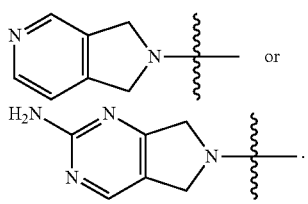

6. The compound of claim 1, wherein $R^1$ is $R^m$, wherein $R^1$ is -alkylenyl-$R^m$.

7. The compound of claim 1, wherein $R^m$ is cycloalkyl, unsubstituted or substituted as in claim 1.

8. The compound of claim 1, wherein $R^m$ is a heterocycloalkyl, unsubstituted or substituted with an alkyl, —C(O) alkyl, or monocyclic heterocycloalkyl group.

9. The compound of claim 1, wherein $R^m$ is phenyl, pyridinyl, pyrazolyl, pyrimidinyl, thiazolyl, or pyrazinyl, each unsubstituted or substituted as in claim 1.

10. The compound of claim 1, wherein the $R^m$ group is substituted with one or more $R^x$ substituents each independently selected from the group consisting of: fluoro, chloro, bromo, hydroxy, hydroxymethyl, hydroxyethyl, cyano, amino, di(alkyl)amino, alkylamino, monofluoroalkyl, trifluoroalkyl, methoxy, ethoxy, trifluoromethoxy, acetyl, propionyl, butyryl, methoxycarbonyl, ethoxycarbonyl, tert-butoxycarbonyl, carboxyl, methylsulfonyl, ethylsulfonyl, trifluoromethylsulfonyl, methylamido, ethylamido, oxetanyl, pyrrolidinyl, tetrahydrofuranyl, piperidinyl, tetrahydropyranyl, morpholinyl, piperazinyl, pyridinyl, imidazolyl, pyrrolyl, pyrimidinyl, and phenyl, each substituted or unsubstituted as in claim 1.

11. The compound of claim 1, wherein the Rm group is substituted with 1, 2, or 3 $R^x$ substituents each independently selected from the group consisting of: fluoro, trifluoromethyl, trifluoromethoxy, morpholinyl, 4-methyl-piperazinyl, piperidinyl, methoxy, cyano, acetyl, ethylamido, methylsulfonyl, ethylsulfonyl, cyano, chloro, dimethylamino, methyl, ethyl, propyl, isopropyl, isobutyl, butyryl, oxetanyl, tetrahydropyranyl, pyrrolidinyl, and 1-(3-oxetanyl)-piperidin-4-yl.

12. The compound of claim 1, wherein $R^1$ is an alkyl, unsubstituted or substituted with one or more substituents selected from the group consisting of halo, hydroxy, cyano, alkoxy, trifluoroalkyl, trifluoroalkoxy, amino, methylamino, dimethylamino, acetyl, methoxycarbonyl, amido, and methylsulfonyl.

13. The compound of claim 1, wherein $R^1$ is —N(R")R°, and R" is $R^m$ or -alkylenyl-$R^m$.

14. The compound of claim 13, wherein R" is hydroxyalkyl, cyanoalkyl, alkoxyalkyl, haloalkyl, —CONR$^h$R$^i$, or —C(O)R$^j$, where R$^h$ and R$^i$ are each independently H or alkyl, and R$^j$ is hydroxymethyl, cycloalkyl, piperidinyl, or phenyl.

15. The compound of claim 1, wherein both $R^2$ and $R^3$ are H.

16. A compound selected from the group consisting of:

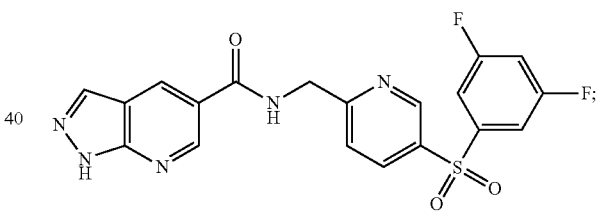

1H-Pyrazolo[3,4-b]pyridine-5-carboxylic acid [5-(3,5-difluoro-benzenesulfonyl)-pyridin-2-ylmethyl]-amide

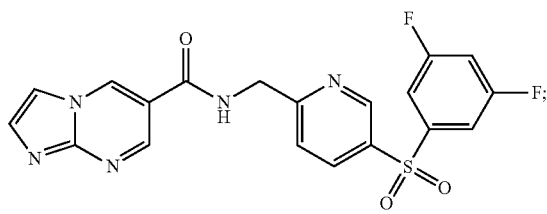

Imidazo[1,2-a]pyrimidine-6-carboxylic acid [5-(3,5-difluoro-benzenesulfonyl)-pyridin-2-ylmethyl]-amide

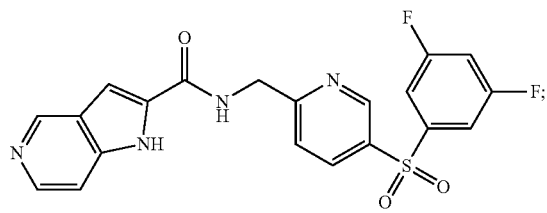

1H-Pyrrolo[3,2-c]pyridine-2-carboxylic acid [5-(3,5-difluoro-benzenesulfonyl)-pyridin-2-ylmethyl]-amide -continued

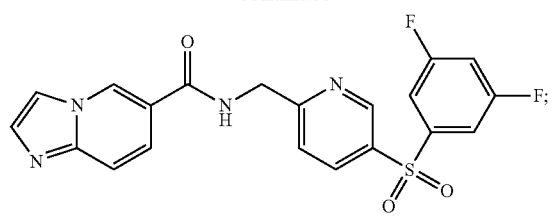

Imidazo[1,2-a]pyridine-6-carboxylic acid [5-(3,5-difluoro-benzenesulfonyl)-pyridin-2-ylmethyl]-amide

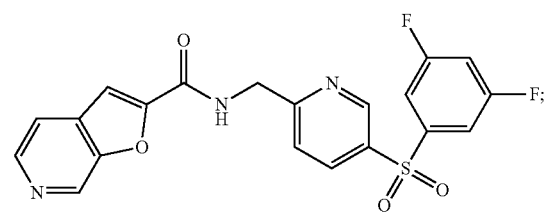

Furo[2,3-c]pyridine-2-carboxylic acid [5-(3,5-difluoro-benzenesulfonyl)-pyridin-2-ylmethyl]-amide

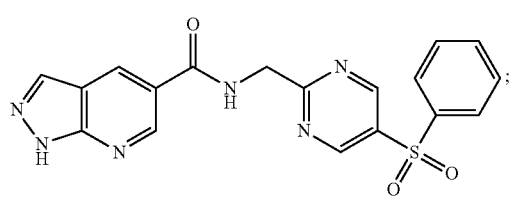

1H-Pyrazolo[3,4-b]pyridine-5-carboxylic acid (5-benzenesulfonyl-pyrimidin-2-ylmethyl)-amide

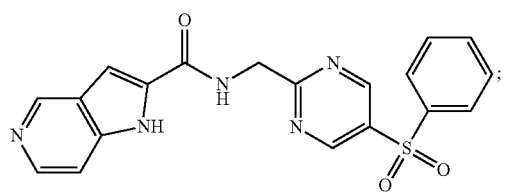

1H-Pyrrolo[3,2-c]pyridine-2-carboxylic acid (5-benzenesulfonyl-pyrimidin-2-ylmethyl)-amide

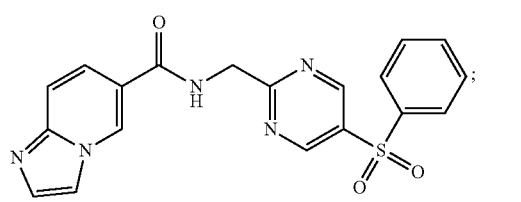

Imidazo[1,2-a]pyridine-6-carboxylic acid (5-benzenesulfonyl-pyrimidin-2-ylmethyl)-amide

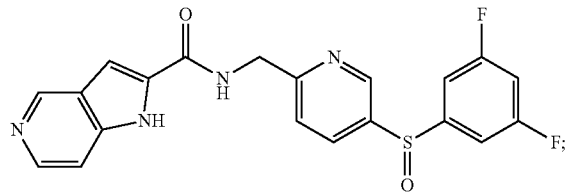

1H-Pyrrolo[3,2-c]pyridine-2-carboxylic acid [5-(3,5-difluoro-benzenesulfonyl)-pyridin-2-ylmethyl]-amide (racemic)

-continued

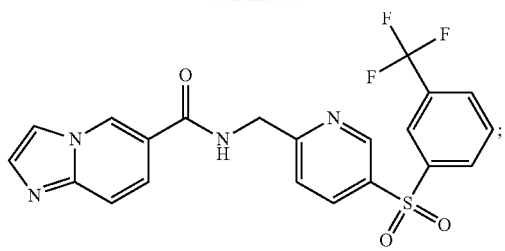

Imidazo[1,2-a]pyridine-6-carboxylic acid [5-(3-trifluoromethyl-benzenesulfonyl)-pyridin-2-ylmethyl]-amide

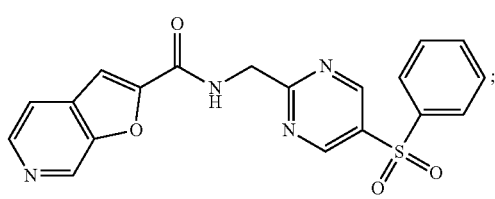

Furo[2,3-c]pyridine-2-carboxylic acid (5-benzenesulfonyl-pyrimidin-2-ylmethyl)-amide

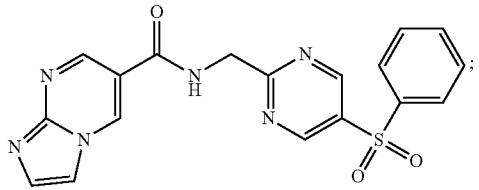

Imidazo[1,2-a]pyrimidine-6-carboxylic acid (5-benzenesulfonyl-pyrimidin-2-ylmethyl)-amide

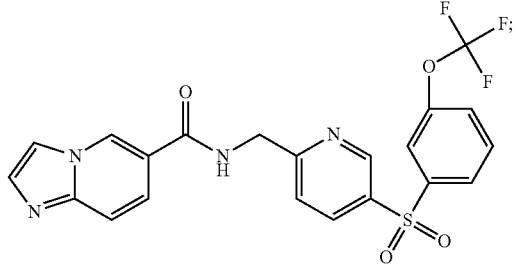

Imidazo[1,2-a]pyridine-6-carboxylic acid [5-(3-trifluoromethoxy-benzenesulfonyl)-pyridin-2-ylmethyl]-amide

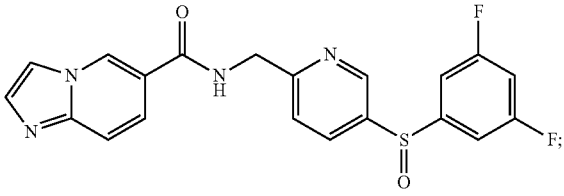

Imidazo[1,2-a]pyridine-6-carboxylic acid [5-(3,5-difluoro-benzenesulfinyl)-pyridin-2-ylmethyl]-amide (racemic)

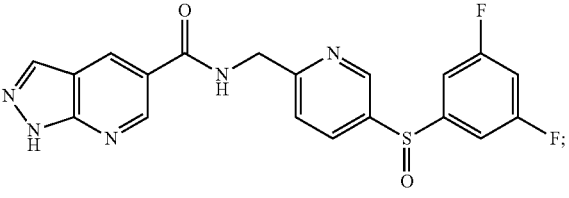

1H-Pyrazolo[3,4-b]pyridine-5-carboxylic acid [5-(3,5-difluoro-benzenesulfinyl)-pyridin-2-ylmethyl]-amide (racemic)

-continued

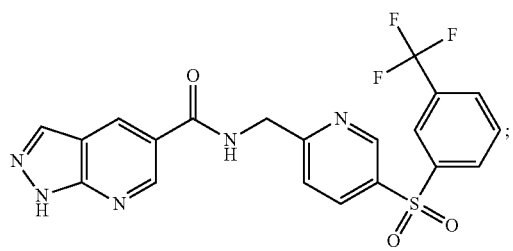

1H-Pyrazolo[3,4-b]pyridine-5-carboxylic acid [5-(3-trifluoromethyl-benzenesulfonyl)-pyridin-2-ylmethyl]-amide

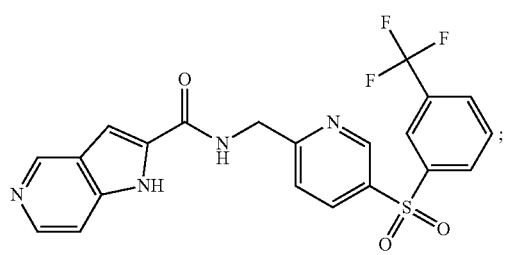

1H-Pyrazolo[3,2-c]pyridine-2-carboxylic acid [5-(3-trifluoromethyl-benzenesulfonyl)-pyridin-2-ylmethyl]-amide

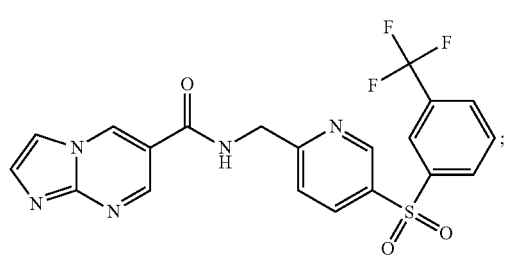

Imidazo[1,2-a]pyrimidine-6-carboxylic acid [5-(3-trifluoromethyl-benzenesulfonyl)-pyridin-2-ylmethyl]-amide

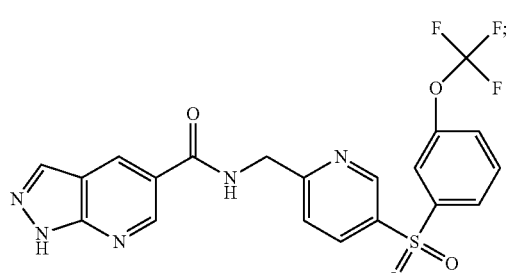

1H-Pyrazolo[3,4-b]pyridine-5-carboxylic acid [5-(3-trifluoromethoxy-benzenesulfonyl)-pyridin-2-ylmethyl]-amide

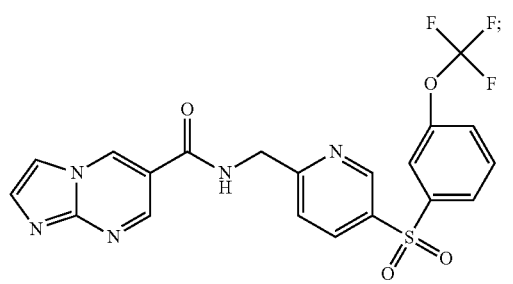

Imidazo[1,2-a]pyrimidine-6-carboxylic acid [5-(3-trifluoromethoxy-benzenesulfonyl)-pyridin-2-ylmethyl]-amide -continued

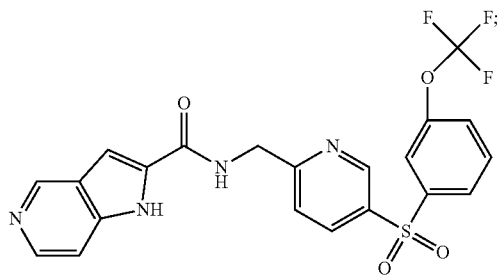

1H-Pyrrolo[3,2-c]pyridine-2-carboxylic acid [5-(3-trifluoromethoxy-benzenesulfonyl)-pyridin-2-ylmethyl]-amide

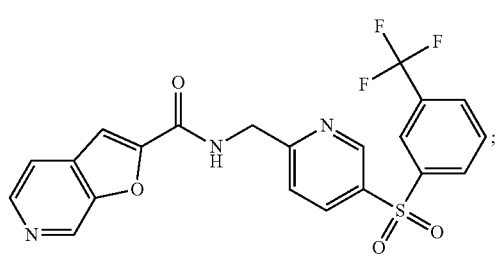

Furo[2,3-c]pyridine-2-carboxylic acid [5-(3-trifluoromethyl-benzenesulfonyl)-pyridin-2-ylmethyl]-amide

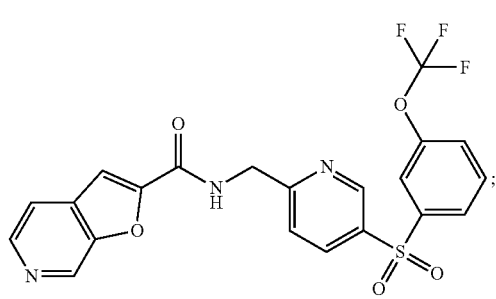

Furo[2,3-c]pyridine-2-carboxylic acid [5-(3-trifluoromethoxy-benzenesulfonyl)-pyridin-2-ylmethyl]-amide

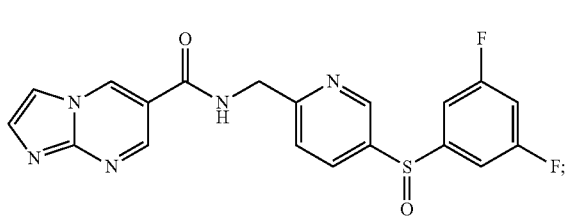

Imidazo[1,2-a]pyrimidine-6-carboxylic acid [5-(3,5-difluoro-benzenesulfonyl)-pyridin-2-ylmethyl]-amide (racemic)

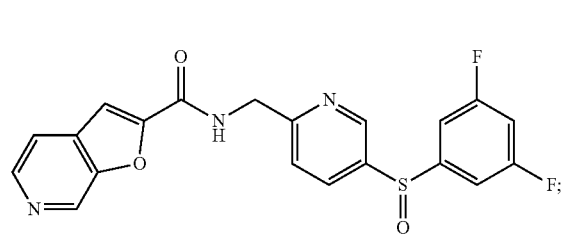

Furo[2,3-c]pyridine-2-carboxylic acid [5-(3,5-difluoro-benzenesulfonyl)-pyridin-2-ylmethyl]-amide (racemic)

-continued

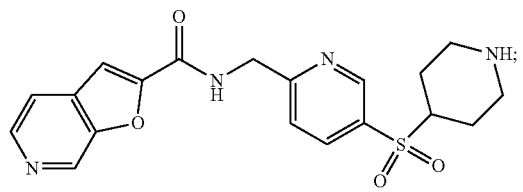

Furo[2,3-c]pyridine-2-carboxylic acid [5-(piperidine-4-sulfonyl)-pyridin-2-ylmethyl]-amide

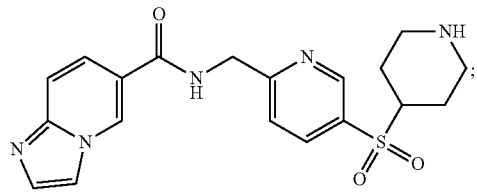

Imidazo[1,2-a]pyridine-6-carboxylic acid [5-(piperidine-4-sulfonyl)-pyridin-2-ylmethyl]-amide

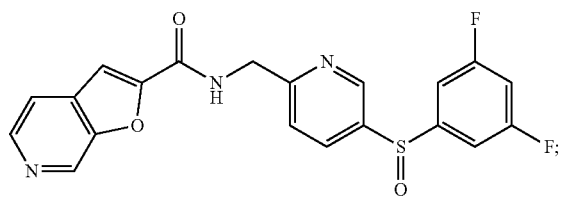

Furo[2,3-c]pyridine-2-carboxylic acid [5-(3,5-difluoro-benzenesulfinyl)-pyridin-2-ylmethyl]-amide (stereoisomer 1)

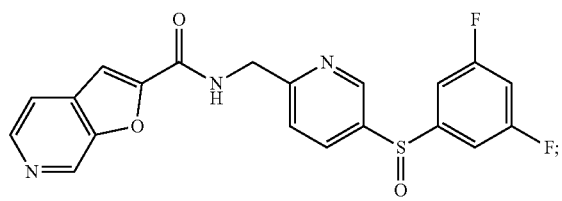

Furo[2,3-c]pyridine-2-carboxylic acid [5-(3,5-difluoro-benzenesulfinyl)-pyridin-2-ylmethyl]-amide (stereoisomer 2)

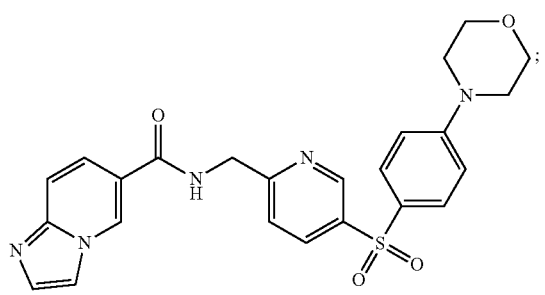

Imidazo[1,2-a]pyridine-6-carboxylic acid [5-(4-morpholin-4-yl-benzenesulfonyl)-pyridin-2-ylmethyl]-amide

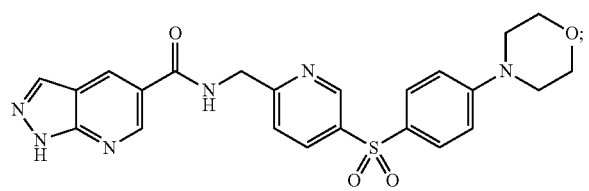

1H-Pyrazolo[3,4-b]pyridine-5-carboxylic acid [5-(4-morpholin-4-yl-benzenesulfonyl)-pyridin-2-ylmethyl]-amide -continued

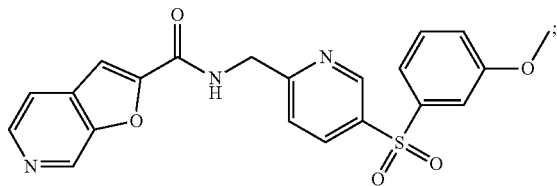

Furo[2,3-c]pyridine-2-carboxylic acid [5-(3-methoxy-benzenesulfonyl)-pyridin-2-ylmethyl]-amide

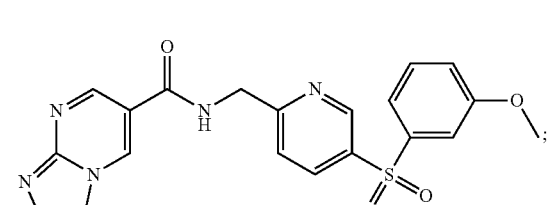

Imidazo[1,2-a]pyrimidine-6-carboxylic acid [5-(3-methoxy-benzenesulfonyl)-pyridin-2-ylmethyl]-amide

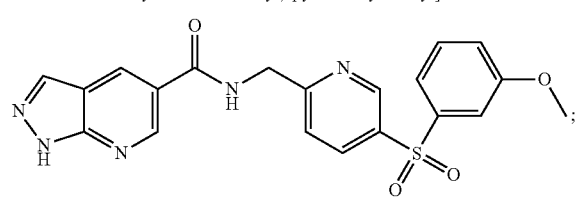

1H-Pyrazolo[3,4-b]pyridine-5-carboxylic acid [5-(3-methoxy-benzenesulfonyl)-pyridin-2-ylmethyl]-amide

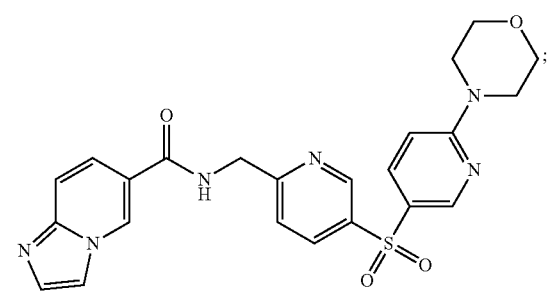

Imidazo[1,2-a]pyridine-6-carboxylic acid [5-(6-morpholin-4-yl-pyridine-3-sulfonyl)-pyridin-2-ylmethyl]-amide

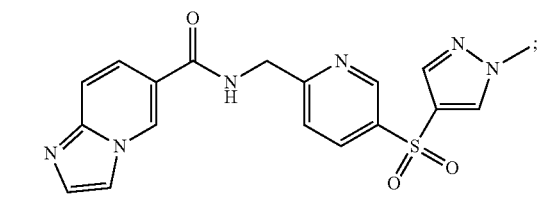

Imidazo[1,2-a]pyridine-6-carboxylic acid [5-(1-methyl-1H-pyrazole-4-sulfonyl)-pyridin-2-ylmethyl]-amide

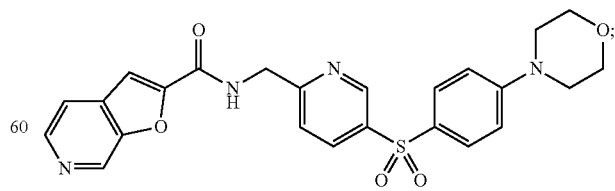

Furo[2,3-c]pyridine-2-carboxylic acid [5-(4-morpholin-4-yl-benzenesulfonyl)-pyridin-2-ylmethyl]-amide -continued

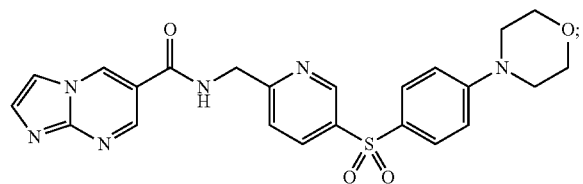

Imidazo[1,2-a]pyrimidine-6-carboxylic acid [5-(4-morpholin-4-yl-benzenesulfonyl)-pyridin-2-ylmethyl]-amide

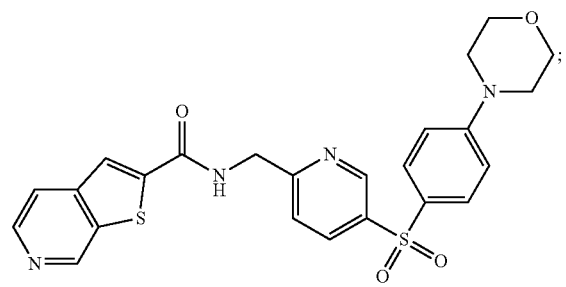

Thieno[2,3-c]pyridine-2-carboxylic acid [5-(4-morpholin-4-yl-benzenesulfonyl)-pyridin-2-ylmethyl]-amide

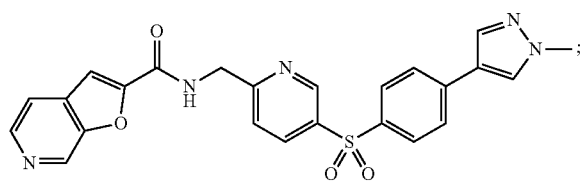

Thieno[2,3-c]pyridine-2-carboxylic acid [5-(1-methyl-1H-pyrazole-4-sulfonyl)-pyridin-2-ylmethyl]-amide

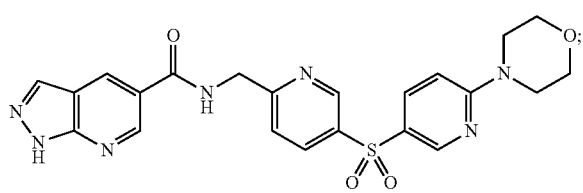

1H-Pyrazolo[3,4-b]pyridine-5-carboxylic acid [5-(6-morpholin-4-yl-pyridine-3-sulfonyl)-pyridin-2-ylmethyl]-amide

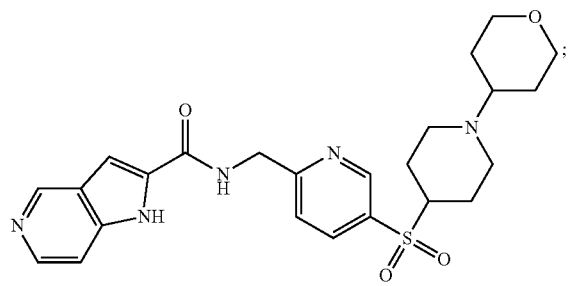

1H-Pyrrolo[3,2-c]pyridine-2-carboxylic acid {5-[1-(tetrahydro-pyran-4-yl)-piperidine-4-sulfonyl]-pyridin-2-ylmethyl}-amide

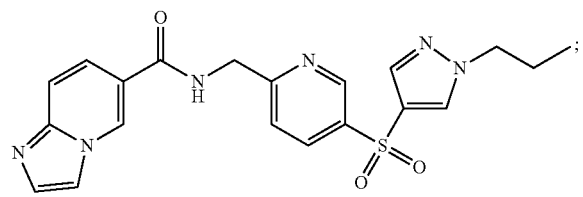

Imidazo[1,2-a]pyridine-6-carboxylic acid [5-(1-propyl-1H-pyrazole-4-sulfonyl)-pyridin-2-ylmethyl]-amide -continued

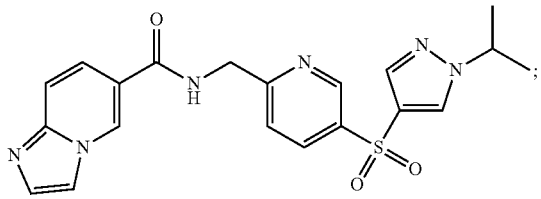

Imidazo[1,2-a]pyridine-6-carboxylic acid [5-(1-isopropyl-1H-pyrazole-4-sulfonyl)-pyridin-2-ylmethyl]-amide

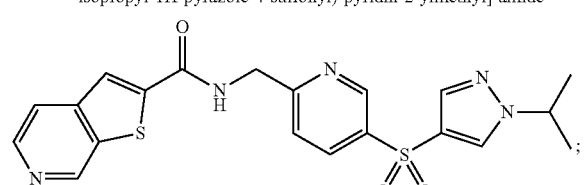

Thieno[2,3-c]pyridine-2-carboxylic acid [5-(1-isopropyl-1H-pyrazole-4-sulfonyl)-pyridin-2-ylmethyl]-amide

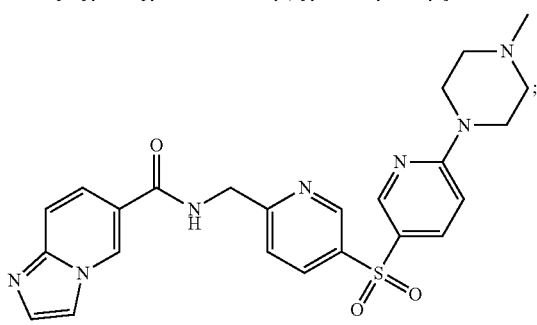

Imidazo[1,2-a]pyridine-6-carboxylic acid {5-[6-(4-methyl-piperazin-1-yl)-pyridine-3-sulfonyl]-pyridin-2-ylmethyl}-amide

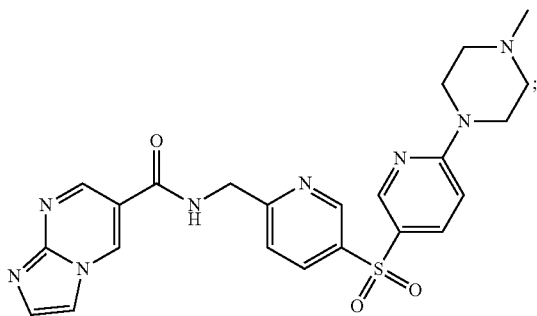

Imidazo[1,2-a]pyrimidine-6-carboxylic acid {5-[6-(4-methyl-piperazin-1-yl)-pyridine-3-sulfonyl]-pyridin-2-ylmethyl}-amide

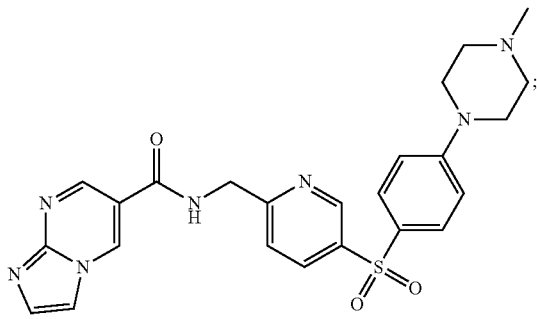

Imidazo[1,2-a]pyrimidine-6-carboxylic acid {5-[4-(4-methyl-piperazin-1-yl)-benzenesulfonyl]-pyridin-2-ylmethyl}-amide 145
-continued

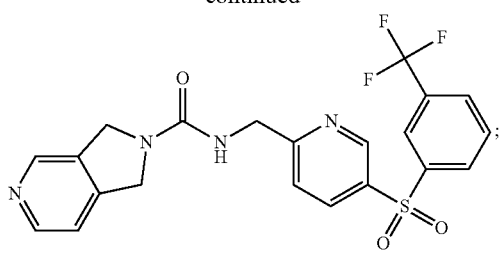

1,3-Dihydro-pyrrolo[3,4-c]pyridine-2-carboxylic acid [5-(3-trifluoromethyl-benzenesulfonyl)-pyridin-2-ylmethyl]-amide

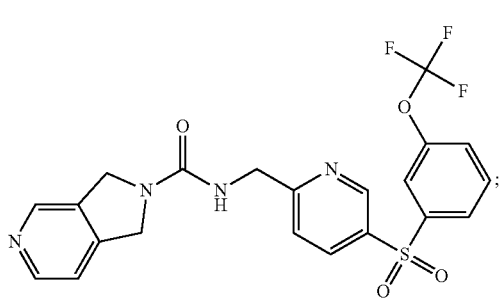

1,3-Dihydro-pyrrolo[3,4-c]pyridine-2-carboxylic acid [5-(3-trifluoromethyl-benzenesulfonyl)-pyridin-2-ylmethyl]-amide

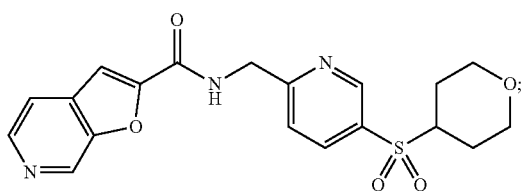

Furo[2,3-c]pyridine-2-carboxylic acid [5-(tetrahydro-pyran-4-sulfonyl)-pyridin-2-ylmethyl]-amide

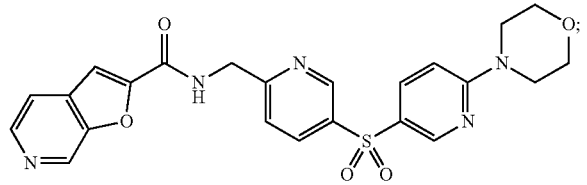

Furo[2,3-c]pyridine-2-carboxylic acid [5-(6-morpholin-4-yl-pyridine-3-sulfonyl)-pyridin-2-ylmethyl]-amide

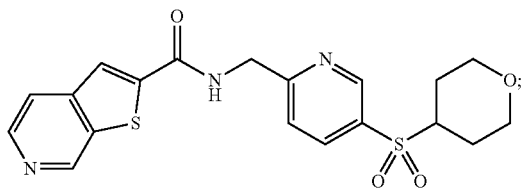

Thieno[2,3-c]pyridine-2-carboxylic acid [5-(tetrahydro-pyran-4-sulfonyl)-pyridin-2-ylmethyl]-amide

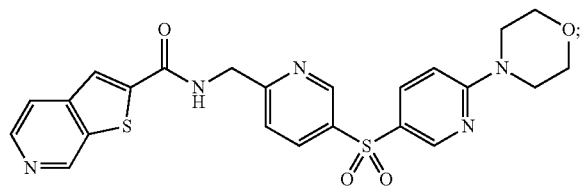

Thieno[2,3-c]pyridine-2-carboxylic acid [5-(6-morpholin-4-yl-pyridine-3-sulfonyl)-pyridin-2-ylmethyl]-amide 146
-continued

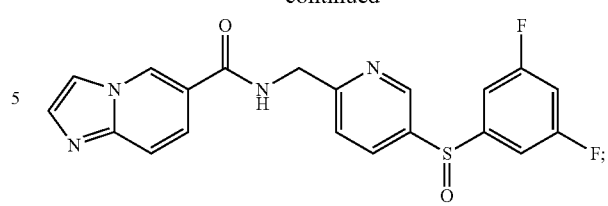

Imidazo[1,2-a]pyridine-6-carboxylic acid [5-(3,5-difluoro-benzenesulfinyl)-pyridin-2-ylmethyl]-amide (racemic)

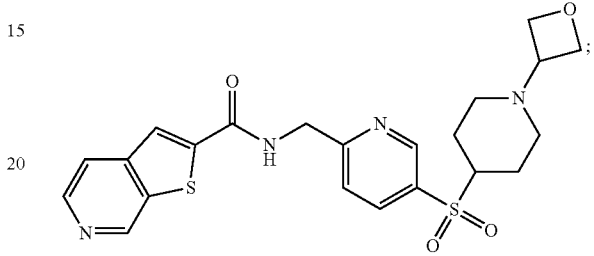

Thieno[2,3-c]pyridine-2-carboxylic acid [5-(1-oxetan-3-yl-piperidine-4-sulfonyl)-pyridin-2-ylmethyl]-amide

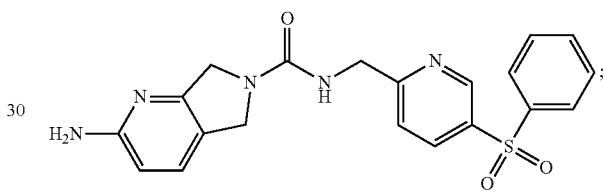

2-Amino-5,7-dihydro-pyrrolo[3,4-d]pyrimidine-6-carboxylic acid (5-benzenesulfonyl-pyridin-2-ylmethyl)-amide

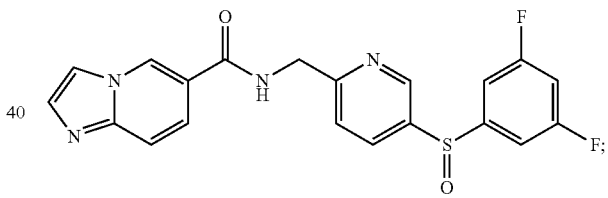

Imidazo[1,2-a]pyridine-6-carboxylic acid [5-(3,5-difluoro-benzenesulfinyl)-pyridin-2-ylmethyl]-amide (racemic)

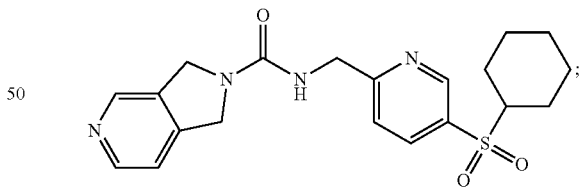

1,3-Dihydro-pyrrolo[3,4-c]pyridine-2-carboxylic acid (5-cyclohexanesulfonyl-pyridin-2-ylmethyl)-amide

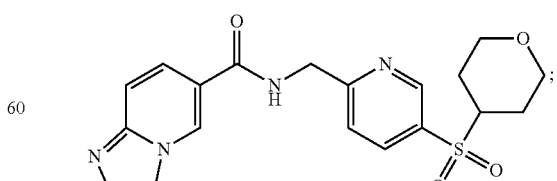

Imidazo[1,2-a]pyridine-6-carboxylic acid [5-(tetrahydro-pyran-4-sulfonyl)-pyridin-2-ylmethyl]-amide -continued

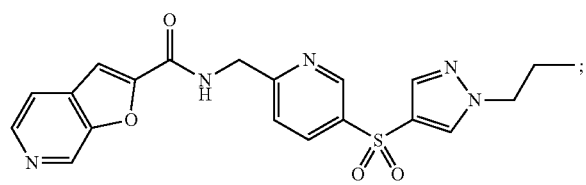

Furo[2,3-c]pyridine-2-carboxylic acid [5-(1-propyl-1H-pyrazole-4-sulfonyl)-pyridin-2-ylmethyl]-amide

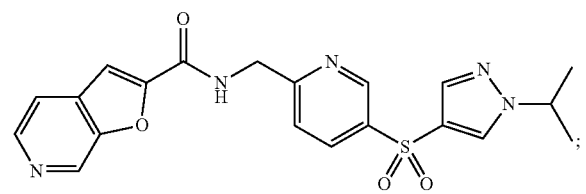

Furo[2,3-c]pyridine-2-carboxylic acid [5-(1-isopropyl-1H-pyrazole-4-sulfonyl)-pyridin-2-ylmethyl]-amide

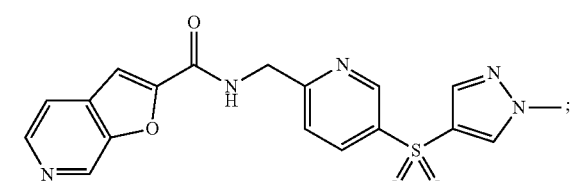

Furo[2,3-c]pyridine-2-carboxylic acid [5-(1-methyl-1H-pyrazole-4-sulfonyl)-pyridin-2-ylmethyl]-amide

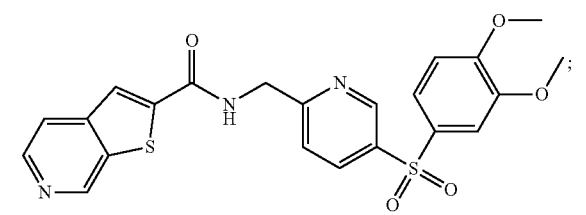

Thieno[2,3-c]pyridine-2-carboxylic acid [5-(3,4-dimethoxy-benzenesulfonyl)-pyridin-2-ylmethyl]-amide

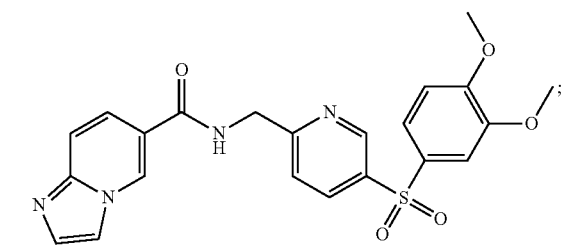

Imidazo[1,2-a]pyridine-6-carboxylic acid [5-(3,4-dimethoxy-benzenesulfonyl)-pyridin-2-ylmethyl]-amide

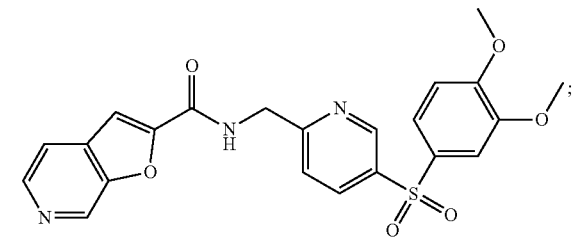

Furo[2,3-c]pyridine-2-carboxylic acid [5-(3,4-dimethoxy-benzenesulfonyl)-pyridin-2-ylmethyl]-amide -continued

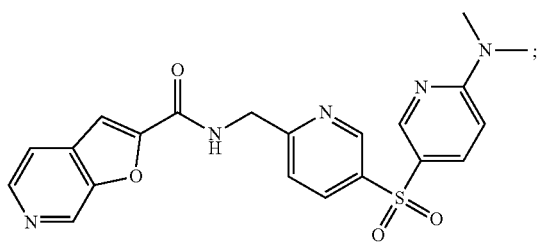

Furo[2,3-c]pyridine-2-carboxylic acid [5-(6-dimethylamino-pyridine-3-sulfonyl)-pyridin-2-ylmethyl]-amide

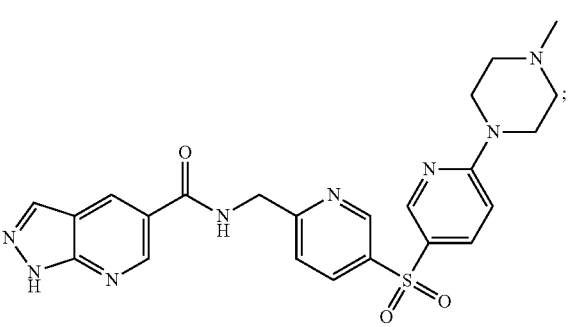

1H-Pyrazolo[3,4-b]pyridine-5-carboxylic acid {5-[6-(4-methyl-piperazin-1-yl)-pyridine-3-sulfonyl]-pyridin-2-ylmethyl}-amide

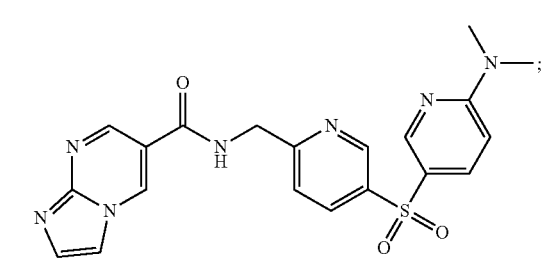

Imidazo[1,2-a]pyrimidine-6-carboxylic acid [5-(6-dimethylamino-pyridine-3-sulfonyl)-pyridin-2-ylmethyl]-amide

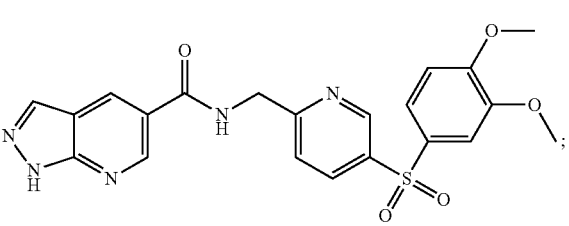

1H-Pyrazolo[3,4-b]pyridine-5-carboxylic acid [5-(3,4-dimethoxy-benzenesulfonyl)-pyridin-2-ylmethyl]-amide

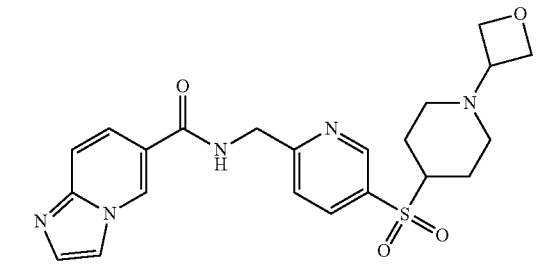

Imidazo[1,2-a]pyridine-6-carboxylic acid [5-(1-oxetan-3-yl-piperidine-4-sulfonyl)-pyridin-2-ylmethyl]-amide

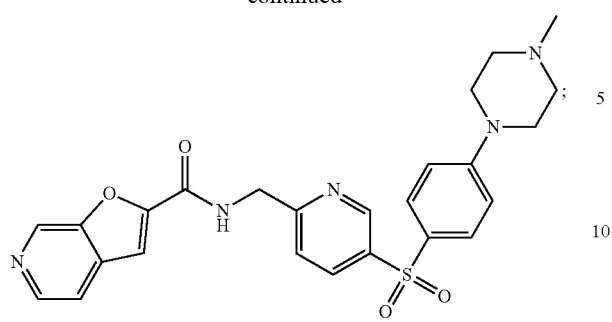

Furo[2,3-c]pyridine-2-carboxylic acid {5-[4-(4-methyl-piperazin-1-yl)-benzenesulfonyl]-pyridin-2-ylmethyl}-amide

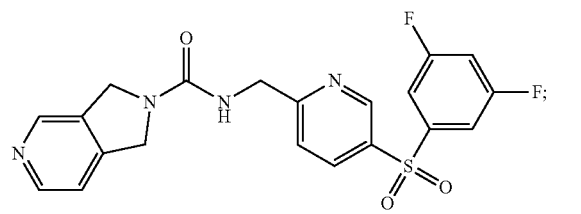

1,3-Dihydro-pyrrolo[3,4-c]pyridine-2-carboxylic acid [5-(3,5-difluoro-benzenesulfonyl)-pyridin-2-ylmethyl]-amide

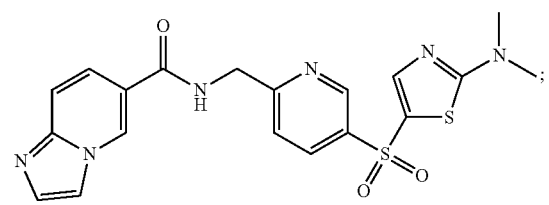

Imidazo[1,2-a]pyridine-6-carboxylic acid [5-(2-dimethylamino-thiazole-5-sulfonyl)-pyridin-2-ylmethyl]-amide

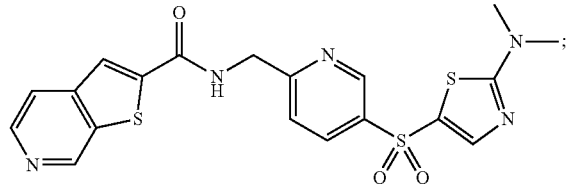

Thieno[2,3-c]pyridine-2-carboxylic acid [5-(2-dimethylamino-thiazole-5-sulfonyl)-pyridin-2-ylmethyl]-amide

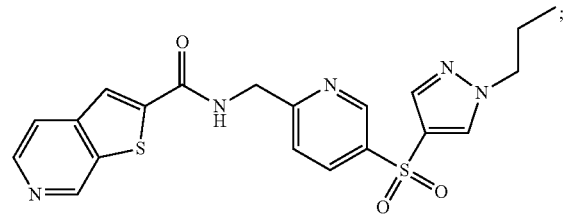

Thieno[2,3-c]pyridine-2-carboxylic acid [5-(1-propyl-1H-pyrazole-4-sulfonyl)-pyridin-2-ylmethyl]-amide

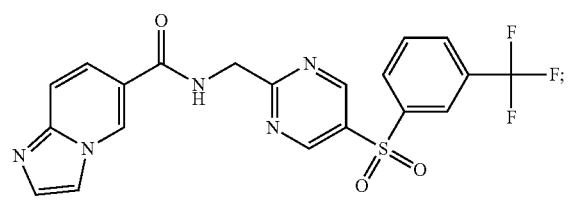

Imidazo[1,2-a]pyridine-6-carboxylic acid [5-(3-trifluoromethyl-benzenesulfonyl)-pyrimidin-2-ylmethyl]-amide

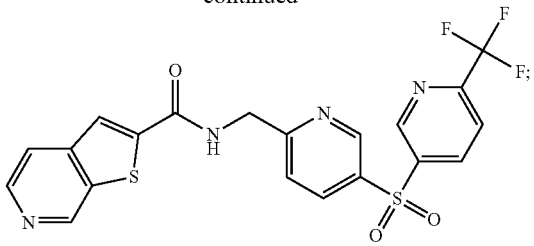

Thieno[2,3-c]pyridine-2-carboxylic acid [5-(6-trifluoromethyl-pyridine-3-sulfonyl)-pyridin-2-ylmethyl]-amide

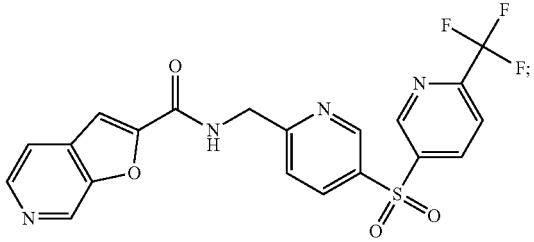

Furo[2,3-c]pyridine-2-carboxylic acid [5-(6-trifluoromethyl-pyridine-3-sulfonyl)-pyridin-2-ylmethyl]-amide

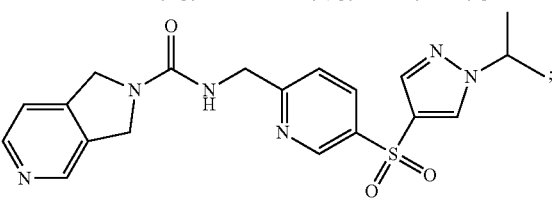

1,3-Dihydro-pyrrolo[3,4-c]pyridine-2-carboxylic acid [5-(1-isopropyl-1H-pyrazole-4-sulfonyl)-pyridin-2-ylmethyl]-amide

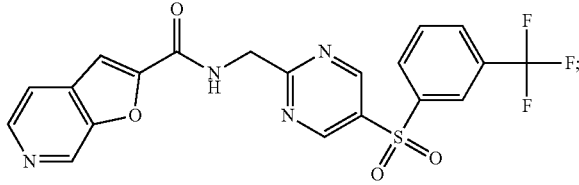

Furo[2,3-c]pyridine-2-carboxylic acid [5-(3-trifluoromethyl-benzenesulfonyl)-pyrimidin-2-ylmethyl]-amide

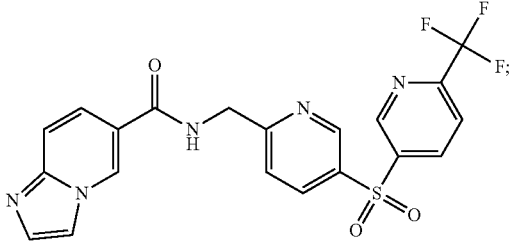

Imidazo[1,2-a]pyridine-6-carboxylic acid [5-(6-trifluoromethyl-pyridine-3-sulfonyl)-pyridin-2-ylmethyl]-amide

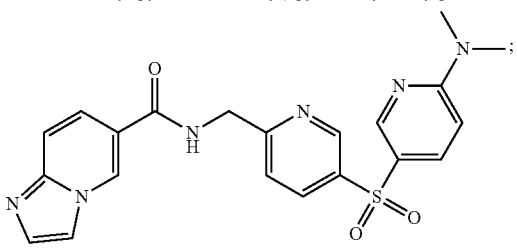

Imidazo[1,2-a]pyridine-6-carboxylic acid [5-(6-dimethylamino-pyridine-3-sulfonyl)-pyridin-2-ylmethyl]-amide 151
-continued

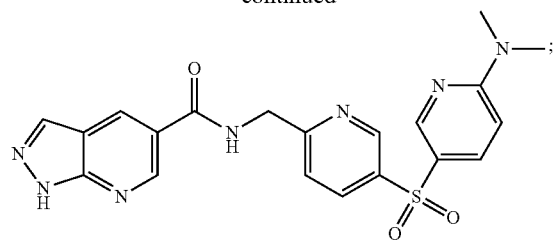

1H-Pyrazolo[3,4-b]pyridine-5-carboxylic acid [5-(6-dimethylamino-pyridine-3-sulfonyl)-pyridin-2-ylmethyl]-amide

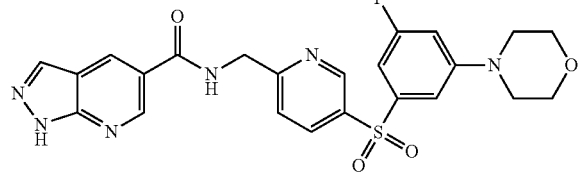

1H-Pyrazolo[3,4-b]pyridine-5-carboxylic acid [5-(3-fluoro-5-morpholin-4-yl-benzenesulfonyl)-pyridin-2-ylmethyl]-amide

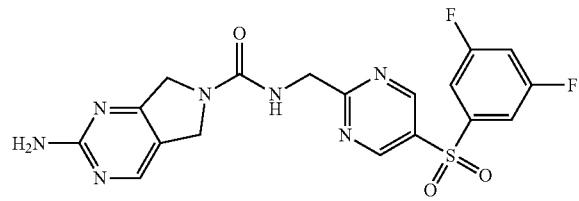

2-Amino-5,7-dihydro-pyrrolo[3,4-d]pyrimidine-6-carboxylic acid [5-(3,5-difluoro-benzenesulfonyl)-pyridin-2-ylmethyl]-amide

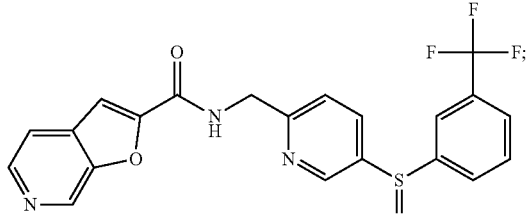

Furo[2,3-c]pyridine-2-carboxylic acid [5-(3-trifluoromethyl-benzenesulfinyl)-pyridin-2-ylmethyl]-amide (racemic)

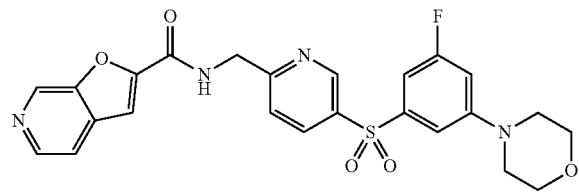

Furo[2,3-c]pyridine-2-carboxylic acid [5-(3-fluoro-5-morpholin-4-yl-benzenesulfonyl)-pyridin-2-ylmethyl]-amide

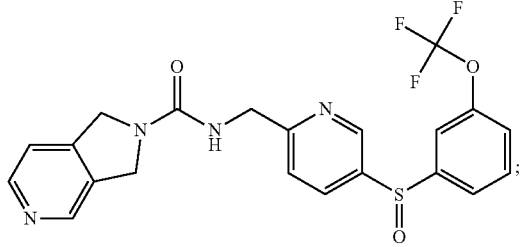

1,3-Dihydro-pyrrolo[3,4-c]pyridine-2-carboxylic acid [5-(3-trifluoromethoxy-benzenesulfinyl)-pyridin-2-ylmethyl]-amide (racemic)

152
-continued

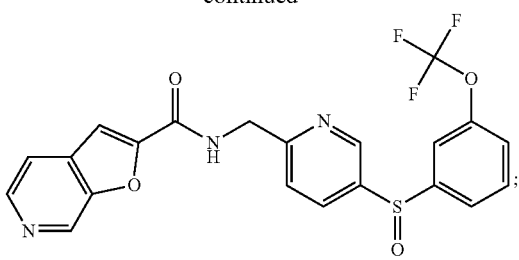

Furo[2,3-c]pyridine-2-carboxylic acid [5-(3-trifluoromethoxy-benzenesulfinyl)-pyridin-2-ylmethyl]-amide (racemic)

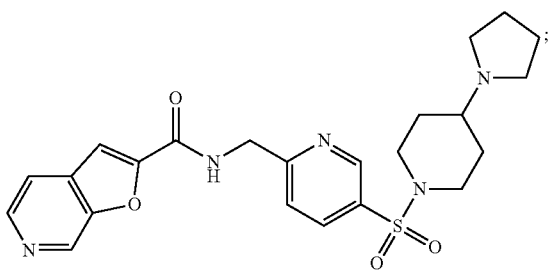

Furo[2,3-c]pyridine-2-carboxylic acid [5-(4-pyrrolidin-1-yl-piperidine-1-sulfonyl)-pyridin-2-ylmethyl]-amide

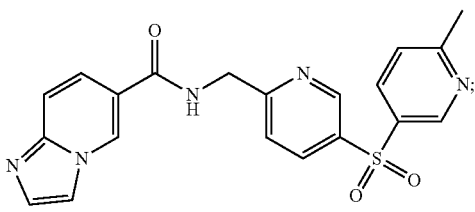

Imidazo[1,2-a]pyridine-6-carboxylic acid [5-(6-methyl-pyridine-3-sulfonyl)-pyridin-2-ylmethyl]-amide

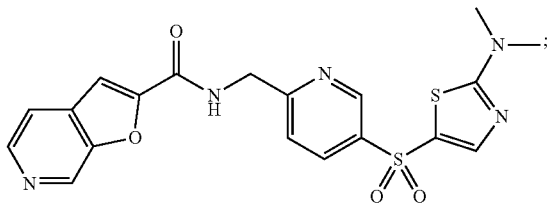

Furo[2,3-c]pyridine-2-carboxylic acid [5-(2-dimethylamino-thiazole-5-sulfonyl)-pyridin-2-ylmethyl]-amide

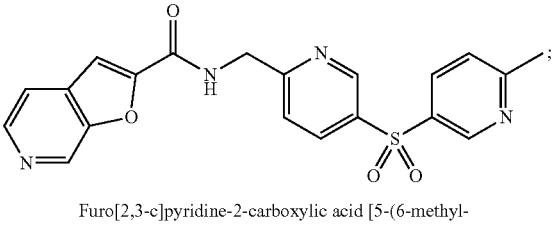

Furo[2,3-c]pyridine-2-carboxylic acid [5-(6-methyl-pyridine-3-sulfonyl)-pyridin-2-ylmethyl]-amide

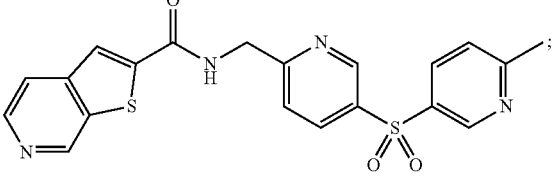

Thieno[2,3-c]pyridine-2-carboxylic acid [5-(6-methyl-pyridine-3-sulfonyl)-pyridin-2-ylmethyl]-amide

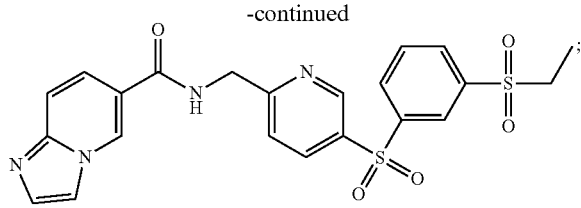

Imidazo[1,2-a]pyridine-6-carboxylic acid [5-(3-ethanesulfonyl-benzenesulfonyl)-pyridin-2-ylmethyl]-amide

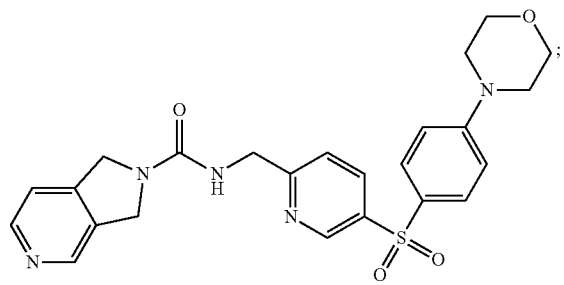

1,3-Dihydro-pyrrolo[3,4-c]pyridine-2-carboxylic acid [5-(4-morpholin-4-yl-benzenesulfonyl)-pyridin-2-ylmethyl]-amide

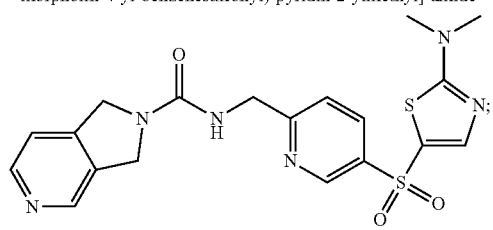

1,3-Dihydro-pyrrolo[3,4-c]pyridine-2-carboxylic acid [5-(2-dimethylamino-thiazole-5-sulfonyl)-pyridin-2-ylmethyl]-amide

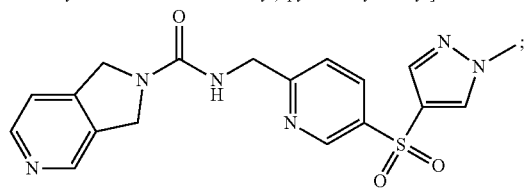

1,3-Dihydro-pyrrolo[3,4-c]pyridine-2-carboxylic acid [5-(1-methyl-1H-pyrazole-4-sulfonyl)-pyridin-2-ylmethyl]-amide

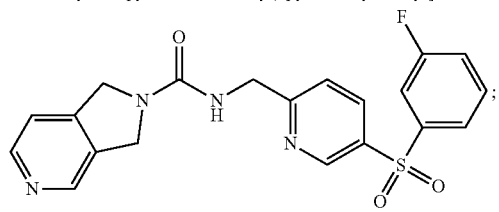

1,3-Dihydro-pyrrolo[3,4-c]pyridine-2-carboxylic acid [5-(3-fluoro-benzenesulfonyl)-pyridin-2-ylmethyl]-amide

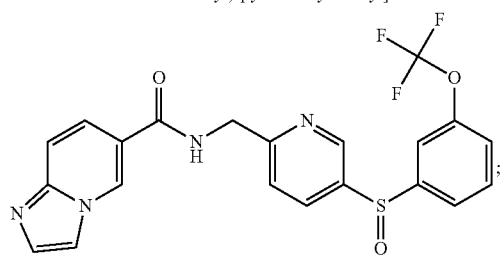

Imidazo[1,2-a]pyridine-6-carboxylic acid [5-(3-trifluoromethoxy-benzenesulfinyl)-pyridin-2-ylmethyl]-amide (racemic)

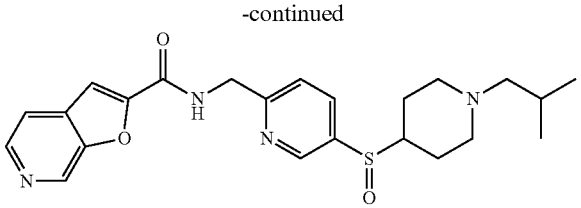

Furo[2,3-c]pyridine-2-carboxylic acid [5-(1-isobutyl-piperidine-4-sulfinyl)-pyridin-2-ylmethyl]-amide (racemic)

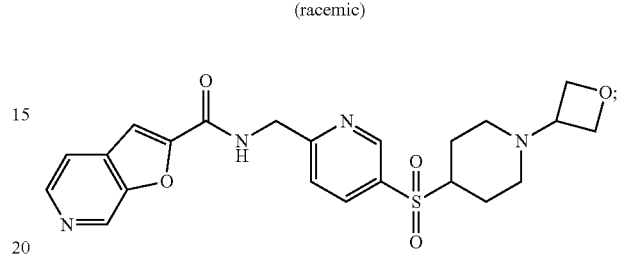

Furo[2,3-c]pyridine-2-carboxylic acid [5-(1-oxetan-3-yl-piperidine-4-sulfonyl)-pyridin-2-ylmethyl]-amide

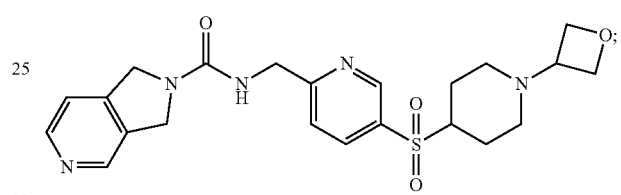

1,3-Dihydro-pyrrolo[3,4-c]pyridine-2-carboxylic acid [5-(1-oxetan-3-yl-piperidine-4-sulfonyl)-pyridin-2-ylmethyl]-amide

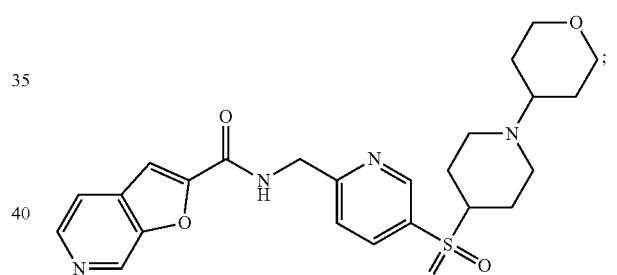

Furo[2,3-c]pyridine-2-carboxylic acid {5-[1-(tetrahydro-pyran-4-yl)-piperidine-4-sulfonyl]-pyridin-2-ylmethyl}-amide

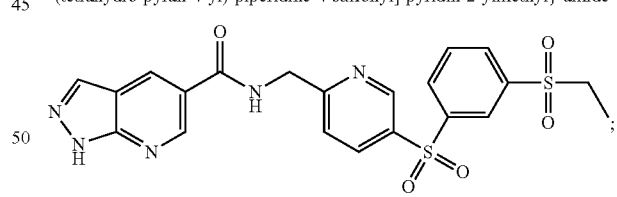

1H-Pyrazole[3,4-b]pyridine-5-carboxylic acid [5-(3-ethanesulfonyl-benzenesulfonyl)-pyridin-2-ylmethyl]-amide

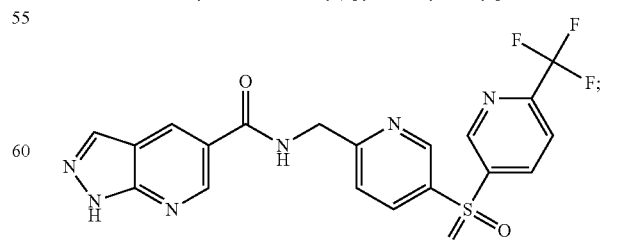

1H-Pyrazole[3,4-b]pyridine-5-carboxylic acid [5-(6-trifluoromethyl-pyridine-3-sulfonyl)-pyridin-2-ylmethyl]-amide

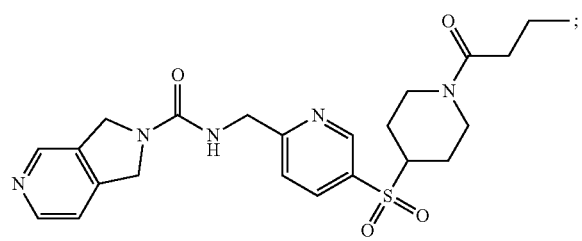

1,3-Dihydro-pyrrolo[3,4-c]pyridine-2-carboxylic acid [5-(1-butyryl-piperidine-4-sulfonyl)-pyridin-2-ylmethyl]-amide

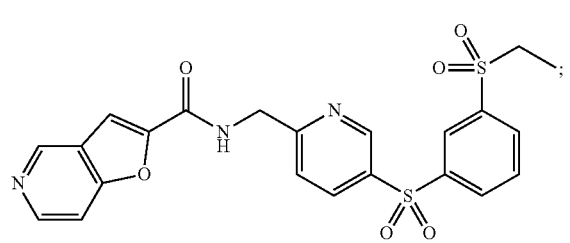

N-[[5-(3-ethylsulfonylphenyl)sulfonyl-2-pyridyl]methyl]furo[2-3-c]pyridine-2-carboxamide

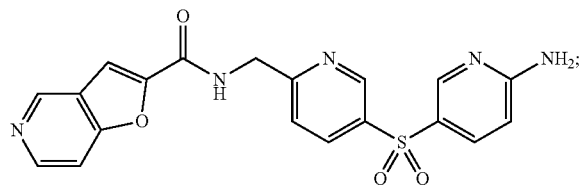

N-[[5-[(6-amino-3-pyridyl)sulfonyl-2-pyridyl]methyl]furo[2-3-c]pyridine-2-carboxamide

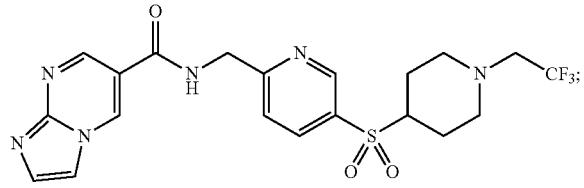

N-[[5-[[1-(2,2,2-trifluoroethyl)-4-piperidyl]sulfonyl]-2-pyridyl]methyl]imidazo[1-2-a]pyridine-2-carboxamide

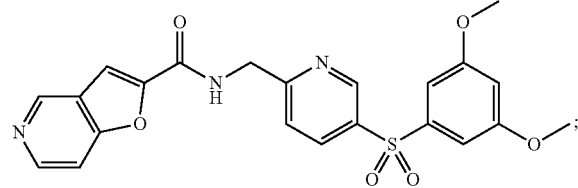

N-[[5-(3,5-dimethoxyphenyl)sulfonyl-2-pyridyl]methyl]furo[2-3-c]pyridine-2-carboxamide

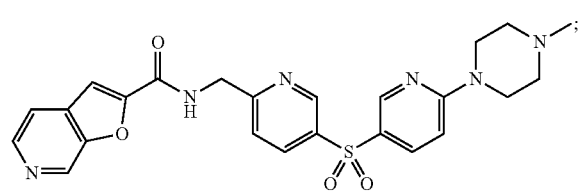

N-[[5-[[6-(4-methylpiperazin-1-yl)-3-pyridyl]sulfonyl]-2-pyridyl]methyl]-1,3-dihydropyrrolo[3,4-c]pyridine-2-carboxamide

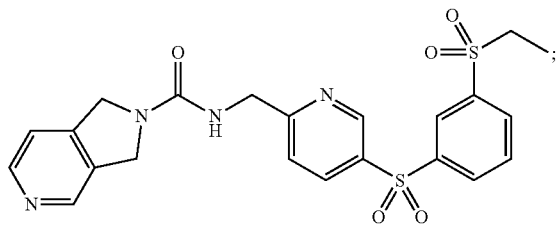

N-[[5-(3-ethylsulfonylphenyl)sulfonyl-2-pyridyl]methyl]-1,3-dihydropyrrolo[3,4-c]pyridine-2-carboxamide

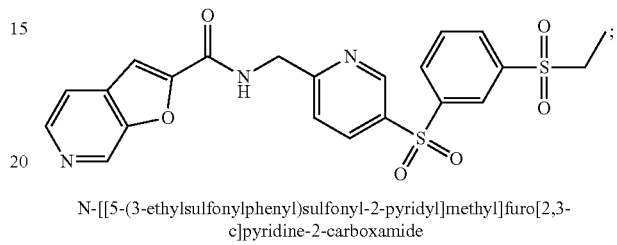

N-[[5-(3-ethylsulfonylphenyl)sulfonyl-2-pyridyl]methyl]furo[2,3-c]pyridine-2-carboxamide

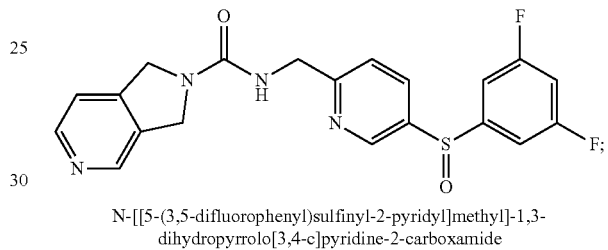

N-[[5-(3,5-difluorophenyl)sulfinyl-2-pyridyl]methyl]-1,3-dihydropyrrolo[3,4-c]pyridine-2-carboxamide

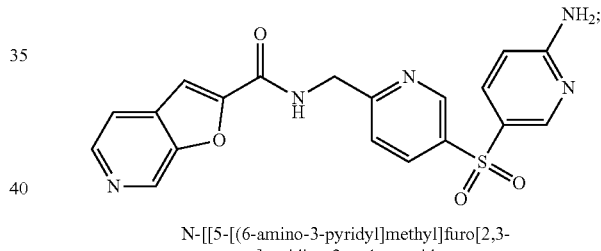

N-[[5-[(6-amino-3-pyridyl)methyl]furo[2,3-c]pyridine-2-carboxamide

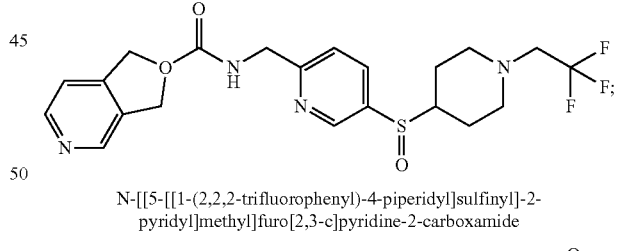

N-[[5-[[1-(2,2,2-trifluorophenyl)-4-piperidyl]sulfinyl]-2-pyridyl]methyl]furo[2,3-c]pyridine-2-carboxamide

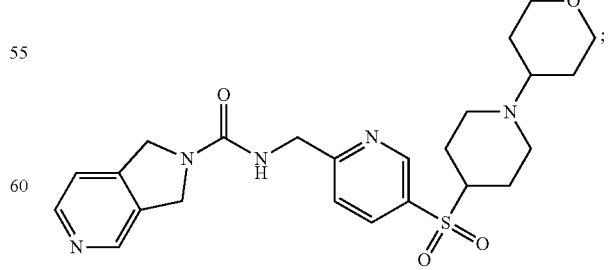

N-[[5-[(1-tetrahydropyran-4-yl-4-piperidyl)sulfonyl]-2-pyridyl]methyl]-1,3-dihydropyrrolo[3,4-c]pyridine-2-carboxamide -continued

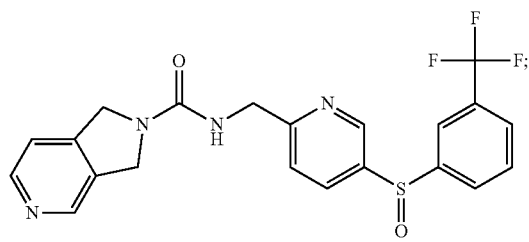

N-[[5-[3-(trifluoromethyl)phenyl]sulfinyl-2-pyridyl]methyl]-1,3-dihydropyrrolo[3,4-c]pyridine-2-carboxamide

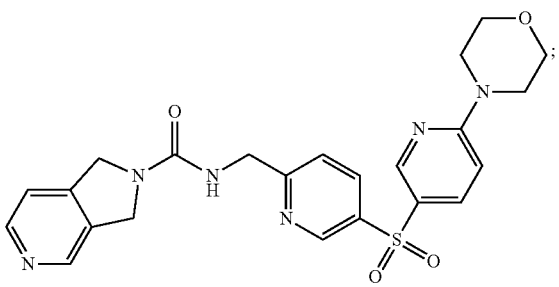

N-[[5-[(6-morpholino-3-pyridyl)sulfonyl]-2-pyridyl]methyl]-1,3-dihydropyrrolo[3,4-c]pyridine-2-carboxamide

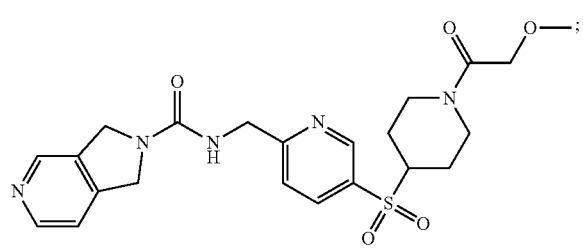

N-[[5-[[1-(2-methoxyacetyl)-4-piperidyl)sulfonyl]-2-pyridyl]methyl]-1,3-dihydropyrrolo[3,4-c]pyridine-2-carboxamide

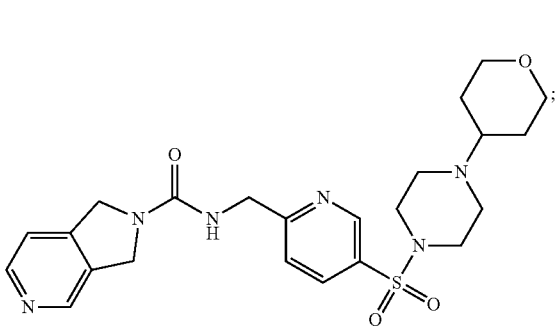

N-[[5-(4-tetrahydropyran-4-ylpiperazin-1-yl)sulfonyl-2-pyridyl]methyl]-1,3-dihydropyrrolo[3,4-c]pyridine-2-carboxamide

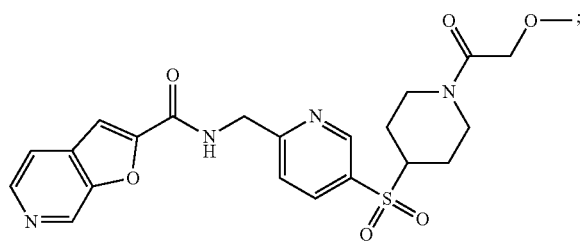

N-[[5-[[1-(2-methoxyacetyl)-4-piperidyl)sulfonyl]-2-pyridyl]methyl]furo[2,3-c]pyridine-2-carboxamide

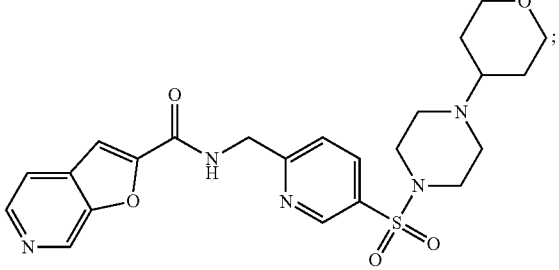

N-[[5-(4-tetrahydropyran-4-ylpiperazin-1-yl)sulfonyl-2-pyridyl]methyl]furo[2,3-c]pyridine-2-carboxamide

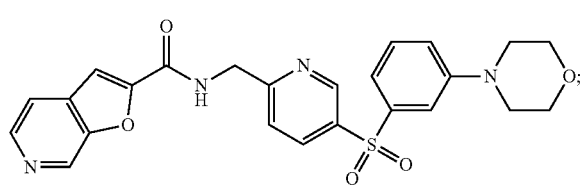

N-[[5-(3-morpholinophenyl)sulfonyl-2-pyridyl]methyl]furo[2,3-c]pyridine-2-carboxamide

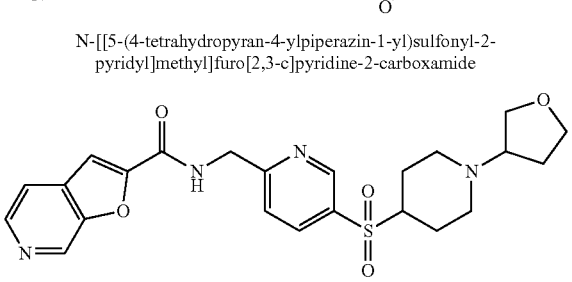

N-[[5-[(1-tetrahydrofuran-3-yl-4-piperidyl)sulfonyl]-2-pyridyl]methyl]furo[2,3-c]pyridine-2-carboxamide

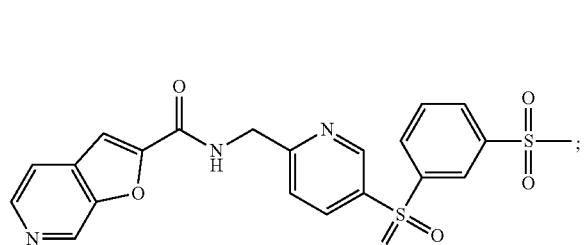

N-[[5-(3-methylsulfonylphenyl)sulfonyl-2-pyridyl]methyl]furo[2,3-c]pyridine-2-carboxamide

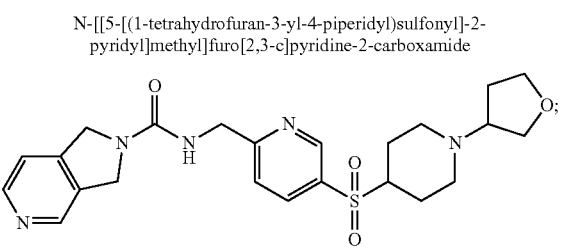

N-[[5-[(1-tetrahydrofuran-3-yl-4-piperidyl)sulfonyl]-2-pyridyl]methyl]-1,3-dihyropyrrolo[3,4-c]pyridine-2-carboxamide

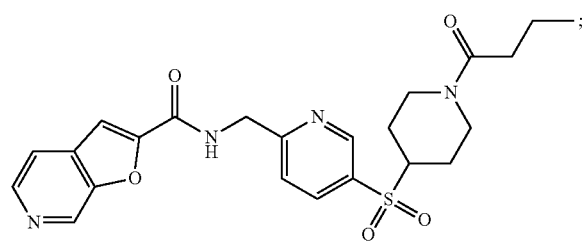

N-[[5-[(1-butanoyl-4-piperidyl)sulfonyl]-2-pyridyl]methyl]furo[2,3-c]pyridine-2-carboxamide

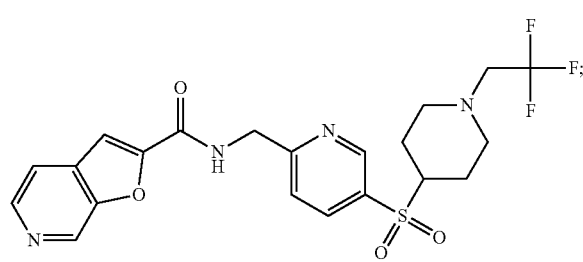

N-[[5-[[1-(2,2,2-trifluoroethyl)-4-piperidyl]sulfonyl]-2-pyridyl]methyl]furo[2,3-c]pyridine-2-carboxamide

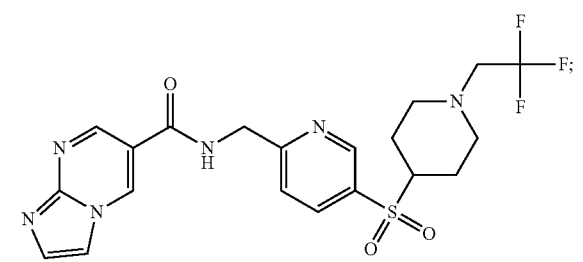

N-[[5-[[1-(2,2,2-trifluoroethyl)-4-piperidyl]sulfonyl]-2-pyridyl]methyl]imidazo[1,2-a]pyrimidine-6-carboxamide

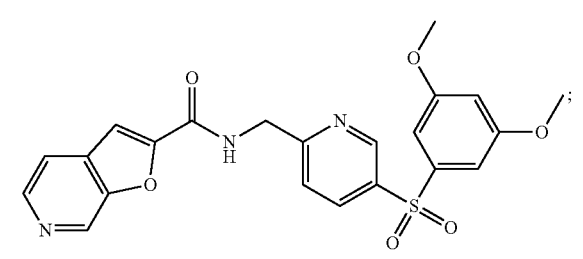

N-[[5-(3,5-dimethoxyphenyl)sulfonyl-2-pyridyl]methyl]furo[2,3-c]pyridine-2-carboxamide

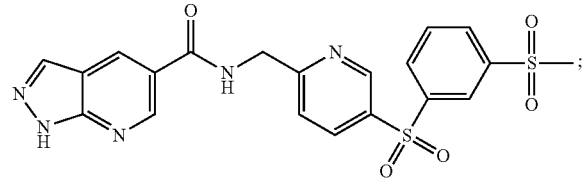

N-[[5-(3-methylsulfonylphenyl)sulfonyl-2-pyridyl]methyl]-1H-pyrazolo[3,4-b]pyridine-5-carboxamide

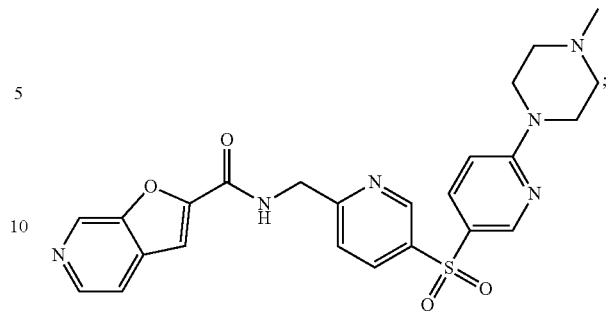

N-[[5-[[6-(4-methylpiperazin-1-yl)-3-pyridyl]sulfonyl]-2-pyridyl]methyl]furo[2,3-c]pyridine-2-carboxamide

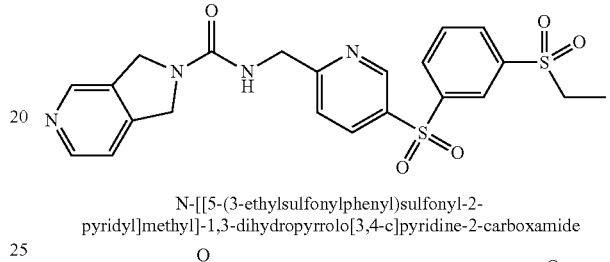

N-[[5-(3-ethylsulfonylphenyl)sulfonyl-2-pyridyl]methyl]-1,3-dihydropyrrolo[3,4-c]pyridine-2-carboxamide

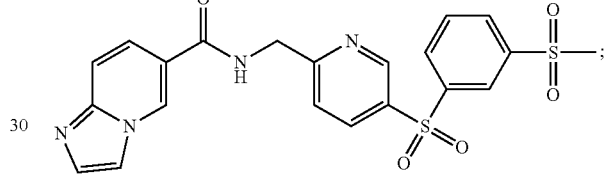

N-[[5-(3-methylsulfonylphenyl)sulfonyl-2-pyridyl]methyl]imidazo[1,2-a]pyridine-6-carboxamide

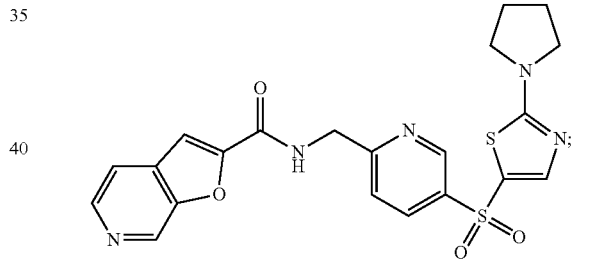

N-[[5-(2-pyrrolidin-1-ylthiazol-5-yl)sulfonyl-2-pyridyl]methyl]furo[2,3-c]pyridine-2-carboxamide

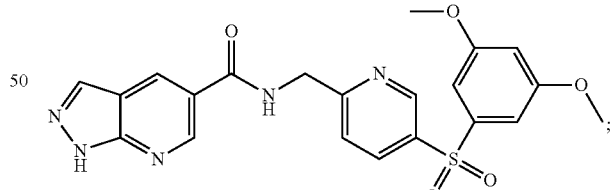

N-[[5-(3,5-dimethoxyphenyl)sulfonyl-2-pyridyl]methyl]-1H-pyrazolo[3,4-b]pyridine-5-carboxamide

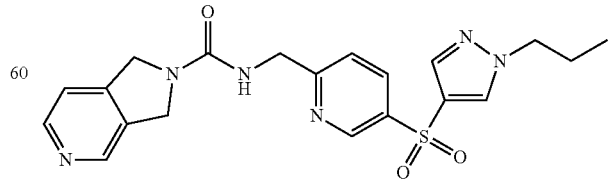

N-[[5-(1-propylpyrazol-4-yl)sulfonyl-2-pyridyl]methyl]-1,3-dihydropyrazolo[3,4-c]pyridine-2-carboxamide

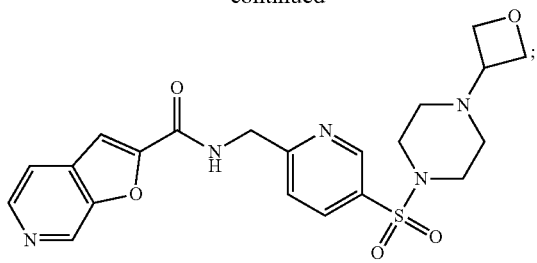

N-[[5-[4-oxetan-3-yl)piperazin-1-yl]sulfonyl-2-
pyridyl]methyl]furo[2,3-c]pyridine-2-carboxamide

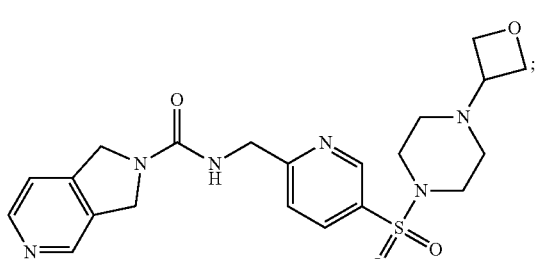

N-[[5-[4-oxetan-3-yl)piperazin-1-yl]sulfonyl-2-
pyridyl]methyl]-1,3-dihydropyrrolo[3,4-c]pyridine-2-carboxamide

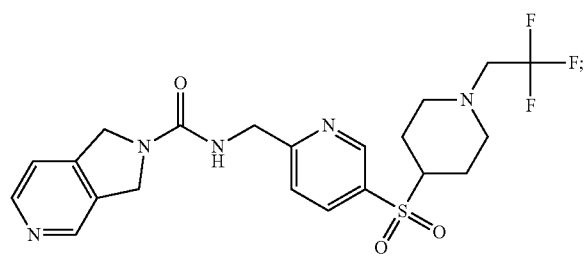

N-[[5-[[1-(2,2,2-trifluoroethyl)-4-piperidyl]sulfonyl]-2-
pyridyl]methyl]-1,3-dihydropyrrolo[3,4-c]pyridine-2-carboxamide

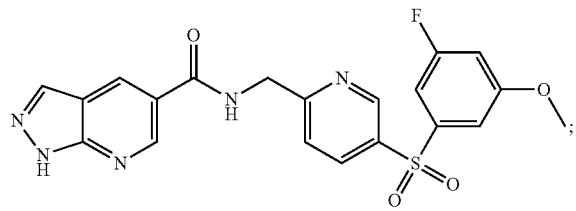

N-[[5-[(3-fluoro-5-methoxy-phenyl)sulfonyl]-2-
pyridyl]methyl]-1H-pyrazolo[3,4-b]pyridine-5-carboxamide

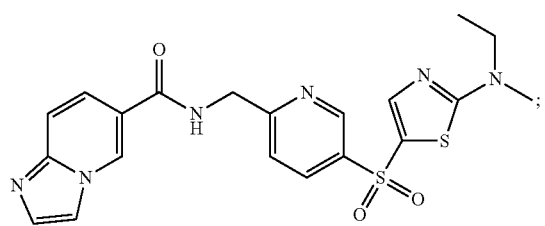

N-[[5-[2-[ethyl(methyl)amino]thiazol-5-yl]sulfonyl-2-
pyridyl]methyl]imidazo[1,2-a]pyridine-6-carboxamide

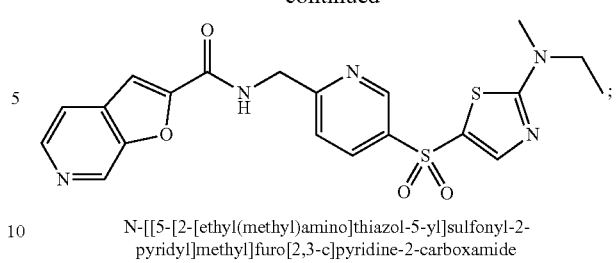

N-[[5-[2-[ethyl(methyl)amino]thiazol-5-yl]sulfonyl-2-
pyridyl]methyl]furo[2,3-c]pyridine-2-carboxamide

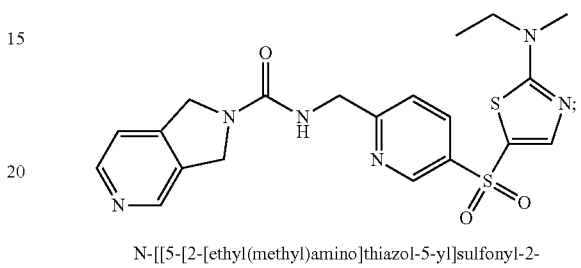

N-[[5-[2-[ethyl(methyl)amino]thiazol-5-yl]sulfonyl-2-
pyridyl]methyl]-1,3-dihydropyrrolo[3,4-c]pyridine-2-carboxamide

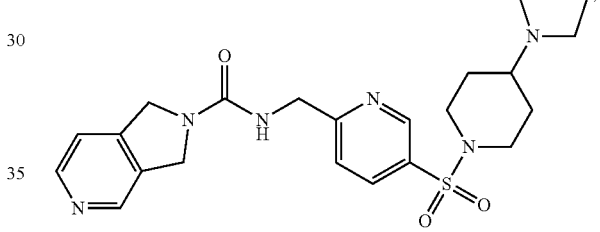

N-[[5-[(4-pyrrolidin-1-yl-1-piperidyl)sulfonyl]-2-
pyridyl]methyl]-1,3-dihydropyrrolo[3,4-c]pyridine-2-carboxamide

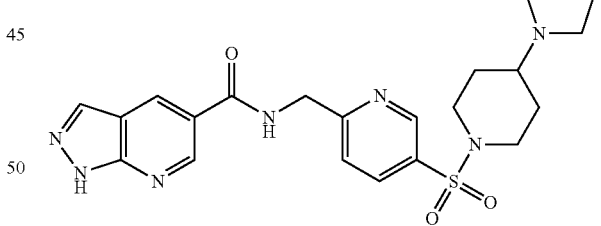

N-[[5-[(4-pyrrolidin-1-yl-1-piperidyl)sulfonyl]-2-
pyridyl]methyl]-1H-pyrazolo[3,4-b]pyridine-5-carboxamide

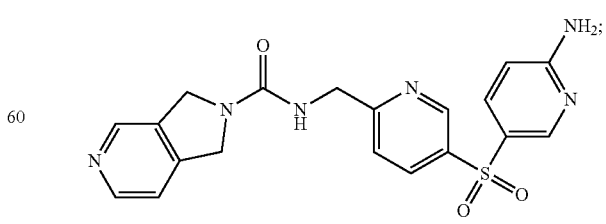

N-[[5-[(6-amino-3-pyridyl)sulfonyl]-2-
pyridyl]methyl]-1,3-dihydropyrrolo[3,4-c]pyridine-2-carboxamide -continued

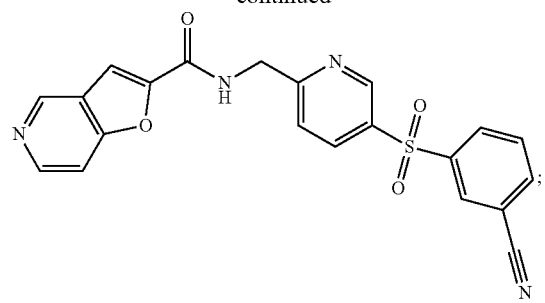

N-[[5-(3-cyanophenyl)sulfonyl-2-
pyridyl]methyl]furo[2,3-c]pyridine-2-carboxamide

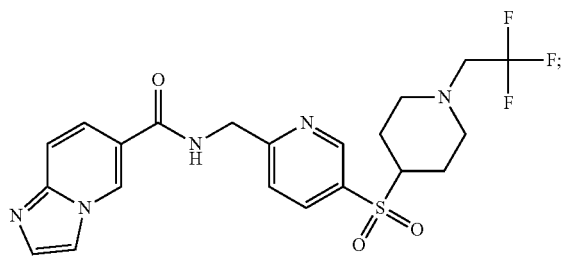

N-[[5-[[1-(2,2,2-trifluoroethyl)-4-piperidyl]sulfonyl]-2-
pyridyl]methyl]imidazo[1,2-a]pyridine-6-carboxamide

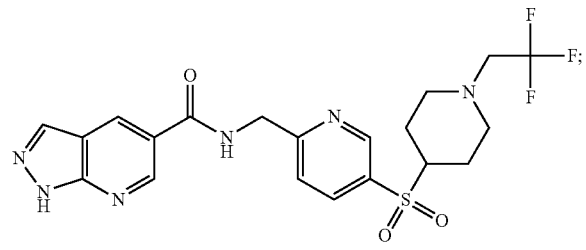

N-[[5-[[1-(2,2,2-trifluoroethyl)-4-piperidyl]sulfonyl]-2-
pyridyl]methyl]-1H-pyrazolo[3,4-b]pyridine-5-carboxamide

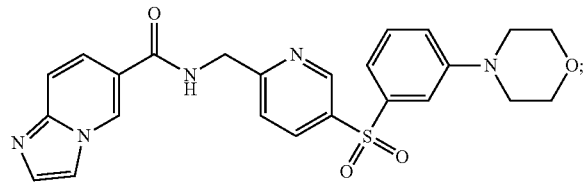

N-[[5-(3-morpholinophenyl)sulfonyl-2-
pyridyl]methyl]imidazo[1,2-a]pyridine-6-carboxamide

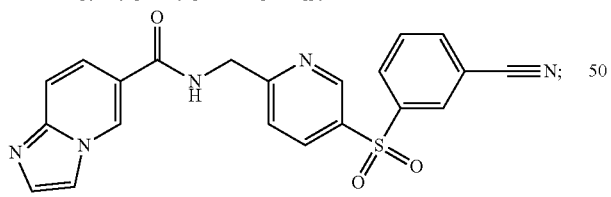

N-[[5-(3-cyanophenyl)sulfonyl-2-
pyridyl]methyl]imidazo[1,2-a]pyridine-6-carboxamide

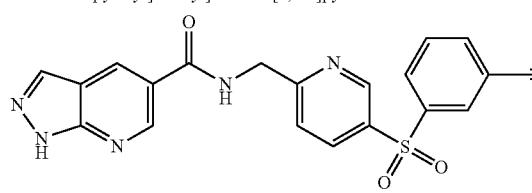

N-[[5-(3-cyanophenyl)sulfonyl-2-
pyridyl]methyl]1H-pyrazolo[3,4-b]pyridine-5-carboxamide -continued

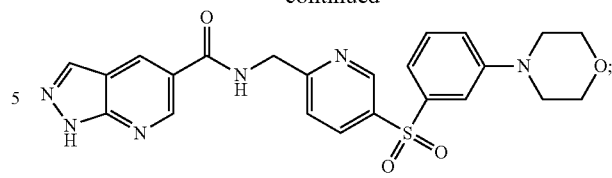

N-[[5-(3-morpholinophenyl)sulfonyl-2-
pyridyl]methyl]-1H-pyrazolo[3,4-b]pyridine-5-carboxamide

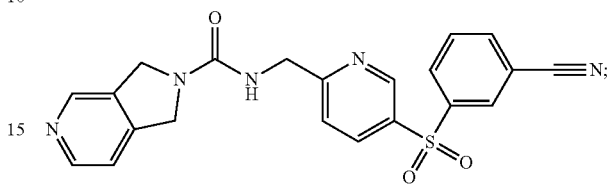

N-[[5-(3-cyanophenyl)sulfonyl-2-
pyridyl]methyl]-1,3-dihydropyrrolo[3,4-c]pyridine-2-carboxamide

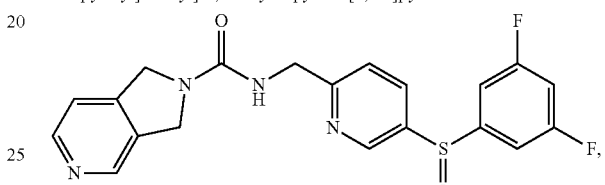

N-[[5-(3,5-difluorophenyl)sulfinyl-2-
pyridyl]methyl]-1,3-dihydropyrrolo[3,4-c]pyridine-2-carboxamide
(enantiomer 1)

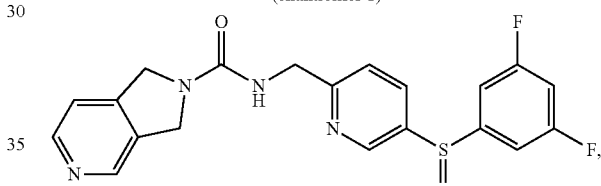

N-[[5-(3,5-difluorophenyl)sulfinyl-2-
pyridyl]methyl]-1,3-dihydropyrrolo[3,4-c]pyridine-2-carboxamide
(enantiomer 2)

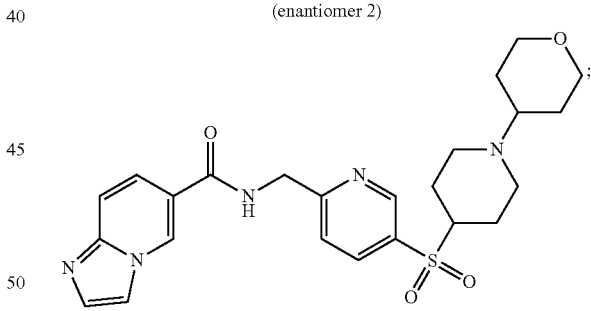

N-[[5-[(1-tetrahydropyran-4-yl-4-piperidyl)sulfonyl]-2-
pyridyl]methyl]imidazo[1,2-c]pyridine-6-carboxamide

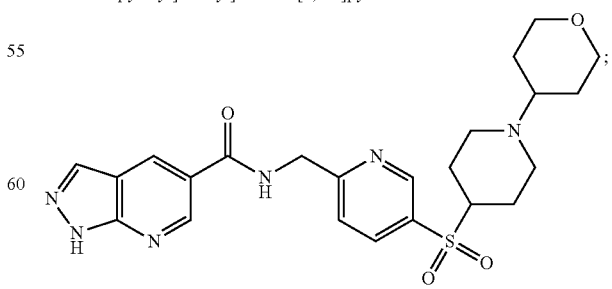

N-[[5-[(1-tetrahydropyran-4-yl-4-piperidyl)sulfonyl]-2-
pyridyl]methyl]-1H-pyrazolo[3,4-b]pyridine-5-carboxamide -continued

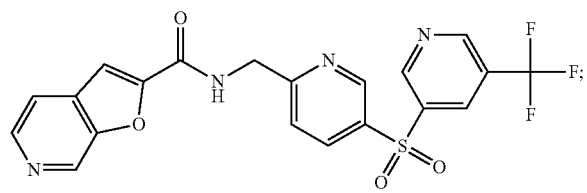

N-[[5-[[5-(trifluoromethyl)-3-pyridyl]sulfonyl]-2-pyridyl]methyl]furo[2,3-c]pyridine-2-carboxamide

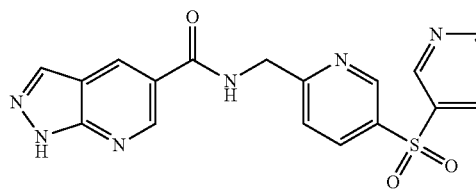

N-[[5-[(5-chloro-3-pyridyl)sulfonyl]-2-pyridyl]methyl]1H-pyrazolo[3,4-b]pyridine-5-carboxamide

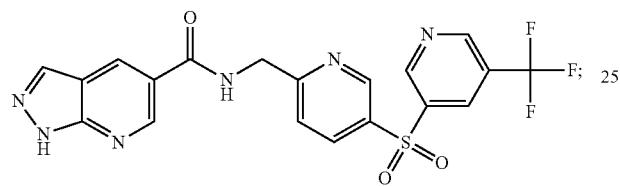

N-[[5-[[5-(trifluoromethyl)-3-pyridyl]sulfonyl]-2-pyridyl]methyl]-1H-pyrazolo[3,4-b]pyridine-5-carboxamide

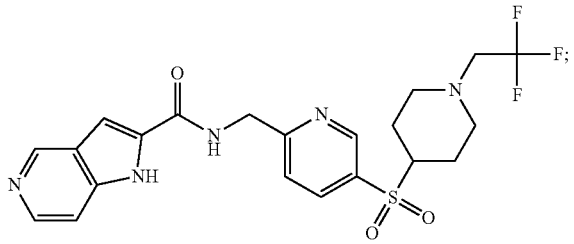

N-[[5-[[1-(2,2,2-trifluoroethyl)-4-piperidyl]sulfonyl]-2-pyridyl]methyl]-1H-pyrrolo[3,2-c]pyridine-2-carboxamide

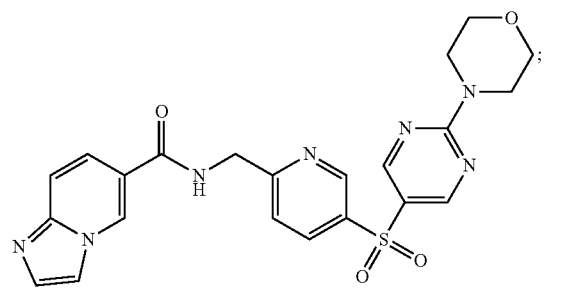

N-[[5-(2-morpholinopyrimidin-5-yl)sulfonyl-2-pyridyl]methyl]imidazo[1,2-a]pyridine-6-carboxamide

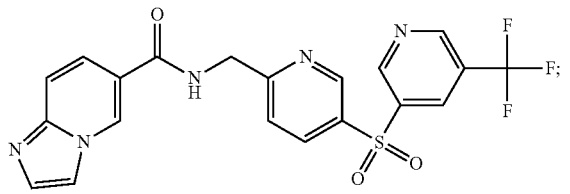

N-[[5-[[5-(trifluoromethyl)-3-pyridyl]sulfonyl]-2-pyridyl]methyl]imidazo[1,2-a]pyridine-6-carboxamide -continued

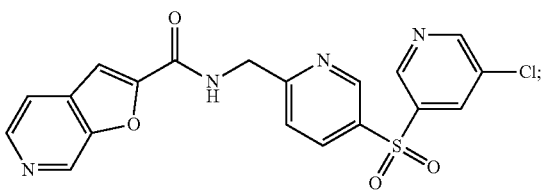

N-[[5-[(5-chloro-3-pyridyl)sulfonyl]-2-pyridyl]methyl]furo[2,3-c]pyridine-2-carboxamide

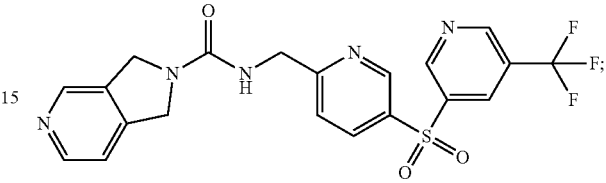

N-[[5-[[5-(trifluoromethyl)-3-pyridyl]sulfonyl]-2-pyridyl]methyl]-1,3-dihydropyrrolo[3,4-c]pyridine-2-carboxamide

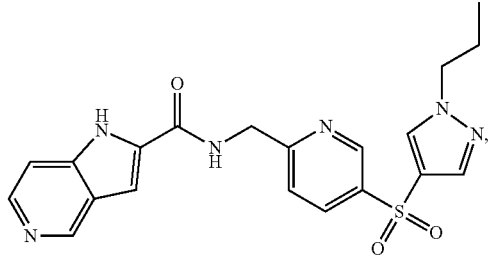

N-[[5-(1-propylpyrazol-4-yl)sulfonyl-2-pyridyl]methyl]-1H-pyrrolo[3,2-c]pyridine-2-carboxamide

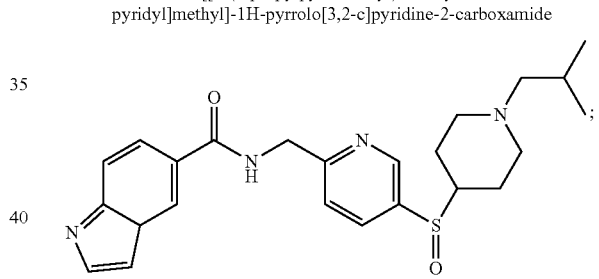

N-[[5-[(1-isobutyl-4-piperidyl)sulfinyl]-2-pyridyl]methyl]imidazo[1,2-a]pyridine-6-carboxamide

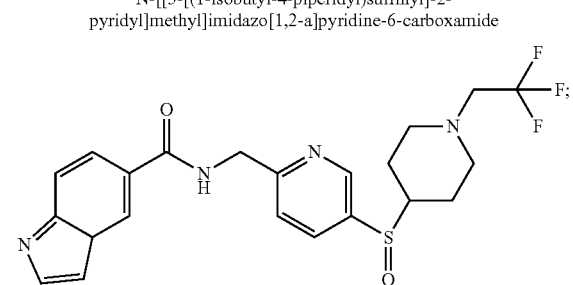

N-[[5-[[1-(2,2,2-trifluoroethyl)-4-piperidyl]sulfinyl]-2-pyridyl]methyl]imidazo[1,2-a]pyridine-6-carboxamide

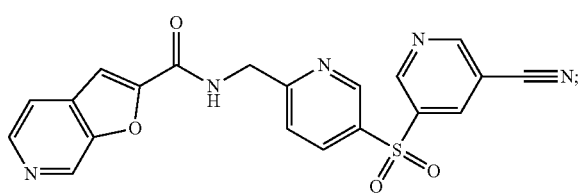

N-[[5-[(5-cyano-3-pyridyl)sulfonyl]-2-pyridyl]methyl]furo[2,3-c]pyridine-2-carboxamide

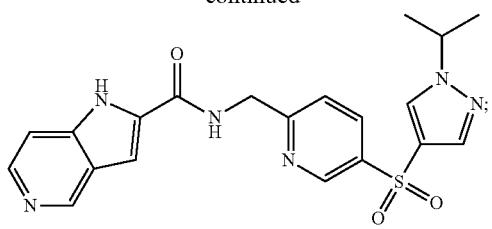

N-[[5-(1-isopropylpyrazol-4-yl)sulfonyl-2-pyridyl]methyl]-1H-pyrrolo[3,2-c]pyridine-2-carboxamide

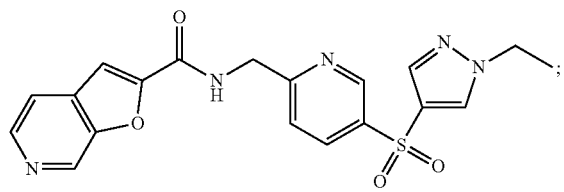

N-[[5-(1-ethylpyrazol-4-yl)sulfonyl-2-pyridyl]methyl]furo[2,3-c]pyridine-2-carboxamide

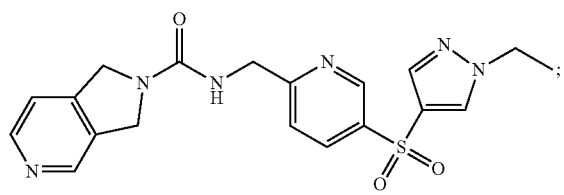

N-[[5-(1-ethylpyrazol-4-yl)sulfonyl-2-pyridyl]methyl]-1,3-dihydropyrrolo[3,4-c]pyridine-2-carboxamide

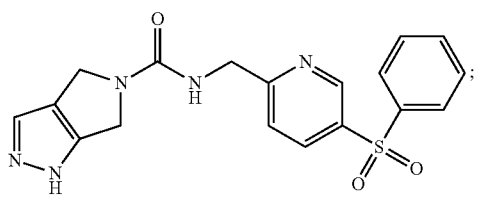

N-[[5-(benzenesulfonyl)-2-pyridyl]methyl]-4,6-dihydro-1H-pyrrolo[3,4-c]pyrazole-5-carboxamide

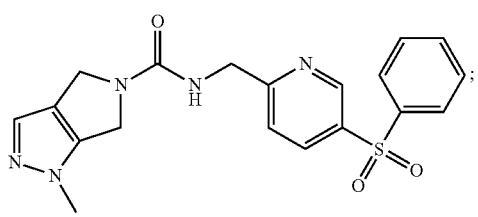

N-[[5-(benzenesulfonyl)-2-pyridyl]methyl]-1-methyl-4,6-dihydropyrrolo[3,4-c]pyrazole-5-carboxamide

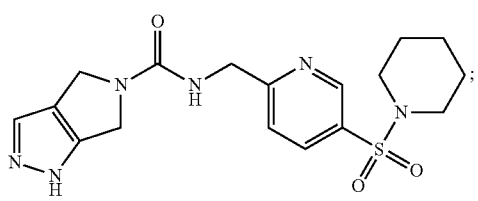

N-[[5-(1-piperidylsulfonyl)-2-pyridyl]methyl]-4,6-dihydro-1H-pyrrolo[3,4-c]pyrazole-5-carboxamide

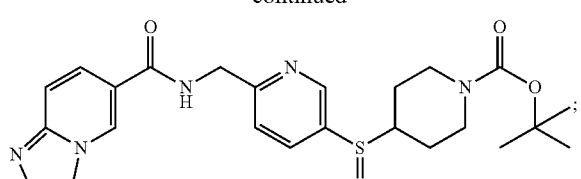

tert-butyl 4-[[6-[(imidazo[1,2-a]pyridine-6-carbonylamino)methyl]-3-pyridyl]sulfinyl]piperidine-1-carboxylate

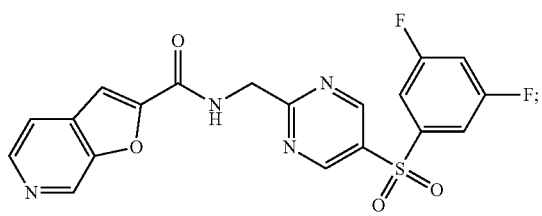

N-[[5-(3,5-difluorophenyl)sulfonylpyrimidin-2-yl]methyl]furo[2,3-c]pyridine-2-carboxamide

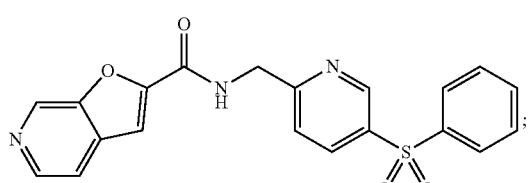

N-[[5-(benzenesulfonyl)-2-pyridyl]methyl]furo[2,3-c]pyridine-2-carboxamide

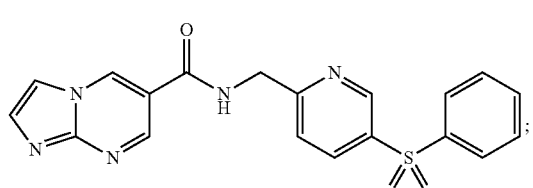

N-[[5-(benzenesulfonyl)-2-pyridyl]methyl]imidazo[1,2-a]pyrimidine-6-carboxamide

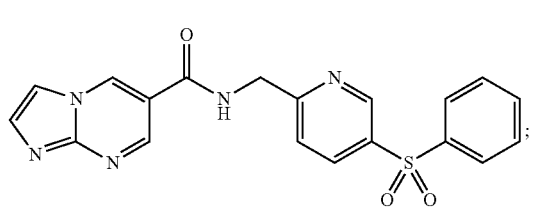

N-[[5-(benzenesulfonyl)-2-pyridyl]methyl]imidazo[1,2-a]pyrimidine-6-carboxamide

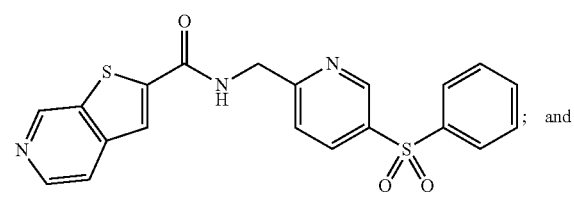

N-[[5-(benzenesulfonyl)-2-pyridyl]methyl]thieno[2,3-c]pyridine-2-carboxamide

-continued

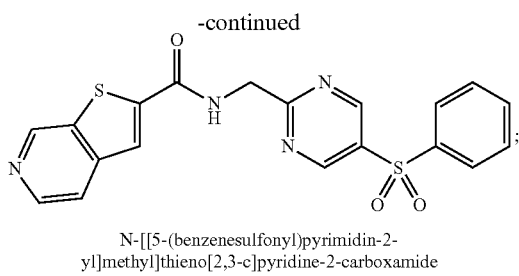

N-[[5-(benzenesulfonyl)pyrimidin-2-yl]methyl]thieno[2,3-c]pyridine-2-carboxamide and pharmaceutically acceptable salts thereof, stereoisomers thereof, and pharmaceutically acceptable salts of stereoisomers thereof.

17. A pharmaceutical composition comprising: (a) an effective amount of at least one compound of claim 1; and (b) a pharmaceutically acceptable carrier.

18. The pharmaceutical composition of claim 17, further comprising therapeutically effective amounts of one or more additional adjunctive active agents, or a rescuing agent, wherein said one or more additional adjunctive active agents are selected from the group consisting of a cytotoxic agent, cisplatin, doxorubicin, taxotere, taxol, etoposide, irinotecan, camptostar, topotecan, paclitaxel, docetaxel, the epothilones, tamoxifen, 5-fluorouracil, methoxtrexate, temozolomide, cyclophosphamide, SCH 66336, tipifarnib, R115777, L778,123, BMS 214662, gefitinib, erlotinib, C225, imatinib, Interferon alfa-2b, PEGinterferon alfa-2b, aromatase combinations, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, leucovirin, oxaliplatin, Pentostatine, vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17a-Ethinylestradiol, Diethylstilbestrol, Testosterone, Prednisone, Fluoxymesterone, Dromostanolone propionate, Testolactone, Megestrol acetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Ifosfomide, Rituximab, C225, Campath, leucovorin, dexamethasone, bicalutamide, chlorambucil, letrozole, megestrol, valrubicin, vinblastine, and niacin extended-release, wherein the rescuing agent is selected from the group consisting of nicotinamide, nicotinic acid, and nicotinamide mononucleotide (NMN).

19. A method of treating a subject suffering from or diagnosed with a disease or medical condition mediated by nicotinamidephosphoribosyltransferase (NAMPT) activity, comprising administering to the subject in need of such treatment an effective amount of at least one compound of claim 1, wherein the disease or medical condition is a solid or liquid tumor, non-small cell lung cancer, leukemia, lymphoma, ovarian cancer, glioma, breast cancer, uterine cancer, colon cancer, cervical cancer, lung cancer, prostate cancer, skin cancer, rhino-gastric tumors, colorectal cancer, CNS cancer, bladder cancer, pancreatic cancer, Hodgkin's disease, rheumatoid arthritis, diabetes, atherosclerosis, sepsis, aging, inflammation.

20. The method of claim 19, further comprising administering to the subject an effective amount of a rescuing agent or at least one compound selected from the group consisting of: a cytotoxic agent, cisplatin, doxorubicin, taxotere, taxol, etoposide, irinotecan, camptostar, topotecan, paclitaxel, docetaxel, the epothilones, tamoxifen, 5-fluorouracil, methoxtrexate, temozolomide, cyclophosphamide, SCH 66336, tipifarnib, R115777, L778,123, BMS 214662, gefitinib, erlotinib, C225, imatinib, Interferon alfa-2b, PEGinterferon alfa-2b, aromatase combinations, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, leucovirin, oxaliplatin, Pentostatine, vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17a-Ethinylestradiol, Diethylstilbestrol, Testosterone, Prednisone, Fluoxymesterone, Dromostanolone propionate, Testolactone, Megestrol acetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Ifosfomide, Rituximab, C225, Campath, leucovorin, dexamethasone, bicalutamide, chlorambucil, letrozole, megestrol, valrubicin, vinblastine, and niacin extended-release, wherein the rescuing agent is selected from the group consisting of nicotinamide, nicotinic acid, and nicotinamide mononucleotide (NMN).

* * * * *